(12) United States Patent
Seo et al.

(10) Patent No.: US 9,493,478 B2
(45) Date of Patent: Nov. 15, 2016

(54) FUSED RING COMPOUND CONTAINING FURAN OR SALT THEREOF AND PHARMACEUTICAL COMPOSITION COMPRISING SAME

(71) Applicant: YUHAN CORPORATION, Seoul (KR)

(72) Inventors: Hyoung Sig Seo, Anyang-si (KR); Tae Kyun Kim, Hwaseong-si (KR); Hyun Joo Lee, Suwon-si (KR); Dong Hoon Kim, Suwon-si (KR); Gyu Jin Lee, Seongnam-si (KR); Jun Chul Park, Yongin-si (KR); Ji Yeong Gal, Yongin-si (KR); Tae-hoon Kim, Bucheon-si (KR); Kwan Hoon Hyun, Incheon (KR); Kyoung Kyu Ahn, Suwon-si (KR); Kaapjoo Park, Seoul (KR); Su Youn Nam, Seoul (KR); Ge Hyeong Lee, Daejeon (KR); Hee Jong Lim, Daejeon (KR)

(73) Assignee: YUHAN CORPORATION, Seoul (KR)

( * ) Notice: Subject to any disclaimer, the term of this patent is extended or adjusted under 35 U.S.C. 154(b) by 0 days.

(21) Appl. No.: 14/416,079

(22) PCT Filed: Jul. 23, 2013

(86) PCT No.: PCT/KR2013/006581
§ 371 (c)(1),
(2) Date: Jan. 21, 2015

(87) PCT Pub. No.: WO2014/017803
PCT Pub. Date: Jan. 30, 2014

(65) Prior Publication Data
US 2015/0191478 A1 Jul. 9, 2015

(30) Foreign Application Priority Data
Jul. 23, 2012 (KR) ........................ 10-2012-0080026

(51) Int. Cl.
*C07D 491/048* (2006.01)
(52) U.S. Cl.
CPC ................................ *C07D 491/048* (2013.01)
(58) Field of Classification Search
CPC .................................................. C07D 491/048
See application file for complete search history.

(56) References Cited

U.S. PATENT DOCUMENTS 7,067,515 B2 * 6/2006 Wishka ................ C07D 519/00
514/228.2

| 2006/0074083 | A1 | 4/2006 | Kalvinsh et al. |
| 2011/0028507 | A1 | 2/2011 | Kim et al. |
| 2012/0010247 | A1 | 1/2012 | Kamata et al. |
| 2012/0015926 | A1 | 1/2012 | Tong et al. |

FOREIGN PATENT DOCUMENTS

| WO | 0109121 A2 | 2/2001 |
| WO | 02100857 A1 | 12/2002 |
| WO | 03022856 A1 | 3/2003 |
| WO | 2004/089939 A1 | 10/2004 |
| WO | 2006024666 A1 | 3/2006 |
| WO | 2009/037570 A2 | 3/2009 |
| WO | 2010/054278 A2 | 5/2010 |
| WO | 2012/031197 A1 | 3/2012 |

OTHER PUBLICATIONS

Michelotti et. al. "Two classes of p38a MAP kinase inhibitors having a common diphenylether core but exhibiting divergent binding modes" 2005, 15, 5274-5279.*
Jiang et. al. "3,5-Disubstituted quinolines as novel c-Jun N-terminal kinase inhibitors." Bioorganic & Medicinal Chemistry Letters 2007, 17, 6378-6382.*
Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*
Miyazaki et. al. "Design and effective synthesis of novel templates, 3,7-diphenyl-4-amino-thieno and furo-[3,2-c]pyridines as protein kinase inhibitors and in vitro evaluation targeting angiogenetic kinases" Bioorganic & Medicinal Chemistry Letters 2007, 17, 250-254.*
Mulvihill et. al. "Novel 2-phenylquinolin-7-yl-derived imidazo[1,5-a]pyrazines as potent insulin-like growth factor-I receptor (IGF-IR) inhibitors" Bioorganic & Medicinal Chemistry 2008, 16, 1359-1375.*
Cheng "Structure-based design, SAR analysis and antitumor activity of PI3K/ mTOR dual inhibitors from 4-methylpyridopyrimidinone series" Bioorganic & Medicinal Chemistry Letters 23 (2013) 2787-2792.*

(Continued)

*Primary Examiner* — David K O'Dell
(74) *Attorney, Agent, or Firm* — Sughrue Mion, PLLC

(57) ABSTRACT

The present invention provides a fused ring compound containing furan or a pharmaceutically acceptable salt thereof, a method for preparing same, a pharmaceutical composition comprising same, and a use thereof. The fused ring compound containing furan or a pharmaceutically acceptable salt thereof inhibits the activity of phosphatidylinositol 3-kinase (PI3K) and can therefore be used in a pharmaceutical composition for treating and preventing respiratory diseases, inflammatory diseases, proliferative diseases, cardiovascular diseases, or central nervous system diseases which occur due to the over-activation of PI3K.

14 Claims, No Drawings

(56) References Cited

OTHER PUBLICATIONS

Baell "New Substructure Filters for Removal of Pan Assay Interference Compounds (PAINS) from Screening Libraries and for Their Exclusion in Bioassays" J. Med. Chem. 2010, 53, 2719-2740.*
Pitt "Heteroaromatic Rings of the Future" J. Med. Chem. 2009, 52, 2952-2963.*
Pozharskii et. al. Heterocycles in Life and Society Wiley, 1997, pp. 1-6.*
Ward et al., "Isoform-specific phosphoinositide 3-kinase inhibitors as therapeutic agents," Current Opinion in Pharmacology, 2003, vol. 3, pp. 426-434 (9 pages total).
Toker et al., "Signalling through the lipid products of phosphoinositide-3-OH kinase," Nature, Jun. 12, 1997, vol. 387 pp. 673-676 (4 pages total).
Bader et al., "Oncogenic PI3K Deregulates Transcription and Translation," Nature Reviews Cancer, Dec. 2005, vol. 5, pp. 921-929 (9 pages total).
Moir et al., "Phosphatidylinositol 3-Kinase Isoform-Specific Effects in Airway Mesenchymal Cell Function," The Journal of Pharmacology and Experimental Therapeutics, 2011, vol. 337, No. 2, pp. 557-566 (10 pages total).
Conte et al., "Inhibition of PI3K Prevents the Proliferation and Differentiation of Human Lung Fibroblasts into Myofibroblasts: The Role of Class I P110 Isoforms," PLoS One, Oct. 2011, vol. 6, No. 10, pp. 110 (10 pages total).
Pal et al., "PI3K and Akt as molecular targets for cancer therapy: current clinical outcomes," Acta Pharmacologica Sinica, 2012, vol. 33, pp. 1441-1458 (18 pages total).
Barberis et al., "Targeting phosphoinositide 3-kinase γ to fight inflammation and more," Thromb Haemost, 2008, pp. 279-285 (7 pages total).
Koyasu, Shigeo "The role of PI3K in immune cells," Nature Immunology, Apr. 2003, vol. 4, No. 4, pp. 313-319 (7 pages total).
Ali et al., "Essential role for the p110δ phosphoinositide 3-kinase in the allergic response," Nature, Oct. 21, 2004, vol. 431, pp. 1007-1011 (5 pages total).
Foukas et al., "Critical role for the p110α phosphoinositide-3-OH kinase in growth and metabolic regulation," Nature, May 18, 2006, vol. 441, pp. 366-370 (5 pages total).
Sheppard et al., "Targeting PI3 Kinase/AKT/mTOR Signaling in Cancer," Critical Reviews in Oncogenesis, 2012, vol. 17, No. 1, pp. 69-95 (27 pages total).
Engelman et al., "The evolution of phosphatidylinositol 3-kinases as regulators of growth and metabolism," Nature Reviews Genetics, Aug. 2006, vol. 7, pp. 606-619 (14 pages total).
Naga Prasad et al., "Role of Phosphoinositide 3-Kinase in Cardiac Function and Heart Failure," Trends in Cardiovascular Medicine, 2003, vol. 13, No. 5, pp. 206-212 (7 pages total).
Lim et al., "PI3Kγ-deficient mice have reduced levels of allergen-induced eosinophilic inflammation and airway remodeling," AJP Lung Cellular and Molecular Physiology, Feb. 2009, vol. 296, pp. L210-L219 (11 pages total).
Lazaar et al., "Airway smooth muscle: A modulator of airway remodeling in asthma," J Allergy Clin Immunol, Sep. 2005, vol. 116, No. 3, pp. 488-495 (8 pages total).
Kim et al., "PI3Kγ is required for NMDA receptor—dependent long-term depression and behavioral flexibility," Nature Neuroscience, Nov. 2011, vol. 14, No. 11, pp. 1447-1454 (10 pages total).
International Searching Authority, International Search Report of PCT/KR2013/006581, dated Nov. 6, 2013. [PCT/ISA/210].
Mladenovic et al., "Cu(I) Substitutions. Furo[3,2-b] pyridines, Furo[3,2-c] pyridines and IH/-Thieno[3,4-b] 2-pyran-I-ones from Cuprous Acetylides," Journal of Heterocyclic Chemistry, vol. 5: 227-230, Apr. 1968, 4 pages total.
European Patent Office, Communication dated Feb. 11, 2016 issued in counterpart European Application No. 13823101.4.

* cited by examiner

FUSED RING COMPOUND CONTAINING FURAN OR SALT THEREOF AND PHARMACEUTICAL COMPOSITION COMPRISING SAME

CROSS REFERENCE TO RELATED APPLICATIONS

This application is a National Stage of International Application No. PCT/KR2013/006581 filed Jul. 23, 2013, claiming priority based on Korean Patent Application No. 10-2012-0080026, filed Jul. 23, 2012, the contents of all of which are incorporated herein by reference in their entirety.

FIELD OF THE INVENTION

The present invention relates to a fused ring compound containing furan or a pharmaceutically acceptable salt thereof, a method for preparing same, a pharmaceutical composition comprising same, and a use thereof.

BACKGROUND OF THE INVENTION

Phosphatidylinositol 3-kinase (PI3K), which is also known as phosphoinositol 3-kinase or phosphoinositide 3-kinase, is a lipid kinase capable of phosphorylating 3-hydroxyl group of an inositol ring and plays an important role in cell proliferation, survival, motility and the like (Nature 387: 673-6 (1997)).

Class I PI3Ks (PI3Kα, PI3Kβ, PI3Kδ and PI3Kγ) are activated by receptor tyrosine kinase or G-protein coupled receptor (GPCR) to produce phosphatidylinositol 3,4,5-triphosphate (PIP3) and activate Akt. The activated Akt controls cell proliferation, survival, vascularization, etc. by phosphorylating TSC2, GSK3β, MDM2, FOXO, BAD and the like (Nature Rev. Cancer 5: 921-929 (2005)).

Class I PI3Ks are heterodimeric molecules composed of p110 catalytic subunits and regulatory subunits. They are further classified into Class IA and Class IB on their regulatory partner and regulation mechanism. Class IA enzymes are composed of five (5) different enzymes based regulatory subunits (p85α, p55α, p50α, p85β and p55γ) and three (3) different catalytic subunits (p110α, p110β and p110δ), and all of the catalytic subunits interact with all of the regulatory subunits to form various types of heterodimer. Class IA PI3Ks are generally activated in response to growth factor-stimulation of receptor tyrosine kinases, via interaction of the regulatory subunit SH2 domains with certain phosphotyrosine residues of the activated receptor or adaptor proteins such as insulin receptor substrate-1 (IRS-1). Both p110α and p110β are mainly expressed in all cell types, whereas the expression of p110δ is more restricted to inflammatory cells including leukocytes and some epithelial cells (Curr. Opin. Pharmacol. 3(4): 426-434 (2003); Thromb Haemost 99: 279-285 (2008)). In contrast, the single Class IB enzymes consist of p120γ catalytic subunits that interact with p101 regulatory subunits (which is commonly referred to as "p110γ"; see Cell 89: 105-114, April 1997, etc.). Moreover, Class IB enzymes are activated in response to G-protein coupled receptor (GPCRs) and its expression appears to be limited to inflammatory cells, including leukocytes and macrophagocytes, and cardiomyocytes (Thromb Haemost 99: 279-285 (2008)).

It is known that overactivity of p110α, a catalytic subunit of PI3Kα, is found in colon cancer, breast cancer, brain tumor, gastric cancer, liver cancer, ovarian cancer, etc. (Acta Pharmacologica Sinica 33: 1441-1458 (2012)). Also, it has been reported that p110α regulates proliferation of smooth muscle cells and cytokine secretion in bronchial smooth muscle cells of patients with severe asthma (J Pharmacol Exp Ther. 337(2): 557-566 (2011)). It is also known to participate in conversion of fibroblast to myofibroblast by TGFβ1 in patients with idiopathic pulmonary fibrosis (PLoS ONE 6(10): e24663 (2011)). Further, it is observed that PI3K-Akt pathway are overactivated in cancers where phosphatase and tensin homolog (PTEN) that dephosphorylates PIP3 is inactivated or p110α is overactivated. Thus, a drug having an inhibitory activity against PI3K can be considered as promising cancer therapeutics because they can block PI3K-Akt pathway by inhibiting Akt activation to inhibit the proliferation, survival, vascularization of cancer cells (Crit Rev Oncog. 17(1): 69-95 (2012)). Furthermore, it has been reported that a drug having an anti-PI3K activity can be useful for treating asthma and chronic obstructive pulmonary disease (COPD) because they can mediate proliferative function of tracheal smooth muscle and prevent fibrogenesis which are causes of the airway remodeling in severe asthmatic patients (Nature Rev. Genet. 7: 606-619 (2006); Nature 441: 366-370 (2006); J Pharmacol Exp Ther. 337(2): 557-566 (2011); J Allergy Clin Immunol 116: 488-495 (2005)).

Both Class IA PI3K and Class IB PI3K enzymes play an important role in immune cells (Koyasu, Nature Immunology, 2003, 4, 313-319) and, thus, they are evaluated as therapeutic targets in inflammatory and allergic conditions. Recent studies have revealed that mice lacking PI3Kγ and PI3Kδ were able to survive, yet their inflammatory and allergic reactions were impaired (Ali et al, Nature, 2004, 431, (7011), 1007-1011). Also, it has been reported that anti-inflammatory and anti-fibrotic effects due to PI3K inhibition can control respiratory diseases such as asthma and COPD and is also useful in treating cardiovascular diseases (Prasad et al, Trends in Cardiovascular Medicine, 13, 206-212 (2003); Am J Physiol Lung Cell Mol Physiol 296: L210-L219, (2009)). Additionally, it has been revealed that Class I PI3K enzyme play an important role not only in basic processes of learning and memory but also in regulation of learning and judgment ability in intracellular signal transduction pathways (Nat Neurosci. 2011 Oct. 23; 14(11):1447-54). Accordingly, Class I PI3K enzyme inhibitors are expected to provide prophylactic and therapeutic benefits against cancer as well as a wide range of diseases including inflammatory disease.

SUMMARY OF THE INVENTION

The present inventors have discovered that a fused ring compound containing furan or a pharmaceutically acceptable salt thereof has an inhibitory activity against PI3K and thus can be used for treating and preventing respiratory disease, inflammatory disease, proliferative disease, cardiovascular disease or central nervous system disease.

Therefore, the present invention provide a fused ring compound containing furan or a pharmaceutically acceptable salt thereof, a method for preparing same, a pharmaceutical composition comprising same and a use thereof.

According to one aspect of the present invention, there is provided a fused ring compound containing furan or a pharmaceutically acceptable salt thereof.

According to another aspect of the present invention, there is provided a method for preparing the fused ring compound containing furan.

According to a further aspect of the present invention, there is provided a pharmaceutical composition comprising the fused ring compound containing furan as an active ingredient.

According to a still further aspect of the present invention, there is provided a use of the fused ring compound containing furan or a pharmaceutically acceptable salt thereof for the manufacture of a medicament for treating and preventing respiratory disease, inflammatory disease, proliferative disease, cardiovascular disease or central nervous system disease.

According to a still further aspect of the present invention, there is provided a method for treating and preventing respiratory disease, inflammatory disease, proliferative disease, cardiovascular disease or central nervous system disease in a mammal, which comprises administering the fused ring compound containing furan or a pharmaceutically acceptable salt thereof to the mammal.

The compound according to the present invention, i.e., the fused ring compound containing furan or a pharmaceutically acceptable salt thereof, exhibits an excellent inhibitory activity against PI3K, and thus can be used effectively for treating and preventing respiratory disease, inflammatory disease, proliferative disease, cardiovascular disease or central nervous system disease.

DETAILED DESCRIPTION OF THE INVENTION

In the present invention, the term "alkyl" refers to a straight or branched hydrocarbon radical containing 1 to 10 carbon atoms. Examples thereof include, but are not limited to, methyl, ethyl, n-propyl, i-propyl, n-butyl, i-butyl, t-butyl, n-pentyl, n-hexyl and the like.

The term "cycloalkyl" refers to a saturated carbocyclic radical having a monocyclic- (e.g., cyclohexyl) or polycyclic- (e.g., norbornyl, adamantyl) ring containing 3 to 10 carbon atoms. Examples thereof include, but are not limited to, cyclopropyl, cyclopentyl, cyclohexyl, norbornyl, adamantyl and the like.

The term "aryl" refers to an organic radical derived by the removal of one hydrogen atom from aromatic hydrocarbons, which contains a monocyclic ring or fused polycyclic ring where each ring containing substituted or unsubstituted 6 to 20, preferably 6 to 12, ring members. Structures where a plurality of aryl groups is linked by single bonds are also included. Particular examples thereof include, but are not limited to, phenyl, naphthyl, biphenyl, terphenyl, indenyl, and the like. Preferably, said aryl may be phenyl or naphthyl.

The term "heteroaryl" refers to a 5- to 12-membered aromatic radical containing one or more, preferably 1 to 4, heteroatoms selected from O, N and S. It may be a 5- to 6-membered monocyclic heteroaryl or a polycyclic heteroaryl condensed with one or more benzene rings, and may be partially saturated. In the present invention, said heteroaryl also includes structures where one or more heteroaryls are linked by single bonds. The heteroatom contained in said heteroaryl may be oxidized or form quaternary salts. Particular examples thereof include, but are not limited to, monocyclic heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, oxotriazolyl, tetrazolyl, furazanyl, pyridyl, pyrazinyl, pyrimidinyl, pyridazinyl and the like; polycyclic heteroaryl such as benzofuranyl, benzothiophenyl, dibenzofuranyl, dibenzothiophenyl, isobenzofuranyl, benzoimidazolyl, benzothiazolyl, benzoisothiazolyl, benzoisoxazolyl, benzoxazolyl, benzodioxolyl, benzothiadiazolyl, dihydrobenzofuranyl, dihydrobenzoxazinyl, benzodioxinyl, dihydrobenzodioxinyl, thioxothiazolidinyl, isoindolyl, indolyl, indazolyl, quinolyl, isoquinolyl, cinnolinyl, quinazolinyl, quinoxalinyl, carbazolyl, phenanthridinyl, benzodioxolyl, acridinyl, phenanthrolinyl, phenazinyl, phenothiazinyl, phenoxazinyl and the like; N-oxide thereof (e.g., pyridyl N-oxide, quinolyl N-oxide); and quaternary salt thereof. Preferably, said heteroaryl may be selected from the group consisting of thiophenyl, imidazolyl, pyrazolyl, thiazolyl, oxotriazolyl, tetrazolyl, pyridyl, pyrimidinyl, pyridazinyl, benzothiophenyl, benzoimidazolyl, benzothiazolyl, benzothiadiazolyl, indolyl, indazolyl, quinolyl, isoquinolyl, benzodioxolyl, dihydrobenzofuranyl, dihydrobenzoxazinyl, benzodioxinyl, dihydrobenzodioxinyl, thioxothiazolidinyl and the like.

Also, the term "heterocycloalkyl" refers to 3- to 12-membered mono- or poly-cyclic radical containing one or more, preferably 1 to 4, heteroatoms selected from O, N and S, and does not include aromatic rings. Particular examples thereof include pyrrolidinyl, imidazolinyl, imidazolidinyl, pyrazolinyl, pyrazolidinyl, piperidinyl, morpholinyl, piperazinyl, tetrahydropyridinyl and the like.

The present invention provides a compound of formula (I) or a pharmaceutically acceptable salt thereof:

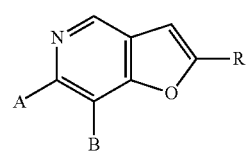

(I)

wherein,

A and B are each independently hydrogen; halogen; —(C≡C)R$_1$; —(CH$_2$)$_m$Q; —(CH=CH)(CH$_2$)$_m$Q; —(C≡C)(CH$_2$)$_m$Q; —NH(CH$_2$)$_p$Q; —O(CH$_2$)$_m$Q; —(CONH)(CH$_2$)$_m$Q; or —CONR$_1$R$_2$ (wherein, one of A and B is hydrogen, and A and B cannot be hydrogen at the same time), m is an integer from 0 to 3, p is an integer from 0 to 3, Q is C$_6$-C$_{12}$ aryl; 3- to 12-membered heterocycloalkyl; or 5- to 12-membered heteroaryl, wherein Q is optionally substituted with one or more substituents selected from the group consisting of hydroxy; amino; halogen; cyano; C$_1$-C$_{10}$alkyl optionally substituted with one or more substituents selected from the group consisting of halogen, hydroxy, cyano, C$_1$-C$_6$alkoxy and C$_1$-C$_6$alkylcarbonyloxy; C$_2$-C$_{10}$alkenyl; 4-oxo-2-thioxothiazolidin-5-ylidenyl; C$_2$-C$_{10}$alkynyl; C$_3$-C$_{10}$cycloalkyl; 5- to 7-membered heterocycloalkyl-C$_1$-C$_4$alkyl (wherein, said heterocycloalkyl is optionally substituted with C$_1$-C$_4$alkyl); C$_6$-C$_{12}$aryl; 5- to 12-membered heteroaryl (wherein, said heteroaryl is optionally substituted with C$_1$-C$_4$alkyl); 3- to 12-membered heterocycloalkyl (wherein, said heterocycloalkyl is optionally substituted with C$_1$-C$_6$alkyl); C$_1$-C$_{10}$alkoxy optionally substituted with one or more substituents selected from halogen and cyano; C$_3$-C$_{10}$cycloalkyloxy; C$_6$-C$_{12}$aryl-C$_1$-C$_{10}$alkyloxy (wherein, said aryl is optionally substituted with C$_1$-C$_3$alkoxy); C$_6$-C$_{12}$aryloxy optionally substituted with one or more substituents selected from the group consisting of hydroxy, amino, halogen, hydroxycarbonyl, cyano and nitro; 5- to 12-membered heteroaryloxy (wherein, said heteroaryl is optionally substituted with one or more substituents selected from the group consisting of hydroxy, amino, halogen, hydroxycarbonyl, cyano and nitro); $C_1$-$C_{10}$alkylcarbonyloxy; $C_1$-$C_{10}$alkylthio; mono- or di-$C_1$-$C_{10}$alkylamino; mono- or di-$C_3$-$C_7$cycloalkylamino; $C_6$-$C_{12}$arylamino; 5- to 12-membered heteroarylamino; $C_1$-$C_{10}$alkylsulfonylamino; $C_6$-$C_{12}$arylsulfonylamino; 5- to 12-membered heteroarylsulfonylamino; $C_1$-$C_{10}$alkylcarbonylamino; $C_6$-$C_{12}$arylcarbonylamino; 5- to 12-membered heteroarylcarbonylamino; formyl; $C_1$-$C_{10}$alkylcarbonyl; $C_6$-$C_{12}$arylcarbonyl; 5- to 12-membered heteroarylcarbonyl; $C_1$-$C_{10}$alkoxycarbonyl; hydroxycarbonyl; $C_6$-$C_{12}$aryloxycarbonyl; 5- to 12-membered heteroaryloxycarbonyl; aminocarbonyl; mono- or di-$C_1$-$C_{10}$alkylaminocarbonyl (wherein said alkyl is optionally substituted with hydroxy); $C_6$-$C_{12}$arylaminocarbonyl; 5- to 12-membered heteroarylaminocarbonyl; aminosulfonyl; mono- or di-$C_1$-$C_{10}$alkylaminosulfonyl (wherein, said alkyl is optionally substituted with hydroxy); $C_3$-$C_7$cycloalkylaminosulfonyl; $C_1$-$C_{10}$alkylsulfonyl optionally substituted with hydroxy; 5- to 7-membered heterocycloalkyl-sulfonyl (wherein, said heterocycloalkyl is optionally substituted with $C_1$-$C_4$alkyl); $C_6$-$C_{12}$arylaminosulfonyl; 5- to 12-membered heteroarylaminosulfonyl; $C_1$-$C_{10}$alkylsulfinyl; $C_1$-$C_{10}$alkylcarbamoyloxy; and $C_1$-$C_{10}$alkylureido, $R_1$ and $R_2$ are each independently hydrogen; $C_1$-$C_{10}$alkyl optionally substituted with one or more substituents selected from hydroxy and $C_1$-$C_6$alkoxy; $C_3$-$C_{10}$cycloalkyl optionally substituted with one or more substituents selected from the group consisting of halogen, hydroxy, $C_1$-$C_6$alkoxy and $C_1$-$C_6$alkylcarbonyloxy; $C_1$-$C_{10}$alkoxycarbonyl; $C_1$-$C_{10}$alkylcarbonyl; or $R_1$ and $R_2$ join together to form a 5- to 12-membered ring optionally containing a heteroatom selected from N and O, R is $C_2$-$C_6$alkenyl optionally substituted with one or more substituents selected from the group consisting of cyano, $C_1$-$C_6$alkoxycarbonyl and hydroxycarbonyl; $C_6$-$C_{12}$aryl; or 5- to 12-membered heteroaryl (wherein, said aryl or heteroaryl is optionally substituted with one or more substituents selected from the group consisting of hydroxy, halogen, $C_1$-$C_4$alkyl optionally substituted with one or more halogens, carboxy, cyano, $C_1$-$C_{10}$alkoxy, amino, $C_1$-$C_{10}$alkylsulfonylamino, $C_6$-$C_{12}$arylsulfonylamino optionally substituted with one or more halogens, $C_1$-$C_{10}$alkylcarbonylamino, $C_6$-$C_{12}$arylcarbonylamino, $C_6$-$C_{12}$arylureido, $C_1$-$C_{10}$alkylcarbonyl, $C_6$-$C_{12}$arylcarbonyl, 5- to 12-membered heteroarylcarbonyl, $C_1$-$C_{10}$alkoxycarbonyl, aminocarbonyl, $C_1$-$C_{10}$alkylaminocarbonyl, $C_6$-$C_{12}$arylaminocarbonyl, 5- to 12-membered heteroarylaminocarbonyl, aminosulfonyl, mono- or di-$C_1$-$C_{10}$alkylaminosulfonyl, $C_3$-$C_7$cycloalkylamino sulfonyl, $C_6$-$C_{12}$arylaminosulfonyl and 5- to 12-membered heteroarylaminosulfonyl); or a substituent selected from the group consisting of the following chemical formulae,

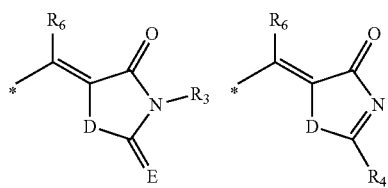

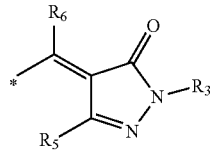

* indicates the binding site in which the compound of formula (I) is connected to, D is $NR_7$, O or S, E is O or S, $R_3$ is hydrogen; or $C_1$-$C_{10}$alkyl optionally substituted with hydroxy, $R_4$ is 3- to 12-membered heterocycloalkyl (said heterocycloalkyl is optionally substituted with $C_1$-$C_{10}$alkyl or halogen); $C_1$-$C_{10}$alkoxy; $C_1$-$C_{10}$alkylthio; or $NR_8R_9$, $R_5$ is hydrogen or $C_1$-$C_{10}$alkyl, $R_6$ is hydrogen or $C_1$-$C_{10}$alkyl, $R_7$ is hydrogen or $C_1$-$C_{10}$alkyl, $R_8$ and $R_9$ are each independently hydrogen; $C_1$-$C_6$alkyl optionally substituted with one or more substituents selected from $C_1$-$C_6$alkoxycarbonyl and $C_6$-$C_{12}$aryl (said aryl is optionally substituted with halogen or $C_1$-$C_6$alkoxy); $C_6$-$C_{12}$aryl (said aryl is optionally substituted with one or more substituents selected from the group consisting of halogen, $C_1$-$C_6$alkyl and $C_1$-$C_6$alkoxy); or 5- to 12-membered heteroaryl (said heteroaryl is optionally substituted with one or more substituents selected from the group consisting of halogen, $C_1$-$C_6$alkyl and $C_1$-$C_6$alkoxy).

In the compound of formula (I) according to the present invention or a pharmaceutically acceptable salt thereof, preferably, each of the heterocycloalkyl and heteroaryl may independently contain 1 to 4 heteroatoms selected from the group consisting of N, O and S.

In the compound of formula (I) according to the present invention or a pharmaceutically acceptable salt thereof, preferably, A and B are each independently hydrogen; halogen; —(C≡C)$R_1$; —(CH$_2$)$_m$Q; —(CH═CH)(CH$_2$)$_m$Q; —(C≡C)(CH$_2$)$_m$Q; —NH(CH$_2$)$_p$Q; —O(CH$_2$)$_m$Q; —(CONH)(CH$_2$)$_m$Q; or —CONR$_1$R$_2$ (wherein, one of A and B is hydrogen, and A and B cannot be hydrogen at the same time), m is an integer from 0 to 3, p is an integer from 0 to 3, Q is $C_6$-$C_{12}$aryl; 5- to 12-membered heterocycloalkyl; or 5- to 12-membered heteroaryl, wherein Q is optionally substituted with one or more substituents selected from the group consisting of hydroxy; amino; halogen; cyano; $C_1$-$C_6$alkyl optionally substituted with one or more substituents selected from the group consisting of halogen, hydroxy, cyano, $C_1$-$C_6$alkoxy and $C_1$-$C_6$alkylcarbonyloxy; $C_2$-$C_6$alkenyl; 4-oxo-2-thioxothiazolidin-5-ylidenyl; $C_2$-$C_6$alkynyl; $C_3$-$C_7$cycloalkyl; 5- to 7-membered heterocycloalkyl-$C_1$-$C_4$alkyl (wherein, said heterocycloalkyl is optionally substituted with $C_1$-$C_4$alkyl); $C_6$-$C_{12}$aryl; 5- to 12-membered heteroaryl (wherein, said heteroaryl is optionally substituted with $C_1$-$C_4$alkyl); 3- to 12-membered heterocycloalkyl (wherein, said heterocycloalkyl is optionally substituted with $C_1$-$C_3$alkyl); $C_1$-$C_6$alkoxy optionally substituted with one or more of halogen and cyano; $C_3$-$C_7$cycloalkyloxy; $C_6$-$C_{12}$aryl-$C_1$-$C_6$alkyloxy (wherein, said aryl is optionally substituted with $C_1$-$C_3$alkoxy); $C_6$-$C_{12}$aryloxy optionally substituted with one or more substituents selected from the group consisting of hydroxy, amino, halogen, hydroxycarbonyl, cyano and nitro; 5- to 12-membered heteroaryloxy (wherein, said heteroaryl is optionally substituted with one or more substituents selected from the group consisting of hydroxy, amino, halogen, hydroxycarbonyl, cyano and nitro); $C_1$-$C_6$alkylcarbonyloxy; $C_1$-$C_6$alkylthio; mono- or di-$C_1$-$C_6$alkylamino; mono- or di-$C_3$-$C_7$cycloalkylamino; $C_6$-$C_{12}$arylamino; 5- to 12-membered heteroarylamino; $C_1$-$C_6$alkylsulfonylamino; $C_6$-$C_{12}$arylsulfonylamino; 5- to 12-membered heteroarylsulfonylamino; $C_1$-$C_6$alkylcarbonylamino; $C_6$-$C_{12}$arylcarbonylamino; 5- to 12-membered heteroarylcarbonylamino; formyl; $C_1$-$C_6$alkylcarbonyl; $C_6$-$C_{12}$arylcarbonyl; 5- to 12-membered heteroarylcarbonyl; $C_1$-$C_6$alkoxycarbonyl; hydroxycarbonyl; $C_6$-$C_{12}$aryloxycarbonyl; 5- to 12-membered heteroaryloxycarbonyl; aminocarbonyl; mono- or di-$C_1$-$C_6$alkylaminocarbonyl (wherein, said alkyl is optionally substituted with hydroxy); $C_6$-$C_{12}$arylaminocarbonyl; 5- to 12-membered heteroarylaminocarbonyl; aminosulfonyl; mono- or di-$C_1$-$C_6$alkylaminosulfonyl (wherein, said alkyl is optionally substituted with hydroxy); $C_3$-$C_7$cycloalkylaminosulfonyl; $C_1$-$C_6$alkylsulfonyl optionally substituted with hydroxy; 5- to 7-membered heterocycloalkyl-sulfonyl (wherein, said heterocycloalkyl is optionally substituted with $C_1$-$C_4$alkyl); $C_6$-$C_{12}$arylaminosulfonyl; 5- to 12-membered heteroarylaminosulfonyl; $C_1$-$C_6$alkylsulfinyl; $C_1$-$C_6$alkylcarbamoyloxy; and $C_1$-$C_6$alkylureido, $R_1$ and $R_2$ are each independently hydrogen; $C_1$-$C_6$alkyl optionally substituted with one or more substituents selected from hydroxy and $C_1$-$C_6$alkoxy; $C_3$-$C_7$cycloalkyl optionally substituted with one or more substituents selected from the group consisting of halogen, hydroxy, $C_1$-$C_6$alkoxy and $C_1$-$C_6$alkylcarbonyloxy; $C_1$-$C_6$alkoxycarbonyl; $C_1$-$C_6$alkylcarbonyl; or $R_1$ and $R_2$ join together to form a 5- to 12-membered ring optionally containing a heteroatom selected from N and O, R is $C_2$-$C_6$alkenyl optionally substituted with one or more substituents selected from the group consisting of cyano, $C_1$-$C_6$alkoxycarbonyl and hydroxycarbonyl; $C_6$-$C_{12}$aryl; or 5- to 12-membered heteroaryl (wherein, said aryl or heteroaryl is optionally substituted with one or more substituents selected from the group consisting of hydroxy, halogen, $C_1$-$C_4$alkyl optionally substituted with one or more halogens, carboxy, cyano, $C_1$-$C_6$alkoxy, amino, $C_1$-$C_6$alkylsulfonylamino, $C_6$-$C_{12}$arylsulfonylamino optionally substituted with one or more halogens, $C_1$-$C_6$alkylcarbonylamino, $C_6$-$C_{12}$arylcarbonylamino, $C_6$-$C_{12}$arylureido, $C_1$-$C_6$alkylcarbonyl, $C_6$-$C_{12}$arylcarbonyl, 5- to 12-membered heteroarylcarbonyl, $C_1$-$C_6$alkoxycarbonyl, aminocarbonyl, $C_1$-$C_6$alkylaminocarbonyl, $C_6$-$C_{12}$arylaminocarbonyl, 5- to 12-membered heteroarylaminocarbonyl, aminosulfonyl, mono- or di-$C_1$-$C_6$alkylaminosulfonyl, $C_3$-$C_7$cycloalkylaminosulfonyl, $C_6$-$C_{12}$arylaminosulfonyl and 5- to 12-membered heteroarylaminosulfonyl); or a substituent selected from the group consisting of the following chemical formulae,

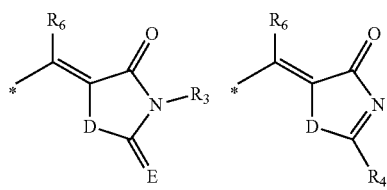

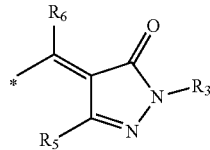

* indicates the binding site in which the compound of formula (I) is connected to, D is $NR_7$, O or S, E is O or S, $R_3$ is hydrogen; or $C_1$-$C_6$alkyl optionally substituted with hydroxy, $R_4$ is 3- to 12-membered heterocycloalkyl (said heterocycloalkyl is optionally substituted with $C_1$-$C_6$alkyl or halogen); $C_1$-$C_6$alkoxy; $C_1$-$C_6$alkylthio; or $NR_8R_9$, $R_5$ is hydrogen or $C_1$-$C_6$alkyl, $R_6$ is hydrogen or $C_1$-$C_6$alkyl, $R_7$ is hydrogen or $C_1$-$C_6$alkyl, $R_8$ and $R_9$ are each independently hydrogen; $C_1$-$C_6$alkyl optionally substituted with one or more substituents selected from $C_1$-$C_6$alkoxycarbonyl and $C_6$-$C_{12}$aryl (said aryl is optionally substituted with halogen or $C_1$-$C_6$alkoxy); $C_6$-$C_{12}$aryl (said aryl is optionally substituted with one or more substituents selected from the group consisting of halogen, $C_1$-$C_6$alkyl and $C_1$-$C_6$alkoxy); or 5- to 12-membered heteroaryl (said heteroaryl is optionally substituted with one or more substituents selected from the group consisting of halogen, $C_1$-$C_6$alkyl and $C_1$-$C_6$alkoxy).

In the compound of formula (I) or a pharmaceutically acceptable salt thereof according to the present invention, more preferably, A and B are each independently hydrogen; —(C≡C)$R_1$; —(CH$_2$)$_m$Q; —(CH═CH)(CH$_2$)$_m$Q; —(C≡C)(CH$_2$)$_m$Q; —NH(CH$_2$)$_p$Q; —O(CH$_2$)$_m$Q; —(CONH)(CH$_2$)$_m$Q; or —CONR$_1$R$_2$ (wherein, one of A and B is hydrogen, and A and B cannot be hydrogen at the same time), m is an integer from 0 to 3, p is an integer from 0 to 3, Q is $C_6$-$C_{12}$aryl; 5- to 12-membered heterocycloalkyl; or 5- to 12-membered heteroaryl, wherein Q is optionally substituted with one or more substituents selected from the group consisting of hydroxy; amino; halogen; cyano; $C_1$-$C_6$alkyl optionally substituted with one or more substituents selected from the group consisting of halogen, hydroxy, cyano, $C_1$-$C_6$alkoxy and $C_1$-$C_6$alkylcarbonyloxy; $C_2$-$C_6$alkenyl; 4-oxo-2-thioxothiazolidin-5-ylidenyl; $C_2$-$C_6$alkynyl; $C_3$-$C_7$cycloalkyl; 5- to 7-membered heterocycloalkyl-$C_1$-$C_4$alkyl (wherein, said heterocycloalkyl is optionally substituted with $C_1$-$C_4$alkyl); $C_6$-$C_{12}$aryl; 5- to 12-membered heteroaryl (wherein, said heteroaryl is optionally substituted with $C_1$-$C_4$alkyl); 3- to 12-membered heterocycloalkyl (wherein, said heterocycloalkyl is optionally substituted with $C_1$-$C_3$alkyl); $C_1$-$C_6$alkoxy optionally substituted with one or more of halogen and cyano; $C_3$-$C_7$cycloalkyloxy; $C_6$-$C_{12}$aryl-$C_1$-$C_6$alkyloxy (wherein, said aryl is optionally substituted with $C_1$-$C_3$alkoxy); $C_6$-$C_{12}$aryloxy optionally substituted with one or more substituents selected from the group consisting of hydroxy, amino, halogen, hydroxycarbonyl, cyano and nitro; 5- to 12-membered heteroaryloxy (wherein, said heteroaryl is optionally substituted with one or more substituents selected from the group consisting of hydroxy, amino, halogen, hydroxycarbonyl, cyano and nitro); $C_1$-$C_6$alkylcarbonyloxy; $C_1$-$C_6$alkylthio; mono- or di-$C_1$-

$C_6$alkylamino; mono- or di-$C_3$-$C_7$cycloalkylamino; $C_6$-$C_{12}$arylamino; 5- to 12-membered heteroarylamino; $C_1$-$C_6$alkylsulfonylamino; $C_6$-$C_{12}$arylsulfonylamino; 5- to 12-membered heteroarylsulfonylamino; $C_1$-$C_6$alkylcarbonylamino; $C_6$-$C_{12}$arylcarbonylamino; 5- to 12-membered heteroarylcarbonylamino; formyl; $C_1$-$C_6$alkylcarbonyl; $C_6$-$C_{12}$arylcarbonyl; 5- to 12-membered heteroarylcarbonyl; $C_1$-$C_6$alkoxycarbonyl; hydroxycarbonyl; $C_6$-$C_{12}$aryloxycarbonyl; 5- to 12-membered heteroaryloxycarbonyl; aminocarbonyl; mono- or di-$C_1$-$C_6$alkylaminocarbonyl (wherein, said alkyl is optionally substituted with hydroxy); $C_6$-$C_{12}$arylaminocarbonyl; 5- to 12-membered heteroarylaminocarbonyl; aminosulfonyl; mono- or di-$C_1$-$C_6$alkylaminosulfonyl (wherein, said alkyl is optionally substituted with hydroxy); $C_3$-$C_7$cycloalkylaminosulfonyl; $C_1$-$C_6$alkylsulfonyl optionally substituted with hydroxy; 5- to 7-membered heterocycloalkyl-sulfonyl (wherein, said heterocycloalkyl is optionally substituted with $C_1$-$C_4$alkyl); $C_6$-$C_{12}$arylaminosulfonyl; 5- to 12-membered heteroarylaminosulfonyl; $C_1$-$C_6$alkylsulfinyl; $C_1$-$C_6$alkylcarbamoyloxy; and $C_1$-$C_6$alkylureido, $R_1$ and $R_2$ are each independently hydrogen; $C_1$-$C_6$alkyl optionally substituted with one or more substituents selected from hydroxy and $C_1$-$C_6$alkoxy; $C_3$-$C_7$cycloalkyl optionally substituted with one or more substituents selected from the group consisting of halogen, hydroxy, $C_1$-$C_6$alkoxy and $C_1$-$C_6$alkylcarbonyloxy; $C_1$-$C_6$alkoxycarbonyl; $C_1$-$C_6$alkylcarbonyl; or $R_1$ and $R_2$ join together to form a 5- to 12-membered ring optionally containing a heteroatom selected from N and O, R is $C_6$-$C_{12}$aryl; or 5- to 12-membered heteroaryl (wherein, said aryl or heteroaryl is optionally substituted with one or more substituents selected from the group consisting of hydroxy, halogen, $C_1$-$C_4$alkyl optionally substituted with one or more halogens, carboxy, cyano, $C_1$-$C_6$alkoxy, amino, $C_1$-$C_6$alkylsulfonylamino, $C_6$-$C_{12}$arylsulfonylamino optionally substituted with one or more halogens, $C_1$-$C_6$alkylcarbonylamino, $C_6$-$C_{12}$arylcarbonylamino, $C_6$-$C_{12}$arylureido, $C_1$-$C_6$alkylcarbonyl, $C_6$-$C_{12}$arylcarbonyl, 5- to 12-membered heteroarylcarbonyl, $C_1$-$C_6$alkoxycarbonyl, aminocarbonyl, $C_1$-$C_6$alkylaminocarbonyl, $C_6$-$C_{12}$arylaminocarbonyl, 5- to 12-membered heteroarylaminocarbonyl, aminosulfonyl, mono- or di-$C_1$-$C_6$alkylaminosulfonyl, $C_3$-$C_7$cycloalkylamino sulfonyl, $C_6$-$C_{12}$arylaminosulfonyl, 5- to 12-membered heteroarylaminosulfonyl); or a substituent selected from the group consisting of the following chemical formulae,

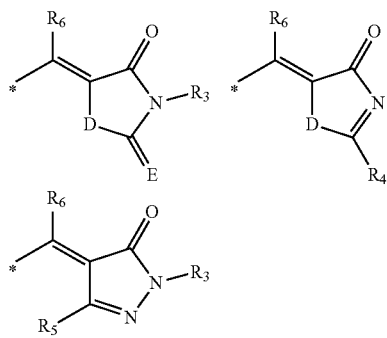

* indicates the binding site in which the compound of formula (I) is connected to, D is $NR_7$, O or S, E is O or S, $R_3$ is hydrogen; or $C_1$-$C_6$alkyl optionally substituted with hydroxy, $R_4$ is 3- to 12-membered heterocycloalkyl (said heterocycloalkyl is optionally substituted with $C_1$-$C_6$alkyl or halogen); $C_1$-$C_6$alkoxy; $C_1$-$C_6$alkylthio; or $NR_8R_9$, $R_5$ is hydrogen or $C_1$-$C_6$alkyl, $R_6$ is hydrogen or $C_1$-$C_6$alkyl, $R_7$ is hydrogen or $C_1$-$C_6$alkyl, $R_8$ and $R_9$ are each independently hydrogen; $C_1$-$C_6$alkyl optionally substituted with one or more substituents selected from $C_1$-$C_6$alkoxycarbonyl and $C_6$-$C_{12}$aryl (said aryl is optionally substituted with halogen or $C_1$-$C_6$alkoxy); $C_6$-$C_{12}$aryl (said aryl is optionally substituted with one or more substituents selected from the group consisting of halogen, $C_1$-$C_6$alkyl and $C_1$-$C_6$alkoxy); or 5- to 12-membered heteroaryl (said heteroaryl is optionally substituted with one or more substituents selected from the group consisting of halogen, $C_1$-$C_6$alkyl and $C_1$-$C_6$alkoxy).

In the compound of formula (I) according to the present invention or a pharmaceutically acceptable salt thereof, more preferably, A and B are each independently hydrogen; —(C≡C)$R_1$; —(CH$_2$)$_m$Q; —(CH═CH)(CH$_2$)$_m$Q; —(C≡C)(CH$_2$)$_m$Q; —NH(CH$_2$)$_p$Q; —O(CH$_2$)$_m$Q; —(CONH)(CH$_2$)$_m$Q; or —CONR$_1$R$_2$ (wherein, one of A and B is hydrogen, and A and B cannot be hydrogen at the same time), m is an integer from 0 to 3, p is an integer from 0 to 3, Q is $C_6$-$C_{12}$aryl; 5- to 12-membered heterocycloalkyl; or 5- to 12-membered heteroaryl, wherein Q is optionally substituted with one or more substituents selected from the group consisting of hydroxy; amino; halogen; cyano; $C_1$-$C_6$alkyl optionally substituted with one or more substituents selected from the group consisting of halogen, hydroxy, cyano, $C_1$-$C_6$alkoxy and $C_1$-$C_6$alkylcarbonyloxy; $C_2$-$C_6$alkenyl; 4-oxo-2-thioxothiazolidin-5-ylidenyl; $C_3$-$C_7$cycloalkyl; 5- to 7-membered heterocycloalkyl-$C_1$-$C_4$alkyl (wherein, said heterocycloalkyl is optionally substituted with $C_1$-$C_4$alkyl); $C_6$-$C_{12}$aryl; 5- to 12-membered heteroaryl (wherein, said heteroaryl is optionally substituted with $C_1$-$C_4$alkyl); 3- to 12-membered heterocycloalkyl (wherein, said heterocycloalkyl is optionally substituted with $C_1$-$C_3$alkyl); $C_1$-$C_6$alkoxy optionally substituted with one or more of halogen and cyano; $C_6$-$C_{12}$aryl-$C_1$-$C_6$alkyloxy (wherein, said aryl is optionally substituted with $C_1$-$C_3$alkoxy); $C_6$-$C_{12}$aryloxy optionally substituted with one or more cyanos; 5- to 12-membered heteroaryloxy; $C_1$-$C_6$alkylthio; mono- or di-$C_1$-$C_6$alkylamino; mono- or di-$C_3$-$C_7$cycloalkylamino; $C_1$-$C_6$alkylsulfonylamino; $C_6$-$C_{12}$arylsulfonylamino; $C_1$-$C_6$alkylcarbonylamino; formyl; $C_1$-$C_6$alkylcarbonyl; $C_1$-$C_6$alkoxycarbonyl; hydroxycarbonyl; aminocarbonyl; mono- or di-$C_1$-$C_6$alkylaminocarbonyl (wherein, said alkyl is optionally substituted with hydroxy); aminosulfonyl; mono- or di-$C_1$-$C_6$alkylaminosulfonyl (wherein, said alkyl is optionally substituted with hydroxy); $C_3$-$C_7$cycloalkylamino sulfonyl; $C_1$-$C_6$alkylsulfonyl; 5- to 7-membered heterocycloalkyl-sulfonyl (wherein, said heterocycloalkyl is optionally substituted with $C_1$-$C_4$alkyl); and $C_1$-$C_6$alkylsulfinyl, $R_1$ and $R_2$ are each independently hydrogen; $C_1$-$C_6$alkyl optionally substituted with one or more of hydroxy and $C_1$-$C_6$alkoxy; $C_3$-$C_7$cycloalkyl; $C_1$-$C_6$alkoxycarbonyl; or $R_1$ and R₂ join together to form a 5- to 12-membered ring optionally containing a heteroatom selected from N and O, R is $C_6$-$C_{12}$aryl; or 5- to 12-membered heteroaryl (wherein, said aryl or heteroaryl is optionally substituted with one or more substituents selected from the group consisting of halogen, $C_1$-$C_6$alkoxy, amino, $C_1$-$C_6$alkylsulfonylamino, $C_6$-$C_{12}$arylsulfonylamino optionally substituted with one or more halogens, $C_1$-$C_6$alkylcarbonylamino, $C_6$-$C_{12}$arylureido and aminocarbonyl); or a substituent selected from the group consisting of the following chemical formulae,

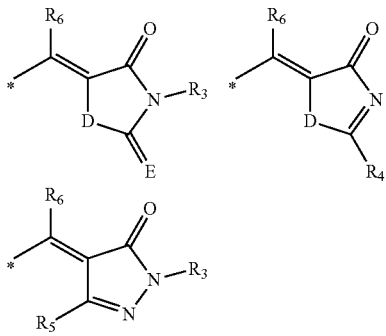

* indicates the binding site in which the compound of formula (I) is connected to, D is $NR_7$, O or S, E is O or S, $R_3$ is hydrogen; or $C_1$-$C_6$alkyl optionally substituted with hydroxy, $R_4$ is 3- to 12-membered heterocycloalkyl or $NR_8R_9$, $R_5$ is hydrogen or $C_1$-$C_6$alkyl, $R_6$ is hydrogen or $C_1$-$C_6$alkyl, $R_7$ is hydrogen or $C_1$-$C_6$alkyl, $R_8$ and $R_9$ are each independently hydrogen; $C_1$-$C_6$alkyl optionally substituted with one or more of $C_6$-$C_{12}$aryl (said aryl is optionally substituted with halogen or $C_1$-$C_6$alkoxy); or $C_6$-$C_{12}$aryl optionally substituted with one or more substituents selected from the group consisting of halogen, $C_1$-$C_6$alkyl and $C_1$-$C_6$alkoxy.

In the compound of formula (I) according to the present invention or a pharmaceutically acceptable salt thereof, more preferably, A and B are each independently hydrogen; —(C≡C)$R_1$; —(CH$_2$)$_m$Q; —(CH=CH)(CH$_2$)$_m$Q; —(C≡C)(CH$_2$)$_m$Q; —NH(CH$_2$)$_p$Q; —(CONH)(CH$_2$)$_m$Q; or —CONR$_1$R$_2$ (wherein, one of A and B is hydrogen, and A and B cannot be hydrogen at the same time), m is an integer from 0 to 3, p is an integer from 0 to 3, Q is $C_6$-$C_{12}$aryl; 5- to 12-membered heterocycloalkyl; or 5- to 12-membered heteroaryl, wherein Q is optionally substituted with one or more substituents selected from the group consisting of hydroxy; amino; halogen; cyano; $C_1$-$C_6$alkyl optionally substituted with one or more substituents selected from the group consisting of halogen, hydroxy, cyano, $C_1$-$C_6$alkoxy and $C_1$-$C_3$alkylcarbonyloxy; $C_2$-$C_6$alkenyl; 4-oxo-2-thioxothiazolidin-5-ylidenyl; $C_3$-$C_7$cycloalkyl; 5- to 7-membered heterocycloalkyl-$C_1$-$C_3$alkyl (wherein, said heterocycloalkyl is optionally substituted with $C_1$-$C_3$alkyl); $C_6$-$C_{12}$aryl; 5- to 6-membered heteroaryl (wherein, said heteroaryl is optionally substituted with $C_1$-$C_4$alkyl); 5- to 7-membered heterocycloalkyl (wherein, said heterocycloalkyl is optionally substituted with $C_1$-$C_3$alkyl); $C_1$-$C_6$alkoxy optionally substituted with one or more of halogen and cyano; $C_6$-$C_{12}$aryl-$C_1$-$C_3$alkyloxy (wherein, said aryl is optionally substituted with $C_1$-$C_3$alkoxy); $C_6$-$C_{12}$aryloxy optionally substituted with one or more cyanos; 5- to 6-membered heteroaryloxy; $C_1$-$C_6$alkylthio; mono- or di-$C_1$-$C_6$alkylamino; mono- or di-$C_3$-$C_7$cycloalkylamino; $C_1$-$C_3$alkylsulfonylamino; $C_6$-$C_{12}$arylsulfonylamino; $C_1$-$C_3$alkylcarbonylamino; formyl; $C_1$-$C_6$alkylcarbonyl; $C_1$-$C_6$alkoxycarbonyl; hydroxycarbonyl; aminocarbonyl; mono- or di-$C_1$-$C_6$alkylaminocarbonyl (wherein, said alkyl is optionally substituted with hydroxy); aminosulfonyl; mono- or di-$C_1$-$C_6$alkylaminosulfonyl (wherein, said alkyl is optionally substituted with hydroxy); $C_3$-$C_7$cycloalkylaminosulfonyl; $C_1$-$C_6$alkylsulfonyl; 5- to 7-membered heterocycloalkylsulfonyl (wherein, said heterocycloalkyl is optionally substituted with $C_1$-$C_4$alkyl); $C_1$-$C_3$alkylsulfinyl, $R_1$ and $R_2$ are each independently hydrogen; $C_1$-$C_6$alkyl optionally substituted with one or more substituents selected from hydroxy and $C_1$-$C_3$alkoxy; $C_3$-$C_7$cycloalkyl; $C_1$-$C_3$alkoxycarbonyl; or $R_1$ and $R_2$ join together to form a 5- to 7-membered ring optionally containing a heteroatom selected from N and O, R is $C_6$-$C_{12}$aryl; 5- to 12-membered heteroaryl (wherein, said aryl or heteroaryl is optionally substituted with one or more substituents selected from the group consisting of halogen, $C_1$-$C_3$alkoxy, amino, $C_1$-$C_3$alkylsulfonylamino, $C_6$-$C_{12}$arylsulfonylamino optionally substituted with one or more halogens, $C_1$-$C_3$alkylcarbonylamino and $C_6$-$C_{12}$arylureido); or a substituent selected from the group consisting of the following chemical formulae,

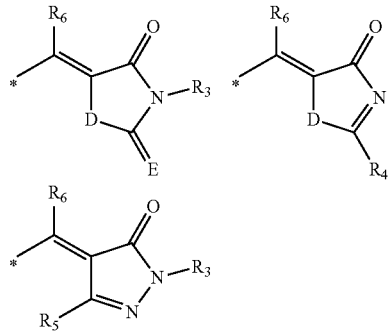

* indicates the binding site in which the compound of formula (I) is connected to, D is $NR_7$ or S, E is O or S, $R_3$ is hydrogen; or $C_1$-$C_6$alkyl optionally substituted with hydroxy, $R_4$ is 5- to 7-membered heterocycloalkyl or $NR_8R_9$, $R_5$ and $R_6$ are each independently hydrogen or $C_1$-$C_3$alkyl, $R_7$ is hydrogen or $C_1$-$C_3$alkyl, $R_8$ and $R_9$ are each independently hydrogen; $C_1$-$C_6$alkyl optionally substituted with one or more of $C_6$-$C_{12}$aryl (said aryl is optionally substituted with halogen or $C_1$-$C_3$alkoxy); or $C_6$-$C_{12}$aryl optionally substituted with one or more substituents selected from the group consisting of halogen, $C_1$-$C_6$alkyl and $C_1$-$C_3$alkoxy.

According to one embodiment of the present invention, there is provided the compound of formula (I) or a pharmaceutically acceptable salt thereof, wherein R is

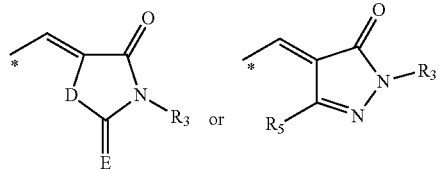

(wherein, * indicates the binding site in which the compound of formula (I) is connected to; and R₃, R₄, R₆, D and E are same as defined in the compound of formula (I) above), i.e., the compound of (Ia) or (Ib) below or a pharmaceutically acceptable salt thereof:

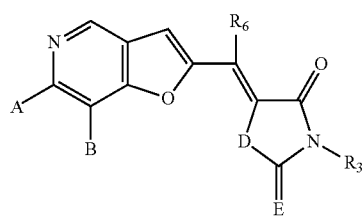

(Ia)

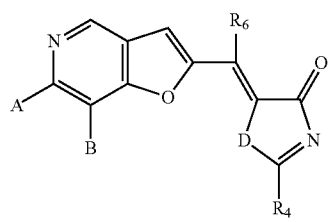

(Ib)

According to another embodiment of the present invention, there is provided the compound of formula (I) or a pharmaceutically acceptable salt thereof, wherein R is

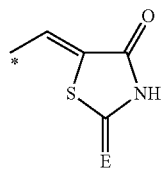

(wherein, * indicates the binding site in which the compound of formula (I) is connected to; and E is O or S), i.e., the compound of (Ic) or a pharmaceutically acceptable salt thereof:

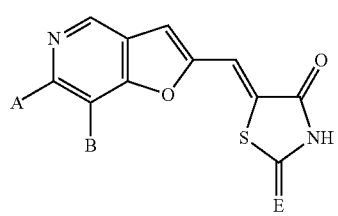

(Ic)

wherein, A and B are same as defined in the compound of formula (I) above.

According to a still another embodiment of the present invention, there is provided the compound of formula (I) or a pharmaceutically acceptable salt thereof, wherein R is

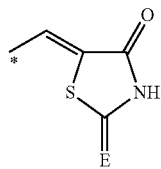

(wherein, * indicates the binding site in which the compound of formula (I) is connected to; and E is O or S), A is hydrogen, and B is B', i.e., the compound of (Id) or a pharmaceutically acceptable salt thereof:

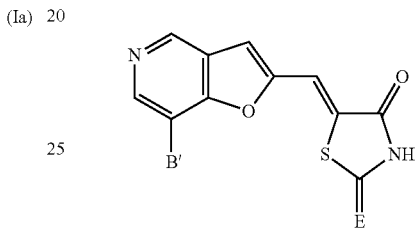

(Id)

wherein,

B' is —(C≡C)R₁; —(CH₂)$_m$Q; —(C≡C)(CH₂)$_m$Q; or —(CONH)(CH₂)$_m$Q, m is 0,

Q is $C_6$-$C_{12}$aryl; 5- to 12-membered heterocycloalkyl; or 5- to 12-membered heteroaryl, wherein Q is optionally substituted with one or more substituents selected from the group consisting of hydroxy; amino; halogen; cyano; $C_1$-$C_6$alkyl optionally substituted with one or more substituents selected from the group consisting of halogen, hydroxy, cyano, $C_1$-$C_6$alkoxy and $C_1$-$C_6$alkylcarbonyloxy; $C_2$-$C_6$alkenyl; 4-oxo-2-thioxothiazolidin-5-ylidenyl; $C_3$-$C_7$cycloalkyl; 5- to 7-membered heterocycloalkyl-$C_1$-$C_4$alkyl (wherein, said heterocycloalkyl is optionally substituted with $C_1$-$C_4$alkyl); $C_6$-$C_{12}$aryl; 5- to 12-membered heteroaryl (wherein, said heteroaryl is optionally substituted with $C_1$-$C_4$alkyl); 3- to 12-membered heterocycloalkyl (wherein, said heterocycloalkyl is optionally substituted with $C_1$-$C_3$alkyl); $C_1$-$C_6$alkoxy optionally substituted with one or more of halogen and cyano; $C_6$-$C_{12}$aryl-$C_1$-$C_6$alkyloxy (wherein, said aryl is optionally substituted with $C_1$-$C_3$alkoxy); $C_6$-$C_{12}$aryloxy optionally substituted with one or more cyanos; 5- to 12-membered heteroaryloxy; $C_1$-$C_6$alkylthio; mono- or di-$C_1$-$C_6$alkylamino; mono- or di-$C_3$-$C_7$cycloalkylamino; $C_1$-$C_6$alkylsulfonylamino; $C_6$-$C_{12}$arylsulfonylamino; $C_1$-$C_6$alkylcarbonylamino; formyl; $C_1$-$C_6$alkylcarbonyl; $C_1$-$C_6$alkoxycarbonyl; hydroxycarbonyl; aminocarbonyl; mono- or di-$C_1$-$C_6$alkylaminocarbonyl (wherein, said alkyl is optionally substituted with hydroxy); aminosulfonyl; mono- or di-$C_1$-$C_6$alkylaminosulfonyl (wherein, said alkyl is optionally substituted with hydroxy); $C_3$-$C_7$cycloalkylaminosulfonyl; $C_1$-$C_6$alkylsulfonyl; 5- to 7-membered heterocycloalkylsulfonyl (wherein, said heterocycloalkyl is optionally substituted with $C_1$-$C_4$alkyl); and $C_1$-$C_6$alkylsulfinyl, $R_1$ is hydrogen; $C_1$-$C_6$alkyl optionally substituted with one or more substituents selected from hydroxy and $C_1$-$C_6$alkoxy; $C_3$-$C_7$cycloalkyl; $C_1$-$C_6$alkoxycarbonyl.

The compound of formula (I) according to the present invention may also form a pharmaceutically acceptable salt. Said salt may be any conventional acid addition salt formed by, e.g., inorganic acids such as hydrochloric acid, hydrobromic acid, sulfuric acid, sodium bisulfate, phosphoric acid, nitric acid, carbonic acid and others; or organic acids such as citric acid, acetic acid, lactic acid, tartaric acid, maleic acid, fumaric acid, gentisic acid, lactobionic acid, salicylic acid, malonic acid, tartaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid or aspartic acid, but not limited thereto. Also, said salt may be any conventional metallic salt, e.g., salts of alkali metals such as lithium, sodium, potassium and the like; or salts of alkali earth metals such as calcium, magnesium and the like; or chromium salts. Additionally, said salt may be formed by any suitable organic ligands, e.g., a quaternary ammonium salt, a dicyclohexylamine salt, a N-methyl-D-glucamine salt, and amino acid salts formed by arginine, lysine, etc.

The compound of formula (I) of the present invention or a pharmaceutically acceptable salt thereof may be prepared by various methods depending on substituents thereof. For example, the compound of formula (I) of the present invention or a pharmaceutically acceptable salt thereof may be prepared by methods disclosed in Reaction Schemes 1 to 7 below, but not limited thereto. In Reaction Schemes 1 to 7, the definitions of substituents are same as defined above unless specified otherwise.

(1) Synthesis Example 1

In the compound of formula (I), a fused ring compound, wherein A is hydrogen, and R is

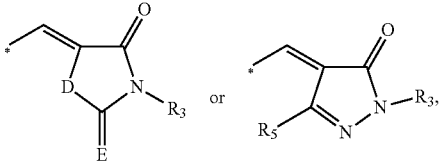

may be prepared by Reaction Scheme 1 below.

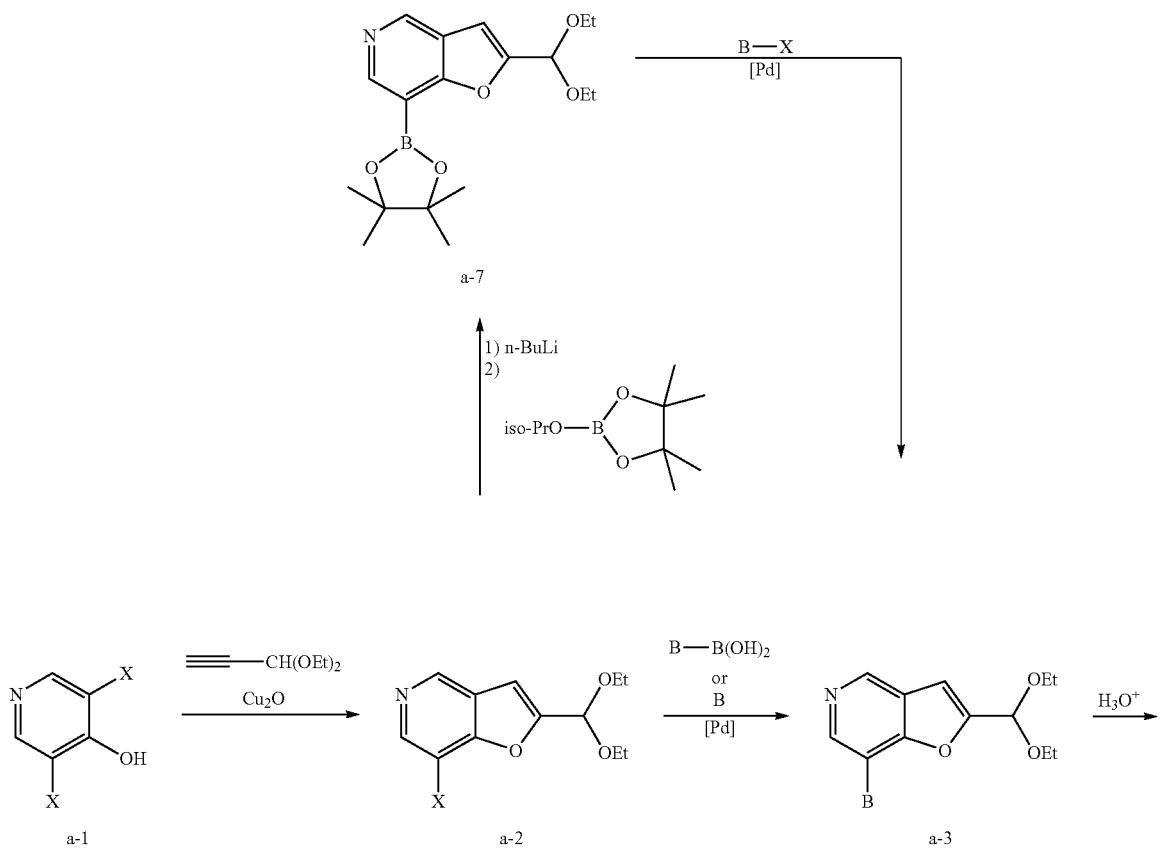

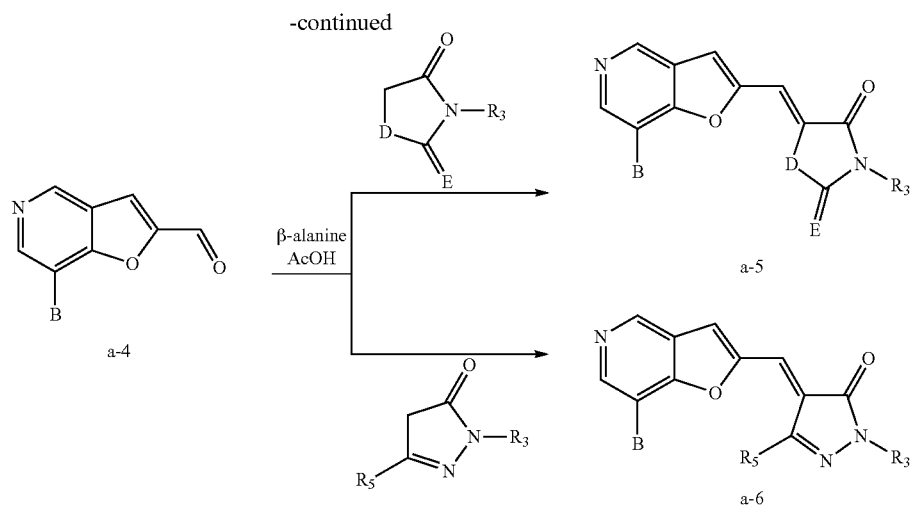

In Reaction Scheme 1 above, $R_3$, $R_5$, D and E are same as defined in the compound of formula (I) above, B is —$(CH_2)_mQ$; —$(CH=CH)(CH_2)_mQ$; or —$NH(CH_2)_pQ$ (wherein, m, p and Q are same as defined in the compound of formula (I) above) and X is halogen.

Specifically, the preparation method may comprise the steps of: (i) subjecting the compound of formula (a-1) to a reaction with alkyne derivative using a metal catalyst such as copper (or palladium) to obtain the compound of formula (a-2); (ii) subjecting the compound of formula (a-2) to a coupling reaction to obtain the compound of formula (a-3) or subjecting the compound of formula (a-2) to a reaction with a boron derivative to obtain the compound of formula (a-7), followed by a reaction with a halide to obtain the compound of formula (a-3); (iii) hydrolyzing the compound of formula (a-3) under an acidic condition to obtain the compound of formula (a-4); and subjecting the compound of formula (a-4) to a Knoevenagel to obtain the compounds of formulae (a-5) and (a-6).

The furan ring formation of the compound of formula (a-2) may be carried out by using an ethyne reagent such as 3,3-diethoxy-1-propyne under a copper oxide catalyst. Such reaction may be conducted by using an organic solvent such as pyridine, N,N-dimethylformamide, pyrolidine, etc., and preferably at a temperature ranging from 120° C. to 130° C. Additionally, in order to improve the yield and/or the rate of the reaction, the reaction may be carried out in the presence of a metal catalyst and ligand such as palladium, etc. and a base such as triethylamine.

The synthesis of the compound of formula (a-3) from the compound of formula (a-2) may be carried out by a coupling reaction of a halide compound and boronic acid under a palladium catalyst or a coupling reaction of a halide compound and amine. Such reaction may be conducted by using a solvent such as toluene, tetrahydrofuran, N,N-dimethylformamide, etc., and preferably at a temperature ranging from 100° C. to 130° C. Additionally, in order to improve the yield and/or the rate of the reaction, the reaction may be carried out in the presence of a base such as sodium carbonate, cesium carbonate, etc.

The synthesis of the boron derivative of formula (a-7) may be carried out by substituting the halide at position 7 with lithium by using a base such as n-butyl lithium, followed by substituting with a boron derivative by adding a boron reagent such as dioxaborolane, etc. Such reaction may be conducted by using an organic solvent such as tetrahydrofuran, diethyl ether, etc. Preferably, the above lithium substitution may be conducted at about −78° C., and the boron derivative substitution reaction may preferably be conducted at about 0° C.

The synthesis of the compound of formula (a-3) from the compound of the formula (a-7) may be carried out by a coupling reaction of a boron derivative and a halide compound under a palladium catalyst. Said reaction may be conducted by using an organic solvent such as toluene, tetrahydrofuran, N,N-dimethylformamide, etc., preferably at a temperature ranging from 100° C. to 130° C. Additionally, in order to improve the yield and/or the rate of the reaction, the reaction may be carried out in the presence of a base such as sodium carbonate, cesium carbonate, etc.

The aldehyde derivative of formula (a-4) can be prepared by hydrolyzing the compound of formula (a-3) in the presence of an acid catalyst such as hydrochloric acid, acetic acid, etc. Such reaction may be conducted by using a solvent such as water, tetrahydrofuran, acetone, etc., at room temperature or under a heating condition (20° C. to 60° C.).

The synthesis of the compound of formula (a-5) or (a-6) may be carried out via a condensation reaction by using a compound containing an active methylene such as thiazolidinedione, rhodanine, pyrazolone, etc. Such reaction may be conducted by using a solvent such as acetic acid, N,N-dimethylformamide, ethanol, etc., and preferably at a temperature ranging from 80° C. to 130° C. In order to improve the yield and/or the rate of the reaction, the reaction may be carried out in the presence of an amine or ammonium salt catalyst such as β-alanine, sodium acetate, piperidine, etc.

(2) Synthesis Example 2

In the compound of formula (I), a fused ring compound, wherein R is

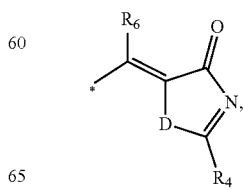

may be prepared by Reaction Scheme 2 below.

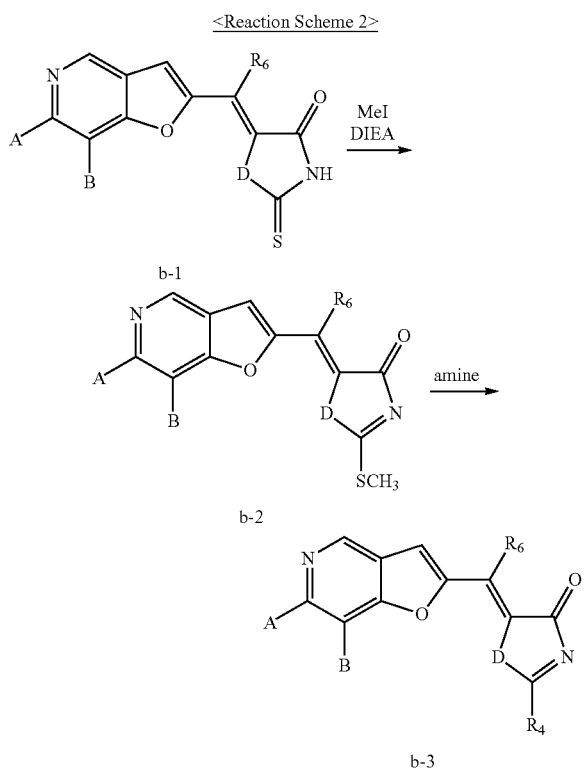

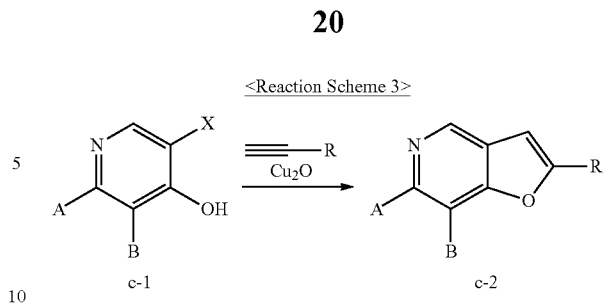

In Reaction Scheme 3 above, A and B are same as defined in the compound of formula (I) above.

Specifically, the preparation method may comprise the step of subjecting the compound of formula (c-1) to a reaction with an alkyne derivative substituted with various R by using a copper catalyst to obtain the compound of formula (c-2).

Such reaction may be carried out by using an ethyne reagent substituted with various aryls or heteroaryls, in the presence of a copper oxide catalyst. The reaction is conducted by using an organic solvent such as pyridine, N,N-dimethylformamide, pyrolidine, etc., and preferably at a temperature ranging from 120° C. to 130° C. Additionally, in order improve the yield and/or the rate of the reaction, the reaction may be carried out in the presence of a metal catalyst and ligand such as palladium, etc. and a base such as triethylamine.

(4) Synthesis Example 4

In the compound of formula (I), a fused ring compound, wherein $R_6$ is $C_1$-$C_{10}$alkyl, may be prepared by Reaction Scheme 4 below.

In Reaction Scheme 2 above, A, B, $R_6$ and D are same as defined in the compound of formula (I) above, $R_4$ is 3- to 12-membered heterocycloalkyl containing one or more heteroatoms selected from the group consisting of N, O and S; or $NR_8R_9$ (wherein, $R_8$ and $R_9$ are same as defined in the compound of formula (I) above).

Specifically, the preparation method may comprise the steps of: (i) introducing a methyl group to the compound of formula (b-1) to obtain the methylsulfide compound of formula (b-2); and (ii) subjecting the compound of formula (b-2) to a substitution reaction with amine to obtain the compound of formula (b-3).

The synthesis of the compound of formula (b-2) may be carried out by subjecting the compound of formula (b-1) to a reaction with iodomethane in the presence of a base such as diisopropylethylamine, potassium carbonate, etc. Such reaction may be conducted by using a solvent such as methanol, dichloromethane, tetrahydrofuran, etc., and preferably at room temperature.

The synthesis of the compound of formula (b-3) may be carried out by subjecting the compound of formula (b-2) to a substitution reaction with amine in the presence of a base such as diisopropylethylamine, piperidine, etc. Such reaction may be conducted by using a solvent such as ethanol, acetonitrile, N,N-dimethylformamide, etc., and preferably at a temperature ranging from 90° C. to 130° C., or in a microwave (200-400 W).

(3) Synthesis Example 3

In the compound of formula (I), a fused ring compound, wherein R is various aryl and heteroaryl, may be prepared by Reaction Scheme 3 below.

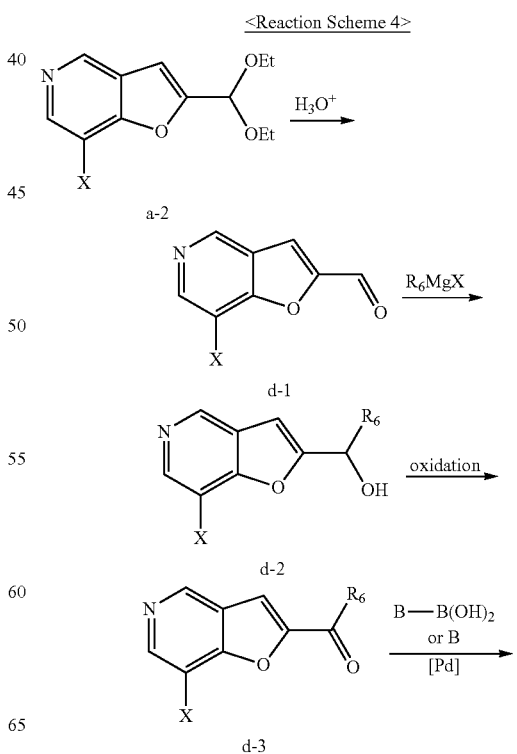

-continued

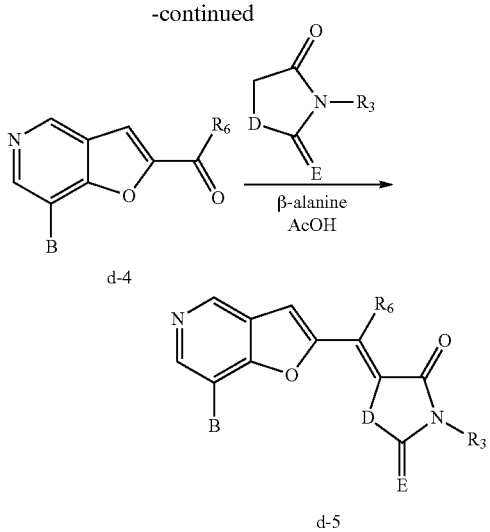

In Reaction Scheme 4 above, $R_3$, $R_6$, D and E are same as defined in the compound of formula (I) above, B is —$(CH_2)_mQ$; —$(CH=CH)(CH_2)_mQ$; or —$NH(CH_2)_pQ$ (wherein, m, Q and P are same as defined in the compound of formula (I)), and X is halogen.

Specifically, the preparation method may comprise the steps of: (i) hydrolyzing the compound of formula (a-2) under acidic condition to obtain the compound of formula (d-1); (ii) subjecting the compound of formula (d-1) to an addition reaction to obtain the compound of formula (d-2); (iii) subjecting the compound of formula (d-2) to an oxidation reaction to obtain the compound of formula (d-3); (iv) subjecting the compound of formula (d-3) to a coupling reaction to obtain the compound of formula (d-4); and (v) subjecting the compound of formula (d-4) to a Knoevenagel reaction to obtain the compound of formula (d-5).

The compound of formula (d-1) may be prepared by hydrolyzing the compound of formula (a-2) in the presence of an acid catalyst such as hydrochloric acid, acetic acid, etc. The reaction may be conducted by using a solvent such as water, tetrahydrofuran, acetone, etc., at a room temperature or under a heating condition (20° C. to 60° C.).

The compound of formula (d-2) may be prepared by subjecting the compound of formula (d-1) to a reaction with an alkyl magnesium halide reagent. Such reaction may be conducted by using an organic solvent such as tetrahydrofuran, diethyl ether, etc., and preferably at a temperature ranging from 0° C. to room temperature.

The synthesis of the compound of formula (d-3) from the compound of the formula (d-2) may be carried out via an oxidation reaction by using a reagent such as tetrapropylammonium perruthenate/N-methylmorpholine-N-oxide, etc. Such reaction may be carried out by using a solvent such as dichloromethane, acetonitrile and the like at room temperature.

The synthesis of the compound of formula (d-4) from the compound of formula (d-3) may be carried out via a coupling reaction of a halide compound of d-3 and boronic acid or amine in the presence of a palladium catalyst. Such reaction may be conducted by using an organic solvent such as toluene, tetrahydrofuran, N,N-dimethylformamide, etc., and preferably at a temperature ranging from 100° C. to 130° C. Additionally, in order to improve the yield and/or the rate of the reaction, the reaction may be carried out in the presence of a base such as sodium carbonate, cesium carbonate, etc.

The synthesis of the compound of formula (d-5) from the compound of formula (d-4) may be carried out via a condensation reaction by using a compound containing an active methylene such as thiazolidinedione, rhodanine, etc. Such reaction may be conducted by using a solvent such as acetic acid, N,N-dimethylformamide, ethanol, etc., and preferably at a temperature ranging from 80° C. to 130° C. Additionally, in order to improve the yield and/or the rate of the reaction, the reaction may be carried out in the presence of an amine or ammonium salt catalyst such as β-alanine, sodium acetate, piperidine, etc.

(5) Synthesis Example 5

In the compound of formula (I), a fused ring compound, wherein B is —$(CONH)(CH_2)mQ$ or —$CONR_1R_2$, may be prepared by Reaction Scheme 5 below.

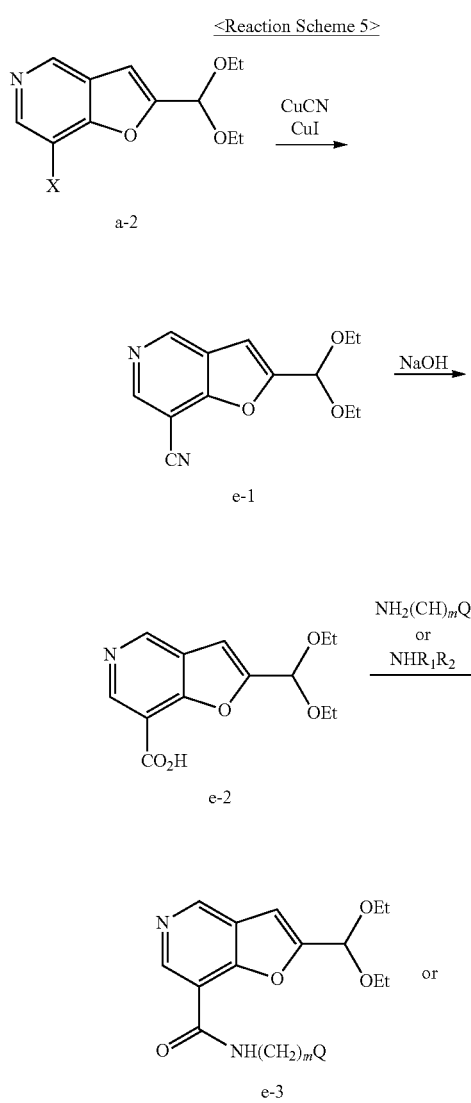

-continued

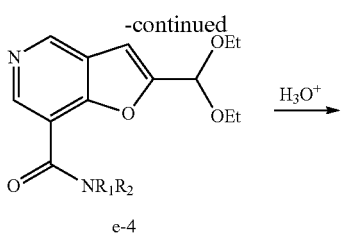
e-4

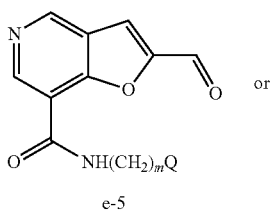
e-5 or

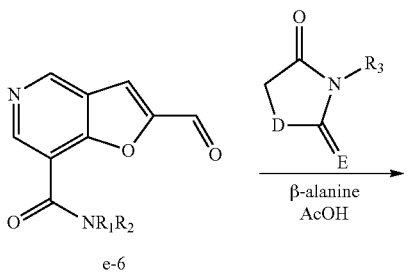
e-6

β-alanine
AcOH

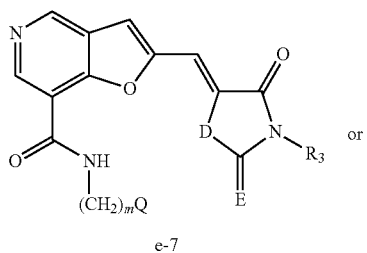
e-7 or

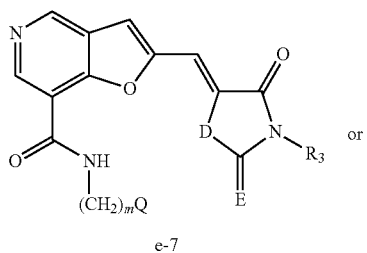
e-8

In Reaction Scheme 5 above, Q, m, $R_1$, $R_2$, $R_3$, D and E are same as defined in the compound of formula (I), and X is halogen.

Specifically, the preparation method may comprise the steps of: (i) substituting the halide of the compound of formula (a-2) with a nitrile to obtain the compound of formula (e-1); (ii) hydrolyzing the compound of formula (e-1) under basic conditions to obtain the compound of formula (e-2); (iii) subjecting the compound of formula (e-2) to a reaction with amine to obtain the compound of formula (e-3) or (e-4); (iv) subjecting the compound of formula (e-3) or (e-4) to a hydrolysis under acidic condition to obtain the compound of formula (e-5) or (e-6); and (v) subjecting the compound of formula (e-5) or (e-6) to a Knoevenagel reaction to obtain the compound of formula (e-7) or (e-8).

The synthesis of the compound of formula (e-1) from the compound of formula (a-2) may be carried out via a substitution reaction by using a reagent such as copper cyanide, etc. Such reaction may be conducted by using a solvent N,N-dimethylformamide, pyridine, etc., and preferably at a temperature ranging from 100° C. to 130° C. Additionally, in order to improve the yield and/or the rate of the reaction, the reaction may be carried out in the presence of a metal catalyst such as copper iodide, palladium, etc.

The synthesis of the compound of formula (e-2) may be carried out by hydrolyzing the compound of formula (e-1) under basic conditions such as sodium hydroxide, etc. Such reaction may be conducted by using a solvent such as a mixed solution of water and ethanol, and preferably at a temperature ranging from 60° C. to 100° C.

The reaction of the compound of formula (e-2) and amine may be carried out via an amide coupling reaction using a coupling agent such as (benzotriazol-1-yloxy)-tris-(dimethylamino)phosphonium hexafluorophosphate, N-(3-dimethylaminopropyl-N'-ethylcarbodiimide hydrochloride, 1-hydroxybenzotriazole hydrate, etc., and a base such as diisopropylethylamine, triethylamine, etc. The coupling reaction may be conducted by using an organic solvent such as dichloromethane, N,N-dimethylformamide, etc. In addition, preferably, the coupling reaction may be carried out at room temperature.

The compound of formula (e-5) or (e-6) may be prepared by hydrolyzing the compound of formula (e-3) or (e-4) in the presence of an acid catalyst such as hydrochloric acid, acetic acid, etc. The hydrolysis reaction may be conducted by using a solvent such as water, tetrahydrofuran, acetone, etc., at room temperature or under a heating condition (20° C. to 60° C.).

The synthesis of the compound of formula (e-7) or (e-8) from the compound of formula (e-5) or (e-6) may be carried out via a condensation reaction by using a compound containing an active methylene such as thiazolidinedione, rhodanine, etc. Such reaction may be conducted by using a solvent such as acetic acid, N,N-dimethylformamide, ethanol, etc., and preferably at a temperature ranging from 80° C. to 130° C. Additionally, in order to improve the yield and/or the rate of the reaction, the reaction may be carried out in the presence of an amine or ammonium salt catalyst such as β-alanine, sodium acetate, piperidine, etc.

(6) Synthesis Example 6

In the compound of formula (I), a fused ring compound, wherein B is —(C≡C)$R_1$; or —(C≡C)(CH$_2$)mQ, may be prepared by Reaction Scheme 6 below.

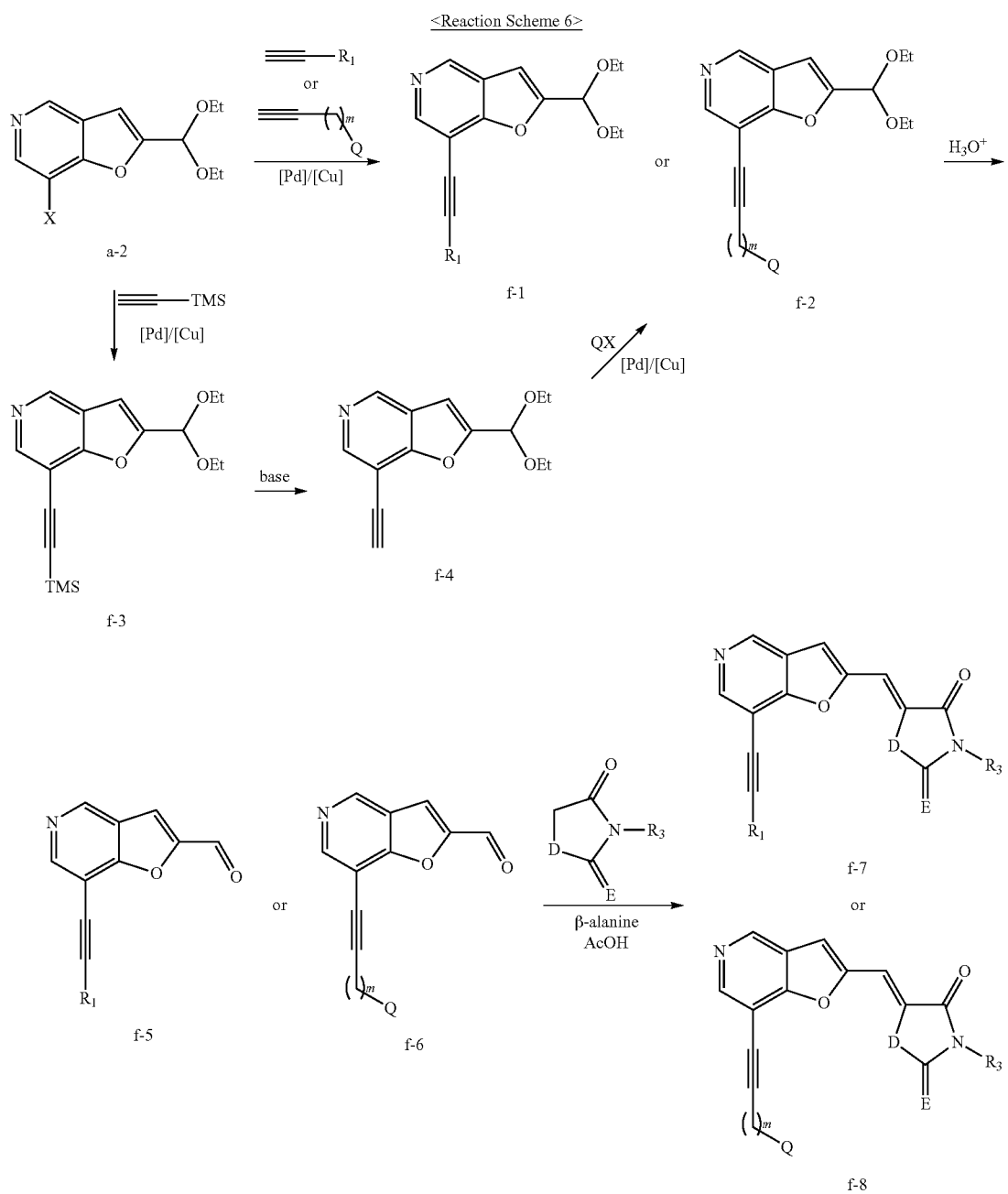

<Reaction Scheme 6>

In Reaction Scheme 6, $R_1$, m, Q, $R_3$, D and E are same as defined in the compound of formula (I) above, and X is halogen.

Specifically, the preparation method may comprise the steps of: (i) subjecting the halide compound of formula (a-2) to a Sonogashira coupling reaction with an ethane reagent to obtain the compound of formula (f-1) or (f-2); (ii) hydrolyzing the compound of formula (f-1) or (f-2) under acidic condition to obtain the compound of formula (f-5) or (f-6); and (iii) subjecting the compound of formula (f-5) or (f-6) to a Knoevenagel reaction to obtain the compound of formula (f-7) or (f-8).

Also, optionally, the preparation method may comprise the steps of: (i) subjecting the halide compound of formula (a-2) to a Sonogashira coupling reaction with ethynyltrimethylsilane to obtain the compound of formula (f-3); (ii) removing trimethylsilane from the compound of formula (f-3) under basic conditions to obtain the compound of formula (f-4); (iii) subjecting the compound of formula (f-4) to a Sonogashira coupling reaction with arylhalide or heteroarylhalide to obtain the compound of formula (f-2); (iv) hydrolyzing the compound of formula (f-2) under acidic condition to obtain the compound of formula (f-6); and (v) subjecting the compound of formula (f-6) to a Knoevenagel reaction to obtain the compound of formula (f-8).

The reaction of the compound of formula (a-2) and an ethyne reagent may be carried out via a Sonogashira coupling reaction by using a palladium reagent such as bis (triphenylphosphine)palladium(II) dichloride, tetrakis(triphenylphosphine)palladium(0), etc. and copper iodide. Such reaction may be conducted at room temperature or under a heating condition (20° C. to 60° C.). Additionally, in order to improve the yield and the rate of the reaction, the reaction may be carried out in the presence of a ligand such as triphenylphosphine and the like under basic conditions such as diisopropylamine, triethylamine, etc.

The synthesis of the compound of formula (f-4) from the compound of formula (f-3) may be carried out by removing trimethylsilane using a base such as potassium carbonate. Such reaction may be conducted by using a solvent such as methanol, water, etc. at room temperature or under a heating condition (20° C. to 60° C.).

The reaction of the compound of formula (f-4) and arylhalide or heteroarylhalide may be carried out via a Sonogashira coupling reaction using a palladium reagent such as bis(triphenylphosphine)palladium(II) dichloride, tetrakis(triphenylphosphine)palladium(0), etc. and copper iodide. Such coupling reaction may be conducted at room temperature or under a heating condition (20° C. to 60° C.) and, in order to improve the yield and the rate of the reaction, the reaction may be carried out in the presence of a ligand such as triphenylphosphine and the like under basic conditions such as diisopropylamine, triethylamine, etc.

The compound of formula (f-5) or (f-6) may be prepared by hydrolyzing the compound of formula (f-1) or (f-2) under acidic condition such as hydrochloric acid, acetic acid, etc. Such reaction may be conducted by using a solvent such as water, tetrahydrofuran, acetone and the like at room temperature or under a heating condition (20° C. to 60° C.).

The synthesis of the compound of formula (f-7) or (f-8) may be carried out by a condensation reaction using a compound containing an active methylene such as thiazolidinedione, rhodanine, etc. Such reaction may be conducted by using a solvent such as acetic acid, N,N-dimethylformamide, ethanol, etc., and preferably at a temperature ranging from 80° C. to 130° C. In order to improve the yield and/or the rate of the reaction, the reaction may be carried out in the presence of an amine or ammonium salt catalyst such as β-alanine, sodium acetate, piperidine, etc.

(7) Synthesis Example 7

In the compound of formula (I), a fused ring compound, wherein B is hydrogen, R is

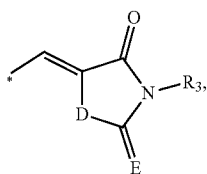

may be prepared by Reaction Scheme 7 below.

<Reaction Scheme 7>

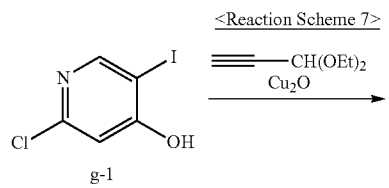

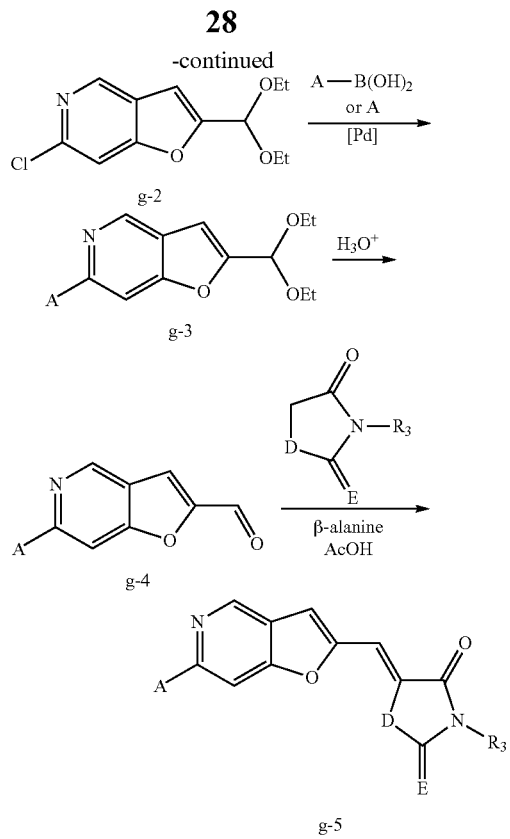

In Reaction Scheme 7, A, $R_3$, D and E are same as defined in the compound of formula (I) above, X is halogen.

Specifically, the preparation method may comprise the steps of: (i) subjecting the compound of formula (g-1) to a reaction with an alkyne derivative in the presence of a metal catalyst such as copper (or palladium) to obtain the compound of formula (g-2); (ii) subjecting the compound of formula (g-2) to a coupling reaction to obtain the compound of formula (g-3); (iii) hydrolyzing the compound of formula (g-3) under acidic condition to obtain the compound of formula (g-4); and (iv) subjecting the compound of formula (g-4) to a Knoevenagel reaction to obtain the compound of formula (g-5).

The furan ring formation of the compound of formula (g-2) may be carried out by using an ethyne reagent such as 3,3-diethoxy-1-propyne under a copper oxide catalyst. Such reaction may be conducted by using an organic solvent such as pyridine, N,N-dimethylformamide, pyrolidine, etc., and preferably at a temperature ranging from 120° C. to 130° C. Additionally, in order to improve the yield and/or the rate of the reaction, the reaction may be carried out in the presence of a metal catalyst such as palladium, etc., ligand and a base such as triethylamine.

The synthesis of the compound of formula (g-3) from the compound of formula (g-2) may be carried out via a coupling reaction of a halide compound and boronic acid under a palladium catalyst or a coupling reaction of a halide compound and amine. Such reaction may be conducted by using a solvent such as toluene, tetrahydrofuran, N,N-dimethylformamide, etc., and preferably by stirring overnight at a temperature ranging from 100° C. to 130° C. Additionally, in order to improve the yield and the rate of the reaction, the reaction may be carried out in the presence of a base such as sodium carbonate, cesium carbonate, etc.

The synthesis of the compound of formula (g-4) may be carried out by hydrolyzing the compound of formula (g-3) in the presence of an acid catalyst such as hydrochloric acid, acetic acid, etc. Such reaction may be conducted by using a solvent such as water, tetrahydrofuran, acetone and the like at room temperature or under a heating condition (20° C. to 60° C.).

The synthesis of the compound of formula (g-5) may be carried out via a condensation reaction by using a compound containing an active methylene such as thiazolidinedione, rhodanine, etc. Such reaction may be conducted by using a solvent such as acetic acid, N,N-dimethylformamide, ethanol, etc., and preferably at a temperature ranging from 80° C. to 130° C. In order to improve the yield and/or the rate of the reaction, the reaction may be carried out in the presence of an amine or ammonium salt catalyst such as β-alanine, sodium acetate, piperidine, etc.

According to one embodiment of the present invention, there is provided a method for preparing the compound of formula (Ie), which comprises the steps of: (i) converting the compound of formula (IIa), e.g., corresponding to the compound of formula (a-3) in Reaction Scheme 1, to the compound of formula (IIb), e.g., corresponding to the compound of formula (a-4) in Reaction Scheme 1; and (ii) converting the compound of formula (IIb) into the compound of formula (Ie), e.g., corresponding to the compounds of formulae (a-5) and (a-6) in Reaction Scheme 1:

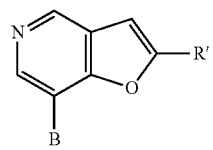
(Ie)

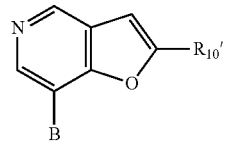
(IIa)

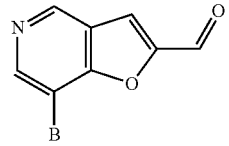
(IIb)

wherein, B is same as defined in the compound of formula (I) above,

R' is

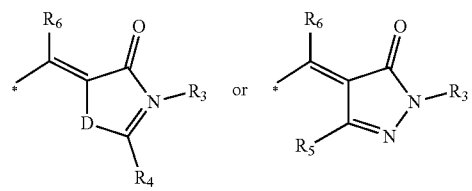

(wherein, D, E, $R_3$, $R_5$, and $R_6$ are same as defined in the compound of formula (I) above), $R_{10}'$ is di-$C_1$-$C_{10}$alkoxymethyl.

The present invention also provides an intermediate compound, i.e., the compound of formula (II) or a salt thereof, which is useful in preparing a fused ring compound containing furan of the present invention, i.e., the compound of formula (I), or a salt thereof:

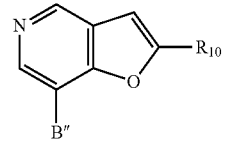
(II)

wherein, B" is —(C≡C)$R_1$; —(C≡C)(CH$_2$)$_m$Q; —(CONH)(CH$_2$)$_m$Q; —CONR$_1$R$_2$; CN; or CO$_2$H (wherein, $R_1$, $R_2$, m and Q are same as defined in the compound of formula (I) above), $R_{10}$ is di-$C_1$-$C_{10}$alkoxymethyl; or formyl.

The fused ring compound containing furan, i.e., the compound of formula (I) or a pharmaceutically acceptable salt thereof has an inhibitory activity against PI3K, and thus can be used for treating and preventing diseases induced by hyperactivity of PI3K such as respiratory disease, inflammatory disease, proliferative disease, cardiovascular disease or central nervous system disease. Accordingly, the present invention also provides a pharmaceutical composition comprising a therapeutically effective amount of the compound of formula (I) or a pharmaceutically acceptable salt thereof for treating and preventing respiratory disease, inflammatory disease, proliferative disease, cardiovascular disease or central nervous system disease.

Said respiratory disease and inflammatory disease include asthma, chronic obstructive pulmonary disease (COPD), idiopathic pulmonary fibrosis, allergy (or anaphylaxis), psoriasis, rheumatoid arthritis, autoimmune disease and the like. Said proliferative disease includes breast cancer, bladder cancer, colon cancer, glioma, glioblastoma, lung cancer, hepatoma, gastric cancer, melanoma, thyroid cancer, endometrial cancer, kidney cancer, cervical cancer, pancreatic cancer, esophageal cancer, prostate cancer, brain cancer, cholangioma, ovarian cancer, tuberous cerebrosclerosis, alveolar rhabdomyosarcoma, leukemia and the like. Said cardiovascular disease includes thrombosis, myocardial infarction, hypertension, cardiomegaly, heart failure and the like. Said central nervous system disease includes post-traumatic stress disorder (PTSD), memory loss, learning disorder, cognitive disorder and the like. More particularly, the pharmaceutical composition according to the present invention may be useful in the treatment and prevention of asthma, idiopathic pulmonary fibrosis and COPD.

The pharmaceutical composition may comprise any pharmaceutically acceptable carriers known in the art such as an excipient, a disintegrant, a sweetner, a lubricant, a flavoring agent and the like. The pharmaceutical composition may be formulated in accordance with conventional methods, and may be prepared in the form of oral formulations such as tablets, capsules, powders, granules, suspensions, oils, syrups and others or parenteral formulations such as inhalants, sprays, injections and others. The pharmaceutical composition may be prepared as various dosage forms, e.g., a single dose formulation or a multidose formulation, etc.

The pharmaceutical composition of the present invention may comprise an excipient such as lactose, corn starch, etc., a lubricant such as magnesium stearate, etc., an emulsifier, a suspending agent, a stabilizer, an isotonic agent and the like. A sweetener and/or a flavoring agent may be added, if necessary.

The pharmaceutical composition of the present invention may be administered orally or parenterally, e.g., intravenous, intraperitoneal, subcutaneous, rectal and local injection. Thus, the pharmaceutical composition of the present invention may be formulated into various forms such as tablets, capsules, aqueous liquid preparations, suspensions and the like. Conventionally, when the pharmaceutical composition is prepared as a tablet for oral administration, it may be added with a carrier such as lactose, corn starch, etc. and a lubricant such as magnesium stearate, etc. When the pharmaceutical composition is prepared as a capsule for oral administration, it may be added with diluents such as lactose and/or dried corn starch. When the pharmaceutical composition is prepared as an aqueous liquid preparation, its active ingredient may be combined with an emulsifier and/or a suspending agent. A sweetener and/or a flavoring agent may be added, if necessary. In the case when the pharmaceutical composition is prepared as an injection for intramuscular, intraperitoneal, subcutaneous and intravenous administration, conventionally, its active ingredient may be prepared as a sterilized solution. The sterilized solution needs to be buffered and its pH must be regulated. When the pharmaceutical composition is prepared as an intravenous injection, the concentration of its solute needs to be regulated so as to give isotonicity to the formulation. The inventive pharmaceutical composition may be in the form of an aqueous liquid preparation containing a pharmaceutically acceptable carrier such as brine having a pH of 7.4. The solution may be administered intramuscularly into the bloodstream by local bolus injection.

The fused ring compound containing furan, i.e., the compound of formula (I), or a pharmaceutically acceptable salt thereof may be administered to a patient at an effective amount of about 0.0001 mg/kg to about 100 mg/kg per day. Of course, said dosage amount may vary depending on various factors including the age, weight, sensitivity, condition of the patient or the effectiveness of the compound.

The present invention also provides a use of the compound of formula (I) or a pharmaceutically acceptable salt thereof for the manufacture of a medicament for treating and preventing respiratory disease, inflammatory disease, proliferative disease, cardiovascular disease or central nervous system disease.

The present invention also provides a method for treating and preventing respiratory disease, inflammatory disease, proliferative disease, cardiovascular disease or central nervous system disease in a mammal, which comprises administering the compound of formula (I) or a pharmaceutically acceptable salt thereof to the mammal.

Particular examples and preferred examples of said respiratory disease, inflammatory disease, proliferative disease, cardiovascular disease or central nervous system disease are same as defined above.

Hereinafter, the present invention is described more specifically by the following Examples and Experimental Examples, but these are provided for illustration purposes only, and the present invention is not limited thereto.

In the following Examples, analysis of the compounds prepared was carried out as follows: NMR spectrum analysis was conducted by using a 400 MHz spectrometer (Bruker), chemical shift was computed in ppm, and column chromatography was carried out on silica gel (Merck, 70-230 mesh) (W. C. Still, J. Org. Chem. 43, 2923-2925 (1978)). In addition, each starting material was prepared using methods known in the art or purchased from Sigma Aldrich.

Reference Example 1

2-(Diethoxymethyl)-7-iodofuro[3,2-c]pyridine

A solution prepared by dissolving 3,5-diiodopyridin-4-ol (20.0 mmol) in anhydrous pyridine (50 ml) was added with propargyl aldehyde diethyl acetal (24.0 mmol) and copper (II) oxide (14.0 mmol), and stirred under reflux for 12 hours under a nitrogen atmosphere. The reaction solution thus obtained was cooled to room temperature, filtered, and the filtrate was concentrated under reduced pressure. The residue was diluted with ethyl acetate, washed with aqueous ammonia, water and brine, in sequence, which was then dried over anhydrous magnesium sulfate and filtered. After the filtrate was concentrated under reduced pressure, the residue thus obtained was purified by silica gel column chromatography (n-hexane/ethyl acetate=10/1, v/v) to obtain the title compound as a light brown solid (yield: 87%).

$^1$H NMR (CDCl$_3$, 300 MHz) δ 8.78 (s, 1H), 8.72 (s, 1H), 6.99 (s, 1H), 5.69 (s, 1H), 3.69 (m, 4H), 1.28 (t, 6H)

Reference Example 2

2-(Diethoxymethyl)-7-(4,4,5,5-tetramethyl-1,3-dioxaborolan-2-yl)furo[3,2-c]pyridine A solution prepared by dissolving 2-(diethoxymethyl)-7-iodofuro[3,2-c]pyridine (10 mmol) obtained in Reference Example 1 and 2-isopropoxy-4,4,5,5-tetramethyl-1,3,2-dioxaborolane (30.0 mmol) in anhydrous tetrahydrofuran (50 ml) was slowly added dropwise with n-butyl lithium (40 mmol, 2.5 M in n-hexane solution) over 20 minutes at −78° C., followed by stirring at −78° C. for 30 minutes. A saturated aqueous ammonium chloride solution was added to the reaction solution to terminate the reaction, which was then extracted with dichloromethane. The extract thus obtained was washed with brine, dried over anhydrous magnesium sulfate, filtered, and the filtrate was concentrated under reduced pressure. The residue was dissolved in dichloromethane, and the solution thus obtained was added with diethyl ether. The resulting solid was filtered and dried to obtain the title compound as a white solid (yield: 81%).

$^1$H NMR (CDCl$_3$, 300 MHz) δ 8.95 (s, 1H), 8.79 (s, 1H), 6.87 (s, 1H), 5.74 (s, 1H), 3.71 (m, 4H), 1.40 (s, 12H), 1.29 (t, 6H)

Reference Example 3

2-(Diethoxymethyl)-7-ethynylfuro[3,2-c]pyridine

Step 1: Synthesis of 2-(diethoxymethyl)-7-(trimethylsilyl)ethynylfuro[3,2-c]pyridine 2-(Diethoxymethyl)-7-iodofuro[3,2-c]pyridine (28.8 mmol) obtained in Reference Example 1, [1,1'-bis(diphenylphosphino)ferrocene]dichloropalladium(II) (2.9 mmol), copper iodide (12.9 mmol) and triphenylphosphine (9.5 mmol) were dissolved in anhydrous triethylamine (100 ml), stirred at room temperature for 20 minutes, and then added dropwise with trimethylsilylacetylene (86.4 mmol). The reaction mixture was heated to 60° C. and stirred for 12 hours. Then, the reaction mixture was cooled to room temperature and filtered through Celite. The filtrate thus obtained was concentrated under reduced pressure to obtain a compound as brown oil. The residue was diluted with ethyl acetate, washed with aqueous ammonia, water and brine, in sequence, which was then dried over anhydrous magnesium sulfate and filtered. After the filtrate was concentrated under reduced pressure, the residue thus obtained was purified by silica gel column chromatography (n-hexane/ethyl acetate=10/1, v/v) to obtain the title compound as light yellow solid (yield: 60%).

$^1$H NMR (CDCl$_3$, 400 MHz) δ 8.81 (s, 1H), 8.56 (s, 1H), 6.88 (s, 1H), 5.70 (s, 1H), 3.71 (m, 4H), 1.28 (t, 6H), 0.30 (s, 9H)

Step 2: Synthesis of 2-(Diethoxymethyl)-7-ethynylfuro[3,2-c]pyridine

A solution prepared by dissolving 2-(diethoxymethyl)-7-(trimethylsilyl)ethynylfuro[3,2-c]pyridine (6.3 mmol) obtained in Step 1 in methanol (80 ml) was added with potassium carbonate (18.9 mmol), and stirred at room temperature for 2 hours. The reaction mixture was filtered to remove solid materials, and the filtrate was concentrated under reduced pressure to obtain a compound as yellow oil. The residue thus obtained was diluted with ethyl acetate, washed with water and brine, in sequence, which was then dried over anhydrous magnesium sulfate and filtered. After the filtrate was concentrated under reduced pressure, the residue thus obtained was purified by silica gel column chromatography (n-hexane/ethyl acetate=10/1, v/v) to obtain the title compound as yellow oil (yield: 75%).

$^1$H NMR (CDCl$_3$, 400 MHz) δ 8.91 (brs, 1H), 8.67 (brs, 1H), 6.91 (s, 1H), 5.69 (s, 1H), 3.67 (m, 4H), 3.47 (s, 1H), 1.28 (t, 6H)

Reference Example 4

Synthesis of 7-(1,2,3,6-tetrahydropyridin-4-yl)furo[3,2-c]pyridine-2-carbaldehyde Step 1: Synthesis of tert-butyl 4-{2-(diethoxymethyl)furo[3,2-c]pyridin-7-yl}-5,6-dihydropyridine-1(2H)-carboxylate A solution prepared by dissolving 2-(diethoxymethyl)-7-iodofuro[3,2-c]pyridine (2.3 mmol) obtained in Reference Example 1, tetrakis(triphenylphosphine)palladium(0) (0.1 mmol) and tert-butyl 4-(4,4,5,5-tetramethyl-1,3,2-dioxaborolan-2-yl)-5,6-dihydropyridine-1(2H)-carboxylate (2.8 mmol) in dimethoxyethyne (40 ml) was added with ethanol (12 ml) and 2M sodium carbonate solution (12 ml), which was then heated to 85° C., followed by stirring for 3 hours. The reaction mixture was cooled to room temperature, diluted with ethyl acetate, washed with water and brine, in sequence, which was then dried over anhydrous magnesium sulfate and filtered. After the filtrate was concentrated under reduced pressure, the residue thus obtained was purified by silica gel column chromatography (n-hexane/ethyl acetate=4/1, v/v) to obtain the title compound as yellow oil (yield: 85%).

$^1$H NMR (CDCl$_3$, 400 MHz) δ 8.77 (s, 1H), 8.43 (s, 1H), 6.89 (s, 1H), 6.55 (brs, 1H), 5.69 (s, 1H), 4.16 (brs, 2H), 3.71 (brs, 2H), 3.66 (m, 4H), 2.70 (brs, 2H), 1.49 (s, 9H), 1.28 (t, 6H)

Step 2: Synthesis of 7-(1,2,3,6-tetrahydropyridin-4-yl)furo[3,2-c]pyridine-2-carbaldehyde A solution prepared by dissolving tert-butyl 4-[2-(diethoxymethyl)furo[3,2-c]pyridin-7-yl]-5,6-dihydropyridine-1(2H)-carboxylate (2.3 mmol) obtained in Step 1 in tetrahydrofuran (6 ml) was slowly added dropwise with a 3N aqueous hydrochloric acid solution (6 ml), and stirred at room temperature for 24 hours. The reaction mixture was added with a saturated sodium bicarbonate solution, which was then filtered and dried to obtain the title compound as yellow solid (yield: 55%)

$^1$H NMR (CDCl$_3$, 400 MHz) δ 9.94 (s, 1H), 8.76 (s, 1H), 8.62 (s, 1H), 7.67 (s, 1H), 6.75 (s, 1H), 3.64 (brs, 2H), 3.19 (t, 2H), 2.66 (brs, 2H)

Reference Example 5

1-(7-Iodofuro[3,2-c]pyridin-2-yl)ethanone

Step 1: 7-Iodofuro[3,2-c]pyridine-2-carbaldehyde

A solution prepared by dissolving 2-(diethoxymethyl)-7-iodofuro[3,2-c]pyridine (2.88 mmol) obtained in Reference Example 1 in tetrahydrofuran (5 ml) was added with a 3N aqueous hydrochloric acid solution (15 ml) and stirred overnight. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered. The resulting filtrate was concentrated under reduced pressure, and the residue thus obtained was used in the following step without any further purification process.

Step 2: 1-(7-Iodofuro[3,2-c]pyridin-2-yl)ethanol

A solution prepared by dissolving 7-iodofuro[3,2-c]pyridine-2-carbaldehyde obtained in Step 1 in tetrahydrofuran (5 ml) was slowly added with methyl magnesium bromide (3M ether solution) at 0° C., and stirred for 1 hour. An aqueous ammonium chloride solution was added to the reaction solution to terminate the reaction, which was then extracted with ethyl acetate. The extract thus obtained was washed with brine, dried over anhydrous magnesium sulfate and filtered. The resulting filtrate was concentrated under reduced pressure, and the residue thus obtained was used in the following step without any further purification process.

$^1$H NMR (CDCl$_3$, 400 MHz) δ 8.77 (s, 2H), 8.72 (s, 2H), 6.85 (s, 1H), 5.09 (m, 1H), 1.68 (d, 3H)

Step 3: 1-(7-Iodofuro[3,2-c]pyridin-2-yl)ethanone

A solution prepared by dissolving 1-(7-iodofuro[3,2-c]pyridin-2-yl)ethanol (1.38 mmol) obtained in Step 2 in dichloromethane (5 ml) was added with 4-methylmorpholine-N-oxide (4.15 mmol) and tetrapropylammonium perruthenate (catalytic amount), and stirred at room temperature for 2 hours. The reaction solution was filtered through Celite, and concentrated under reduced pressure. The residue thus obtained was purified by silica gel column chromatography (n-hexane/ethyl acetate=1/1, v/v) to obtain the title compound as a white solid (yield: 46%).

$^1$H NMR (CDCl$_3$, 400 MHz) δ 8.95 (s, 1H), 8.89 (s, 1H), 7.63 (s, 1H), 2.68 (s, 3H)

Reference Example 6

2-(Diethoxymethyl)furo[3,2-c]pyridine-7-carboxylic acid

Step 1: Synthesis of 2-(diethoxymethyl)furo[3,2-c]pyridine-7-carbonitrile

A solution prepared by dissolving 2-(diethoxymethyl)-7-iodofuro[3,2-c]pyridine (14.4 mmol) obtained in Reference Example 1 in N,N-dimethylformamide (96 ml) was added with copper cyanide (28.8 mmol) and copper iodide (28.8 mmol), and stirred overnight under reflux. The reaction mixture was cooled to room temperature, diluted with ethyl acetate, washed with water and brine, in sequence, which was then dried over anhydrous magnesium sulfate and filtered. After the filtrate was concentrated under reduced pressure, the residue thus obtained was purified by silica gel column chromatography (n-hexane/ethyl acetate=4/1, v/v) to obtain the title compound as yellow oil (yield: 85%).

$^1$H NMR (CDCl$_3$, 400 MHz) δ 9.07 (s, 1H), 8.77 (s, 1H), 7.00 (s, 1H), 5.69 (s, 1H), 3.72 (m, 4H), 1.29 (t, 6H)

Step 2:
2-(Diethoxymethyl)furo[3,2-c]pyridine-7-carboxylic acid

A solution prepared by dissolving 2-(diethoxymethyl)furo[3,2-c]pyridine-7-carbonitrile (9.3 mmol) obtained in Step 1 in a solution of ethanol/water (10 ml/5 ml) was added with sodium hydroxide (28.02 mmol), and stirred at 80° C. for 2 hours. The reaction solution was neutralized by adding a 3N aqueous hydrochloric acid solution, added with sodium chloride, and extracted with acetonitrile. The extract was washed with brine, dried over anhydrous magnesium sulfate and filtered. The resulting filtrate was concentrated under reduced pressure to obtain the title compound as a white solid (yield: 94%).

$^1$H NMR (CDCl$_3$, 400 MHz) δ 11.76 (brs, 1H), 9.30 (s, 1H), 9.26 (s, H), 7.06 (s, 1H), 5.80 (s, 1H), 3.74 (m, 4H), 1.30 (t, 6H)

Reference Example 7

6-Chloro-2-(diethoxymethyl)furo[3,2-c]pyridine

A solution prepared by dissolving 2-chloro-5-iodo-4-pyridinol (7.83 mmol) in anhydrous pyridine (20 ml) was added with propargyl aldehyde diethyl acetal (7.83 mmol) and copper(II) oxide (5.48 mmol) and stirred under reflux for 12 hours under nitrogen. The reaction solution was cooled to room temperature, filtered, and the filtrate was concentrated under reduced pressure. The residue was diluted with ethyl acetate, washed with aqueous ammonia, water and brine, in sequence, which was then dried over anhydrous magnesium sulfate and filtered. After the filtrate was concentrated under reduced pressure, the residue thus obtained was purified by silica gel column chromatography (n-hexane/ethyl acetate=5/1, v/v) to obtain the title compound as a light yellow solid (yield: 55%).

$^1$H NMR (CDCl$_3$, 400 MHz) δ 8.64 (s, 1H), 7.47 (s, 1H), 6.87 (s, 1H), 5.65 (s, 1H), 3.68 (q, 4H), 1.27 (t, 6H)

Example 1

(Z)-5-([7-{4-(Trifluoromethoxy)phenyl}furo[3,2-c]pyridin-2-yl]methylene)-thiazolidine-2,4-dione Step 1: Synthesis of 2-(diethoxymethyl)-7-{4-(trifluoromethoxy)phenyl}furo[3,2-c]pyridine A solution prepared by dissolving 2-(diethoxymethyl)-7-iodofuro[3,2-c]pyridine (1.0 mmol) obtained in Reference Example 1 in a mixed solution of tetrahydrofuran/water (4/1, v/v, 5 ml) was added with 4-trifluoromethoxyphenylboronic acid (1.2 mmol), sodium carbonate (2.2 mmol) and tetrakis(triphenylphosphine)palladium(0) (5.0 mol %), and stirred overnight under reflux. The organic layer was separated and concentrated under reduced pressure. The residue thus obtained was purified by silica gel column chromatography (n-hexane/ethyl acetate=4/1, v/v) to obtain the title compound as light brown oil (yield: 84%).

$^1$H NMR (CDCl$_3$, 300 MHz) δ 8.89 (s, 1H), 8.65 (s, 1H), 7.91 (d, 2H), 7.38 (d, 2H), 6.98 (s, 1H), 5.70 (s, 1H), 3.66-3.74 (m, 4H), 1.28 (t, 6H)

Step 2: Synthesis of 7-{4-(trifluoromethoxy)phenyl}furo[3,2-c]pyridine-2-carbaldehyde A solution prepared by dissolving 2-(diethoxymethyl)-7-{4-(trifluoromethoxy)phenyl}furo[3,2-c]pyridine (0.5 mmol) obtained in Step 1 in a tetrahydrofuran solution (5 ml) was added with a 3N aqueous hydrochloric acid solution (5 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract was washed with brine, dried over anhydrous magnesium sulfate, filtered, and the filtrate was concentrated under reduced pressure. The residue thus obtained was purified by silica gel column chromatography (n-hexane/ethyl acetate=4/1, v/v) to obtain the title compound as light brown oil (yield: 90%).

$^1$H NMR (CDCl$_3$, 300 MHz) δ 9.99 (s, 1H), 9.12 (brs, 1H), 8.85 (brs, 1H), 7.93 (d, 2H), 7.72 (s, 1H), 7.42 (d, 2H)

Step 3: Synthesis of (Z)-5-([7-{4-(trifluoromethoxy)phenyl}furo[3,2-c]pyridin-2-yl]methylene)-thiazolidine-2,4-dione A solution prepared by dissolving 7-{4-(trifluoromethoxy)phenyl}furo[3,2-c]pyridine-2-carbaldehyde (0.4 mmol) obtained in Step 2 in an acetic acid solution (3 ml) was added with thiazolidinedione (0.5 mmol) and β-alanine (0.4 mmol), and stirred under reflux for 4 hours. After cooled to room temperature, the resulting solid was filtered, washed with acetic acid and water, and dried to obtain the title compound as a light yellow solid (yield: 80%).

$^1$H NMR (DMSO-d$_6$, 300 MHz) δ 12.71 (brs, 1H), 9.08 (s, 1H), 8.81 (s, 1H), 8.09 (d, 2H), 7.88 (s, 1H), 7.71 (s, 1H), 7.63 (d, 2H)

Examples 2 to 130

The title compounds of Examples 2 to 130 were prepared in the same manner as described in Example 1 above, except for using each of the following compounds: 2,4-difluorophenylboronic acid, 4-(methoxycarbonyl)phenylboronic acid, 4-cyanophenylboronic acid, 3-cyanophenylboronic acid, 3-(benzyloxy)phenylboronic acid, 4-(benzyloxy)phenylboronic acid, 4-acetamidophenylboronic acid, phenylboronic acid, 4-tert-butylphenylboronic acid, 6-hydroxypyridine-3-boronic acid, 1-methylpyrazole-4-boronic acid, 3-thiophene boronic acid, benzo[b]thiophene-2-boronic acid, 4-aminophenylboronic acid pinacol ester, 5-chloro-2-thiophene boronic acid, 3-chloro-4-methylphenylboronic acid, 3,4-dichlorophenylboronic acid, N, N-dimethyl-4-(4,4,5,5-tetramethyl-1,3,2-dioxaborolan-2-yl)aniline, 4-fluoro-3-methylphenylboronic acid, 4-fluoro-3-(trifluoromethyl)phenylboronic acid, trans-2-[3,5-bis(trifluoromethyl)phenyl]vinylboronic acid pinacol ester, 4-(methylthio)phenylboronic acid, 3-(methylthio)phenylboronic acid, 4-methoxyphenylboronic acid, 3-methoxyphenylboronic acid, 2-methoxyphenylboronic acid, 4-chlorophenylboronic acid, 4-acetylphenylboronic acid, 6-methoxypyridine-3-boronic acid, 4-ethoxyphenylboronic acid, 3,5-dimethoxyphenylboronic acid, 3,4-dimethoxyphenylboronic acid, p-tolylboronic acid, 4-vinylphenylboronic acid, 3,4-(methylenedioxy)-phenylboronic acid, 5-bromo-3-pyridine boronic acid pinacol ester, 1-propyl-4-(4,4,5,5-tetramethyl-1,3,2-dioxaborolan-2-yl)-1H-1,2,4-triazol-5(4H)-one, 5-pyrimidylboronic acid, {4-(methylsulfonyl)phenyl}boronic acid, 6-(methylsulfanyl)-3-pyridinylboronic acid, 2-fluoropyridine-5-boronic acid, 2-chloropyridine-4-boronic acid, 2-bromopyridine-5-boronic acid, 2-chloropyridine-5-boronic acid, 3-chloro-4-methoxyphenylboronic acid, 3-fluoro-4-methoxyphenylboronic acid, 4-methoxy-3-methylphenylboronic acid, 3-chloro-4-isopropoxyphenylboronic acid, 2,3-dimethoxypyridine-5-boronic acid pinacol ester, 3-chloro-4-ethoxyphenylboronic acid, 3-fluoro-4-isopropoxyphenylboronic acid, 2-aminopyridine-5-boronic acid pinacol ester, 4-ethoxy-3-fluorophenylboronic acid, 4-ethoxy-3,5-dimethylphenylboronic acid, 4-(ethylthio)benzeneboronic acid, 4-methoxy-3-(trifluoromethyl)benzeneboronic acid, 3-amino-2-methoxypyridine-5-boronic acid pinacol ester, 5-chloro-6-methoxypyridine-3-boronic acid pinacol ester, 2-cyanopyridine-5-boronic acid pinacol ester, 2-(methylthio)pyrimidine-5-boronic acid pinacol ester, 2,4-dimethoxypyrimidine-5-boronic acid, 2-fluoro-3-methylpyridine-5-boronic acid, 2-chloro-3-methylpyridine-5-boronic acid, 2-chloro-3-fluoropyridine-5-boronic acid pinacol ester, 2-methylpyridine-5-boronic acid pinacol ester, 2-chloro-3-methoxypyridine-5-boronic acid, 2-methoxy-3-(trifluoromethyl)pyridine-5-boronic acid, 2,3-dihydrobenzofuran-5-boronic acid, 4-(methoxymethyl)phenylboronic acid, 3,5-dimethylphenylboronic acid, 4-(tert-butylamino)sulfonylphenylboronic acid pinacol ester, 3,5-dimethyl-4-methoxyphenylboronic acid, 3,5-dimethyl-4-propoxyphenylboronic acid, 3,5-dimethyl-4-isopropoxyphenylboronic acid, [6-(2,2,2-trifluoroethoxyl)pyridin-3-yl]boronic acid, 3,4,5-trimethoxyphenylboronic acid, 2-fluoro-4-(methylthio)benzeneboronic acid, 2-methoxy-4-(4,4,5,5-tetramethyl-1,3,2-dioxaborolan-2-yl)phenol, 2,6-dimethyl-4-(4,4,5,5-tetramethyl-1,3,2-dioxaborolan-2-yl)phenol, 2-methoxypyrimidine-5-boronic acid, 4-methyl-7-(4,4,5,5-tetramethyl-1,3,2-dioxaborolan-2-yl)-3,4-dihydro-2H-1,4-benzoxazine, 4-isopropoxy-3-methylphenylboronic acid, 4-ethoxy-3-methylphenylboronic acid, 4-hydroxyphenylboronic acid, 3-amino-2-chloropyridine-5-boronic acid, 3,5-dichloro-4-methoxybenzene boronic acid, 4-hydroxymethyl-3-methylphenylboronic acid, 3-fluoro-4-(trifluoromethyl)benzene boronic acid, (4-methoxy-3-trifluoromethyl)phenylboronic acid, 6-(5,5-dimethyl-1,3,2-dioxaborinan-2-yl)-4H-1,3-benzodioxine, 5-(5,5-dimethyl-1,3,2-dioxaborinan-2-yl)-2-methoxybenzonitrile, 3-chloro-4-hydroxy-5-methoxyphenylboronic acid pinacol ester, 4-ethoxy-3-(trifluoromethyl)benzeneboronic acid, 2,2-difluoro-benzo[1,3]dioxole-5-boronic acid, 4-(tert-butoxymethyl)phenylboronic acid, 2-ethoxypyrimidine-5-boronic acid, 3-fluoro-2-methoxypyridine-5-boronic acid, 2,6-chloropyridine-4-boronic acid pinacol ester, 4-cyclopropyl-benzene boronic acid, 5-chloro-6-ethoxypyridine-3-boronic acid, 6-methoxy-5-methylpyridine-3-boronic acid, 6-ethoxy-5-methylpyridine-3-boronic acid, 5-chloro-6-isopropoxypyridine-3-boronic acid, 2-methoxypyridine-4-boronic acid, 2-picoline-4-boronic acid, 2-(trifluoromethyl)pyridine-4-boronic acid, 2-ethoxy-6-fluoropyridine-4-boronic acid, 3-cyanomethylphenylboronic acid, 3-(2,2,2-trifluoroethoxyl)phenylboronic acid, (3-fluoro-5-methylphenyl)boronic acid, 3-(methylsulfonamido)phenylboronic acid, 3-amino-4-methylphenylboronic acid, 4-amino-3-fluorophenylboronic acid hydrochloride, 3,5-bis(trifluoromethyl)phenylboronic acid, benzo[c][1,2,5]thiadiazole-5-boronic acid pinacol ester, 6-quinoline boronic acid pinacol ester, N-cyclopropyl-5-(4,4,5,5-tetramethyl-1,3,2-dioxaborolan-2-yl)pyrimidin-2-amine, 3-methoxy-1-propyn-1-ylboronic acid pinacol ester, 5-methyl-6-(morpholin-4-yl)-pyridine-3-boronic acid pinacol ester, 6-(dimethylamino)pyridine-3-boronic acid pinacol ester, 1H-indazole-5-boronic acid pinacol ester, 1H-benzo[d]imidazole-5-boronic acid pinacol ester, 1H-pyrazole-4-boronic acid pinacol ester, 4,4,5,5-tetramethyl-2-(phenylethynyl)-1,3,2-dioxaborolane, 4,4,5,5-tetramethyl-2-(propyn-1-yl)-1,3,2-dioxaborolane, 6-morpholinopyridin-3-ylboronic acid, 2-aminopyrimidine-5-boronic acid, 1-{4-(4,4,5,5-tetramethyl-1,3,2-dioxaborolan-2-yl)phenyl)-1H-tetrazole and 3-hydroxyphenylboronic acid, instead of 4-trifluoromethoxyphenylboronic acid in Step 1 of Example 1.

Example 2

(Z)-5-[{7-(2,4-Difluorophenyl)furo[3,2-c]pyridin-2-yl}methylene]thiazolidine-2,4-dione $^1$H NMR (DMSO-$d_6$, 300 MHz) δ 12.66 (brs, 1H), 9.09 (s, 1H), 8.63 (s, 1H), 7.84 (m, 1H), 7.81 (s, 1H), 7.67 (s, 1H), 7.60 (m, 1H), 7.36 (m, 1H); (yield: 62%)

Example 3

(Z)-Methyl 4-[2-{(2,4-dioxothiazolidin-5-ylidene)methyl}furo[3,2-c]pyridin-7-yl]benzoate $^1$H NMR (DMSO-$d_6$, 300 MHz) δ 12.72 (brs, 1H), 9.10 (s, 1H), 8.87 (s, 1H), 8.15 (m, 4H), 7.87 (s, 1H), 7.71 (s, 1H), 3.93 (s, 3H); (yield: 62%)

Example 4

(Z)-4-[2-{(2,4-Dioxothiazolidin-5-ylidene)methyl}furo[3,2-c]pyridin-7-yl]benzonitrile $^1$H NMR (DMSO-$d_6$, 300 MHz) δ 12.71 (brs, 1H), 9.12 (s, 1H), 8.87 (s, 1H), 8.14 (m, 4H), 7.89 (s, 1H), 7.73 (s, 1H); (yield: 70%)

Example 5

(Z)-3-[2-{(2,4-Dioxothiazolidin-5-ylidene)methyl}furo[3,2-c]pyridin-7-yl]benzonitrile $^1$H NMR (DMSO-$d_6$, 300 MHz) δ 12.72 (brs, 1H), 9.11 (s, 1H), 8.89 (s, 1H), 8.46 (s, 1H), 8.31 (d, 1H), 8.01 (d, 1H), 7.83 (m, 2H), 7.12 (s, 1H); (yield: 72%)

Example 6

(Z)-5-([7-{3-(Benzyloxy)phenyl}furo[3,2-c]pyridin-2-yl]methylene)thiazolidine-2,4-dione $^1$H NMR (DMSO-$d_6$, 300 MHz) δ 12.70 (brs, 1H), 9.05 (s, 1H), 8.79 (s, 1H), 7.85 (s, 1H), 7.68 (s, 1H), 7.62 (s, 1H), 7.52 (m, 4H), 7.38 (m, 3H), 7.17 (m, 1H), 5.24 (s, 2H); (yield: 40%)

Example 7

(Z)-5-([7-{4-(Benzyloxy)phenyl}furo[3,2-c]pyridin-2-yl]methylene)thiazolidine-2,4-dione $^1$H NMR (DMSO-d$_6$, 300 MHz) δ 12.69 (brs, 1H), 8.99 (s, 1H), 8.75 (s, 1H), 7.94 (d, 2H), 7.85 (s, 1H), 7.67 (s, 1H), 7.52 (m, 2H), 7.38 (m, 3H), 7.25 (d, 2H), 5.22 (s, 2H); (yield: 52%)

Example 8

(Z)—N-(4-[2-{(2,4-Dioxothiazolidin-5-ylidene)methyl}furo[3,2-c]pyridin-7-yl]phenyl)acetamide $^1$H NMR (DMSO-d$_6$, 300 MHz) δ 10.21 (s, 1H), 9.02 (s, 1H), 8.79 (s, 1H), 7.94 (d, 2H), 7.89 (s, 1H), 7.83 (d, 2H), 7.70 (s, 1H), 2.11 (s, 3H); (yield: 40%)

Example 9

(Z)-5-{(7-Phenylfuro[3,2-c]pyridin-2-yl)methylene}thiazolidine-2,4-dione $^1$H NMR (DMSO-d$_6$, 300 MHz) δ 9.05 (s, 1H), 8.79 (s, 1H), 7.97 (d, 2H), 7.85 (s, 1H), 7.69 (s, 1H), 7.62 (t, 2H), 7.53 (t, 1H); (yield: 53%)

Example 10

(Z)-5-[{7-(4-tert-Butylphenyl)furo[3,2-c]pyridin-2-yl}methylene]thiazolidine-2,4-dione $^1$H NMR (DMSO-d$_6$, 300 MHz) δ 9.03 (s, 1H), 8.79 (s, 1H), 7.92 (d, 2H), 7.87 (s, 1H), 7.69 (s, 1H), 7.62 (d, 2H), 1.37 (s, 9H); (yield: 54%)

Example 11

(Z)-5-[{7-(6-Hydroxypyridin-3-yl)furo[3,2-c]pyridin-2-yl}methylene]thiazolidine-2,4-dione $^1$H NMR (DMSO-d$_6$, 400 MHz) δ 12.68 (brs, 1H), 12.30 (brs, 1H), 9.95 (s, 1H), 8.73 (s, 1H), 8.07 (d, 2H), 7.84 (s, 1H), 7.66 (s, 1H), 6.55 (d, 1H); (yield: 58%)

Example 12

(Z)-5-[{7-(1-Methyl-1H-pyrazol-4-yl)furo[3,2-c]pyridin-2-yl}methylene]thiazolidine-2,4-dione $^1$H NMR (DMSO-d$_6$, 400 MHz) δ 12.75 (brs, 1H), 8.89 (s, 1H), 8.85 (s, 1H), 8.47 (s, 1H), 8.25 (s, 1H), 7.89 (s, 1H), 7.66 (s, 1H), 3.98 (s, 1H); (yield: 22%)

Example 13

(Z)-5-[{7-(Thiophen-3-yl)furo[3,2-c]pyridin-2-yl}methylene]thiazolidine-2,4-dione $^1$H NMR (DMSO-d$_6$, 400 MHz) δ 12.76 (brs, 1H), 8.98 (d, 2H), 8.30 (s, 1H), 7.88-7.91 (m, 3H), 7.69 (s, 1H); (yield: 64%)

Example 14

(Z)-5-[{7-(Benzo[b]thiophen-2-yl)furo[3,2-c]pyridin-2-yl}methylene]thiazolidine-2,4-dione $^1$H NMR (DMSO-d$_6$, 400 MHz) δ 12.76 (brs, 1H), 9.67 (s, 1H), 8.95 (s, 1H), 8.32 (s, 1H), 8.12 (d, 1H), 7.90-7.95 (m, 2H), 7.72 (s, 1H), 7.46-7.53 (m, 2H); (yield: 27%)

Example 15

(Z)-5-[{7-(4-Aminophenyl)furo[3,2-c]pyridin-2-yl}methylene]thiazolidine-2,4-dione $^1$H NMR (DMSO-d$_6$, 400 MHz) δ 10.17 (s, 1H), 9.00 (s, 1H), 8.78 (s, 1H), 7.93 (d, 2H), 7.81-7.87 (m, 3H), 7.69 (s, 1H); (yield: 32%)

Example 16

(Z)-5-[{7-(5-Chlorothiophen-2-yl)furo[3,2-c]pyridin-2-yl}methylene]thiazolidine-2,4-dione $^1$H NMR (DMSO-d$_6$, 400 MHz) δ 12.73 (brs, 1H), 8.99 (s, 1H), 8.87 (s, 1H), 7.87 (s, 1H), 7.81 (s, 1H), 7.69 (s, 1H), 7.38 (s, 1H); (yield: 14%)

Example 17

(Z)-5-[{7-(3-Chloro-4-methylphenyl)furo[3,2-c]pyridin-2-yl}methylene]thiazolidine-2,4-dione $^1$H NMR (DMSO-d$_6$, 400 MHz) δ 12.77 (brs, 1H), 9.06 (s, 1H), 8.85 (s, 1H), 8.12 (s, 1H), 7.84-7.88 (m, 2H), 7.70 (s, 1H), 7.60 (s, 1H), 2.46 (s, 3H); (yield: 59%)

Example 18

(Z)-5-[{7-(3,4-Dichlorophenyl)furo[3,2-c]pyridin-2-yl}methylene]thiazolidine-2,4-dione $^1$H NMR (DMSO-d$_6$, 400 MHz) δ 9.09 (s, 1H), 8.88 (s, 1H), 8.36 (s, 1H), 7.73-7.95 (m, 4H); (yield: 66%)

Example 19

(Z)-5-[{7-(4-(Dimethylamino)phenyl}furo[3,2-c]pyridin-2-yl]methylene)thiazolidine-2,4-dione $^1$H NMR (DMSO-d$_6$, 400 MHz) δ 8.95 (s, 1H), 8.74 (s, 1H), 7.84-7.87 (m, 2H), 7.68 (s, 1H), 6.92 (s, 2H), 3.02 (s, 6H); (yield: 53%)

Example 20

(Z)-5-[{7-(4-Fluoro-3-methylphenyl)furo[3,2-c]pyridin-2-yl}methylene]thiazolidine-2,4-dione $^1$H NMR (DMSO-d$_6$, 400 MHz) δ 12.67 (brs, 1H), 9.05 (s, 1H), 8.79 (s, 1H), 7.70-8.06 (m, 4H), 7.38-7.41 (m, 1H), 2.38 (s, 3H); (yield: 76%)

Example 21

(Z)-5-([7-{4-Fluoro-3-(trifluoromethyl)phenyl}furo[3,2-c]pyridin-2-yl]methylene)thiazolidine-2,4-dione $^1$H NMR (DMSO-$d_6$, 400 MHz) δ 12.64 (brs, 1H), 9.09 (s, 1H), 8.85 (s, 1H), 8.36 (s, 1H), 8.30 (s, 1H), 7.71-7.87 (m, 3H); (yield: 71%)

Example 22

(Z)-5-([7-{(E)-3,5-Bis(trifluoromethyl)styryl}furo[3,2-c]pyridin-2-yl]methylene)thiazolidine-2,4-dione $^1$H NMR (DMSO-$d_6$, 400 MHz) δ 12.77 (brs, 1H), 9.01 (s, 1H), 8.71 (s, 1H), 8.34 (s, 2H), 8.08 (s, 1H), 7.99-7.88 (m, 3H), 7.69 (s, 1H); (yield: 74%)

Example 23

(Z)-5-([7-{4-(Methylthio)phenyl}furo[3,2-c]pyridin-2-yl]methylene)thiazolidine-2,4-dione $^1$H NMR (DMSO-$d_6$, 400 MHz) δ 12.70 (brs, 1H), 9.04 (s, 1H), 8.89 (s, 1H), 7.93 (d, 2H), 7.87 (s, 1H), 7.70 (s, 1H), 7.50 (d, 2H), 2.58 (s, 3H); (yield: 69%)

Example 24

(Z)-5-([7-{3-(Methylthio)phenyl}furo[3,2-c]pyridin-2-yl]methylene)thiazolidine-2,4-dione $^1$H NMR (DMSO-d6, 400 MHz) δ 12.68 (brs, 1H), 9.07 (s, 1H), 8.82 (s, 1H), 7.87 (s, 2H), 7.71 (m, 2H), 7.57 (m, 1H), 7.42 (m, 1H), 2.59 (s, 3H); (yield: 57%)

Example 25

(Z)-5-[{7-(4-Methoxyphenyl)furo[3,2-c]pyridin-2-yl}methylene]thiazolidine-2,4-dione $^1$H NMR (DMSO-$d_6$, 400 MHz) δ 12.65 (brs, 1H), 9.00 (s, 1H), 8.76 (s, 1H), 7.93 (d, 2H), 7.87 (s, 1H), 7.69 (s, 1H) m 7.18 (d, 2H), 3.88 (s, 3H); (yield: 62%)

Example 26

(Z)-5-[{7-(3-Methoxyphenyl)furo[3,2-c]pyridin-2-yl}methylene]thiazolidine-2,4-dione $^1$H NMR (DMSO-$d_6$, 400 MHz) δ 12.70 (brs, 1H), 9.06 (s, 1H), 8.80 (s, 1H), 7.87 (s, 1H), 7.70 (s, 1H), 7.51 (m, 3H), 7.12 (s, 1H), 3.89 (s, 3H); (yield: 57%)

Example 27

(Z)-5-[{7-(2-Methoxyphenyl)furo[3,2-c]pyridin-2-yl}methylene]thiazolidine-2,4-dione $^1$H NMR (DMSO-d6, 400 MHz) δ 12.60 (brs, 1H), 9.05 (s, 1H), 8.57 (s, 1H), 7.83 (s, 1H), 7.67 (s, 1H), 7.53 (m, 2H), 7.27 (m, 1H), 7.15 (m, 1H), 3.80 (s, 3H); (yield: 68%)

Example 28

(Z)-5-[{7-(4-Chlorophenyl)furo[3,2-c]pyridin-2-yl}methylene]thiazolidine-2,4-dione $^1$H NMR (DMSO-$d_6$, 400 MHz) δ 12.72 (brs, 1H), 9.07 (s, 1H), 8.80 (s, 1H), 8.00 (m, 2H), 7.87 (s, 1H), 7.70 (s, 3H); (yield: 67%)

Example 29

(Z)-5-[{7-(4-Acetylphenyl)furo[3,2-c]pyridin-2-yl}methylene]thiazolidine-2,4-dione $^1$H NMR (DMSO-$d_6$, 400 MHz) δ 12.72 (brs, 1H), 9.11 (s, 1H), 8.88 (s, 1H), 8.17 (m, 4H), 7.88 (s, 1H), 7.72 (s, 1H), 2.68 (s, 3H); (yield: 60%)

Example 30

(Z)-5-[{7-(6-Methoxypyridin-3-yl)furo[3,2-c]pyridin-2-yl}methylene]thiazolidine-2,4-dione $^1$H NMR (DMSO-$d_6$, 400 MHz) δ 12.82 (brs, 1H), 9.05 (s, 1H), 8.80 (m, 2H), 8.30 (d, 1H), 7.87 (s, 1H), 7.70 (s, 1H), 7.09 (d, 1H), 3.97 (s, 3H); (yield: 57%)

Example 31

(Z)-5-[{7-(4-Ethoxyphenyl)furo[3,2-c]pyridin-2-yl}methylene]thiazolidine-2,4-dione $^1$H NMR (DMSO-$d_6$, 400 MHz) δ 12.63 (brs, 1H), 8.98 (s, 1H), 8.73 (s, 1H), 7.89 (d, 2H), 7.84 (s, 1H), 7.66 (w, 1H), 7.15 (d, 2H), 4.14 (m, 2H), 1.38 (t, 3H); (yield: 66%)

Example 32

(Z)-5-[{7-(3,5-Dimethoxyphenyl)furo[3,2-c]pyridin-2-yl}methylene]thiazolidine-2,4-dione $^1$H NMR (DMSO-$d_6$, 400 MHz) δ 12.67 (brs, 1H), 9.06 (s, 1H), 8.79 (s, 1H), 7.87 (s, 1H), 7.70 (s, 1H), 7.09 (s, 2H), 6.67 (s, 1H), 3.87 (s, 6H); (yield: 60%)

Example 33

(Z)-5-[{7-(3,4-Dimethoxyphenyl)furo[3,2-c]pyridin-2-yl}methylene]thiazolidine-2,4-dione $^1$H NMR (DMSO-$d_6$, 400 MHz) δ 12.71 (brs, 1H), 9.01 (s, 1H), 8.77 (s, 1H), 7.88 (s, 1H), 7.70 (s, 12H), 7.51 (s, 2H), 7.20 (m, 1H), 3.91 (s, 3H), 3.87 (s, 3H); (yield: 67%)

Example 34

(Z)-5-[{7-(p-Tolyl)furo[3,2-c]pyridin-2-yl}methylene]thiazolidine-2,4-dione $^1$H NMR (DMSO-$d_6$, 400 MHz) δ 12.75 (brs, 1H), 9.03 (s, 1H), 8.78 (s, 1H), 7.88 (m, 3H), 7.70 (m, 1H), 7.43 (m, 2H), 2.44 (s, 3H); (yield: 61%)

Example 35

(Z)-5-[{7-(4-Vinylphenyl)furo[3,2-c]pyridin-2-yl}methylene]thiazolidine-2,4-dione $^1$H NMR (DMSO-d$_6$, 400 MHz) δ 12.70 (brs, 1H), 9.05 (s, 1H), 8.83 (s, 1H), 7.98 (m, 2H), 7.87 (s, 1H), 7.72 (m, 3H), 6.89 (m, 1H), 6.02 (d, 1H), 5.40 (d, 1H); (yield: 65%)

Example 36

(Z)-5-[{7-(Benzo[d][1,3]dioxol-5-yl)furo[3,2-c]pyridin-2-yl}methylene]thiazolidine-2,4-dione $^1$H NMR (DMSO-d$_6$, 400 MHz) δ 12.62 (brs, 1H), 8.95 (s, 1H), 8.68 (s, 1H), 7.81 (s, 1H), 7.62 (s, 1H), 7.50 (s, 1H), 7.42 (d, 1H), 7.10 (d, 1H), 6.09 (s, 2H); (yield: 60%)

Example 37

(Z)-5-[{7-(5-Bromopyridin-3-yl)furo[3,2-c]pyridin-2-yl}methylene]thiazolidine-2,4-dione $^1$H NMR (DMSO-d$_6$, 400 MHz) δ 12.72 (brs, 1H), 9.19 (s, 1H), 9.13 (s, 1H), 8.96 (s, 1H), 8.87 (s, 1H), 8.73 (s, 1H), 7.89 (s, 1H), 7.73 (s, 1H); (yield: 67%)

Example 38

(Z)-5-([7-{3-Fluoro-4-(5-oxo-1-propyl-1H-1,2,4-triazol-4(5H)-yl)phenyl}furo[3,2-c]pyridin-2-yl]methylene)thiazolidine-2,4-dione $^1$H NMR (DMSO-d$_6$, 400 MHz) δ 12.63 (brs, 1H), 9.04 (s, 1H), 8.85 (s, 1H), 8.29 (s, 1H), 8.07 (d, 1H), 7.93 (m, 1H), 7.83 (m, 2H), 7.66 (s, 1H), 3.66 (m, 2H), 1.66 (m, 2H), 0.84 (t, 3H); (yield: 66%)

Example 39

(Z)-5-[{7-(Pyrimidin-5-yl)furo[3,2-c]pyridin-2-yl}methylene]thiazolidine-2,4-dione $^1$H NMR (DMSO-d$_6$, 400 MHz) δ 12.70 (brs, 1H), 9.43 (s, 2H), 9.33 (s, 1H), 9.15 (s, 1H), 8.96 (s, 1H), 7.89 (s, 1H), 7.73 (s, 1H); (yield: 60%)

Example 40

(Z)-5-([7-{4-(Methylsulfonyl)phenyl}furo[3,2-c]pyridin-2-yl]methylene)thiazolidine-2,4-dione $^1$H NMR (DMSO-d$_6$, 400 MHz) δ 12.70 (brs, 1H), 9.13 (s, 1H), 8.89 (s, 1H), 8.25 (m, 2H), 8.16 (m, 2H), 7.89 (s, 1H), 7.73 (s, 1H), 3.34 (s, 3H); (yield: 61%)

Example 41

(Z)-5-([7-{6-(Methylthio)pyridin-3-yl}furo[3,2-c]pyridin-2-yl]methylene)thiazolidine-2,4-dione $^1$H NMR (DMSO-d$_6$, 400 MHz) δ 12.75 (brs, 1H), 9.07 (s, 1H), 9.04 (s, 1H), 8.84 (s, 1H), 8.23 (d, 1H), 7.88 (s, 1H), 7.71 (s, 1H), 7.56 (d, 1H), 2.61 (s, 3H); (yield: 59%)

Example 42

(Z)-5-[{7-(6-Fluoropyridin-3-yl)furo[3,2-c]pyridin-2-yl}methylene]thiazolidine-2,4-dione $^1$H NMR (DMSO-d$_6$, 400 MHz) δ 12.69 (brs, 1H), 9.11-8.97 (m, 1H), 8.86-8.74 (m, 2H), 8.09 (m, 1H), 7.88 (m, 1H), 7.71-7.70 (m, 2H), 6.55 (m, 1H); (yield: 58%)

Example 43

(Z)-5-[{7-(2-Chloropyridin-4-yl)furo[3,2-c]pyridin-2-yl}methylene]thiazolidine-2,4-dione $^1$H NMR (DMSO-d$_6$, 400 MHz) δ 12.73 (brs, 1H), 9.16 (s, 1H), 9.00 (s, 1H), 8.65 (brs, 1H), 8.21 (s, 1H), 8.04 (brs, 1H), 7.89 (s, 1H), 7.73 (s, 1H); (yield: 59%)

Example 44

(Z)-5-[{7-(6-Bromopyridin-3-yl)furo[3,2-c]pyridin-2-yl}methylene]thiazolidine-2,4-dione $^1$H NMR (DMSO-d$_6$, 400 MHz) δ 12.72 (brs, 1H), 9.11 (s, 1H), 9.02 (s, 1H), 8.87 (s, 1H), 9.33 (m, 1H), 7.93 (m, 1H), 7.84 (s, 1H), 7.68 (s, 1H); (yield: 56%)

Example 45

(Z)-5-[{7-(6-Chloropyridin-3-yl)furo[3,2-c]pyridin-2-yl}methylene]thiazolidine-2,4-dione $^1$H NMR (DMSO-d$_6$, 400 MHz) δ 12.75 (brs, 1H), 9.11 (s, 1H), 9.04 (s, 1H), 8.88 (s, 1H), 8.44 (d, 1H), 7.88 (s, 1H), 7.81 (d, 1H), 7.72 (s, 1H); (yield: 67%)

Example 46

(Z)-5-[{7-(3-Chloro-4-methoxyphenyl)furo[3,2-c]pyridin-2-yl}methylene]thiazolidine-2,4-dione $^1$H NMR (DMSO-d$_6$, 400 MHz) δ 12.67 (brs, 1H), 9.02 (s, 1H), 8.82 (s, 1H), 8.15 (s, 1H), 7.92 (d, 1H), 7.87 (s, 1H), 7.69 (s, 1H), 7.38 (d, 1H), 3.97 (s, 3H); (yield: 64%)

Example 47

(Z)-5-[{7-(3-Fluoro-4-methoxyphenyl)furo[3,2-c]pyridin-2-yl}methylene]thiazolidine-2,4-dione $^1$H NMR (DMSO-d$_6$, 400 MHz) δ 12.69 (brs, 1H), 9.02 (s, 1H), 8.81 (s, 1H), 7.88 (m, 1H), 7.88 (s, 1H), 7.79 (d, 1H), 7.69 (s, 1H), 7.39 (m, 1H), 3.95 (s, 3H); (yield: 58%)

Example 48

(Z)-5-[{7-(4-Methoxy-3-methylphenyl)furo[3,2-c]pyridin-2-yl}methylene]thiazolidine-2,4-dione $^1$H NMR (DMSO-d$_6$, 400 MHz) δ 12.65 (brs, 1H), 8.98 (s, 1H), 8.76 (s, 1H), 7.86 (s, 1H), 7.79 (m, 1H), 7.67 (s, 1H), 7.15 (m, 1H), 3.89 (s, 3H); (yield: 57%)

Example 49

(Z)-5-[{7-(3-Chloro-4-isopropoxyphenyl)furo[3,2-c]pyridin-2-yl}methylene]thiazolidine-2,4-dione $^1$H NMR (DMSO-d$_6$, 400 MHz) δ 12.66 (brs, 1H), 9.02 (s, 1H), 8.81 (s, 1H), 8.13 (s, 1H), 7.88 (m, 2H), 7.68 (s, 1H), 7.39 (m, 1H), 4.83 (m, 1H), 1.36 (d, 6H); (yield: 56%)

Example 50

(Z)-5-[{7-(5,6-Dimethoxypyridin-3-yl)furo[3,2-c]pyridin-2-yl}methylene]thiazolidine-2,4-dione $^1$H NMR (DMSO-d$_6$, 400 MHz) δ 12.69 (brs, 1H), 9.05 (s, 1H), 8.82 (s, 1H), 8.28 (s, 1H), 7.88 (s, 1H), 7.82 (s, 1H), 7.71 (s, 1H), 3.97 (s, 3H), 3.94 (s, 3H); (yield: 64%)

Example 51

(Z)-5-[{7-(3-Chloro-4-ethoxyphenyl)furo[3,2-c]pyridin-2-yl}methylene]thiazolidine-2,4-dione $^1$H NMR (DMSO-d$_6$, 400 MHz) δ 12.64 (brs, 1H), 9.01 (s, 1H), 8.80 (s, 1H), 8.14 (s, 1H), 7.90 (m, 1H), 7.86 (s, 1H), 7.68 (s, 1H), 7.35 (m, 1H), 4.24 (m, 2H), 1.42 (t, 3H); (yield: 68%)

Example 52

(Z)-5-[{7-(3-Fluoro-4-isopropoxyphenyl)furo[3,2-c]pyridin-2-yl}methylene]thiazolidine-2,4-dione $^1$H NMR (DMSO-d$_6$, 400 MHz) δ 12.69 (brs, 1H), 9.01 (s, 1H), 8.80 (s, 1H), 7.90 (m, 1H), 7.87 (s, 1H), 7.75 (m, 1H), 7.68 (s, 1H), 7.40 (m, 1H), 4.78 (m, 1H), 1.35 (d, 6H); (yield: 60%)

Example 53

(Z)-5-[{7-(6-Aminopyridin-3-yl)furo[3,2-c]pyridin-2-yl}methylene]thiazolidine-2,4-dione $^1$H NMR (DMSO-d$_6$, 400 MHz) δ 12.72 (brs, 1H), 8.995 (s, 1H), 8.74 (s, 1H), 8.63 (s, 1H), 8.00 (m, 1H), 7.87 (s, 1H), 7.67 (s, 1H), 6.67 (m, 1H), 6.48 (s, 1H); (yield: 57%)

Example 54

(Z)-5-[{7-(4-Ethoxy-3-fluorophenyl)furo[3,2-c]pyridin-2-yl}methylene]thiazolidine-2,4-dione $^1$H NMR (DMSO-d$_6$, 400 MHz) δ 12.66 (brs, 1H), 9.01 (s, 1H), 8.80 (s, 1H), 7.91 (m, 1H), 7.87 (s, 1H), 7.75 (d, 1H), 7.68 (s, 1H), 7.38 (m, 1H), 4.23 (m, 2H), 1.41 (t, 3H); (yield: 57%)

Example 55

(Z)-5-[{7-(4-Ethoxy-3,5-dimethylphenyl)furo[3,2-c]pyridin-2-yl}methylene]thiazolidine-2,4-dione $^1$H NMR (DMSO-d$_6$, 400 MHz) δ 12.69 (brs, 1H), 8.99 (s, 1H), 8.77 (s, 1H), 7.87 (s, 1H), 7.68 (m, 3H), 3.89 (m, 2H), 2.35 (s, 6H), 1.39 (t, 3H); (yield: 57%)

Example 56

(Z)-5-[{7-(4-Ethylsulfanylphenyl)furo[3,2-c]pyridin-2-yl}methylene]thiazolidine-2,4-dione $^1$H NMR (DMSO-d$_6$, 400 MHz) δ 12.68 (brs, 1H), 9.03 (s, 1H), 8.78 (s, 1H), 7.92 (m, 2H), 7.86 (s, 1H), 7.69 (s, 1H), 7.51 (d, 2H), 3.10 (m, 2H), 1.30 (t, 3H); (yield: 56%)

Example 57

(Z)-5-[{7-(4-Methoxy-3-trifluoromethylphenyl)furo[3,2-c]pyridin-2-yl}methylene]thiazolidine-2,4-dione $^1$H NMR (DMSO-d$_6$, 400 MHz) δ 12.66 (brs, 1H), 9.05 (s, 1H), 8.81 (s, 1H), 8.20 (m, 2H), 7.86 (s, 1H), 7.70 (s, 1H), 7.51 (m, 1H), 4.01 (s, 3H); (yield: 60%)

Example 58

5-[{7-(5-Amino-6-methoxypyridin-3-yl)furo[3,2-c]pyridin-2-yl}methylene]thiazolidine-2,4-dione $^1$H NMR (DMSO-d$_6$, 400 MHz) δ 12.67 (brs, 1H), 9.01 (s, 1H), 8.67 (s, 1H), 7.95 (s, 1H), 7.86 (s, 1H), 7.68 (s, 1H), 7.40 (s, 1H), 5.21 (brs, 2H), 3.96 (s, 3H); (yield: 49%)

Example 59

(Z)-5-[{7-(5-Chloro-6-methoxypyridin-3-yl)furo[3,2-c]pyridin-2-yl}methylene]thiazolidine-2,4-dione $^1$H NMR (DMSO-d$_6$, 400 MHz) δ 12.68 (brs, 1H), 9.07 (s, 1H), 8.88 (s, 1H), 8.75 (s, 1H), 8.57 (s, 1H), 7.88 (s, 1H), 7.70 (s, 1H), 4.06 (s, 3H); (yield: 59%)

Example 60

(Z)-5-[2-{(2,4-Dioxothiazolidin-5-ylidene)methyl}furo[3,2-c]pyridin-7-yl]picolinonitrile $^1$H NMR (DMSO-d$_6$, 400 MHz) δ 12.63 (brs, 1H), 8.96 (s, 1H), 8.74 (s, 1H), 8.10-8.06 (m, 2H), 7.85 (s, 1H), 7.67 (s, 1H), 6.55 (m, 1H); (yield: 53%)

Example 61

(Z)-5-([7-{2-(Methylthio)pyrimidin-5-yl}furo[3,2-c]pyridin-2-yl]methylene)thiazolidine-2,4-dione $^1$H NMR (DMSO-d$_6$, 400 MHz) δ 12.74 (brs, 1H), 9.25 (s, 2H), 9.11 (s, 1H), 8.92 (s, 1H), 7.89 (s, 1H), 7.72 (s, 1H), 2.62 (s, 3H); (yield: 57%)

Example 62

(Z)-5-([7-{2,4-(Dimethoxy)pyrimidin-5-yl}furo[3,2-c]pyridin-2-yl]methylene)thiazolidine-2,4-dione $^1$H NMR (DMSO-d$_6$, 400 MHz) δ 12.65 (brs, 1H), 9.07 (s, 1H), 8.63 (s, 2H), 7.84 (s, 1H), 7.67 (s, 1H), 4.01 (s, 3H), 3.97 (s, 3H); (yield: 61%)

Example 63

(Z)-5-[{7-(6-Fluoro-5-methylpyridin-3-yl)furo[3,2-c]pyridin-2-yl}methylene]thiazolidine-2,4-dione $^1$H NMR (DMSO-d$_6$, 400 MHz) δ 12.70 (brs, 1H), 8.95 (s, 1H), 8.75 (s, 1H), 8.00 (d, 2H), 7.86 (s, 1H), 7.67 (s, 1H), 2.11 (s, 3H); (yield: 63%)

Example 64

(Z)-5-[{7-(6-Chloro-5-methylpyridin-3-yl)furo[3,2-c]pyridin-2-yl}methylene]thiazolidine-2,4-dione $^1$H NMR (DMSO-d$_6$, 400 MHz) δ 12.71 (brs, 1H), 9.09 (s, 1H), 8.87 (d, 2H), 8.43 (s, 1H), 7.88 (s, 1H), 7.70 (s, 1H), 2.47 (s, 3H); (yield: 56%)

Example 65

(Z)-5-[{7-(6-Chloro-5-fluoropyridin-3-yl)furo[3,2-c]pyridin-2-yl}methylene]thiazolidine-2,4-dione $^1$H NMR (DMSO-d$_6$, 400 MHz) δ 12.74 (brs, 1H), 9.13 (s, 1H), 8.95 (m, 2H), 8.60 (d, 1H), 7.89 (s, 1H), 7.72 (s, 1H); (yield: 56%)

Example 66

(Z)-5-[{7-(6-Methylpyridin-3-yl)furo[3,2-c]pyridin-2-yl}methylene]thiazolidine-2,4-dione $^1$H NMR (DMSO-d$_6$, 400 MHz) δ 12.67 (brs, 1H), 9.07 (s, 2H), 8.84 (s, 1H), 8.26 (d, 1H), 7.86 (s, 1H), 7.70 (s, 1H), 7.51 (d, 1H), 2.60 (s, 3H); (yield: 60%)

Example 67

(Z)-5-[{7-(6-Chloro-5-methoxypyridin-3-yl)furo[3,2-c]pyridin-2-yl}methylene]thiazolidine-2,4-dione $^1$H NMR (DMSO-d$_6$, 400 MHz) δ 12.71 (brs, 1H), 9.15 (m, 1H), 8.93 (s, 1H), 8.59 (s, 1H), 8.10 (m, 1H), 7.89 (m, 1H), 7.73 (s, 1H), 4.06 (s, 3H); (yield: 62%)

Example 68

(Z)-5-([7-{6-Methoxy-5-(trifluoromethyl)pyridin-3-yl}furo[3,2-c]pyridin-2-yl]methylene)thiazolidine-2,4-dione $^1$H NMR (DMSO-d$_6$, 400 MHz) δ 12.69 (brs, 1H), 9.09 (s, 1H), 9.01 (s, 1H), 8.90 (s, 1H), 8.69 (s, 1H), 7.86 (s, 1H), 7.71 (s, 1H), 4.10 (s, 3H); (yield: 67%)

Example 69

(Z)-5-[{7-(2,3-Dihydrobenzofuran-5-yl)furo[3,2-c]pyridin-2-yl}methylene]thiazolidine-2,4-dione $^1$H NMR (DMSO-d$_6$, 400 MHz) δ 12.71 (brs, 1H), 8.98 (s, 1H), 8.73 (s, 1H), 7.87 (d, 2H), 7.70 (m, 1H), 7.67 (s, 1H), 6.68 (m, 1H), 4.66 (m, 2H), 3.34 (m, 2H); (yield: 66%)

Example 70

(Z)-5-([7-{4-(Methoxymethyl)phenyl}furo[3,2-c]pyridin-2-yl]methylene)thiazolidine-2,4-dione $^1$H NMR (DMSO-d$_6$, 400 MHz) δ 12.69 (brs, 1H), 9.05 (m, 1H), 8.80 (m, 1H), 7.96 (m, 2H), 7.88 (m, 1H), 7.71 (m, 1H), 7.55 (m, 2H), 4.54 (s, 2H), 3.37 (s, 3H); (yield: 59%)

Example 71

(Z)-5-[{7-(3,5-Dimethylphenyl)furo[3,2-c]pyridin-2-yl}methylene]thiazolidine-2,4-dione $^1$H NMR (DMSO-d$_6$, 400 MHz) δ 12.69 (brs, 1H), 9.03 (m, 1H), 8.80 (m, 1H), 7.87 (m, 1H), 7.74 (m, 1H), 7.62 (s, 2H), 7.16 (s, 2H), 2.41 (s, 6H); (yield: 56%)

Example 72

(Z)—N-(tert-Butyl)-4-[2-{(2,4-dioxothiazolidin-5-ylidene)methyl}furo[3,2-c]pyridin-7-yl]benzenesulfonamide $^1$H NMR (DMSO-d$_6$, 400 MHz) δ 12.69 (brs, 1H), 9.11 (m, 1H), 8.86 (s, 1H), 8.13 (m, 2H), 8.05 (m, 2H), 7.78 (m, 1H), 7.72 (m, 2H), 1.15 (s, 9H); (yield: 51%)

Example 73

(Z)-5-[{7-(4-Methoxy-3,5-dimethylphenyl)furo[3,2-c]pyridin-2-yl}methylene]thiazolidine-2,4-dione $^1$H NMR (DMSO-d$_6$, 400 MHz) δ 12.70 (brs, 1H), 9.03 (m, 1H), 8.79 (s, 1H), 8.07-7.89 (m, 1H), 7.71 (m, 3H), 3.75 (s, 3H), 2.37 (s, 6H); (yield: 5%)

Example 74

(Z)-5-[{7-(3,5-Dimethyl-4-propoxyphenyl)furo[3,2-c]pyridin-2-yl}methylene]thiazolidine-2,4-dione $^1$H NMR (DMSO-d$_6$, 400 MHz) δ 12.69 (brs, 1H), 9.00 (m, 1H), 8.77 (m, 1H), 8.05-7.86 (m, 1H), 7.69 (m, 3H), 3.79 (m, 2H), 2.35 (s, 6H), 1.80 (m, 2H), 1.07 (t, 3H); (yield: 56%)

Example 75

(Z)-5-[{7-(4-Isopropoxy-3,5-dimethylphenyl)furo[3,2-c]pyridin-2-yl}methylene]thiazolidine-2,4-dione $^1$H NMR (DMSO-d$_6$, 400 MHz) δ 12.69 (brs, 1H), 9.01 (m, 1H), 8.79 (s, 1H), 8.07-7.88 (m, 1H), 7.69 (m, 3H), 4.26 (m, 1H), 2.35 (s, 6H), 1.29 (d, 6H); (yield: 50%)

Example 76

(Z)-5-([7-{6-(2,2,2-Trifluoroethoxy)pyridin-3-yl}furo[3,2-c]pyridin-2-yl]methylene)thiazolidine-2,4-dione $^1$H NMR (DMSO-d$_6$, 400 MHz) δ 12.70 (brs, 1H), 9.08 (m, 1H), 8.82 (m, 2H), 8.40 (m, 1H), 8.07-7.88 (m, 1H), 7.77 (m, 1H), 7.26 (m, 1H), 5.11 (m, 2H); (yield: 58%)

Example 77

(Z)-5-[{7-(3,4,5-Trimethoxyphenyl)furo[3,2-c]pyridin-2-yl}methylene]thiazolidine-2,4-dione $^1$H NMR (DMSO-$d_6$, 400 MHz) δ 12.69 (brs, 1H), 9.05 (s, 1H), 8.79 (s, 1H), 7.88 (s, 1H), 7.71 (s, 1H), 7.18 (s, 2H), 3.92 (s, 6H), 3.77 (s, 3H); (yield: 65%)

Example 78

(Z)-5-([7-{2-Fluoro-4-(methylthio)phenyl}furo[3,2-c]pyridin-2-yl]methylene)thiazolidine-2,4-dione $^1$H NMR (DMSO-$d_6$, 400 MHz) δ 12.64 (brs, 1H), 9.01 (s, 1H), 8.63 (s, 1H), 7.84 (s, 1H), 7.69 (m, 2H), 7.40 (d, 1H), 7.31 (d, 1H), 2.59 (s, 3H); (yield: 60%)

Example 79

(Z)-5-[{7-(4-Hydroxy-3-methoxyphenyl)furo[3,2-c]pyridin-2-yl}methylene]thiazolidine-2,4-dione $^1$H NMR (DMSO-$d_6$, 400 MHz) δ 12.67 (brs, 1H), 9.43 (s, 1H), 8.97 (s, 1H), 8.73 (s, 1H), 7.86 (s, 1H), 7.68 (s, 1H), 7.47 (s, 1H), 7.38 (d, 1H), 6.98 (d, 1H), 3.91 (s, 3H); (yield: 60%)

Example 80

(Z)-5-[{7-(4-Hydroxy-3,5-dimethylphenyl)furo[3,2-c]pyridin-2-yl}methylene]thiazolidine-2,4-dione $^1$H NMR (DMSO-$d_6$, 400 MHz) δ 12.66 (brs, 1H), 8.94 (s, 1H), 8.73 (s, 1H), 7.60 (s, 1H), 7.86 (s, 1H), 7.66 (s, 1H), 7.60 (s, 2H), 2.30 (s, 6H); (yield: 46%)

Example 81

(Z)-5-[{7-(2-Methoxypyrimidin-5-yl)furo[3,2-c]pyridin-2-yl}methylene]thiazolidine-2,4-dione $^1$H NMR (DMSO-$d_6$, 400 MHz) δ 12.72 (brs, 1H), 9.22 (s, 2H), 9.09 (s, 1H), 8.89 (s, 1H), 7.89 (s, 1H), 7.71 (s, 1H), 4.04 (s, 3H); (yield: 68%)

Example 82

(Z)-5-([7-{4-Methyl-3,4-dihydro-2H-benzo[b][1,4]oxazin-7-yl}furo[3,2-c]pyridin-2-yl]methylene)thiazolidine-2,4-dione $^1$H NMR (DMSO-$d_6$, 400 MHz) δ 12.67 (brs, 1H), 8.92 (s, 1H), 8.72 (s, 1H), 7.86 (s, 1H), 7.66 (s, 1H), 7.46 (d, 1H), 7.37 (s, 1H), 6.87 (d, 1H), 4.29 (brs, 2H), 3.32 (brs, 2H), 2.94 (s, 3H); (yield: 58%)

Example 83

(Z)-5-[{7-(4-Isopropoxy-3-methylphenyl)furo[3,2-c]pyridin-2-yl}methylene]thiazolidine-2,4-dione $^1$H NMR (DMSO-$d_6$, 400 MHz) δ 12.70 (brs, 1H), 8.98 (s, 1H), 8.75 (s, 1H), 7.85 (d, 2H), 7.73 (d, 1H), 7.67 (s, 1H), 7.16 (d, 1H), 4.72 (m, 1H), 2.26 (s, 3H), 1.34 (s, 6H); (yield: 80%)

Example 84

(Z)-5-[{7-(4-Ethoxy-3-methylphenyl)furo[3,2-c]pyridin-2-yl}methylene]thiazolidine-2,4-dione $^1$H NMR (DMSO-$d_6$, 400 MHz) δ 12.70 (brs, 1H), 8.96 (s, 1H), 8.75 (s, 1H), 7.86 (s, 1H), 7.76 (m, 2H), 7.61 (s, 1H), 7.13 (d, 1H), 4.14 (m, 2H), 2.29 (s, 3H), 1.40 (t, 3H); (yield: 66%)

Example 85

(Z)-5-[{7-(4-Hydroxyphenyl)furo[3,2-c]pyridin-2-yl}methylene]thiazolidine-2,4-dione $^1$H NMR (DMSO-$d_6$, 400 MHz) δ 12.70 (brs, 1H), 9.88 (s, 1H), 8.97 (s, 1H), 8.72 (s, 1H), 7.87 (s, 1H), 7.80 (m, 2H), 7.68 (s, 1H), 6.98 (m, 2H); (yield: 67%)

Example 86

(Z)-5-[{7-(5-Amino-6-chloropyridin-3-yl)furo[3,2-c]pyridin-2-yl}methylene]thiazolidine-2,4-dione $^1$H NMR (DMSO-d6, 400 MHz) δ 12.72 (brs, 1H), 9.10 (s, 1H), 8.74 (s, 1H), 8.17 (s, 1H), 7.88 (s, 1H), 7.71 (s, 1H), 7.62 (s, 1H), 5.85 (brs, 2H); (yield: 53%)

Example 87

(Z)-5-[{7-(3,5-Dichloro-4-methoxyphenyl)furo[3,2-c]pyridin-2-yl}methylene]thiazolidine-2,4-dione $^1$H NMR (DMSO-$d_6$, 400 MHz) δ 12.69 (brs, 1H), 9.07 (s, 1H), 8.90 (s, 1H), 8.18 (s, 2H), 7.87 (s, 1H), 7.70 (s, 1H), 3.94 (s, 3H); (yield: 49%)

Example 88

(Z)-5-([7-{4-(Hydroxymethyl)-3-methylphenyl}furo[3,2-c]pyridin-2-yl]methylene)thiazolidine-2,4-dione $^1$H NMR (DMSO-$d_6$, 400 MHz) δ 12.71 (brs, 1H), 9.05 (s, 1H), 8.82 (s, 1H), 7.90 (d, 2H), 7.79 (m, 1H), 7.70 (s, 1H), 7.54 (d, 1H), 5.20 (s, 2H), 2.11 (s, 3H); (yield: 48%)

Example 89

(Z)-5-([7-{3-Fluoro-4-(trifluoromethoxy)phenyl}furo[3,2-c]pyridin-2-yl]methylene)thiazolidine-2,4-dione $^1$H NMR (DMSO-$d_6$, 400 MHz) δ 12.71 (brs, 1H), 9.11 (s, 1H), 8.87 (s, 1H), 8.16 (d, 1H), 7.95-7.85 (m, 3H), 7.71 (s, 1H); (yield: 89%)

Example 90

(Z)-5-([7-{4-Methoxy-3-(trifluoromethyl)phenyl}furo[3,2-c]pyridin-2-yl]methylene)thiazolidine-2,4-dione $^1$H NMR (DMSO-$d_6$, 400 MHz) δ 12.67 (brs, 1H), 9.05 (s, 1H), 8.81 (s, 1H), 8.20 (m, 2H), 7.86 (s, 1H), 7.53 (s, 1H), 7.51 (d, 1H), 4.1 (s, 3H); (yield: 45%)

Example 91

(Z)-5-[{7-(4H-Benzo[d][1,3]dioxin-6-yl)furo[3,2-c]pyridin-2-yl}methylene]thiazolidine-2,4-dione $^1$H NMR (DMSO-$d_6$, 400 MHz) δ 12.70 (brs, 1H), 9.00 (s, 1H), 8.75 (s, 1H), 7.87 (s, 1H), 7.79 (d, 1H), 7.75 (s, 1H), 7.68 (s, 1H), 7.08 (d, 1H), 5.37 (s, 2H), 5.01 (s, 2H); (yield: 40%)

Example 92

(Z)-5-[2-{(2,4-Dioxothiazolidin-5-ylidene)methyl}furo[3,2-c]pyridin-7-yl]-2-methoxybenzonitrile $^1$H NMR (DMSO-$d_6$, 400 MHz) δ 12.69 (brs, 1H), 9.04 (s, 1H), 8.83 (s, 1H), 8.37 (s, 1H), 8.27 (d, 1H), 7.88 (s, 1H), 7.70 (s, 1H), 7.50 (d, 1H), 4.03 (s, 3H); (yield: 49%)

Example 93

(Z)-5-[{7-(3-Chloro-4-hydroxy-5-methoxyphenyl)furo[3,2-c]pyridin-2-yl}methylene]thiazolidine-2,4-dione $^1$H NMR (DMSO-$d_6$, 400 MHz) δ 12.69 (brs, 1H), 9.87 (s, 1H), 9.03 (s, 1H), 8.85 (s, 1H), 7.88 (s, 1H), 7.69 (d, 2H), 7.48 (s, 1H), 3.97 (s, 3H); (yield: 47%)

Example 94

(Z)-5-([7-{4-Ethoxy-3-(trifluoromethyl)phenyl}furo[3,2-c]pyridin-2-yl]methylene)thiazolidine-2,4-dione $^1$H NMR (DMSO-$d_6$, 400 MHz) δ 12.70 (brs, 1H), 9.05 (d, 1H), 8.87-8.80 (d, 1H), 8.17 (m, 2H), 7.86 (s, 1H), 7.70 (s, 1H), 7.49 (d, 1H), 4.29 (m, 2H), 1.40 (t, 3H); (yield: 30%)

Example 95

(Z)-5-[{7-(2,2-Difluorobenzo[d][1,3]dioxol-5-yl)furo[3,2-c]pyridin-2-yl}methylene]thiazolidine-2,4-dione $^1$H NMR (DMSO-$d_6$, 400 MHz) δ 12.70 (brs, 1H), 9.07 (m, 1H), 8.80 (m, 1H), 8.01 (m, 1H), 7.84 (m, 2H), 7.68 (m, 2H); (yield: 50%)

Example 96

(Z)-5-([7-{4-(tert-Butoxymethyl)phenyl}furo[3,2-c]pyridin-2-yl]methylene)thiazolidine-2,4-dione $^1$H NMR (DMSO-$d_6$, 400 MHz) δ 12.69 (brs, 1H), 9.05 (s, 1H), 8.79 (s, 1H), 7.95 (m, 2H), 7.88 (s, 1H), 7.70 (s, 1H), 7.54 (d, 2H), 4.54 (s, 2H), 1.27 (s, 9H); (yield: 49%)

Example 97

(Z)-5-[{7-(2-Ethoxypyrimidin-5-yl)furo[3,2-c]pyridin-2-yl}methylene]thiazolidine-2,4-dione $^1$H NMR (DMSO-$d_6$, 400 MHz) δ 12.72 (brs, 1H), 9.20 (s, 2H), 9.08 (s, 1H), 8.88 (s, 1H), 7.87 (s, 1H), 7.69 (s, 1H), 4.46 (m, 2H), 1.40 (t, 3H); (yield: 50%)

Example 98

(Z)-5-[{7-(5-Fluoro-6-methoxypyridin-3-yl)furo[3,2-c]pyridin-2-yl}methylene]thiazolidine-2,4-dione $^1$H NMR (DMSO-$d_6$ 400 MHz) δ 12.72 (brs, 1H), 9.06 (s, 1H), 8.86 (s, 1H), 8.64 (s, 1H), 8.36 (d, 1H), 7.88 (s, 1H), 7.70 (s, 1H), 4.06 (s, 3H); (yield: 57%)

Example 99

(Z)-5-[{7-(2,6-Dichloropyridin-4-yl)furo[3,2-c]pyridin-2-yl}methylene]thiazolidine-2,4-dione $^1$H NMR (DMSO-$d_6$, 400 MHz) δ 12.73 (brs, 1H), 9.18 (s, 1H), 9.06 (s, 1H), 8.26 (s, 2H), 7.90 (s, 1H), 7.73 (s, 1H); (yield: 54%)

Example 100

(Z)-5-[{7-(4-Cyclopropylphenyl)furo[3,2-c]pyridin-2-yl}methylene]thiazolidine-2,4-dione $^1$H NMR (DMSO-$d_6$, 400 MHz) δ 12.69 (brs, 1H), 9.02 (s, 1H), 8.76 (s, 1H), 7.85 (m, 3H), 7.69 (s, 1H), 7.30 (d, 2H), 2.06 (m, 1H), 1.04 (m, 2H), 0.80 (m, 2H); (yield: 47%)

Example 101

(Z)-5-[{7-(5-Chloro-6-ethoxypyridin-3-yl)furo[3,2-c]pyridin-2-yl}methylene]thiazolidine-2,4-dione $^1$H NMR (DMSO-$d_6$, 400 MHz) δ 12.70 (brs, 1H), 9.06 (s, 1H), 8.87 (s, 1H), 8.72 (m, 1H), 8.55 (m, 1H), 7.88 (s, 2H), 7.69 (s, 1H), 4.50 (m, 2H), 1.41 (t, 3H); (yield: 89%)

Example 102

(Z)-5-[{7-(6-Methoxy-5-methylpyridin-3-yl)furo[3,2-c]pyridin-2-yl}methylene]thiazolidine-2,4-dione $^1$H NMR (DMSO-$d_6$, 400 MHz) δ 12.62 (brs, 1H), 9.01 (s, 1H), 8.80 (s, 1H), 8.61 (s, 1H), 8.19 (s, 1H), 7.84 (s, 1H), 7.66 (s, 1H), 3.99 (s, 3H), 2.29 (s, 3H); (yield: 40%)

Example 103

(Z)-5-[{7-(6-Ethoxy-5-methylpyridin-3-yl)furo[3,2-c]pyridin-2-yl}methylene]thiazolidine-2,4-dione $^1$H NMR (DMSO-$d_6$, 400 MHz) δ 12.65 (brs, 1H), 9.02 (s, 1H), 8.80 (s, 1H), 8.58 (s, 1H), 8.18 (s, 1H), 7.86 (s, 1H), 7.67 (s, 1H), 4.45 (m, 2H), 2.28 (s, 3H), 1.39 (t, 3H); (yield: 39%)

Example 104

(Z)-5-[{7-(5-Chloro-6-isopropoxypyridin-3-yl)furo[3,2-c]pyridin-2-yl}methylene]thiazolidine-2,4-dione $^1$H NMR (DMSO-$d_6$, 400 MHz) δ 12.70 (brs, 1H), 9.05 (s, 1H), 8.86 (s, 1H), 8.72 (m, 1H), 8.53 (m, 1H), 7.85 (s, 1H), 7.67 (s, 1H), 5.42 (m, 1H), 1.40 (d, 6H); (yield: 89%)

Example 105

(Z)-5-[{7-(2-Methoxypyridin-4-yl)furo[3,2-c]pyridin-2-yl}methylene]thiazolidine-2,4-dione $^1$H NMR (DMSO-d$_6$, 400 MHz) δ 12.71 (brs, 1H), 9.13 (s, 1H), 8.92 (s, 1H), 8.39 (m, 1H), 7.88 (s, 1H), 7.72 (s, 1H), 7.59 (m, 1H), 7.45 (s, 1H), 3.95 (s, 3H); (yield: 50%)

Example 106

(Z)-5-[{7-(2-Methylpyridin-4-yl)furo[3,2-c]pyridin-2-yl}methylene]thiazolidine-2,4-dione $^1$H NMR (DMSO-d$_6$, 400 MHz) δ 12.70 (brs, 1H), 9.14 (s, 1H), 8.94 (s, 1H), 8.67 (m, 1H), 7.94 (s, 1H), 7.90 (s, 1H), 7.80 (m, 1H), 7.73 (s, 1H), 2.62 (s, 3H); (yield: 58%)

Example 107

(Z)-5-([7-{2-(Trifluoromethyl)pyridin-4-yl}furo[3,2-c]pyridin-2-yl]methylene)thiazolidine-2,4-dione $^1$H NMR (DMSO-d$_6$, 400 MHz) δ 12.71 (brs, 1H), 9.18 (s, 1H), 9.03 (s, 1H), 9.01 (m, 1H), 8.54 (s, 1H), 8.32 (m, 1H), 7.83 (s, 1H), 7.70 (s, 1H); (yield: 54%)

Example 108

(Z)-5-[{7-(2-Ethoxy-6-fluoropyridin-4-yl)furo[3,2-c]pyridin-2-yl}methylene]thiazolidine-2,4-dione $^1$H NMR (DMSO-d$_6$, 400 MHz) δ 12.71 (brs, 1H), 9.15 (s, 1H), 8.97 (s, 1H), 7.89 (s, 1H), 7.71 (s, 1H), 7.42 (s, 1H), 7.35 (s, 1H), 4.36 (m, 2H), 1.38 (t, 3H); (yield: 54%)

Example 109

(Z)-2-(3-[2-{(2,4-Dioxothiazolidin-5-ylidene)methyl}furo[3,2-c]pyridin-7-yl]phenyl)acetonitrile $^1$H NMR (DMSO-d$_6$, 400 MHz) δ 12.68 (brs, 1H), 9.07 (s, 1H), 8.78 (s, 1H), 7.93 (m, 2H), 7.85 (s, 1H), 7.66 (m, 2H), 7.53 (m, 1H), 4.16 (s, 2H); (yield: 49%)

Example 110

(Z)-5-([7-{3-(2,2,2-Trifluoroethoxyl)phenyl}furo[3,2-c]pyridin-2-yl]methylene)thiazolidine-2,4-dione $^1$H NMR (DMSO-d$_6$, 400 MHz) δ 12.68 (brs, 1H), 9.07 (s, 1H), 8.85 (s, 1H), 7.88 (s, 1H), 7.71 (s, 1H), 7.65 (m, 2H), 7.59 (t, 1H), 7.25 (m, 1H), 4.90 (m, 2H); (yield: 50%)

Example 111

(Z)-5-[{7-(3-Fluoro-5-methylphenyl)furo[3,2-c]pyridin-2-yl}methylene]thiazolidine-2,4-dione $^1$H NMR (DMSO-d$_6$, 400 MHz) δ 12.68 (brs, 1H), 9.05 (s, 1H), 8.84 (s, 1H), 7.81 (s, 1H), 7.73 (s, 1H), 7.64 (m, 2H), 7.20 (d, 1H), 2.47 (s, 3H); (yield: 52%)

Example 112

(Z)—N-(3-[2-{(2,4-Dioxothiazolidin-5-ylidene)methyl}furo[3,2-c]pyridin-7-yl]phenyl)methanesulfonamide $^1$H NMR (DMSO-d$_6$, 400 MHz) δ 12.68 (brs, 1H), 9.98 (s, 1H), 9.06 (s, 1H), 8.71 (s, 1H), 7.84 (s, 1H), 7.68 (m, 2H), 7.59 (m, 1H), 7.40 (d, 1H), 3.08 (s, 3H); (yield: 47%)

Example 113

(Z)-5-[{7-(3-Amino-4-methylphenyl)furo[3,2-c]pyridin-2-yl}methylene]thiazolidine-2,4-dione $^1$H NMR (DMSO-d$_6$, 400 MHz) δ 12.70 (brs, 1H), 9.00 (s, 1H), 8.66 (s, 1H), 7.87 (s, 1H), 7.68 (s, 1H), 7.16 (m, 2H), 7.11 (m, 1H), 2.16 (s, 3H); (yield: 49%)

Example 114

(Z)-5-[{7-(4-Amino-3-fluorophenyl)furo[3,2-c]pyridin-2-yl}methylene]thiazolidine-2,4-dione $^1$H NMR (DMSO-d$_6$, 400 MHz) δ 12.69 (brs, 1H), 8.94 (s, 1H), 8.75 (s, 1H), 7.87 (s, 1H), 7.71 (m, 1H), 7.67 (s, 1H), 7.57 (m, 1H), 6.96 (t, 1H), 5.59 (brs, 1H); (yield: 51%)

Example 115

(Z)-5-([7-{3,5-Bis(trifluoromethyl)phenyl}furo[3,2-c]pyridin-2-yl]methylene)thiazolidine-2,4-dione $^1$H NMR (DMSO-d$_6$, 400 MHz) δ 12.67 (brs, 1H), 9.14 (s, 1H), 8.98 (s, 1H), 8.64 (s, 1H), 8.27 (s, 1H), 7.87 (s, 1H), 7.73 (s, 1H); (yield: 54%)

Example 116

(Z)-5-[{7-(Benzo[c][1,2,5]thiadiazol-5-yl)furo[3,2-c]pyridin-2-yl}methylene]thiazolidine-2,4-dione $^1$H NMR (DMSO-d$_6$, 400 MHz) δ 12.76 (brs, 1H), 9.16 (s, 1H), 8.98 (s, 1H), 7.66 (s, 1H), 8.31 (d, 1H), 8.20 (d, 1H), 7.89 (s, 1H), 7.73 (s, 1H); (yield: 51%)

Example 117

(Z)-5-[{7-(Quinolin-6-yl)furo[3,2-c]pyridin-2-yl}methylene]thiazolidine-2,4-dione $^1$H NMR (DMSO-d$_6$, 400 MHz) δ 12.76 (brs, 1H), 9.11 (s, 1H), 8.98 (d, 1H), 8.94 (s, 1H), 8.63 (s, 1H), 8.46 (d, 1H), 8.35 (d, 2H), 8.22 (d, 1H), 7.90 (s, 1H), 7.73 (s, 1H), 7.66 (m, 1H); (yield: 49%)

Example 118

(Z)-5-([7-{2-(Cyclopropylamino)pyrimidin-5-yl}furo[3,2-c]pyridin-2-yl]methylene)thiazolidine-2,4-dione $^1$H NMR (DMSO-d$_6$, 400 MHz) δ 9.00 (s, 1H), 8.95 (s, 2H), 8.82 (s, 1H), 7.90 (d, 1H), 7.88 (s, 1H), 7.69 (s, 1H), 2.83 (m, 1H), 0.72 (m, 2H), 0.53 (m, 2H); (yield: 54%)

Example 119

(Z)-5-[{7-(3-Methoxypropyn-1-yl)furo[3,2-c]pyridin-2-yl}methylene]thiazolidine-2,4-dione $^1$H NMR (DMSO-d$_6$, 400 MHz) δ 9.06 (s, 1H), 8.65 (s, 1H), 7.82 (s, 1H), 7.63 (s, 1H), 4.50 (s, 2H), 3.44 (s, 3H); (yield: 48%)

Example 120

(Z)-5-[{7-(5-Methyl-6-morpholinopyridin-3-yl)furo[3,2-c]pyridin-2-yl}methylene]thiazolidine-2,4-dione $^1$H NMR (DMSO-d$_6$, 400 MHz) δ 9.02 (s, 1H), 8.82 (s, 1H), 8.70 (d, 1H), 8.17 (d, 1H), 7.87 (s, 1H), 7.68 (s, 1H), 3.78 (t, 4H), 3.19 (t, 4H), 2.39 (s, 3H); (yield: 56%)

Example 121

(Z)-5-([7-{6-(Dimethylamino)pyridin-3-yl}furo[3,2-c]pyridin-2-yl]methylene)thiazolidine-2,4-dione $^1$H NMR (DMSO-d$_6$, 400 MHz) δ 8.96 (s, 1H), 8.75 (s, 1H), 8.73 (d, 1H), 8.11 (d, 1H), 7.87 (s, 1H), 7.68 (s, 1H), 6.86 (d, 1H), 3.13 (s, 6H); (yield: 45%)

Example 122

(Z)-5-[{7-(1H-Indazol-5-yl)furo[3,2-c]pyridin-2-yl}methylene]thiazolidine-2,4-dione $^1$H NMR (DMSO-d$_6$, 400 MHz) δ 9.03 (s, 1H), 8.83 (s, 1H), 8.37 (s, 1H), 8.18 (s, 1H), 7.93 (d, 1H), 7.88 (s, 1H), 7.75 (d, 1H), 7.70 (s, 1H); (yield: 52%)

Example 123

(Z)-5-[{7-(1H-Benzo[d]imidazol-5-yl)furo[3,2-c]pyridin-2-yl}methylene]thiazolidine-2,4-dione $^1$H NMR (DMSO-d$_6$, 400 MHz) δ 9.03 (s, 1H), 8.82 (s, 1H), 8.37 (s, 1H), 8.19 (s, 1H), 7.88 (s, 1H), 7.80 (s, 2H), 7.71 (s, 1H); (yield: 47%)

Example 124

(Z)-5-[{7-(1H-Pyrazol-4-yl)furo[3,2-c]pyridin-2-yl}methylene]thiazolidine-2,4-dione $^1$H NMR (DMSO-d$_6$, 400 MHz) δ 13.39 (brs, 1H), 8.92 (d, 2H), 8.55 (brs, 1H), 8.35 (brs, 1H), 7.90 (s, 1H), 7.68 (s, 1H); (yield: 59%)

Example 125

(Z)-5-[{7-(Phenylethynyl)furo[3,2-c]pyridin-2-yl}methylene]thiazolidine-2,4-dione $^1$H NMR (DMSO-d$_6$, 400 MHz) δ 12.71 (brs, 1H), 9.07 (s, 1H), 8.74 (s, 1H), 7.87 (s, 1H), 7.72-7.67 (m, 3H), 7.53-7.52 (m, 3H); (yield: 44%)

Example 126

(Z)-5-[{7-(Propyn-1-yl)furo[3,2-c]pyridin-2-yl}methylene]thiazolidine-2,4-dione $^1$H NMR (DMSO-d$_6$, 400 MHz) δ 12.82 (brs, 1H), 9.00 (s, 1H), 8.57 (s, 1H), 7.83 (s, 1H), 7.63 (s, 1H), 2.24 (s, 3H); (yield: 52%)

Example 127

(Z)-5-[{7-(6-Morpholinopyridin-3-yl)furo[3,2-c]pyridin-2-yl}methylene]thiazolidine-2,4-dione $^1$H NMR (400 MHz, DMSO-d$_6$) δ 8.98 (s, 1H), 8.77 (s, 2H), 8.17 (d, 1H), 7.86 (s, 1H), 7.68 (s, 1H), 7.07 (d, 1H), 3.75 (brs, 4H), 3.59 (brs, 4H); (yield: 55%)

Example 128

(Z)-5-[{7-(2-Aminopyrimidin-5-yl)furo[3,2-c]pyridin-2-yl}methylene]thiazolidine-2,4-dione $^1$H NMR (DMSO-d$_6$, 400 MHz) δ 8.99-8.81 (m, 4H), 7.86 (s, 1H), 7.68 (s, 1H), 7.07 (brs, 2H); (yield: 56%)

Example 129

(Z)-5-([7-{4-(1H-Tetrazol-1-yl)phenyl}furo[3,2-c]pyridin-2-yl]methylene)thiazolidine-2,4-dione $^1$H NMR (DMSO-d$_6$, 400 MHz) δ 12.71 (brs, 1H), 10.26 (s, 1H), 9.11 (s, 1H), 8.90 (s, 1H), 8.27 (d, 1H), 8.19 (d, 1H), 7.90 (s, 1H), 7.74 (s, 1H); (yield: 52%)

Example 130

(Z)-5-[{7-(3-Hydroxyphenyl)furo[3,2-c]pyridin-2-yl}methylene]thiazolidine-2,4-dione $^1$H NMR (DMSO-d$_6$, 400 MHz) δ 12.68 (brs, 1H), 9.71 (s, 1H), 9.03 (s, 1H), 8.72 (s, 1H), 7.86 (s, 1H), 7.68 (s, 1H), 7.45-7.30 (s, 3H), 6.93 (d, 1H)

Example 131

(Z)-5-([7-{3-(Morpholinomethyl)phenyl}furo[3,2-c]pyridin-2-yl]methylene)thiazolidine-2,4-dione Step 1: Synthesis of 3-{2-(diethoxymethyl)furo[3,2-c]pyridin-7-yl}benzaldehyde A solution prepared by dissolving 2-(diethoxymethyl)-7-iodofuro[3,2-c]pyridine (1.0 mmol) obtained in Reference Example 1 in a solution of toluene/ethanol/water (5/1/2, v/v, 5 ml) was added with 3-formylphenylboronic acid (1.2 mmol), sodium carbonate (2.2 mmol) and tetrakis(triphenylphosphine)palladium(0) (5.0 mol %), which was then stirred overnight under reflux. The organic layer was separated and concentrated under reduced pressure. The residue thus obtained was purified by silica gel column chromatography (n-hexane/ethyl acetate=4/1, v/v) to obtain the title compound as light brown oil (yield: 50%).

Step 2: Synthesis of 2-(diethoxymethyl)-7-{3-(morpholinomethyl)phenyl}furo[3,2-c]pyridine A solution prepared by mixing 3-{2-(diethoxymethyl)furo[3,2-c]pyridin-7-yl}benzaldehyde (0.5 mmol) obtained in Step 1, morpholine (1.0 mmol) and acetic acid (catalytic amount) in a tetrahydrofuran solution (2.5 ml) was stirred for 30 minutes at room temperature, and added with sodium triacetoxyborohydride (1.5 mmol). The reaction solution was stirred at room temperature for 20 hours, and the reaction was terminated by adding a saturated sodium bicarbonate solution. The reaction was added with dichloromethane, extracted, and the extract was dried over anhydrous magnesium sulfate, filtered, and concentrated under reduced pressure. The residue thus obtained was purified by silica gel column chromatography (dichloromethane/methanol=50/1, v/v) to obtain the title compound as light brown oil (yield: 65%).

$^1$H NMR (CDCl$_3$, 300 MHz) δ 8.86 (s, 1H), 8.67 (s, 1H), 7.83 (s, 1H), 7.70 (d, 1H), 7.48 (dd, 1H), 7.41 (d, 1H), 6.96 (s, 1H), 5.69 (s, 1H), 3.77-3.62 (m, 8H), 2.51 (dd, 4H), 1.26 (t, 6H)

Step 3: Synthesis of 7-{3-(morpholinomethyl) phenyl}furo[3,2-c]pyridine-2-carbaldehyde A solution prepared by dissolving 2-(diethoxymethyl)-7-{3-(morpholinomethyl)phenyl}furo[3,2-c]pyridine (0.5 mmol) obtained in Step 2 in a tetrahydrofuran (5 ml) was added with a 3N aqueous hydrochloric acid solution (5 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract washed with brine, dried over anhydrous magnesium sulfate, filtered, and concentrated under reduced pressure. The residue thus obtained was purified by silica gel column chromatography (n-hexane/ethyl acetate=4/1, v/v) to obtain the title compound as light brown oil (yield: 80%).

$^1$H NMR (CDCl$_3$, 300 MHz) δ 9.97 (s, 1H), 9.09 (s, 1H), 8.85 (s, 1H), 7.85 (s, 1H), 7.79 (d, 1H), 7.70 (s, 1H), 7.46-4.53 (m, 1H), 6.98 (s, 1H), 3.77-3.64 (m, 6H), 2.53 (brs, 2H)

Step 4: Synthesis of (Z)-5-([7-{3-(morpholinomethyl)phenyl}furo[3,2-c]pyridin-2-yl]methylene) thiazolidine-2,4-dione A solution prepared by dissolving 7-{3-(morpholinomethyl)phenyl}furo[3,2-c]pyridine-2-carbaldehyde (0.4 mmol) obtained in Step 3 in an acetic acid solution (3 ml) was added with thiazolidinedione (0.5 mmol) and β-alanine (0.4 mmol), and stirred under reflux for 4 hours. The reaction solution was cooled to room temperature, and the resulting solid was filtered, washed with acetic acid and water, and dried to obtain the title compound as a light yellow solid (yield: 77%).

$^1$H NMR (DMSO-d$_6$, 300 MHz) δ 9.02 (s, 1H), 8.79 (s, 1H), 7.98 (s, 1H), 7.85 (m, 1H), 7.72 (s, 1H), 7.57 (m, 2H), 7.48 (m, 1H), 3.64 (s, 2H), 3.59 (s, 4H), 2.46 (s, 4H)

Example 132

(Z)-5-([7-{3-(Piperidin-1-ylmethyl)phenyl}furo[3,2-c]pyridin-2-yl]methylene)thiazolidine-2,4-dione The title compound was prepared in the same manner as described in Example 131 above, except for using piperidine instead of morpholine in Step 2 of Example 131.

$^1$H NMR (DMSO-d$_6$, 300 MHz) δ 9.01 (s, 1H), 8.78 (s, 1H), 8.06 (s, 1H), 7.99 (d, 1H), 7.66 (t, 1H), 7.56 (m, 2H), 7.47 (s, 1H), 4.05 (s, 2H), 2.84 (brs, 4H), 1.64 (brs, 4H), 1.47 (brs, 2H); (yield: 22%)

Example 133

(Z)-5-([7-{4-(Morpholinomethyl)phenyl}furo[3,2-c]pyridin-2-yl]methylene)thiazolidine-2,4-dione The title compound was prepared in the same manner as described in Example 131 above, except for using 4-formylphenylboronic acid instead of 3-formylphenylboronic acid in Step 1 of Example 131.

$^1$H NMR (DMSO-d$_6$, 300 MHz) δ 9.02 (s, 1H), 8.79 (s, 1H), 7.95 (d, 2H), 7.77 (s, 1H), 7.62 (s, 1H), 7.55 (d, 1H), 3.66 (s, 2H), 3.63 (s, 4H), 2.50 (s, 4H); (yield: 23%)

Example 134

(Z)-5-{(7-[4-{(4-Methylpiperazin-1-yl)methyl}phenyl]furo[3,2-c]pyridin-2-yl)methylene}thiazolidine-2,4-dione The title compound was prepared in the same manner as described in Example 131 above, except for using 4-formylphenylboronic acid and 1-methylpiperizine instead of 3-formylphenylboronic acid in Step 1 and morpholine in Step 2, respectively.

$^1$H NMR (DMSO-d$_6$, 300 MHz) δ 8.98 (s, 1H), 8.78 (s, 1H), 8.03 (d, 2H), 7.55 (d, 2H), 7.47 (s, 1H), 7.40 (s, 1H), 3.69 (s, 2H), 3.47 (brs, 4H), 2.95 (brs, 4H), 2.59 (s, 3H); (yield: 23%)

Example 135

(Z)-4-[2-{(2,4-Dioxothiazolidin-5-ylidene)methyl}furo[3,2-c]pyridin-7-yl]benzoic acid A solution prepared by dissolving (Z)-methyl 4-[2-{(2,4-dioxothiazolidin-5-ylidene)methyl}furo[3,2-c]pyridin-7-yl]benzoate (0.2 mmol) obtained in Example 3 in tetrahydrofuran/methanol (1/1, 2 ml) was added with a 3N aqueous sodium hydroxide solution (1 ml), and stirred at room temperature overnight. The organic solvent was removed from the reaction solution under reduced pressure, and the remaining aqueous layer was diluted with water. The aqueous layer was added with 1N aqueous hydrochloric acid until the pH of the solution became 3-4, which was then extracted with dichloromethane. The extract was washed with brine, dried over anhydrous magnesium sulfate and filtered. The residue thus obtained was concentrated under reduced pressure to obtain the title compound as a light yellow solid (yield: 68%).

$^1$H NMR (DMSO-d$_6$, 300 MHz) δ 12.76 (brs, 1H) 9.17 (s, 1H), 8.93 (s, 1H), 8.16 (m, 4H), 7.92 (s, 1H), 7.76 (s, 1H)

Example 136

(Z)-5-[{7-(4-Isopropoxyphenyl)furo[3,2-c]pyridin-2-yl}methylene]thiazolidine-2,4-dione Step 1: Synthesis of 7-{4-(benzyloxy)phenyl}-2-(diethoxymethyl)furo[3,2-c]pyridine A solution prepared by dissolving 2-(diethoxymethyl)-7-iodofuro[3,2-c]pyridine (1.0 mmol) obtained in Reference Example 1 in toluene/ethanol/water (5/1/2, v/v, 5 ml) was added with 4-(benzyloxy)phenylboronic acid (1.2 mmol), sodium carbonate (2.2 mmol) and tetrakis(triphenylphosphine)palladium(0) (5.0 mol %), and stirred overnight under reflux. The organic layer was separated and concentrated under reduced pressure. The residue thus obtained was purified by silica gel column chromatography (n-hexane/ethyl acetate=4/1, v/v) to obtain the title compound as light brown oil (yield: 83%).

Step 2: Synthesis of 4-{2-(diethoxymethyl)furo[3,2-c]pyridin-7-yl}phenol

A solution of 7-{4-(benzyloxy)phenyl}-2-(diethoxymethyl)furo[3,2-c]pyridine (2.0 mmol) obtained in Step 1 and 10 wt % palladium/charcoal (10 mol %) in ethyl acetate (10 ml) was stirred at room temperature for 3 hours under a hydrogen atmosphere. The reaction mixture was filtered through Celite, and concentrated under reduced pressure. The residue thus obtained was purified by silica gel column chromatography (n-hexane/ethyl acetate=2/1, v/v) to obtain the title compound as a yellow solid (yield: 90%).

Step 3: Synthesis of 2-(diethoxymethyl)-7-(4-isopropoxyphenyl)furo[3,2-c]pyridine A solution prepared by dissolving 4-{2-(diethoxymethyl)furo[3,2-c]pyridin-7-yl}phenol (1.5 mmol) prepared in Step 2 in dimethyl sulfoxide (4.5 ml) was added with 2-iodopropane (3.0 mmol) and potassium carbonate (3.3 mmol), and subjected to a reaction at 50° C. for 12 hours. The reaction was terminated by adding water, and the reaction solution was extracted with ethyl acetate. The extract was washed with brine, dried over anhydrous magnesium sulfate, filtered, and the filtrate was concentrated under reduced pressure. The residue thus obtained was purified by silica gel column chromatography (n-hexane/ethyl acetate=6/1, v/v) to obtain the title compound as light brown oil (yield: 91%).

$^1$H NMR (CDCl$_3$, 300 MHz) δ 8.81 (s, 1H), 8.64 (s, 1H), 7.8 (d, 2H), 7.04 (d, 2H), 6.94 (s, 1H), 5.70 (s, 1H), 4.68-4.60 (m, 1H), 3.74-3.66 (m, 2H), 1.39 (d, 6H), 1.25 (t, 6H)

Step 4: Synthesis of 7-(4-isopropoxyphenyl)furo[3,2-c]pyridine-2-carbaldehyde

A solution prepared by dissolving 2-(diethoxymethyl)-7-(4-isopropoxyphenyl)furo[3,2-c]pyridine (1.0 mmol) obtained in Step 3 in tetrahydrofuran (5 ml) was added with a 3N aqueous hydrochloric acid solution (5 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, which was then concentrated under reduced pressure. The resulting residue was purified by silica gel column chromatography (n-hexane/ethyl acetate=4/1, v/v) to obtain the title compound as light brown oil (yield: 88%).

$^1$H NMR (CDCl$_3$, 300 MHz) δ 9.97 (s, 1H), 9.03 (s, 1H), 8.82 (s, 1H), 7.84 (d, 2H), 7.69 (s, 1H), 7.07 (d, 2H), 4.62-4.70 (m, 1H), 1.40 (d, 6H)

Step 5: Synthesis of (Z)-5-[{7-(4-isopropoxyphenyl)furo[3,2-c]pyridin-2-yl}methylene]thiazolidine-2,4-dione A solution prepared by dissolving 7-(4-isopropoxyphenyl)furo[3,2-c]pyridine-2-carbaldehyde (0.5 mmol) obtained in Step 4 in acetic acid (3 ml) was added with thiazolidinedione (0.6 mmol) and β-alanine (0.5 mmol), and stirred under reflux for 4 hours. After the reaction solution was cooled to room temperature, the solid thus obtained was filtered, washed with acetic acid and water, and dried to obtain the title compound as a light yellow solid (yield: 77%).

$^1$H NMR (DMSO-d$_6$, 300 MHz) δ 12.69 (brs, 1H), 8.99 (s, 1H), 8.74 (s, 1H), 7.87 (m, 3H), 7.68 (s, 1H), 7.13 (d, 2H), 4.76 (m, 1H), 1.32 (d, 6H)

Example 137

(Z)-5-[{7-(3-Isopropoxyphenyl)furo[3,2-c]pyridin-2-yl}methylene]thiazolidine-2,4-dione Step 1: Synthesis of 7-{3-(benzyloxy)phenyl}-2-(diethoxymethyl)furo[3,2-c]pyridine A solution prepared by dissolving 2-(diethoxymethyl)-7-iodofuro[3,2-c]pyridine (1.0 mmol) obtained in Reference Example 1 in toluene/ethanol/water (5/1/2, v/v, 5 ml) was added with 3-(benzyloxy)phenylboronic acid (1.2 mmol), sodium carbonate (2.2 mmol) and tetrakis(triphenylphosphine)palladium(0) (5.0 mol %), and stirred overnight under reflux. The organic layer was separated and concentrated under reduced pressure. The residue thus obtained was purified by silica gel column chromatography (n-hexane/ethyl acetate=4/1, v/v) to obtain the title compound as light brown oil (yield: 66%).

$^1$H NMR (CDCl$_3$, 300 MHz) δ 8.86 (s, 1H), 8.66 (s, 1H), 7.50-7.32 (m, 8H), 7.08-7.04 (m, 1H), 6.96 (s, 1H), 5.70 (s, 1H), 5.16 (s, 2H), 3.75-3.65 (m, 4H), 1.27 (t, 6H)

Step 2: Synthesis of 3-{2-(diethoxymethyl)furo[3,2-c]pyridin-7-yl}phenol

A solution prepared by dissolving 7-{3-(benzyloxy)phenyl}-2-(diethoxymethyl)furo[3,2-c]pyridine (2.0 mmol) obtained in Step 1 and 10 wt % palladium/charcoal (10 mol %) in ethyl acetate (10 ml) was stirred at room temperature under a hydrogen atmosphere for 3 hours. The reaction mixture was filtered through Celite, and concentrated under reduced pressure. The residue thus obtained was purified by silica gel column chromatography (n-hexane/ethyl acetate=2/1, v/v) to obtain the title compound as a yellow solid (yield: 91%).

Step 3: Synthesis of 2-(diethoxymethyl)-7-(3-isopropoxyphenyl)furo[3,2-c]pyridine A solution prepared by dissolving 3-{2-(diethoxymethyl)furo[3,2-c]pyridin-7-yl}phenol (1.5 mmol) obtained in Step 2 in dimethyl sulfoxide (4.5 ml) was added with 2-iodopropane (3.0 mmol) and potassium carbonate (3.3 mmol), and subjected to a reaction at 50° C. for 12 hours. The reaction was terminated by adding water, and the reaction solution was extracted with ethyl acetate. The extract was washed with brine, dried over anhydrous magnesium sulfate, filtered, and the filtrate was concentrated under reduced pressure. The residue thus obtained was purified by silica gel column chromatography (n-hexane/ethyl acetate=6/1, v/v) to obtain the title compound as light brown oil (yield: 94%).

$^1$H NMR (CDCl$_3$, 300 MHz) δ 8.85 (s, 1H), 8.67 (s, 1H), 7.42 (s, 3H), 6.96 (s, 2H), 5.70 (s, 1H), 4.60-4.68 (m, 1H), 3.66-3.74 (m, 2H), 1.40 (d, 6H), 1.25 (t, 6H)

Step 4: Synthesis of 7-(3-isopropoxyphenyl)furo[3,2-c]pyridine-2-carbaldehyde A solution prepared by dissolving 2-(diethoxymethyl)-7-(3-isopropoxyphenyl)furo[3,2-c]pyridine (1.0 mmol) obtained in Step 3 in tetrahydrofuran (5 ml) was added with a 3N aqueous hydrochloric acid solution (5 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, and the filtrate was concentrated under reduced pressure. The residue thus obtained was purified by silica gel column chromatography (n-hexane/ethyl acetate=4/1, v/v) to obtain the title compound as light brown oil (yield: 92%).

$^1$H NMR (CDCl$_3$, 300 MHz) δ 9.97 (s, 1H), 9.08 (s, 1H), 8.84 (s, 1H), 7.70 (s, 1H), 7.49-7.40 (m, 3H), 7.03-6.99 (m, 1H), 4.72-4.60 (m, 1H), 1.41 (d, 6H)

Step 5: Synthesis of (Z)-5-[{7-(3-isopropoxyphenyl)furo[3,2-c]pyridin-2-yl}methylene]thiazolidine-2,4-dione A solution prepared by dissolving 7-(3-isopropoxyphenyl)furo[3,2-c]pyridine-2-carbaldehyde (0.5 mmol) obtained in Step 4 in acetic acid (3 ml) was added with thiazolidinedione (0.6 mmol) and β-alanine (0.5 mmol), and stirred under reflux for 4 hours. After cooled to room temperature, the resulting solid was filtered, washed with acetic acid and water, and dried to obtain the title compound as a light yellow solid (yield: 70%).

$^1$H NMR (DMSO-d$_6$, 300 MHz) δ 12.67 (brs, 1H), 9.05 (s, 1H), 8.80 (s, 1H), 7.87 (s, 1H), 7.69 (s, 1H), 7.50 (m, 3H), 7.09 (d, 1H), 4.80 (m, 1H), 1.32 (d, 6H)

Example 138

(Z)-2-(3-[2-{(2,4-Dioxothiazolidin-5-ylidene)methyl}furo[3,2-c]pyridin-7-yl]phenoxy)benzonitrile

Step 1: Synthesis of 2-[3-{2-(diethoxymethyl)furo[3,2-c]pyridin-7-yl}phenoxy]benzonitrile A solution prepared by dissolving 3-{2-(diethoxymethyl)furo[3,2-c]pyridin-7-yl}phenol (2.0 mmol) obtained in Step 2 of Example 137 in tetrahydrofuran (10 ml) was added with sodium hydride (5.0 mmol) at room temperature, and stirred for 30 minutes. The reaction solution was added with 2-fluorobenzonitrile (2.4 mmol), and stirred at room temperature for 1 hour. The reaction was terminated by adding water, and the reaction solution was extracted with ethyl acetate. The extract was washed with brine, dried over anhydrous magnesium sulfate, filtered. The filtrate was concentrated under reduced pressure, and the residue thus obtained was purified by silica gel column chromatography (n-hexane/ethyl acetate=4/1, v/v) to obtain the title compound as light brown oil (yield: 80%).

$^1$H NMR (CDCl$_3$, 300 MHz) δ 8.88 (s, 1H), 8.66 (s, 1H), 7.72 (dd, 2H), 7.62-7.50 (m, 3H), 7.14-7.19 (m, 2H), 7.01 (d, 1H), 6.96 (s, 1H), 5.67 (s, 1H), 3.64-3.73 (m, 4H), 1.26 (t, 6H)

Step 2: Synthesis of 2-{3-(2-formylfuro[3,2-c]pyridin-7-yl)phenoxy}benzonitrile A solution prepared by dissolving 2-[3-{2-(diethoxymethyl)furo[3,2-c]pyridin-7-yl}phenoxy]benzonitrile (1.0 mmol) obtained in Step 1 in tetrahydrofuran (10 ml) was added with a 3N aqueous hydrochloric acid solution (10 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, which was then concentrated under reduced pressure. The resulting residue was purified by silica gel column chromatography (n-hexane/ethyl acetate=2/1, v/v) to obtain the title compound as light brown oil (yield: 81%).

$^1$H NMR (CDCl$_3$, 300 MHz) δ 9.67 (s, 1H), 9.11 (s, 1H), 9.84 (s, 1H), 7.75-7.70 (m, 3H), 7.63-7.57 (m, 3H), 7.23-7.17 (m, 2H), 7.09 (d, 1H)

Step 3: Synthesis of (Z)-2-(3-[2-{(2,4-dioxothiazolidin-5-ylidene)methyl}furo[3,2-c]pyridin-7-yl]phenoxy)benzonitrile A solution prepared by dissolving 2-{3-(2-formylfuro[3,2-c]pyridin-7-yl)phenoxy}benzonitrile (0.4 mmol) obtained in Step 2 in acetic acid (3 ml) was added with thiazolidinedione (0.5 mmol) and β-alanine (0.4 mmol), and stirred under reflux for 4 hours. After cooled to room temperature, the resulting solid was filtered, washed with acetic acid and water, and dried to obtain the title compound as a light yellow solid (yield: 75%).

$^1$H NMR (DMSO-d$_6$, 300 MHz) δ 12.66 (brs, 1H), 9.07 (s, 1H), 8.86 (s, 1H), 7.92 (m, 2H), 7.86 (s, 2H), 7.71 (m, 3H), 7.30 (m, 2H), 7.09 (d, 1H)

Example 139

(Z)-5-([7-{3-(Pyridin-4-yloxy)phenyl}furo[3,2-c]pyridin-2-yl]methylene)thiazolidine-2,4-dione

Step 1: Synthesis of 2-(diethoxymethyl)-7-{3-(pyridin-4-yloxy)phenyl}furo[3,2-c]pyridine A solution prepared by dissolving 3-{2-(diethoxymethyl)furo[3,2-c]pyridin-7-yl}phenol (2.0 mmol) obtained in Step 2 of Example 137 in dimethyl sulfoxide (10 ml) was added with 4-bromopyridine (2.4 mmol), cesium carbonate (8.0 mmol) and potassium iodide (4.0 mmol), and stirred under reflux for 6 hours. The reaction was terminated by adding water, and the reaction solution was extracted with ethyl acetate. The extract was washed with brine, dried over anhydrous magnesium sulfate and filtered. After the filtrate was concentrated under reduced pressure, the residue thus obtained was purified by silica gel column chromatography (n-hexane/ethyl acetate=4/1, v/v) to obtain the title compound as light brown oil (yield: 40%).

$^1$H NMR (CDCl$_3$, 300 MHz) δ 8.88 (s, 1H), 8.68 (s, 1H), 8.51 (d, 2H), 7.75 (d, 1H), 7.65 (s, 1H), 7.59 (dd, 1H), 7.18 (dd, 1H), 6.96-6.94 (m, 3H), 5.67 (s, 1H), 3.72-3.63 (m, 4H), 1.24 (t, 6H)

Step 2: Synthesis of 7-{3-(pyridin-4-yloxy)phenyl}furo[3,2-c]pyridine-2-carbaldehyde A solution prepared by dissolving 2-(diethoxymethyl)-7-{3-(pyridin-4-yloxy)phenyl}furo[3,2-c]pyridine (0.6 mmol) obtained in Step 1 in tetrahydrofuran (6 ml) was added with a 3N aqueous hydrochloric acid solution (6 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, and the filtrate was concentrated under reduced pressure. The residue thus obtained was purified by silica gel column chromatography (n-hexane/ethyl acetate=2/1, v/v) to obtain the title compound as light brown oil (yield: 75%).

$^1$H NMR (CDCl$_3$, 300 MHz) δ 9.97 (s, 1H), 9.11 (s, 1H), 8.84 (s, 1H), 8.53 (d, 2H), 7.78 (d, 1H), 7.76 (s, 1H), 7.63 (dd, 2H), 7.26-7.22 (m, 1H), 6.97 (d, 2H)

Step 3: Synthesis of (Z)-5-([7-{3-(pyridin-4-yloxy) phenyl}furo[3,2-c]pyridin-2-yl]methylene)thiazolidine-2,4-dione A solution prepared by dissolving 7-{3-(pyridin-4-yloxy) phenyl}furo[3,2-c]pyridine-2-carbaldehyde (0.4 mmol) obtained in Step 2 in acetic acid (3 ml) was added with thiazolidinedione (0.5 mmol) and β-alanine (0.4 mmol), and stirred under reflux for 4 hours. After cooled to room temperature, the resulting solid was filtered, washed with acetic acid and water, and dried to obtain the title compound as a light yellow solid (yield: 75%).

$^1$H NMR (DMSO-d$_6$, 300 MHz) δ 9.06 (s, 1H), 8.87 (s, 1H), 8.48 (m, 2H), 7.92 (d, 1H), 7.88 (s, 1H), 7.82 (s, 1H), 7.73 (d, 1H), 7.67 (s, 2H), 7.35 (d, 1H), 7.02 (m, 2H)

Example 140

(Z)-5-([7-{3-(Pyrimidin-5-yloxy)phenyl}furo[3,2-c] pyridin-2-yl]methylene)thiazolidine-2,4-dione Step 1: Synthesis of 2-(diethoxymethyl)-7-{3-(pyrimidin-5-yloxy)phenyl}furo[3,2-c]pyridine A solution prepared by dissolving 3-{2-(diethoxymethyl) furo[3,2-c]pyridin-7-yl}phenol (2.0 mmol) obtained in Step 2 of Example 137 in dimethyl sulfoxide (10 ml) was added with 5-bromopyrimidine (4.0 mmol), copper iodide (5 mol %), pyridine-2-carboxylic acid (10 mol %) and potassium phosphate (3.0 mmol), and stirred at 80° C. for 24 hours. The reaction was terminated by adding water, and the reaction solution was extracted with ethyl acetate. The extract was washed with brine, dried over anhydrous magnesium sulfate and filtered. The filtrate was concentrated under reduced pressure, and the residue thus obtained was purified by silica gel column chromatography (n-hexane/ethyl acetate=4/1, v/v) to obtain the title compound as light brown oil (yield: 40%).

Step 2: Synthesis of 7-{3-(pyrimidin-5-yloxy) phenyl}furo[3,2-c]pyridine-2-carbaldehyde A solution prepared by dissolving 2-(diethoxymethyl)-7-{3-(pyrimidin-5-yloxy)phenyl}furo[3,2-c]pyridine (0.6 mmol) obtained in Step 1 in tetrahydrofuran (6 ml) was added with a 3N aqueous hydrochloric acid solution (6 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, and the filtrate was concentrated under reduced pressure. The residue thus obtained was purified by silica gel column chromatography (n-hexane/ethyl acetate=2/1, v/v) to obtain the title compound as light brown oil (yield: 70%).

Step 3: Synthesis of (Z)-5-([7-{3-(pyrimidin-5-yloxy)phenyl}furo[3,2-c]pyridin-2-yl]methylene) thiazolidine-2,4-dione A solution prepared by dissolving 7-{3-(pyrimidin-5-yloxy)phenyl}furo[3,2-c]pyridine-2-carbaldehyde (0.4 mmol) obtained in Step 2 in acetic acid (3 ml) was added with thiazolidinedione (0.5 mmol) and β-alanine (0.4 mmol), and stirred under reflux for 4 hours. The reaction solution was cooled to room temperature, and the resulting solid was filtered, washed with acetic acid and water, and dried to obtain the title compound as a light yellow solid (yield: 68%).

$^1$H NMR (DMSO-d$_6$, 300 MHz) δ 12.67 (brs, 1H), 9.07 (s, 1H), 9.02 (s, 1H), 8.86 (s, 1H), 8.70 (s, 2H), 7.85 (m, 3H), 7.69 (m, 2H), 7.23 (d, 1H)

Example 141

(Z)—N-(3-[2-{(2,4-Dioxothiazolidin-5-ylidene) methyl}furo[3,2-c]pyridin-7-yl]phenyl)benzenesulfonamide Step 1: Synthesis of 2-(diethoxymethyl)-7-(3-nitrophenyl)furo[3,2-c]pyridine A solution prepared by dissolving 2-(diethoxymethyl)-7-iodofuro[3,2-c]pyridine (2.0 mmol) obtained in Reference Example 1 in toluene/ethanol/water (5/1/2, v/v, 10 ml) was added with 3-nitrophenylboronic acid (2.4 mmol), sodium carbonate (4.4 mmol) and tetrakis(triphenylphosphine)palladium(0) (5.0 mol %), which was then stirred overnight under reflux. The organic layer was separated and concentrated under reduced pressure. The residue thus obtained was purified by silica gel column chromatography (n-hexane/ethyl acetate=4/1, v/v) to obtain the title compound as light brown oil (yield: 86%).

Step 2: Synthesis of 3-{2-(diethoxymethyl)furo[3,2-c]pyridin-7-yl}aniline

A solution prepared by dissolving 2-(diethoxymethyl)-7-(3-nitrophenyl)furo[3,2-c]pyridine (1.6 mmol) obtained in Step 1 and 10 wt % palladium/charcoal (10 mol %) in methanol (8.0 ml) was stirred at room temperature for 3 hours under a hydrogen atmosphere. The reaction mixture was filtered through Celite, and concentrated under reduced pressure. The residue thus obtained was purified by silica gel column chromatography (dichloromethane/methanol=40/1, v/v) to obtain the title compound as a yellow solid (yield: 90%).

Step 3: Synthesis of N-[3-{2-(diethoxymethyl)furo [3,2-c]pyridin-7-yl}phenyl]benzenesulfonamide A solution prepared by dissolving 3-{2-(diethoxymethyl) furo[3,2-c]pyridin-7-yl}aniline (2.0 mmol) obtained in Step 2 in pyridine (10 ml) was added with benzenesulfonyl chloride (2.2 mmol), and stirred for 1 hour at room temperature. The reaction was terminated by adding water, and the reaction solution was extracted with ethyl acetate. The extract was washed with a 1N aqueous hydrochloric acid solution and brine, dried over anhydrous magnesium sulfate, filtered. The filtrate was concentrated under reduced pressure, and the residue thus obtained was purified by silica gel column chromatography (n-hexane/ethyl acetate=2/1, v/v) to obtain the title compound as light brown oil (yield: 83%).

$^1$H NMR (CDCl$_3$, 300 MHz) δ 8.97 (s, 1H), 8.61 (s, 1H), 8.08 (s, 1H), 7.86 (d, 2H), 7.67 (d, 1H), 7.57-7.39 (m, 6H), 6.98 (s, 1H), 5.70 (s, 1H), 3.71-3.64 (m, 4H), 1.27 (t, 6H)

Step 4: Synthesis of N-{3-(2-formylfuro[3,2-c]pyridin-7-yl)phenyl}benzene sulfonamide A solution prepared by dissolving N-[3-{2-(diethoxymethyl)furo[3,2-c]pyridin-7-yl}phenyl]benzenesulfonamide (1.0 mmol) obtained in Step 3 in tetrahydrofuran (10 ml) was added with a 3N aqueous hydrochloric acid solution (10 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, which was then concentrated under reduced pressure. The resulting residue was purified by silica gel column chromatography (n-hexane/ethyl acetate=2/1, v/v) to obtain the title compound as light brown oil (yield: 83%).

Step 5: Synthesis of (Z)—N-(3-(2-((2,4-dioxothiazolin-5-ylidene)methyl)furo[3,2-c]pyridin-7-yl)phenyl)benzenesulfonamide A solution prepared by dissolving N-(3-(2-formylfuro[3,2-c]pyridin-7-yl)phenyl)benzenesulfonamide (0.4 mmol) obtained in Step 4 in acetic acid (3 ml) was added with thiazolidinedione (0.5 mmol) and β-alanine (0.4 mmol), and stirred under reflux for 4 hours. After cooled to room temperature, the resulting solid was filtered, washed with acetic acid and water, and dried to obtain the title compound as a light yellow solid (yield: 75%).

$^1$H NMR (DMSO-d$_6$, 300 MHz) δ 12.71 (brs, 1H), 10.61 (s, 1H), 9.05 (s, 1H), 8.57 (s, 1H), 7.84 (m, 3H), 7.68 (s, 1H), 7.62 (m, 5H), 7.47 (t, 1H), 7.24 (d, 1H)

Example 142

(Z)-2-Thioxo-5-([7-{4-(trifluoromethoxy)phenyl}furo[3,2-c]pyridin-2-yl]methylene)thiazolidin-4-one Step 1: Synthesis of 2-(diethoxymethyl)-7-{4-(trifluoromethoxy)phenyl}furo[3,2-c]pyridine A solution prepared by dissolving 2-(diethoxymethyl)-7-iodofuro[3,2-c]pyridine (1.0 mmol) obtained in Reference Example 1 in tetrahydrofuran/water (4/1, v/v, 5 ml) was added with 4-trifluoromethoxyphenylboronic acid (1.2 mmol), sodium carbonate (2.2 mmol) and tetrakis(triphenylphosphine)palladium(0) (5.0 mol %), which was then stirred overnight under reflux. The organic layer was separated and concentrated under reduced pressure. The residue thus obtained was purified by silica gel column chromatography (n-hexane/ethyl acetate=4/1, v/v) to obtain the title compound as light brown oil (yield: 84%).

$^1$H NMR (CDCl$_3$, 300 MHz) δ 8.89 (s, 1H), 8.65 (s, 1H), 7.91 (d, 2H), 7.38 (d, 2H), 6.98 (s, 1H), 5.70 (s, 1H), 3.66-3.74 (m, 4H), 1.28 (t, 6H)

Step 2: Synthesis of 7-{4-(trifluoromethoxy)phenyl}furo[3,2-c]pyridine-2-carbaldehyde A solution prepared by dissolving 2-(diethoxymethyl)-7-{4-(trifluoromethoxy)phenyl}furo[3,2-c]pyridine (0.5 mmol) obtained in Step 1 in tetrahydrofuran (5 ml) was added with a 3N aqueous hydrochloric acid solution (5 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, which was then concentrated under reduced pressure. The resulting residue was purified by silica gel column chromatography (n-hexane/ethyl acetate=4/1, v/v) to obtain the title compound as light brown oil (yield: 90%).

$^1$H NMR (CDCl$_3$, 300 MHz) δ 9.99 (s, 1H), 9.12 (brs, 1H), 8.85 (brs, 1H), 7.93 (d, 2H), 7.72 (s, 1H), 7.42 (d, 2H)

Step 3: Synthesis of (Z)-2-thioxo-5-([7-{4-(trifluoromethoxy)phenyl}furo[3,2-c]pyridin-2-yl]methylene)thiazolidin-4-one A solution prepared by dissolving 7-{4-(trifluoromethoxy)phenyl}furo[3,2-c]pyridine-2-carbaldehyde (0.1 mmol) obtained in Step 2 in acetic acid (3 ml) was added with rhodanine (0.11 mmol) and sodium acetate (0.12 mmol), and stirred under reflux for 5 hours. After cooled to room temperature, the resulting solid was filtered, washed with acetic acid and water, and dried to obtain the title compound as a yellow solid (yield: 87%).

$^1$H NMR (DMSO-d$_6$, 300 MHz) δ 9.07 (s, 1H), 8.81 (s, 1H), 8.10 (d, 2H), 7.74 (d, 2H), 7.58 (d, 2H)

Examples 143 to 250

The title compounds of Examples 143 to 250 were prepared in the same manner as described in Example 142 above, except for using each of the following compounds: 4-aminophenylboronic acid pinacol ester, 5-chloro-2-thiophene boronic acid, 3-chloro-4-fluorophenylboronic acid, 3-fluoro-4-methylphenylboronic acid, 4-fluoro-3-(trifluoromethyl)phenylboronic acid, thiazole-2-boronic acid, 4-(methylthio)phenylboronic acid, {4-(methylsulfonyl)phenyl}boronic acid, 5-bromo-3-pyridine boronic acid pinacol ester, 4-methoxyphenylboronic acid, 2-fluoropyridine-5-boronic acid, 3-thiopheneboronic acid, 3-pyridinylboronic acid, 2-bromopyridine-5-boronic acid, 2-chloropyridine-5-boronic acid, 4-isopropoxyphenylboronic acid, 3-isopropoxyphenylboronic acid, 3-chloro-4-methoxyphenylboronic acid, 3-fluoro-4-methoxyphenylboronic acid, 1,4-benzodioxane-6-boronic acid, 2,3-dimethoxypyridine-5-boronic acid pinacol ester, 3-fluoro-4-isopropoxyphenylboronic acid, 2-aminopyridine-5-boronic acid pinacol ester, 4-ethoxy-3-fluorophenylboronic acid, 3-formyl-4-isopropoxyphenylboronic acid, 2-(dimethylamino)pyrimidine-5-boronic acid pinacol ester, 6-methoxypyridine-3-boronic acid, 6-ethoxypyridine-3-boronic acid, 4-cyano-3-fluorobenzeneboronic acid, 4-methoxy-3-(trifluoromethyl)benzene boronic acid, 5-amino-6-methoxypyridine-3-boronic acid, 2-isopropoxypyridine-5-boronic acid pinacol ester, 5-chloro-6-methoxypyridine-3-boronic acid, 2-cyanopyridine-5-boronic acid pinacol ester, 3-formyl-4-methoxybenzene boronic acid, 4-(ethylsulfonyl)benzene boronic acid, 4-cyclohexylphenylboronic acid, 2-(methylthio)pyrimidine-5-boronic acid pinacol ester, 2,4- dimethoxypyrimidine-5-boronic acid, 2-chloro-3-methylpyridine-5-boronic acid, 2-chloro-3-fluoropyridine-5-boronic acid pinacol ester, 4-hydroxyphenylboronic acid, 2-(N,N-dimethylamino)-3-fluoropyridine-5-boronic acid pinacol ester hydrochloride, 2-methoxy-3-(trifluoromethyl)pyridine-5-boronic acid, 2,3-dihydrobenzofuran-5-boronic acid, 2-chloro-3-methoxypyridine-5-boronic acid, 2,5-difluoro-4-methoxyphenylboronic acid, 4-(methoxymethyl)phenylboronic acid, 4-(N-methylsulfamoyl)phenylboronic acid pinacol ester, 4-(tert-butylamino)sulfonylphenylboronic acid pinacol ester, 4-(morpholinosulfonyl)phenylboronic acid pinacol ester, 4-(piperidin-1-yl)sulfonylphenylboronic acid pinacol ester, 2-fluoro-3-methylpyridine-5-boronic acid, 3,5-dimethyl-4-methoxyphenylboronic acid, 3,5-dimethyl-4-isopropoxyphenylboronic acid, [6-(2,2,2-trifluoroethoxyl)pyridin-3-yl]boronic acid, 3-(4'-methoxybenzyloxy)phenylboronic acid, 3,4,5-trimethoxyphenylboronic acid, 2-methoxy-4-(4,4,5,5-tetramethyl-1,3,2-dioxaborolan-2-yl)phenol, 2,6-dimethyl-4-(4,4,5,5-tetramethyl-1,3,2-dioxaborolan-2-yl)phenol, 2-methoxypyrimidine-5-boronic acid, 4-methyl-7-(4,4,5,5-tetramethyl-1,3,2-dioxaborolan-2-yl)-3,4-dihydro-2H-1,4-benzoxazine, 4-isopropoxy-3-methylphenylboronic acid, 4-ethoxy-3-methylphenylboronic acid, 4-(tert-butoxymethyl)phenylboronic acid, 3-amino-2-chloropyridine-5-boronic acid, 3,5-dichloro-4-methoxybenzene boronic acid, 3-methyl-4-trifluoromethoxyphenylboronic acid, 4-cyanomethoxyphenylboronic acid, 4-hydroxymethyl-3-methylphenylboronic acid, 3-fluoro-4-(trifluoromethoxy)benzene boronic acid, (4-methoxy-3-trifluoromethylphenyl)boronic acid, 6-(5,5-dimethyl-1,3,2-dioxaborinan-2-yl)-4H-1,3-benzodioxine, 5-(5,5-dimethyl-1,3,2-dioxaborinan-2-yl)-2-methoxybenzonitrile, 3-chloro-4-hydroxy-5-methoxyphenylboronic acid pinacol ester, 4-ethoxy-3-(trifluoromethyl)benzeneboronic acid, 2,2-difluoro-benzo[1,3]dioxol-5-boronic acid, 4-acetoxymethylbenzeneboronic acid, 2-ethoxypyrimidine-5-boronic acid, 2,6-chloropyridine-4-boronic acid pinacol ester, 4-cyclopropyl benzene boronic acid, 5-chloro-6-ethoxypyridine-3-boronic acid, 6-methoxy-5-methylpyridine-3-boronic acid, 3-fluoro-2-methoxypyridine-5-boronic acid, 5-chloro-6-isopropoxypyridine-3-boronic acid, 2-methoxypyridine-4-boronic acid, 2-picoline-4-boronic acid, 3-amino-4-fluorophenylboronic acid pinacol ester, 2-(trifluoromethyl)pyridine-4-boronic acid, 2-ethoxy-6-fluoropyridine-4-boronic acid, 3-cyanomethylphenylboronic acid, 3-(2,2,2-trifluoroethoxyl)phenylboronic acid, 3-methylsulfinylphenylboronic acid, 3-fluoro-5-methylphenylboronic acid, 3-(methylsulfonamido)phenylboronic acid, 2-fluoropyridine-4-boronic acid, 3-amino-4-methylphenylboronic acid, 4-amino-3-fluorophenylboronic acid, 3,5-bis(trifluoromethyl)phenylboronic acid, benzoimidazole-5-boronic acid pinacol ester, 1H-pyrazole-4-boronic acid pinacol ester, 4,4,5,5-tetramethyl-2-(phenylethynyl)-1,3,2-dioxaborolane, 4,4,5,5-tetramethyl-2-(propyn-1-yl)-1,3,2-dioxaborolane, 1-methylpyrazole-4-boronic acid pinacol ester, 6-morpholinopyridin-3-ylboronic acid, 2-aminopyrimidine-5-boronic acid, 1-{4-(4,4,5,5-tetramethyl-1,3,2-dioxaborolan-2-yl)phenyl}-1H-tetrazole and 3-hydroxyphenylboronic acid, instead of 4-trifluoromethoxyphenylboronic acid in Step 1 of Example 142.

Example 143

(Z)-5-[{7-(4-Aminophenyl)furo[3,2-c]pyridin-2-yl}methylene]-2-thioxothiazolidin-4-one $^1$H NMR (DMSO-d$_6$, 400 MHz) δ 8.90 (s, 1H), 8.69 (s, 1H), 7.95 (d, 1H), 7.84 (d, 1H), 7.70-7.74 (m, 4H), 6.77 (d, 2H); (yield: 21%)

Example 144

(Z)-5-[{7-(5-Chlorothiophen-2-yl)furo[3,2-c]pyridin-2-yl}methylene]-2-thioxothiazolidin-4-one $^1$H NMR (DMSO-d$_6$, 400 MHz) δ 9.02 (s, 1H), 8.92 (s, 1H), 7.74-7.96 (m, 3H), 7.39 (s, 1H); (yield: 30%)

Example 145

(Z)-5-[{7-(3-Chloro-4-fluorophenyl)furo[3,2-c]pyridin-2-yl}methylene]-2-thioxothiazolidin-4-one $^1$H NMR (DMSO-d$_6$, 400 MHz) δ 9.08 (s, 1H), 8.85 (s, 1H), 8.29-8.33 (m, 1H), 7.98 (s, 1H), 7.73 (d, 2H), 7.65 (dd, 1H); (yield: 33%)

Example 146

(Z)-5-[{7-(3-Fluoro-4-methylphenyl)furo[3,2-c]pyridin-2-yl}methylene]-2-thioxothiazolidin-4-one $^1$H NMR (DMSO-d$_6$, 400 MHz) δ 9.08 (s, 1H), 8.86 (s, 1H), 7.72-7.94 (m, 4H), 7.52 (brs, 1H), 2.37 (s, 3H); (yield: 27%)

Example 147

(Z)-5-([7-{4-Fluoro-3-(trifluoromethyl)phenyl}furo[3,2-c]pyridin-2-yl]methylene)-2-thioxothiazolidin-4-one $^1$H NMR (DMSO-d$_6$, 400 MHz) δ 9.10 (s, 1H), 8.84 (s, 1H), 8.37 (d, 1H), 8.29 (s, 1H), 7.71-7.92 (m, 3H); (yield: 34%)

Example 148

(Z)-5-[{7-(Thiazol-2-yl)furo[3,2-c]pyridin-2-yl}methylene]-2-thioxothiazolidin-4-one $^1$H NMR (DMSO-d$_6$, 400 MHz) δ 9.27 (s, 1H), 9.14 (s, 1H), 8.21 (s, 1H), 8.16 (s, 1H), 7.83 (s, 1H), 7.76 (s, 1H); (yield: 30%)

Example 149

(Z)-5-([7-{4-(Methylthio)phenyl}furo[3,2-c]pyridin-2-yl]methylene)-2-thioxothiazolidin-4-one $^1$H NMR (DMSO-d$_6$, 400 MHz) δ 9.05 (brs, 1H), 8.79 (brs, 1H), 7.94 (m, 2H), 7.74 (m, 2H), 7.46 (m, 2H), 2.58 (s, 3H); (yield: 47%)

Example 150

(Z)-5-([7-{4-(Methylsulfonyl)phenyl}furo[3,2-c]pyridin-2-yl]methylene)-2-thioxothiazolidin-4-one $^1$H NMR (DMSO-d$_6$, 400 MHz) δ 9.13 (s, 1H), 8.90 (s, 1H), 8.27 (m, 2H), 8.14 (m, 2H), 7.76 (s, 1H), 7.72 (s, 1H), 3.33 (s, 3H); (yield: 37%)

Example 151

(Z)-5-[{7-(5-Bromopyridin-3-yl)furo[3,2-c]pyridin-2-yl}methylene]-2-thioxothiazolidin-4-one $^1$H NMR (DMSO-d$_6$, 400 MHz) δ 9.18 (s, 1H), 9.14 (s, 1H), 8.96 (s, 1H), 8.88 (s, 1H), 8.74 (s, 1H), 7.75 (d, 2H); (yield: 48%)

Example 152

(Z)-5-[{7-(4-Methoxyphenyl)furo[3,2-c]pyridin-2-yl}methylene]-2-thioxothiazolidin-4-one $^1$H NMR (DMSO-d$_6$, 400 MHz) δ 9.02 (s, 1H), 8.76 (s, 1H), 7.93 (m, 2H), 7.73 (m, 2H), 7.15 (m, 2H), 3.87 (s, 3H); (yield: 50%)

Example 153

(Z)-5-[{7-(6-Fluoropyridin-3-yl)furo[3,2-c]pyridin-2-yl}methylene]-2-thioxothiazolidin-4-one $^1$H NMR (DMSO-d$_6$, 400 MHz) δ 8.99 (s, 1H), 8.72 (s, 1H), 8.05 (m, 2H), 7.73 (s, 2H), 6.53 (m, 1H); (yield: 57%)

Example 154

(Z)-5-[{7-(Thiophen-3-yl)furo[3,2-c]pyridin-2-yl}methylene]-2-thioxothiazolidin-4-one $^1$H NMR (DMSO-d$_6$, 400 MHz) δ 9.01 (s, 1H), 8.96 (s, 1H), 8.31 (s, 1H), 7.01 (m, 1H), 7.88 (m, 1H), 7.75 (s, 2H); (yield: 92%)

Example 155

(Z)-5-[{7-(Pyridin-3-yl)furo[3,2-c]pyridin-2-yl}methylene]-2-thioxothiazolidin-4-one $^1$H NMR (DMSO-d$_6$, 400 MHz) δ 9.20 (s, 1H), 9.12 (s, 1H), 8.87 (s, 1H), 8.75 (m, 1H), 3.38 (m, 1H), 7.78 (s, 1H), 7.75 (s, 1H), 7.63 (m, 1H); (yield: 57%)

Example 156

(Z)-5-[{7-(6-Bromopyridin-3-yl)furo[3,2-c]pyridin-2-yl}methylene]-2-thioxothiazolidin-4-one $^1$H NMR (DMSO-d$_6$, 400 MHz) δ 9.13 (s, 1H), 9.02 (s, 1H), 8.88 (s, 1H), 8.34 (m, 1H), 7.90 (m, 1H), 7.77 (s, 1H), 7.73 (s, 1H); (yield: 50%)

Example 157

(Z)-5-[{7-(6-Chloropyridin-3-yl)furo[3,2-c]pyridin-2-yl}methylene]-2-thioxothiazolidin-4-one $^1$H NMR (DMSO-d$_6$, 400 MHz) δ 9.13 (s, 1H), 9.05 (s, 1H), 8.88 (s, 1H), 8.46 (d, 1H), 7.78~7.75 (m, 3H); (yield: 58%)

Example 158

(Z)-5-[{7-(4-Isopropoxyphenyl)furo[3,2-c]pyridin-2-yl}methylene]-2-thioxothiazolidin-4-one $^1$H NMR (DMSO-d$_6$, 400 MHz) δ 9.01 (s, 1H), 8.75 (s, 1H), 7.89 (d, 2H), 7.72 (m, 2H), 7.11 (d, 2H), 4.75 (m, 1H), 1.34 (d, 6H); (yield: 55%)

Example 159

(Z)-5-[{7-(3-Isopropoxyphenyl)furo[3,2-c]pyridin-2-yl}methylene]-2-thioxothiazolidin-4-one $^1$H NMR (DMSO-d$_6$, 400 MHz) δ 9.06 (s, 1H), 8.80 (s, 1H), 7.74 (d, 2H), 7.53 (s, 1H), 7.48 (m, 2H), 7.10 (m, 1H), 4.80 (m, 1H), 1.34 (d, 6H); (yield: 50%)

Example 160

(Z)-5-[{7-(3-Chloro-4-methoxyphenyl)furo[3,2-c]pyridin-2-yl}methylene]-2-thioxothiazolidin-4-one $^1$H NMR (DMSO-d$_6$, 400 MHz) δ 9.04 (s, 1H), 8.83 (s, 1H), 8.19 (s, 1H), 7.91 (d, 1H), 7.73 (m, 2H), 7.36 (d, 1H), 3.97 (s, 3H); (yield: 49%)

Example 161

(Z)-5-[{7-(3-Fluoro-4-methoxyphenyl)furo[3,2-c]pyridin-2-yl}methylene]-2-thioxothiazolidin-4-one $^1$H NMR (DMSO-d$_6$, 400 MHz) δ 9.03 (s, 1H), 8.80 (s, 1H), 7.93 (d, 1H), 7.77 (d, 1H), 7.71 (m, 2H), 7.38 (m, 1H), 3.95 (s, 3H); (yield: 47%)

Example 162

(Z)-5-[{7-(2,3-Dihydrobenzo[1,4]dioxin-6-yl)furo[3,2-c]pyridin-2-yl}methylene]-2-thioxothiazolidin-4-one $^1$H NMR (DMSO-d$_6$, 400 MHz) δ 9.01 (s, 1H), 8.74 (s, 1H), 7.71 (m, 2H), 7.50 (s, 1H), 7.46 (d, 1H), 7.04 (d, 1H), 4.34 (s, 3H); (yield: 40%)

Example 163

(Z)-5-[{7-(5,6-Dimethoxypyridin-3-yl)furo[3,2-c]pyridin-2-yl}methylene]-2-thioxothiazolidin-4-one $^1$H NMR (DMSO-d$_6$, 400 MHz) δ 9.07 (s, 1H), 8.81 (s, 1H), 8.26 (s, 1H), 7.85 (s, 1H), 7.74 (d, 2H), 3.97 (s. 3H); (yield: 58%)

Example 164

(Z)-5-[{7-(3-Fluoro-4-isopropoxyphenyl)furo[3,2-c]pyridin-2-yl}methylene]-2-thioxothiazolidin-4-one $^1$H NMR (DMSO-d$_6$, 400 MHz) δ 9.03 (s, 1H), 8.80 (s, 1H), 7.90 (d, 1H), 7.73 (m, 3H), 7.38 (m, 1H), 4.78 (m, 1H), 1.36 (d, 6H); (yield: 54%)

Example 165

(Z)-5-[{7-(6-Aminopyridin-3-yl)furo[3,2-c]pyridin-2-yl}methylene]-2-thioxothiazolidin-4-one $^1$H NMR (DMSO-d$_6$, 400 MHz) δ 8.96 (s, 1H), 8.74 (s, 1H), 8.60 (s, 1H), 8.05 (d, 1H), 7.70 (d, 2H), 6.69 (d, 1H), 6.56 (brs, 2H); (yield: 50%)

Example 166

(Z)-5-[{7-(4-Ethoxy-3-fluorophenyl)furo[3,2-c]pyridin-2-yl}methylene]-2-thioxothiazolidin-4-one $^1$H NMR (DMSO-d$_6$, 400 MHz) δ 9.03 (s, 1H), 8.80 (s, 1H), 7.92 (d, 1H), 7.74 (m, 3H), 7.35 (m, 1H), 4.22 (m, 2H), 1.42 (t, 3H); (yield: 54%)

Example 167

(Z)-2-Isopropoxy-5-[2-{(4-oxo-2-thioxothiazolidin-5-ylidene)methyl}furo[3,2-c]pyridin-7-yl]benzaldehyde $^1$H NMR (DMSO-d$_6$, 400 MHz) δ 10.48 (s, 1H), 9.04 (s, 1H), 8.77 (s, 1H), 8.25 (m, 1H), 8.17 (m, 1H), 7.72 (d, 2H), 7.47 (d, 1H), 4.95 (m, 1H), 1.42 (d, 6H); (yield: 48%)

Example 168

(Z)-5-[{7-(2-Dimethylaminopyrimidin-5-yl)furo[3,2-c]pyridin-2-yl}methylene]-2-thioxothiazolidin-4-one $^1$H NMR (DMSO-d$_6$, 400 MHz) δ 9.01 (s, 1H), 8.96 (s, 2H), 8.79 (s, 1H), 7.73 (m, 2H), 3.24 (s, 6H); (yield: 55%)

Example 169

(Z)-5-[{7-(6-Methoxypyridin-3-yl)furo[3,2-c]pyridin-2-yl}methylene]-2-thioxothiazolidin-4-one $^1$H NMR (DMSO-d$_6$, 400 MHz) δ 9.06 (s, 1H), 8.80 (m, 2H), 8.32 (m, 1H), 7.74 (d, 2H), 7.05 (d, 1H), 3.97 (s, 3H); (yield: 54%)

Example 170

(Z)-5-[{7-(6-Ethoxypyridin-3-yl)furo[3,2-c]pyridin-2-yl}methylene]-2-thioxothiazolidin-4-one $^1$H NMR (DMSO-d$_6$, 400 MHz) δ 9.05 (d, 1H), 8.80 (d, 2H), 8.28 (d, 1H), 7.73 (d, 2H), 7.01 (d, 2H), 4.42 (m, 2H), 1.39 (t, 3H); (yield: 50%)

Example 171

(Z)-2-Fluoro-4-[2-{(4-oxo-2-thioxothiazolidin-5-ylidene)methyl}furo[3,2-c]pyridin-7-yl]benzonitrile $^1$H NMR (DMSO-d$_6$, 400 MHz) δ 9.15 (s, 1H), 8.93 (s, 1H), 8.24~8.16 (m, 2H), 8.05 (m, 1H), 7.77 (s, 1H), 7.73 (s, 1H); (yield: 50%)

Example 172

(Z)-5-[{7-(4-Methoxy-3-trifluoromethylphenyl)furo[3,2-c]pyridin-2-yl}methylene]-2-thioxothiazolidin-4-one $^1$H NMR (DMSO-d$_6$, 400 MHz) δ 9.06 (s, 1H), 8.80 (s, 1H), 8.23 (s, 1H), 8.18 (d, 1H), 7.76 (d, 2H), 7.50 (d, 1H), 4.01 (s, 3H); (yield: 47%)

Example 173

(Z)-5-[{7-(5-Amino-6-methoxypyridin-3-yl)furo[3,2-c]pyridin-2-yl}methylene]-2-thioxothiazolidin-4-one $^1$H NMR (DMSO-d$_6$, 400 MHz) δ 9.02 (s, 1H), 8.67 (s, 1H), 7.96 (s, 1H), 7.73 (d, 2H), 7.40 (s, 1H), 5.19 (m, 2H), 3.97 (s, 3H); (yield: 47%)

Example 174

(Z)-5-[{7-(6-Isopropoxypyridin-3-yl)furo[3,2-c]pyridin-2-yl}methylene]-2-thioxothiazolidin-4-one $^1$H NMR (DMSO-d$_6$, 400 MHz) δ 9.06 (s, 1H), 8.79 (s, 1H), 8.77 (s, 1H), 8.26 (m, 1H), 7.73 (m, 2H), 6.96 (m, 1H), 5.36 (m, 1H), 1.37 (d, 6H); (yield: 50%)

Example 175

(Z)-5-[{7-(5-Chloro-6-methoxypyridin-3-yl)furo[3,2-c]pyridin-2-yl}methylene]-2-thioxothiazolidin-4-one $^1$H NMR (DMSO-d$_6$, 400 MHz) δ 9.08 (s, 1H), 8.89 (s, 1H), 8.74 (m, 1H), 8.60 (s, 1H), 4.06 (s, 3H); (yield: 52%)

Example 176

(Z)-5-[2-{(4-Oxo-2-thioxothiazolidin-5-ylidene)methyl}furo[3,2-c]pyridin-7-yl]picolinonitrile $^1$H NMR (DMSO-d$_6$, 400 MHz) δ 8.99 (s, 1H), 8.71 (s, 1H), 8.06 (m, 2H), 7.72 (m, 2H), 6.53 (m, 1H); (yield: 51%)

Example 177

(Z)-5-{(7-[4-Methoxy-3-{(E)-(4-oxo-2-thioxothiazolidin-5-ylidene)methyl}phenyl]furo[3,2-c]pyridin-2-yl)methylene}-2-thioxothiazolidin-4-one $^1$H NMR (DMSO-d$_6$, 400 MHz) δ 9.05 (s, 1H), 8.79 (s, 1H), 8.31 (s, 1H), 8.25 (m, 1H), 7.73 (s, 1H), 7.68 (m, 1H), 7.47 (m, 1H), 4.04 (s, 3H); (yield: 49%)

Example 178

(Z)-5-[{7-(4-Ethansulfonylphenyl)furo[3,2-c]pyridin-2-yl}methylene]-2-thioxothiazolidin-4-one $^1$H NMR (DMSO-$d_6$, 400 MHz) δ 9.15 (s, 1H), 8.89 (s, 1H), 8.26 (m, 2H), 8.09 (m, 2H), 7.76 (d, 2H), 2.99 (m, 2H), 1.17 (t, 3H); (yield: 50%)

Example 179

(Z)-5-[{7-(4-Cyclohexylphenyl)furo[3,2-c]pyridin-2-yl}methylene]-2-thioxothiazolidin-4-one $^1$H NMR (DMSO-$d_6$, 400 MHz) δ 9.04 (s, 1H), 8.79 (s, 1H), 7.91 (d, 2H), 7.73 (d, 2H), 7.44 (d, 2H), 2.66 (m, 1H), 1.91~1.83 (m, 4H), 1.72 (m, 1H), 1.53~1.41 (m, 4H), 1.31 (m, 1H); (yield: 54%)

Example 180

(Z)-5-([7-{2-(Methylthio)pyrimidin-5-yl}furo[3,2-c]pyridin-2-yl]methylene)-2-thioxothiazolidin-4-one $^1$H NMR (DMSO-$d_6$, 400 MHz) δ 9.26 (s, 1H), 9.12 (s, 1H), 8.92 (s, 1H), 7.76 (d, 2H), 2.63 (s, 3H); (yield: 53%)

Example 181

(Z)-5-[{7-(2,4-Dimethoxypyrimidin-5-yl)furo[3,2-c]pyridin-2-yl}methylene]-2-thioxothiazolidin-4-one $^1$H NMR (DMSO-$d_6$, 400 MHz) δ 9.09 (s, 1H), 8.64 (s, 2H), 7.70 (d, 2H), 4.02 (s, 3H), 3.98 (s, 3H); (yield: 50%)

Example 182

(Z)-5-[{7-(6-Chloro-5-methylpyridin-3-yl)furo[3,2-c]pyridin-2-yl}methylene]-2-thioxothiazolidin-4-one $^1$H NMR (DMSO-$d_6$, 400 MHz) δ 9.12 (s, 1H), 8.91 (s, 1H), 8.85 (s, 1H), 8.49 (s, 1H), 7.75 (d, 2H), 2.50 (s, 3H); (yield: 52%)

Example 183

(Z)-5-[{7-(6-Chloro-5-fluoropyridin-3-yl)furo[3,2-c]pyridin-2-yl}methylene]-2-thioxothiazolidin-4-one $^1$H NMR (DMSO-$d_6$, 400 MHz) δ 9.14 (s, 1H), 8.95 (s, 2H), 8.61 (d, 1H), 7.76 (d, 2H); (yield: 49%)

Example 184

(Z)-5-[{7-(4-Hydroxyphenyl)furo[3,2-c]pyridin-2-yl}methylene]-2-thioxothiazolidin-4-one $^1$H NMR (DMSO-$d_6$, 400 MHz) δ 9.92 (s, 1H), 8.99 (s, 1H), 8.73 (s, 1H), 7.83 (m, 2H), 7.73 (s, 2H), 6.98 (d, 2H); (yield: 43%)

Example 185

(Z)-5-[{7-(6-Dimethylamino-5-fluoropyridin-3-yl)furo[3,2-c]pyridin-2-yl}methylene]-2-thioxothiazolidin-4-one $^1$H NMR (DMSO-$d_6$, 400 MHz) δ 9.02 (s, 1H), 8.84 (s, 1H), 8.62 (s, 1H), 8.12 (d, 1H), 7.74 (s, 2H), 3.16 (s, 6H); (yield: 41%)

Example 186

(Z)-5-[{7-(6-Methoxy-5-trifluoromethylpyridin-3-yl)furo[3,2-c]pyridin-2-yl}methylene]-2-thioxothiazolidin-4-one $^1$H NMR (DMSO-$d_6$, 400 MHz) δ 9.11 (s, 1H), 9.01 (s, 1H), 8.89 (s, 1H), 8.69 (s, 1H), 7.74 (d, 2H), 4.11 (s, 3H); (yield: 50%)

Example 187

(Z)-5-[{7-(2,3-Dihydrobenzofuran-5-yl)furo[3,2-c]pyridin-2-yl}methylene]-2-thioxothiazolidin-4-one $^1$H NMR (DMSO-$d_6$, 400 MHz) δ 8.99 (s, 1H), 8.75 (s, 1H), 7.95 (s, 1H), 7.72 (m, 3H), 6.96 (d, 1H), 4.67 (m, 2H), 3.33 (m, 2H); (yield: 57%)

Example 188

(Z)-5-[{7-(6-Chloro-5-methoxypyridin-3-yl)furo[3,2-c]pyridin-2-yl}methylene]-2-thioxothiazolidin-4-one $^1$H NMR (DMSO-$d_6$, 400 MHz) δ 9.14 (s, 1H), 8.92 (s, 1H), 8.57 (s, 1H), 8.14 (s, 1H), 7.75 (d, 2H), 4.08 (s, 3H); (yield: 53%)

Example 189

(Z)-5-[{7-(2,5-Difluoro-4-methoxyphenyl)furo[3,2-c]pyridin-2-yl}methylene]-2-thioxothiazolidin-4-one $^1$H NMR (DMSO-$d_6$, 400 MHz) δ 9.10 (s, 1H), 8.67 (s, 1H), 7.80 (m, 1H), 7.75 (s, 1H), 7.72 (s, 1H), 7.42 (m, 1H), 3.97 (s, 3H); (yield: 56%)

Example 190

(Z)-5-[{7-(4-Methoxymethylphenyl)furo[3,2-c]pyridin-2-yl}methylene]-2-thioxothiazolidin-4-one $^1$H NMR (DMSO-$d_6$, 400 MHz) δ 9.06 (s, 1H), 8.81 (s, 1H), 7.98 (m, 2H), 7.73 (m, 2H), 7.54 (m, 2H), 4.55 (s. 2H), 3.37 (s, 3H); (yield: 52%)

Example 191

(Z)—N-Methyl-4-[2-{(4-oxo-2-thioxothiazolidin-5-ylidene)methyl}furo[3,2-c]pyridin-7-yl]benzenesulfonamide $^1$H NMR (DMSO-$d_6$, 400 MHz) δ 9.13 (s, 1H), 8.88 (s, 1H), 8.21 (m, 2H), 7.98 (m, 2H), 7.76 (d, 2H), 7.66 (m, 1H), 2.50 (s, 3H); (yield: 49%)

Example 192

(Z)—N-(tert-Butyl)-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.12 (s, 1H), 8.86 (s, 1H), 8.15 (m, 2H), 8.03 (m, 2H), 7.77 (s, 1H), 7.74 (s, 2H), 1.16 (s, 9H); (yield: 40%)

Example 193

(Z)-5-([7-{4-(Morpholinosulfonyl)phenyl}furo[3,2-c]pyridin-2-yl]methylene)-2-thioxothiazolidin-4-one $^1$H NMR (DMSO-d$_6$, 400 MHz) δ 9.15 (s, 1H), 8.88 (s, 1H), 8.24 (d, 2H), 7.93 (m, 2H), 7.75 (m, 2H), 3.67 (m, 4H), 2.95 (m, 4H); (yield: 40%)

Example 194

(Z)-5-[7-{4-(Piperidine-1-sulfonyl)phenyl}-furo[3,2-c]pyridin-2-ylmethylene]-2-thioxothiazolidin-4-one $^1$H NMR (DMSO-d$_6$, 400 MHz) δ 9.14 (s, 1H) 8.86 (s, 1H), 8.20 (m, 2H), 7.92 (m, 2H), 7.75 (d, 2H), 2.97 (m, 4H), 1.59 (m, 4H), 1.38 (brs, 2H); (yield: 46%)

Example 195

(Z)-5-[7-(6-Fluoro-5-methylpyridin-3-yl)-furo[3,2-c]pyridin-2-ylmethylene]-2-thioxothiazolidin-4-one $^1$H NMR (DMSO-d$_6$, 400 MHz) δ 9.10 (m, 1H), 8.88 (m, 1H), 8.65 (m, 1H), 8.53 (m, 1H), 7.73 (m, 2H), 2.42 (s, 3H); (yield: 54%)

Example 196

(Z)-5-[7-(4-Methoxy-3,5-dimethylphenyl)furo[3,2-c]pyridin-2-ylmethylene]-2-thioxothiazolidin-4-one $^1$H NMR (DMSO-d$_6$, 400 MHz) δ 9.04 (s, 1H), 8.80 (s, 1H), 7.94 (s, 1H), 7.79 (s, 1H), 7.72 (m, 2H), 6.81 (s, 1H), 3.75 (s, 3H), 2.39 (s, 6H); (yield: 53%)

Example 197

(Z)-5-[{7-(4-Isopropoxy-3,5-dimethylphenyl)furo[3,2-c]pyridin-2-yl}methylene]-2-thioxothiazolidin-4-one $^1$H NMR (DMSO-d$_6$, 400 MHz) δ 9.03 (m, 1H), 8.78 (m, 1H), 7.93~7.78 (m, 1H), 7.70 (m, 3H), 4.26 (m, 1H), 2.37 (s, 6H), 1.30 (m, 6H); (yield: 50%)

Example 198

(Z)-2-Thioxo-5-([7-{6-(2,2,2-trifluoroethoxy)pyridin-3-yl}furo[3,2-c]pyridin-2-ylmethylene)thiazolidin-4-one $^1$H NMR (DMSO-d$_6$, 400 MHz) δ 9.10 (m, 1H), 8.83 (t, 2H), 8.42 (m, 1H), 7.95~7.83 (m, 1H), 7.75 (m, 2H), 7.24 (m, 1H), 5.12 (m, 2H); (yield: 54%)

Example 199

(Z)-5-{(7-[3-{(4-Methoxybenzyl)oxy}phenyl]furo[3,2-c]pyridin-2-yl)methylene}-2-thioxothiazolidin-4-one $^1$H NMR (DMSO-d$_6$, 400 MHz) δ 9.09 (m, 1H), 8.80 (m, 1H), 7.96~7.83 (m, 1H), 7.76 (d, 1H), 7.62 (d, 1H), 7.52 (m, 2H), 7.45 (m, 2H), 7.17 (m, 1H), 6.95 (m, 2H), 5.16 (s, 2H), 3.76 (s, 3H); (yield: 51%)

Example 200

(Z)-2-Thioxo-5-[{7-(3,4,5-trimethoxyphenyl)furo[3,2-c]pyridin-2-yl}methylene]thiazolidin-4-one $^1$H NMR (DMSO-d$_6$, 400 MHz) δ 9.11 (s, 1H), 8.84 (s, 1H), 7.75 (d, 2H), 7.21 (s, 2H), 3.94 (s, 6H), 3.77 (s, 3H); (yield: 49%)

Example 201

(Z)-5-[{7-(4-Hydroxy-3-methoxyphenyl)furo[3,2-c]pyridin-2-yl}methylene]-2-thioxothiazolidin-4-one $^1$H NMR (DMSO-d$_6$, 400 MHz) δ 9.46 (s, 1H), 8.99 (s, 1H), 8.74 (s, 1H), 7.73 (d, 2H), 7.50 (s, 1H), 7.38 (d, 1H), 7.00 (d, 1H), 3.94 (s, 3H); (yield: 44%)

Example 202

(Z)-5-[{7-(4-Hydroxy-3,5-dimethylphenyl)furo[3,2-c]pyridin-2-yl}methylene]-2-thioxothiazolidin-4-one $^1$H NMR (DMSO-d$_6$, 400 MHz) δ 8.96 (s, 1H), 8.75 (s, 1H), 8.67 (s, 1H), 7.71 (s, 2H), 7.62 (s, 2H), 2.32 (s, 6H); (yield: 42%)

Example 203

(Z)-5-[{7-(2-Methoxypyrimidin-5-yl)furo[3,2-c]pyridin-2-yl}methylene]-2-thioxothiazolidin-4-one $^1$H NMR (DMSO-d$_6$, 400 MHz) δ 9.25 (s, 2H), 9.11 (s, 1H), 8.89 (s, 1H), 7.76 (d, 2H), 4.04 (s, 3H); (yield: 40%)

Example 204

(Z)-5-[{7-(4-Methyl-3,4-dihydro-2H-benzo[b][1,4]oxazin-7-yl)furo[3,2-c]pyridin-2-yl}methylene]-2-thioxothiazolidin-4-one $^1$H NMR (DMSO-d$_6$, 400 MHz) δ 8.94 (s, 1H), 8.72 (s, 1H), 7.71 (s, 2H), 7.43 (d, 1H), 7.39 (s, 1H), 6.84 (d, 1H), 4.30 (brs, 2H), 3.40 (brs, 2H), 2.94 (s, 3H); (yield: 54%)

Example 205

(Z)-5-[{7-(4-Isopropoxy-3-methylphenyl)furo[3,2-c]pyridin-2-yl}methylene]-2-thioxothiazolidin-4-one $^1$H NMR (DMSO-d$_6$, 400 MHz) δ 9.00 (s, 1H), 8.77 (s, 1H), 7.89 (s, 1H), 7.72 (m, 3H), 7.15 (d, 1H), 4.71 (m, 1H), 2.31 (s, 3H), 1.35 (d, 6H); (yield: 49%)

Example 206

(Z)-5-[{7-(4-Ethoxy-3-methylphenyl)furo[3,2-c]pyridin-2-yl}methylene]-2-thioxothiazolidin-4-one ¹H NMR (DMSO-d₆, 400 MHz) δ 9.00 (s, 1H), 8.77 (s, 1H), 7.90 (s, 1H), 7.72 (s, 2H), 7.12 (d, 1H), 4.14 (m, 2H), 2.33 (s, 3H), 1.41 (t, 3H); (yield: 48%)

Example 207

(Z)-5-([7-{4-(tert-Butoxymethyl)phenyl}furo[3,2-c]pyridin-2-yl]methylene)-2-thioxothiazolidin-4-one ¹H NMR (DMSO-d₆, 400 MHz) δ 9.06 (s, 1H), 8.80 (s, 1H), 7.95 (d, 2H), 7.74 (d, 2H), 7.53 (d, 2H), 4.55 (s, 2H), 1.20 (s, 9H); (yield: 52%)

Example 208

(Z)-5-[{7-(5-Amino-6-chloropyridin-3-yl)furo[3,2-c]pyridin-2-yl}methylene]-2-thioxothiazolidin-4-one ¹H NMR (DMSO-d₆, 400 MHz) δ 9.11 (s, 1H), 8.75 (s, 1H), 8.18 (s, 1H), 7.76 (d, 2H), 7.63 (s, 1H), 5.85 (brs, 2H); (yield: 51%)

Example 209

(Z)-5-[{7-(3,5-Dichloro-4-methoxyphenyl)furo[3,2-c]pyridin-2-yl}methylene]-2-thioxothiazolidin-4-one ¹H NMR (DMSO-d₆, 400 MHz) δ 9.09 (s, 1H), 8.92 (s, 1H), 8.21 (s, 2H), 7.74 (d, 2H), 3.94 (s, 3H); (yield: 50%)

Example 210

(Z)-5-([7-{3-Methyl-4-(trifluoromethoxy)phenyl}furo[3,2-c]pyridin-2-yl]methylene)-2-thioxothiazolidin-4-one ¹H NMR (DMSO-d₆, 400 MHz) δ 9.09 (s, 1H), 8.84 (s, 1H), 8.12 (s, 1H), 7.88 (m, 1H), 7.74 (m, 2H), 7.53 (m, 1H), 2.47 (s, 3H); (yield: 47%)

Example 211

(Z)-2-(4-[2-{(4-Oxo-2-thioxothiazolidin-5-ylidene)methyl}furo[3,2-c]pyridin-7-yl]phenoxy)acetonitrile ¹H NMR (DMSO-d₆, 400 MHz) δ 9.03 (s, 1H), 8.78 (s, 1H), 7.01 (d, 2H), 7.70 (d, 2H), 7.29 (d, 2H), 5.31 (s, 2H); (yield: 49%)

Example 212

(Z)-5-([7-{4-(Hydroxymethyl)-3-methylphenyl}furo[3,2-c]pyridin-2-yl]methylene)-2-thioxothiazolidin-4-one ¹H NMR (DMSO-d₆, 400 MHz) δ 9.06 (s, 1H), 8.34 (s, 1H), 7.96 (s, 1H), 7.76 (m, 3H), 7.52 (m, 1H), 5.21 (s, 2H), 2.12 (s, 3H); (yield: 21%)

Example 213

(Z)-5-([7-{3-Fluoro-4-(trifluoromethoxy)phenyl}furo[3,2-c]pyridin-2-yl]methylene)-2-thioxothiazolidin-4-one ¹H NMR (DMSO-d₆, 400 MHz) δ 9.12 (s, 1H), 8.87 (s, 1H), 8.20 (m, 1H), 7.94~7.89 (m, 2H), 7.82~7.76 (m, 2H); (yield: 50%)

Example 214

(Z)-5-([7-{4-Methoxy-3-(trifluoromethyl)phenyl}furo[3,2-c]pyridin-2-yl]methylene)-2-thioxothiazolidin-4-one ¹H NMR (DMSO-d₆, 400 MHz) δ 9.06 (s, 1H), 8.80 (s, 1H), 8.23~8.17 (m, 2H), 7.87~7.72 (m, 2H), 7.51 (m, 1H), 4.00 (m, 3H); (yield: 47%)

Example 215

(Z)-5-[{7-(4H-Benzo[d][1,3]dioxin-6-yl)furo[3,2-c]pyridin-2-yl}methylene]-2-thioxothiazolidin-4-one ¹H NMR (DMSO-d₆, 400 MHz) δ 9.03 (s, 1H), 8.77 (m, 1H), 7.85~7.74 (m, 4H), 7.07 (m, 1H), 5.36 (m, 2H), 5.07~5.00 (m, 2H); (yield: 43%)

Example 216

(Z)-2-Methoxy-5-[2-{(4-oxo-2-thioxothiazolidin-5-ylidene)methyl}furo[3,2-c]pyridin-7-yl]benzonitrile ¹H NMR (DMSO-d₆, 400 MHz) δ 9.05 (s, 1H), 8.81 (s, 1H), 8.35 (s, 1H), 8.25 (m, 1H), 7.73 (d, 2H), 7.46 (d, 1H), 4.04 (s, 3H); (yield: 45%)

Example 217

(Z)-5-[{7-(3-Chloro-4-hydroxy-5-methoxyphenyl)furo[3,2-c]pyridin-2-yl}-methylene]-2-thioxothiazolidin-4-one ¹H NMR (DMSO-d₆, 400 MHz) δ 9.88 (s, 1H), 9.04 (s, 1H), 8.85 (s, 1H), 7.75 (d, 2H), 7.70 (s, 1H), 7.51 (s, 1H), 3.99 (s, 3H); (yield: 40%)

Example 218

(Z)-5-[{7-(4-Ethoxy-3-(trifluoromethyl)phenyl)furo[3,2-c]pyridin-2-yl}-methylene]-2-thioxothiazolidin-4-one ¹H NMR (DMSO-d₆, 400 MHz) δ 9.06 (s, 1H), 8.85 (d, 1H), 8.21~8.14 (m, 2H), 7.87 (s, 1H), 7.74 (d, 1H), 7.49 (t, 1H), 4.29 (m, 2H), 1.40 (t, 3H); (yield: 40%)

Example 219

(Z)-5-[{7-(2,2-Difluorobenzo[d][1,3]dioxol-5-yl)furo[3,2-c]pyridin-2-yl}methylene]-2-thioxothiazolidin-4-one ¹H NMR (DMSO-d₆, 400 MHz) δ 9.09 (s, 1H), 8.82 (d, 1H), 8.00 (d, 1H), 7.88 (s, 1H), 7.81 (t, 1H), 7.74 (d, 1H), 7.65 (m, 1H); (yield: 47%)

Example 220

(Z)-4-[2-{(4-Oxo-2-thioxothiazolidin-5-ylidene)methyl}furo[3,2-c]pyridin-7-yl]benzyl acetate $^1$H NMR (DMSO-$d_6$, 400 MHz) δ 13.15 (brs, 1H), 9.08 (s, 1H), 8.82 (s, 1H), 8.00 (d, 2H), 7.75 (d, 2H), 7.60 (d, 2H), 5.22 (s, 2H), 2.12 (s, 3H); (yield: 40%)

Example 221

(Z)-5-[{7-(2-Ethoxypyrimidin-5-yl)furo[3,2-c]pyridin-2-yl}methylene]-2-thioxothiazolidin-4-one $^1$H NMR (DMSO-$d_6$, 400 MHz) δ 9.21 (s, 2H), 9.10 (s, 1H), 8.889 (s, 1H), 7.76 (d, 2H), 4.50 (m, 2H), 1.45 (t, 3H); (yield: 43%)

Example 222

(Z)-5-[{7-(2,6-Dichloropyridin-4-yl)furo[3,2-c]pyridin-2-yl}methylene]-2-thioxothiazolidin-4-one $^1$H NMR (DMSO-$d_6$, 400 MHz) δ 9.19 (s, 1H), 9.07 (s, 1H), 8.28 (s, 2H), 7.78 (s, 1H), 7.75 (s, 1H); (yield: 40%)

Example 223

(Z)-5-[{7-(4-Cyclopropylphenyl)furo[3,2-c]pyridin-2-yl}methylene]-2-thioxothiazolidin-4-one $^1$H NMR (DMSO-$d_6$, 400 MHz) δ 13.90 (brs, 1H), 9.03 (s, 1H), 8.76 (s, 1H), 7.86 (d, 2H), 7.73 (d, 2H), 7.29 (d, 2H), 2.06 (m, 1H), 1.05 (m, 2H), 0.78 (m, 2H); (yield: 50%)

Example 224

(Z)-5-[{7-(5-Chloro-6-ethoxypyridin-3-yl)furo[3,2-c]pyridin-2-yl}methylene]-2-thioxothiazolidin-4-one $^1$H NMR (DMSO-$d_6$, 400 MHz) δ 9.07 (s, 1H), 8.88 (s, 1H), 8.72 (m, 1H), 8.57 (m, 1H), 7.73 (d, 2H), 4.52 (m, 2H), 1.42 (t, 3H); (yield: 49%)

Example 225

(Z)-5-[{7-(6-Methoxy-5-methylpyridin-3-yl)furo[3,2-c]pyridin-2-yl}methylene]-2-thioxothiazolidin-4-one $^1$H NMR (DMSO-$d_6$, 400 MHz) δ 9.05 (s, 1H), 8.83 (s, 1H), 8.59 (s, 1H), 8.24 (s, 1H), 7.73 (d, 2H), 3.99 (s, 3H), 2.32 (s, 3H); (yield: 47%)

Example 226

(Z)-5-[{7-(5-Fluoro-6-methoxypyridin-3-yl)furo[3,2-c]pyridin-2-yl}methylene]-2-thioxothiazolidin-4-one $^1$H NMR (DMSO-$d_6$, 400 MHz) δ 9.09 (s, 1H), 8.86 (s, 1H), 8.63 (s, 1H), 8.38 (d, 1H), 7.75 (d, 2H), 4.06 (s, 3H); (yield: 47%)

Example 227

(Z)-5-[{7-(5-Chloro-6-isopropoxypyridin-3-yl)furo[3,2-c]pyridin-2-yl}methylene]-2-thioxothiazolidin-4-one $^1$H NMR (DMSO-$d_6$, 400 MHz) δ 9.07 (s, 1H), 8.88 (s, 1H), 8.72 (s, 1H), 8.56 (m, 1H), 7.74 (d, 2H), 5.42 (m, 1H), 1.41 (d, 6H); (yield: 44%)

Example 228

(Z)-5-[{7-(2-Methoxypyridin-4-yl)furo[3,2-c]pyridin-2-yl}methylene]-2-thioxothiazolidin-4-one $^1$H NMR (DMSO-$d_6$, 400 MHz) δ 9.14 (s, 1H), 8.92 (s, 1H), 8.38 (m, 1H), 7.75 (d, 2H), 7.58 (m, 1H), 7.50 (m, 1H), 3.96 (s, 3H); (yield: 40%)

Example 229

(Z)-5-[{7-(2-Methylpyridin-4-yl)furo[3,2-c]pyridin-2-yl}methylene]-2-thioxothiazolidin-4-one $^1$H NMR (DMSO-$d_6$, 400 MHz) δ 9.15 (s, 1H), 8.94 (s, 1H), 8.66 (m, 1H), 8.00 (s, 1H), 7.79 (m, 1H), 7.75 (d, 2H), 2.66 (s, 3H); (yield: 44%)

Example 230

(Z)-5-[{7-(3-Amino-4-fluorophenyl)furo[3,2-c]pyridin-2-yl}methylene]-2-thioxothiazolidin-4-one $^1$H NMR (DMSO-$d_6$, 400 MHz) δ 9.03 (s, 1H), 8.65 (s, 1H), 7.73 (d, 2H), 7.29 (m, 1H), 7.20 (m, 1H), 7.10 (m, 1H), 5.37 (brs, 2H); (yield: 47%)

Example 231

(Z)-2-Thioxo-5-([7-{2-(trifluoromethyl)pyridin-4-yl}furo[3,2-c]pyridin-2-yl]methylene)thiazolidin-4-one $^1$H NMR (DMSO-$d_6$, 400 MHz) δ 9.20 (s, 1H), 9.02 (s, 1H), 9.00 (m, 1H), 8.54 (s, 1H), 8.31 (m, 1H), 7.80 (s, 1H), 7.75 (s, 1H); (yield: 47%)

Example 232

(Z)-5-[{7-(2-Ethoxy-6-fluoropyridin-4-yl)furo[3,2-c]pyridin-2-yl}methylene]-2-thioxothiazolidin-4-one $^1$H NMR (DMSO-$d_6$, 400 MHz) δ 9.16 (s, 1H), 8.98 (s, 1H), 7.75 (d, 2H), 7.45 (s, 1H), 7.36 (s, 1H), 4.37 (m, 2H), 1.41 (t, 3H); (yield: 50%)

Example 233

(Z)-2-(3-[2-{(4-Oxo-2-thioxothiazolidin-5-ylidene)methyl}furo[3,2-c]pyridin-7-yl]phenyl)acetonitrile $^1$H NMR (DMSO-$d_6$, 400 MHz) δ 9.09 (s, 1H), 8.82 (s, 1H), 7.98~7.94 (m, 2H), 7.75 (d, 2H), 7.65 (t, 1H), 7.56 (m, 1H), 4.19 (s, 2H); (yield: 58%)

Example 234

(Z)-2-Thioxo-5-([7-{3-(2,2,2-trifluoroethoxy)phenyl}furo[3,2-c]pyridin-2-yl]methylene)thiazolidin-4-one $^1$H NMR (DMSO-d$_6$, 400 MHz) δ 9.06 (s, 1H), 8.82 (s, 1H), 7.70~7.64 (m, 4H), 7.56 (t, 1H), 7.24 (d, 1H), 4.90 (m, 2H); (yield: 40%)

Example 235

(Z)-5-([7-{3-(Methylsulfinyl)phenyl}furo[3,2-c]pyridin-2-yl]methylene)-2-thioxothiazolidin-4-one $^1$H NMR (DMSO-d$_6$, 400 MHz) δ 9.11 (s, 1H), 8.86 (s, 1H), 8.23 (s, 1H), 8.12 (d, 1H), 7.88 (m, 1H), 7.83 (m, 1H), 7.78 (s, 1H), 7.74 (s, 1H), 2.89 (s, 3H); (yield: 50%)

Example 236

(Z)-5-[{7-(3-Fluoro-5-methylphenyl)furo[3,2-c]pyridin-2-yl}methylene]-2-thioxothiazolidin-4-one $^1$H NMR (DMSO-d$_6$, 400 MHz) δ 9.07 (s, 1H), 8.86 (s, 1H), 7.78 (s, 1H), 7.72~7.69 (m, 2H), 7.63 (m, 1H), 7.22 (d, 1H); (yield: 49%)

Example 237

(Z)—N-(3-[2-{(4-Oxo-2-thioxothiazolidin-5-ylidene)methyl}furo[3,2-c]pyridin-7-yl]phenyl)methanesulfonamide $^1$H NMR (DMSO-d$_6$, 400 MHz) δ 10.00 (s, 1H), 9.09 (s, 1H), 8.72 (s, 1H), 7.77~7.67 (m, 4H), 7.56 (m, 1H), 7.42 (m, 1H), 3.11 (s, 3H); (yield: 51%)

Example 238

(Z)-5-[{7-(2-Fluoropyridin-4-yl)furo[3,2-c]pyridin-2-yl}methylene]-2-thioxothiazolidin-4-one $^1$H NMR (DMSO-d$_6$, 400 MHz) δ 9.19 (s, 1H), 8.99 (s, 1H), 8.48 (m, 1H), 8.00 (m, 1H), 7.87 (s, 1H), 7.77 (m, 2H); (yield: 51%)

Example 239

(Z)-5-[{7-(3-Amino-4-methylphenyl)furo[3,2-c]pyridin-2-yl}methylene]-2-thioxothiazolidin-4-one $^1$H NMR (DMSO-d$_6$, 400 MHz) δ 8.99 (s, 1H), 8.66 (s, 1H), 7.70 (d, 2H), 7.17 (s, 1H), 7.12 (s, 2H), 2.17 (s, 3H); (yield: 58%)

Example 240

(Z)-5-[{7-(4-Amino-3-fluorophenyl)furo[3,2-c]pyridin-2-yl}methylene]-2-thioxothiazolidin-4-one $^1$H NMR (DMSO-d$_6$, 400 MHz) δ 8.94 (s, 1H), 8.75 (s, 1H), 7.76 (d, 1H), 7.68 (m, 2H), 7.60 (d, 1H), 6.97 (t, 1H), 5.63 (brs, 2H); (yield: 45%)

Example 241

(Z)-5-([7-{3,5-Bis(trifluoromethyl)phenyl}furo[3,2-c]pyridin-2-yl]methylene)-2-thioxothiazolidin-4-one $^1$H NMR (DMSO-d$_6$, 400 MHz) δ 9.15 (s, 1H), 8.97 (s, 1H), 8.64 (s, 2H), 8.27 (s, 1H), 7.79 (s, 1H), 7.72 (s, 1H); (yield: 40%)

Example 242

(Z)-5-[{7-(1H-Benzo[d]imidazol-5-yl)furo[3,2-c]pyridin-2-yl}methylene]-2-thioxothiazolidin-4-one $^1$H NMR (DMSO-d$_6$, 400 MHz) δ 9.01 (s, 1H), 8.78 (s, 1H), 8.56 (s, 1H), 8.13 (s, 1H), 7.80 (dd, 1H), 7.69 (d, 1H); (yield: 46%)

Example 243

(Z)-5-[{7-(1H-Pyrazol-4-yl)furo[3,2-c]pyridin-2-yl}methylene]-2-thioxothiazolidin-4-one $^1$H NMR (DMSO-d$_6$, 400 MHz) δ 13.39 (brs, 1H), 8.86 (d, 2H), 8.39 (brs, 2H), 7.69 (d, 2H); (yield: 49%)

Example 244

(Z)-5-[{7-(Phenylethynyl)furo[3,2-c]pyridin-2-yl}methylene]-2-thioxothiazolidin-4-one $^1$H NMR (DMSO-d$_6$, 400 MHz) δ 9.07 (s, 1H), 8.73 (s, 1H), 7.72 (m, 4H), 7.53 (m, 3H); (yield: 50%)

Example 245

(Z)-5-[{7-(Propyn-1-yl)furo[3,2-c]pyridin-2-yl}methylene]-2-thioxothiazolidin-4-one $^1$H NMR (DMSO-d$_6$, 400 MHz) δ 9.01 (s, 1H), 8.59 (s, 1H), 7.69 (m, 2H), 2.25 (s, 3H); (yield: 40%)

Example 246

(Z)-5-[{7-(1-Methyl-1H-pyrazol-4-yl)furo[3,2-c]pyridin-2-yl}methylene]-2-thioxothiazolidin-4-one $^1$H NMR (DMSO-d$_6$, 400 MHz) δ 8.91 (s, 1H), 8.86 (s, 1H), 8.50 (s, 1H), 8.26 (s, 1H), 7.73 (d, 2H); (yield: 50%)

Example 247

(Z)-5-[{7-(6-Morpholinopyridin-3-yl)furo[3,2-c]pyridin-2-yl}methylene]-2-thioxothiazolidin-4-one $^1$H NMR (DMSO-d$_6$, 400 MHz) δ 9.00 (s, 1H), 8.78 (s, 2H), 8.16 (d, 1H), 7.71 (d, 2H), 7.03 (d, 1H), 3.76 (brs, 4H), 3.60 (brs, 4H); (yield: 45%)

Example 248

(Z)-5-[{7-(2-Aminopyrimidin-5-yl)furo[3,2-c]pyridin-2-yl}methylene]-2-thioxothiazolidin-4-one $^1$H NMR (DMSO-d$_6$, 400 MHz) δ 9.01 (s, 1H), 8.90 (s, 2H), 8.81 (s, 1H), 7.74 (d, 2H), 7.11 (s, 2H); (yield: 51%)

Example 249

(Z)-5-([7-{4-(1H-Tetrazol-1-yl)phenyl}furo[3,2-c]pyridin-2-yl]methylene)-2-thioxothiazolidin-4-one ¹H NMR (DMSO-d₆, 400 MHz) δ 10.26 (s, 1H), 9.13 (s, 1H), 8.91 (s, 1H), 8.28 (d, 2H), 8.18 (d, 2H), 7.78 (d, 2H); (yield: 54%)

Example 250

(Z)-5-[{7-(3-Hydroxyphenyl)furo[3,2-c]pyridin-2-yl}methylene]-2-thioxothiazolidin-4-one ¹H NMR (DMSO-d₆, 400 MHz) δ 9.73 (s, 1H), 9.05 (s, 1H), 8.73 (s, 1H), 7.73 (d, 1H), 7.45-7.30 (m, 3H), 6.95 (s, 1H)

Example 251

(Z)-Ethyl 3-[2-{(2,4-dioxothiazolidin-5-ylidene)methyl}furo[3,2-c]pyridin-7-yl]benzoate Step 1: Synthesis of ethyl 3-{2-(diethoxymethyl)furo[3,2-c]pyridin-7-yl}benzoate A solution prepared by dissolving 2-(diethoxymethyl)-7-(4,4,5,5-tetramethyl-1,3-dioxaborolan-2-yl)furo[3,2-c]pyridine (1.0 mmol) obtained in Reference Example 2 in terahydrofuran/water (4/1, v/v, 5 ml) was added with ethyl-3-iodo-benzoate (1.2 mmol), sodium carbonate (2.2 mmol) and tetrakis(triphenylphosphine)palladium(0) (5.0 mol %), and stirred under reflux for 12 hours under a nitrogen atmosphere. The organic layer was separated and concentrated under reduced pressure. The residue thus obtained was purified by silica gel column chromatography (n-hexane/ethyl acetate=4/1, v/v) to obtain the title compound as light brown oil (yield: 83%).

¹H NMR (CDCl₃, 300 MHz) δ 8.89 (s, 1H), 8.70 (s, 1H), 8.52 (s, 1H), 8.13 (d, 1H), 8.07 (d, 1H), 7.61 (dd, 1H), 6.98 (s, 1H), 5.71 (s, 1H), 4.47-4.39 (m, 2H), 3.76-3.66 (m, 4H), 1.43 (t, 3H), 1.28 (t, 6H)

Step 2: Synthesis of ethyl 3-(2-formylfuro[3,2-c]pyridin-7-yl)benzoate

A solution prepared by dissolving ethyl 3-(2-(diethoxymethyl)furo[3,2-c]pyridin-7-yl)benzoate (0.5 mmol) obtained in Step 1 in tetrahydrofuran (5 ml) was added with a 3N aqueous hydrochloric acid solution (5 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, which was then concentrated under reduced pressure. The resulting residue was purified by silica gel column chromatography (n-hexane/ethyl acetate=4/1, v/v) to obtain the title compound as light brown oil (yield: 95%).

¹H NMR (CDCl₃, 300 MHz) δ 10.00 (s, 1H), 9.17 (brs, 1H), 8.93 (brs, 1H), 8.53 (s, 1H), 8.17 (d, 1H), 8.11 (d, 1H), 7.73 (s, 1H), 7.66 (dd, 1H), 4.48-4.41 (m, 2H), 1.44 (t, 3H)

Step 3: Synthesis of (Z)-ethyl 3-[2-{(2,4-dioxothiazolidin-5-ylidene)methyl}furo[3,2-c]pyridin-7-yl]benzoate A solution prepared by dissolving ethyl 3-(2-formylfuro[3,2-c]pyridin-7-yl)benzoate (0.4 mmol) obtained in Step 2 in acetic acid (3 ml) was added with thiazolidinedione (0.5 mmol) and β-alanine (0.4 mmol), and stirred under reflux for 4 hours. After cooled to room temperature, the resulting solid was filtered, washed with acetic acid and water, and dried to obtain the title compound as a light yellow solid (yield: 81%).

¹H NMR (DMSO-d₆, 300 MHz) δ 12.65 (brs, 1H), 9.09 (s, 1H), 8.83 (s, 1H), 8.56 (s, 1H), 8.18 (d, 1H), 8.11 (d, 1H), 7.86 (s, 1H), 7.77 (t, 1H), 4.38 (q, 2H), 1.34 (t, 3H)

Examples 252 to 315

The title compounds of Examples 252 to 315 were prepared in the same manner as described in Example 251 above, except for using each of the following compounds: 1-iodo-3-(trifluoromethoxy)benzene, 4-bromobenzenesulfonylamide, 3-bromobenzenesulfonamide, 4-bromo-3-chlorobenzenesulfonamide, 4-bromo-1-chloro-2-(trifluoromethyl)-benzene, 4-bromo-3-chloro-N-isopropyl-benzene sulfonamide, 4-(4-bromo-3-chlorophenylsulfonyl)-morpholine, 1-(4-bromo-3-chlorophenylsulfonyl)-piperidine, 4-bromo-3-chloro-N-(2-hydroxyethyl)-benzenesulfonamide, 1-(4-bromophenylsulfonyl)-4-propylpiperazine, 1-(4-bromophenylsulfonyl)piperidine, 4-bromo-N-(2-hydroxyethyl)benzenesulfonamide, 4-(4-bromophenylsulfonyl)morpholine, 4-bromo-N-methylbenzenesulfonamide, 4-bromo-N-isopropylbenzenesulfonamide, 4-bromobenzamide, 5-bromothiophene-2-sulfonamide, 2-bromobenzothiazole, 3-chloro-6-methoxypyridazine, N-tert-butoxycarbonyl-5-bromoindole, 4-bromo-N,N-dimethylbenzenesulfonamide, 4-bromo-2-chlorophenol, 4-bromo-o-cresol, 4-bromo-2-fluorophenol, 5-bromo-2-hydroxybenzonitrile, 1-(5-bromo-2-hydroxyphenyl)propen-1-one, 5-bromo-2-methoxypyridine-3-carbonitrile, 4-bromo-2-fluoro-N-methylbenzenesulfonamide, 4-bromo-2-fluoro-N,N-dimethylbenzenesulfonamide, 4-(4-bromo-2-fluorophenylsulfonyl)morpholine, 5-bromo-1,3-difluoro-2-(methylsulfonyl)benzene, 4-bromo-2-fluoro-1-(methylsulfonyl)benzene, methyl 4-bromo-2,6-difluorobenzoate, 4-bromo-2,6-difluoroaniline, 4-bromo-2,6-dimethylaniline, 4-bromo-2,6-dichloro-N-methylbenzenesulfonamide, 4-bromo-2,6-dichloro-N,N-dimethylbenzenesulfonamide, 4-(4-bromo-2,6-dichlorophenylsulfonyl)morpholine, 4-bromo-2,6-dichloro-N-ethylbenzene sulfonamide, 4-bromo-2,6-dichloro-N-isopropylbenzenesulfonamide, 4-bromo-N-methyl-2-(trifluoromethoxy)benzenesulfonamide, 4-bromo-N,N-dimethyl-2-(trifluoromethoxy)benzenesulfonamide, 4-{4-bromo-2-(trifluoromethoxy)phenylsulfonyl}morpholine, 4-bromo-3-fluoro-N,N-dimethylbenzenesulfonamide, 4-bromo-N-tert-butyl-2,6-dichlorobenzenesulfonamide, 4-bromo-2,6-dichloro-N-(2-hydroxyethyl)benzenesulfonamide, 4-bromo-N,N,3-trimethylbenzenesulfonamide, methyl 4-bromo-2-methoxybenzoate, methyl 4-bromo-2-fluorobenzoate, methyl 3-bromo-5-fluorobenzoate, methyl 5-bromo-2-chlorobenzoate, N-(4-bromophenyl)methanesulfonamide, 3-bromo-N,N-dimethylbenzamide, N-(4-bromo-2,6-dimethylphenyl)methanesulfonamide, 4-bromo-N,2-dimethylbenzenesulfonamide, 4-(4-bromo-2-methylphenylsulfonyl)morpholine, 4-bromo-N-ethyl-2-methylbenzenesulfonamide, 4-bromo-N-isopropyl-2-methylbenzenesulfonamide, 4-bromo-N-tert-butyl-2-methylbenzenesulfonamide, 2-amino-5-bromobenzonitrile, 4-bromo-2-(trifluoromethyl)aniline, 2-amino-5-bromo-3-methylpyridine, 4-(4-bromophenyl)-1-methyl-1H-1,2,4-triazol-5(4H)-one and 4-(4-bromophenyl)-1-isopropyl-1H-1,2,4-triazol-5(4H)-one, instead of ethyl-3-iodo-benzoate in Step 1 of Example 251.

Example 252

(Z)-5-([7-{3-(Trifluoromethoxy)phenyl}furo[3,2-c]pyridin-2-yl]methylene)thiazolidine-2,4-dione $^1$H NMR (DMSO-$d_6$, 300 MHz) δ 12.71 (brs, 1H), 9.09 (s, 1H), 8.86 (s, 1H), 8.01 (m, 2H), 7.88 (s, 1H), 7.76 (t, 1H), 7.72 (s, 1H), 7.56 (d, 1H); (yield: 65%)

Example 253

(Z)-4-[2-{(2,4-Dioxothiazolidin-5-ylidene)methyl}furo[3,2-c]pyridin-7-yl]benzenesulfonamide $^1$H NMR (DMSO-$d_6$, 300 MHz) δ 12.74 (brs, 1H), 9.12 (s, 1H), 8.88 (s, 1H), 8.19 (d, 2H), 8.05 (d, 2H), 7.91 (s, 1H), 7.74 (s, 1H), 7.57 (s, 2H); (yield: 68%)

Example 254

(Z)-3-[2-{(2,4-Dioxothiazolidin-5-ylidene)methyl}furo[3,2-c]pyridin-7-yl]benzenesulfonamide $^1$H NMR (DMSO-$d_6$, 300 MHz) δ 12.49 (brs, 1H), 9.13 (s, 1H), 8.82 (s, 1H), 8.44 (s, 1H), 8.30 (d, 1H), 7.99 (d, 1H), 7.93 (s, 2H), 7.70 (s, 1H), 7.48 (s, 2H); (yield: 70%)

Example 255

(Z)-3-Chloro-4-[2-{(2,4-dioxothiazolidin-5-ylidene)methyl}furo[3,2-c]pyridin-7-yl]benzenesulfonamide $^1$H NMR (DMSO-$d_6$, 300 MHz) δ 12.67 (brs, 1H), 9.18 (s, 1H), 8.62 (s, 1H), 8.13 (s, 1H), 7.95 (m, 1H), 7.87 m, 2H), 7.73 (m, 3H); (yield: 25%)

Example 256

(Z)-5-([7-{4-Chloro-3-(trifluoromethyl)phenyl}furo[3,2-c]pyridin-2-yl]methylene)thiazolidine-2,4-dione $^1$H NMR (DMSO-$d_6$, 300 MHz) δ 12.69 (brs, 1H), 9.11 (s, 1H), 8.87 (s, 1H), 8.41 (s, 1H), 8.23 (d, 1H), 7.99 (d, 1H), 7.87 (s, 1H), 7.72 (s, 1H); (yield: 26%)

Example 257

(Z)-3-Chloro-4-[2-{(2,4-dioxothiazolidin-5-ylidene)methyl}furo[3,2-c]pyridin-7-yl]-N-isopropylbenzenesulfonamide $^1$H NMR (DMSO-$d_6$, 300 MHz) δ 12.62 (brs, 1H), 9.17 (s, 1H), 8.64 (s, 1H), 8.10 (s, 1H), 7.90 (m, 4H), 7.72 (s, 1H), 3.35 (m, 1H), 1.02 (d, 6H); (yield: 37%)

Example 258

(Z)-5-([7-{2-Chloro-4-(morpholinosulfonyl)phenyl}furo[3,2-c]pyridin-2-yl]methylene)thiazolidine-2,4-dione $^1$H NMR (DMSO-$d_6$, 300 MHz) δ 12.65 (brs, 1H), 9.18 (s, 1H), 8.68 (s, 1H), 8.07 (s, 1H), 7.96 (m, 2H), 7.85 (s, 1H), 7.71 (s, 1H), 3.68 (brs, 4H), 2.99 (brs, 4H); (yield: 30%)

Example 259

(Z)-5-([7-{2-Chloro-4-(piperidin-1-ylsulfonyl)phenyl}furo[3,2-c]pyridin-2-yl]methylene)thiazolidine-2,4-dione $^1$H NMR (DMSO-$d_6$, 300 MHz) δ 12.65 (brs, 1H), 9.19 (s, 1H), 8.68 (s, 1H), 8.04 (s, 1H), 7.92 (m, 2H), 7.85 (s, 1H), 7.72 (s, 1H), 3.00 (m, 4H), 1.58 (brs, 4H), 1.41 (brs, 2H); (yield: 35%)

Example 260

(Z)-3-Chloro-4-[2-{(2,4-dioxothiazolidin-5-ylidene)methyl}furo[3,2-c]pyridin-7-yl]-N-(2-hydroxyethyl)benzenesulfonamide $^1$H NMR (DMSO-$d_6$, 300 MHz) δ 12.63 (brs, 1H), 9.17 (s, 1H), 8.63 (s, 1H), 8.20 (m, 1H), 8.10 (s, 1H), 7.91 (m, 2H), 7.83 (s, 1H), 7.71 (s, 1H), 4.02 (m, 2H), 3.14 (m, 2H); (yield: 21%)

Example 261

(Z)-5-([7-{4-(4-Propylpiperazin-1-ylsulfonyl)phenyl}furo[3,2-c]pyridin-2-yl]methylene)thiazolidine-2,4-dione $^1$H NMR (DMSO-$d_6$, 400 MHz) δ 9.12 (s, 1H), 8.87 (s, 1H), 8.26 (d, 2H), 7.98 (d, 2H), 7.84 (s, 1H), 7.69 (s, 1H), 3.11 (s, 4H), 2.81 (s, 4H), 2.54 (m, 2H), 1.46 (m, 2H), 0.81 (t, 3H); (yield: 54%)

Example 262

(Z)-5-([7-{4-(Piperidin-1-ylsulfonyl)phenyl}furo[3,2-c]pyridin-2-yl]methylene)thiazolidine-2,4-dione $^1$H NMR (DMSO-$d_6$, 400 MHz) δ 9.12 (s, 1H), 8.86 (s, 1H), 8.20 (d, 2H), 7.95 (d, 2H), 7.87 (s, 1H), 7.08 (s, 1H), 2.98 (s, 4H), 1.57 (s, 4H), 1.39 (s, 2H); (yield: 51%)

Example 263

(Z)-4-[2-{(2,4-Dioxothiazolidin-5-ylidene)methyl}furo[3,2-c]pyridin-7-yl]-N-(2-hydroxyethyl)benzenesulfonamide $^1$H NMR (DMSO-$d_6$, 400 MHz) δ 9.11 (s, 1H), 8.88 (s, 1H), 8.20 (d, 2H), 8.01 (d, 2H), 7.88 (s, 1H), 7.82 (s, 1H), 7.72 (s, 1H), 4.74 (s, 1H), 3.34 (s, 2H), 2.88 (d, 2H); (yield: 50%)

Example 264

(Z)-5-([7-{4-(Morpholinosulfonyl)phenyl}furo[3,2-c]pyridin-2-yl]methylene)thiazolidine-2,4-dione $^1$H NMR (DMSO-$d_6$, 400 MHz) δ 9.12 (s, 1H), 8.88 (s, 1H), 8.23 (d, 2H), 7.96 (d, 2H), 7.87 (s, 1H), 7.71 (s, 1H), 3.67 (s, 4H), 2.96 (s, 4H); (yield: 49%)

Example 265

(Z)-4-[2-{(2,4-Dioxothiazolidin-5-ylidene)methyl}furo[3,2-c]pyridin-7-yl]-N-methylbenzenesulfonamide $^1$H NMR (DMSO-d$_6$, 400 MHz) δ 9.11 (s, 1H), 8.88 (s, 1H), 8.21 (d, 2H), 8.00 (d, 2H), 7.88 (s, 1H), 7.72 (s, 1H), 7.65 (d, 1H), 2.51 (s, 3H); (yield: 48%)

Example 266

(Z)-4-[2-{(2,4-Dioxothiazolidin-5-ylidene)methyl}furo[3,2-c]pyridin-7-yl]-N-isopropylbenzenesulfonamide $^1$H NMR (DMSO-d$_6$, 400 MHz) δ 9.11 (s, 1H), 8.86 (s, 1H), 8.16 (d, 2H), 8.02 (d, 2H), 7.88 (s, 1H), 7.78 (d, 1H), 7.72 (s, 1H), 3.36 (m, 1H), 1.01 (d, 6H); (yield: 58%)

Example 267

(Z)-4-[2-{(2,4-Dioxothiazolidin-5-ylidene)methyl}furo[3,2-c]pyridin-7-yl]benzamide $^1$H NMR (DMSO-d$_6$, 400 MHz) δ 12.69 (brs, 1H), 9.08 (s, 1H), 8.87 (s, 1H), 8.06-8.18 (m, 5H), 7.88 (s, 1H), 7.71 (s, 1H), 7.50 (brs, 1H); (yield: 45%)

Example 268

(Z)-5-[2-{(2,4-Dioxothiazolidin-5-ylidene)methyl}furo[3,2-c]pyridin-7-yl]thiophene-2-sulfonamide $^1$H NMR (DMSO-d$_6$, 400 MHz) δ 12.73 (brs, 1H), 9.67 (s, 1H), 8.96 (s, 1H), 7.87-7.94 (m, 4H), 7.74 (d, 2H); (yield: 36%)

Example 269

(Z)-5-[{7-(Benzo[d]thiazol-2-yl)furo[3,2-c]pyridin-2-yl}methylene]thiazolidine-2,4-dione $^1$H NMR (DMSO-d$_6$, 400 MHz) δ 12.74 (brs, 1H), 9.34 (s, 1H), 9.21 (s, 1H), 8.33 (d, 1H), 8.18 (d, 1H), 7.91 (s, 1H), 7.78 (s, 1H), 7.66 (m, 1H), 7.56 (m, 1H); (yield: 20%)

Example 270

(Z)-5-[{7-(6-Methoxypyridazin-3-yl)furo[3,2-c]pyridin-2-yl}methylene]thiazolidine-2,4-dione $^1$H NMR (DMSO-d$_6$, 400 MHz) δ 12.73 (brs, 1H), 9.10-9.17 (m, 2H), 8.36 (d, 1H), 7.88 (s, 1H), 7.72 (s, 1H), 7.60 (t, 1H), 4.15 (s, 3H); (yield: 23%)

Example 271

(Z)-5-[{7-(1H-Indol-5-yl)furo[3,2-c]pyridin-2-yl}methylene]thiazolidine-2,4-dione $^1$H NMR (DMSO-d$_6$, 300 MHz) δ 11.32 (s, 1H), 8.99 (d, 1H), 8.81 (s, 1H), 8.21 (s, 1H), 7.88 (s, 1H), 7.69-7.76 (m, 3H), 7.58-7.62 (m, 1H), 7.48 (s, 1H), 6.54 (s, 1H); (yield: 22%)

Example 272

(Z)-4-[2-{(2,4-Dioxothiazolidin-5-ylidene)methyl}furo[3,2-c]pyridin-7-yl]-N,N-dimethylbenzenesulfonamide $^1$H NMR (DMSO-d$_6$, 400 MHz) δ 12.71 (brs, 1H), 9.12 (s, 1H), 8.88 (s, 1H), 8.22 (d, 2H), 7.96 (d, 2H), 7.88 (s, 1H), 7.71 (s, 1H), 2.69 (s, 6H); (yield: 66%)

Example 273

(Z)-5-[{7-(3-Chloro-4-hydroxyphenyl)furo[3,2-c]pyridin-2-yl}methylene]thiazolidine-2,4-dione $^1$H NMR (DMSO-d$_6$, 400 MHz) δ 12.69 (brs, 1H), 10.66 (s, 1H), 9.00 (s, 1H), 8.78 (s, 1H), 8.06 (s, 1H), 7.87 (s, 1H), 7.78 (d, 1H), 7.68 (s, 1H), 7.17 (d, 1H); (yield: 55%)

Example 274

(Z)-5-[{7-(4-Hydroxy-3-methylphenyl)furo[3,2-c]pyridin-2-yl}methylene]thiazolidine-2,4-dione $^1$H NMR (DMSO-d$_6$, 400 MHz) δ 12.69 (brs, 1H), 9.77 (s, 1H), 8.945 (s, 1H), 8.72 (s, 1H), 7.87 (s, 1H), 7.78 (s, 1H), 7.67 (s, 1H), 7.62 (d, 1H), 6.98 (d, 1H), 2.26 (s, 3H); (yield: 51%)

Example 275

(Z)-5-[{7-(3-Fluoro-4-hydroxyphenyl)furo[3,2-c]pyridin-2-yl}methylene]thiazolidine-2,4-dione $^1$H NMR (DMSO-d$_6$, 400 MHz) δ 12.70 (brs, 1H), 10.34 (s, 1H), 9.00 (s, 1H), 8.77 (s, 1H), 7.87 (s, 1H), 7.83 (d, 1H), 7.68 (s, 1H), 7.64 (d, 1H), 7.16 (d, 1H); (yield: 50%)

Example 276

(Z)-5-[2-{(2,4-Dioxothiazolidin-5-ylidene)methyl}furo[3,2-c]pyridin-7-yl]-2-hydroxybenzonitrile $^1$H NMR (DMSO-d$_6$, 400 MHz) δ 12.65 (brs, 1H), 11.53 (brs, 1H), 8.99 (s, 1H), 8.77 (s, 1H), 8.25 (m, 1H), 8.14 (d, 1H), 7.75 (s, 1H), 7.59 (s, 1H), 7.22 (d, 1H); (yield: 47%)

Example 277

(Z)-5-[{7-(4-Hydroxy-3-propionylphenyl)furo[3,2-c]pyridin-2-yl}methylene]thiazolidine-2,4-dione $^1$H NMR (DMSO-d$_6$, 400 MHz) δ 12.68 (brs, 1H), 11.97 (s, 1H), 9.03 (s, 1H), 8.79 (s, 1H), 8.35 (m, 1H), 8.07 (d, 1H), 7.87 (s, 1H), 7.70 (s, 1H), 7.20 (d, 1H), 3.25 (m, 2H), 1.13 (t, 3H); (yield: 21%)

Example 278

(Z)-5-[2-{(2,4-Dioxothiazolidin-5-ylidene)methyl}furo[3,2-c]pyridin-7-yl]-2-methoxynicotinonitrile $^1$H NMR (DMSO-d$_6$, 400 MHz) δ 12.72 (brs, 1H), 9.01 (s, 1H), 8.88 (s, 1H), 7.89 (s, 1H), 7.71 (s, 1H), 4.11 (s, 3H), 1.91 (s, 3H); (yield: 46%)

Example 279

(Z)-4-[2-{(2,4-Dioxothiazolidin-5-ylidene)methyl}furo[3,2-c]pyridin-7-yl]-2-fluoro-N-methyl-benzenesulfonamide $^1$H NMR (DMSO-d$_6$, 400 MHz) δ 12.72 (brs, 1H), 9.14 (s, 1H), 8.93 (s, 1H), 8.13 (d, 1H), 8.02 (dd, 1H), 7.97 (d, 2H), 7.73 (s, 1H), 2.58 (d, 3H); (yield: 52%)

Example 280

(Z)-4-[2-{(2,4-Dioxothiazolidin-5-ylidene)methyl}furo[3,2-c]pyridin-7-yl]-2-fluoro-N,N-dimethylbenzenesulfonamide $^1$H NMR (DMSO-d$_6$, 400 MHz) δ 12.73 (brs, 1H), 9.14 (s, 1H), 8.94 (s, 1H), 8.17 (d, 1H), 8.05 (d, 1H), 8.00 (m, 1H), 7.88 (s, 1H), 7.72 (s, 1H), 2.80 (s, 6H); (yield: 57%)

Example 281

(Z)-5-([7-{3-Fluoro-4-(morpholinosulfonyl)phenyl}furo[3,2-c]pyridin-2-yl]methylene)thiazolidine-2,4-dione $^1$H NMR (DMSO-d$_6$, 400 MHz) δ 12.73 (brs, 1H), 9.14 (s, 1H), 8.94 (s, 1H), 8.18 (d, 1H), 8.06 (d, 1H), 7.98 (t, 1H), 7.89 (s, 1H), 7.72 (s, 1H), 3.68 (brs, 4H), 3.12 (brs, 4H); (yield: 50%)

Example 282

(Z)-5-([7-{3,5-Difluoro-4-(methylsulfonyl)phenyl}furo[3,2-c]pyridin-2-yl]methylene)thiazolidine-2,4-dione $^1$H NMR (DMSO-d$_6$, 400 MHz) δ 12.75 (brs, 1H), 9.16 (s, 1H), 9.01 (s, 1H), 8.08 (d, 2H), 7.90 (s, 1H), 7.73 (s, 1H), 3.53 (s, 3H); (yield: 51%)

Example 283

(Z)-5-([7-{3-Fluoro-4-(methylsulfonyl)phenyl}furo[3,2-c]pyridin-2-yl]methylene)thiazolidine-2,4-dione $^1$H NMR (DMSO-d$_6$, 400 MHz) δ 12.73 (brs, 1H), 9.14 (s, 1H), 8.94 (s, 1H), 8.20 (d, 1H), 8.12-8.05 (m, 2H), 7.89 (s, 1H), 7.73 (s, 1H), 3.44 (s, 3H); (yield: 53%)

Example 284

(Z)-Methyl 4-[2-{(2,4-dioxothiazolidin-5-ylidene)methyl}furo[3,2-c]pyridin-7-yl]-2,6-difluorobenzoate $^1$H NMR (DMSO-d$_6$, 400 MHz) δ 11.96 (brs, 1H), 9.12 (s, 1H), 8.95 (s, 1H), 7.97 (d, 2H), 7.80 (s, 1H), 7.65 (s, 1H), 3.95 (s, 3H); (yield: 55%)

Example 285

(Z)-5-[{7-(4-Amino-3,5-difluorophenyl)furo[3,2-c]pyridin-2-yl}methylene]thiazolidine-2,4-dione $^1$H NMR (DMSO-d$_6$, 400 MHz) δ 12.72 (brs, 1H), 8.98 (s, 1H), 8.81 (s, 1H), 7.89 (s, 1H), 7.71-7.65 (m, 3H), 5.70 (brs, 2H); (yield: 54%)

Example 286

(Z)-5-[{7-(4-Amino-3,5-dimethylphenyl)furo[3,2-c]pyridin-2-yl}methylene]thiazolidine-2,4-dione $^1$H NMR (DMSO-d$_6$, 400 MHz) δ 8.88 (s, 1H), 8.71 (s, 1H), 7.87 (s, 1H), 7.64 (s, 1H), 7.54 (s, 2H), 5.00 (brs, 2H), 2.21 (s, 6H); (yield: 50%)

Example 287

(Z)-2,6-Dichloro-4-[2-{(2,4-dioxothiazolidin-5-ylidene)methyl}furo[3,2-c]pyridin-7-yl]-N-methyl-benzenesulfonamide $^1$H NMR (DMSO-d$_6$, 400 MHz) δ 12.72 (brs, 1H), 9.14 (s, 1H), 9.00 (s, 1H), 8.32 (s, 2H), 8.11 (t, 1H), 7.89 (s, 1H), 7.73 (s, 1H), 2.62 (d, 3H); (yield: 52%)

Example 288

(Z)-2,6-Dichloro-4-[2-{(2,4-dioxothiazolidin-5-ylidene)methyl}furo[3,2-c]pyridin-7-yl]-N,N-dimethylbenzenesulfonamide $^1$H NMR (DMSO-d$_6$, 400 MHz) δ 12.72 (brs, 1H), 9.14 (s, 1H), 9.01 (s, 1H), 8.34 (s, 2H), 7.88 (s, 1H), 7.72 (s, 1H), 2.94 (s, 3H); (yield: 51%)

Example 289

(Z)-5-([7-{3,5-Dichloro-4-(morpholinosulfonyl)phenyl}furo[3,2-c]pyridin-2-yl]methylene)thiazolidine-2,4-dione $^1$H NMR (DMSO-d$_6$, 400 MHz) δ 12.71 (brs, 1H), 9.14 (s, 1H), 9.00 (s, 1H), 8.35 (s, 2H), 7.88 (s, 1H), 7.71 (s, 1H), 3.66 (t, 4H), 3.35 (t, 4H); (yield: 52%)

Example 290

(Z)-2,6-Dichloro-4-[2-{(2,4-dioxothiazolidin-5-ylidene)methyl}furo[3,2-c]pyridin-7-yl]-N-ethylbenzenesulfonamide $^1$H NMR (DMSO-d$_6$, 400 MHz) δ 12.71 (brs, 1H), 9.14 (s, 1H), 8.30 (s, 1H), 8.25 (t, 1H), 7.89 (s, 1H), 7.72 (s, 1H), 3.02 (q, 2H), 1.04 (t, 3H); (yield: 53%)

Example 291

(Z)-2,6-Dichloro-4-[2-{(2,4-dioxothiazolidin-5-ylidene)methyl}furo[3,2-c]pyridin-7-yl]-N-isopropylbenzenesulfonamide $^1$H NMR (DMSO-d$_6$, 400 MHz) δ 12.70 (brs, 1H), 9.13 (s, 1H), 8.98 (s, 1H), 8.29 (s, 1H), 8.22 (d, 1H), 7.88 (s, 1H), 7.71 (s, 1H), 3.47 (m, 1H), 1.06 (d, 6H); (yield: 56%)

Example 292

(Z)-4-[2-{(2,4-Dioxothiazolidin-5-ylidene)methyl}furo[3,2-c]pyridin-7-yl]-N-methyl-2-(trifluoromethoxy)benzenesulfonamide $^1$H NMR (DMSO-d$_6$, 400 MHz) δ 9.15 (s, 1H), 8.88 (s, 1H), 8.16-8.10 (m, 3H), 7.88-7.87 (m, 2H), 7.73 (s, 1H), 2.59 (d, 3H); (yield: 54%)

Example 293

(Z)-4-[2-{(2,4-Dioxothiazolidin-5-ylidene)methyl}furo[3,2-c]pyridin-7-yl]-N,N-dimethyl-2-(trifluoromethoxy)benzenesulfonamide $^1$H NMR (DMSO-d$_6$, 400 MHz) δ 12.71 (brs, 1H), 9.15 (s, 1H), 8.89 (s, 1H), 8.15 (m, 3H), 7.87 (s, 1H), 7.73 (s, 1H), 2.82 (s, 6H); (yield: 52%)

Example 294

(Z)-5-([7-{4-(Morpholinosulfonyl)-3-(trifluoromethoxy)phenyl}furo[3,2-c]pyridin-2-yl]methylene)thiazolidine-2,4-dione $^1$H NMR (DMSO-d$_6$, 400 MHz) δ 12.71 (brs, 1H), 9.16 (s, 1H), 8.89 (s, 1H), 8.17-8.15 (m, 3H), 7.87 (s, 1H), 7.72 (s, 1H), 3.66 (t, 4H), 3.13 (t, 4H); (yield: 52%)

Example 295

(Z)-4-[2-{(2,4-Dioxothiazolidin-5-ylidene)methyl}furo[3,2-c]pyridin-7-yl]-3-fluoro-N,N-dimethylbenzenesulfonamide $^1$H NMR (DMSO-d$_6$, 400 MHz) δ 12.67 (brs, 1H), 9.17 (s, 1H), 8.74 (s, 1H), 8.04 (t, 1H), 7.89 (d, 1H), 7.85 (s, 1H), 7.81 (d, 1H), 7.71 (s, 1H), 2.72 (s, 6H); (yield: 50%)

Example 296

(Z)—N-tert-Butyl-2,6-dichloro-4-[2-{(2,4-dioxothiazolidin-5-ylidene)methyl}furo[3,2-c]pyridin-7-yl]benzenesulfonamide $^1$H NMR (DMSO-d$_6$, 400 MHz) δ 12.69 (brs, 1H), 9.13 (s, 1H), 8.97 (s, 1H), 8.26 (s, 2H), 8.08 (s, 1H), 7.88 (s, 1H), 7.71 (s, 1H), 1.21 (s, 9H); (yield: 51%)

Example 297

(Z)-2,6-Dichloro-4-[2-{(2,4-dioxothiazolidin-5-ylidene)methyl}furo[3,2-c]pyridin-7-yl]-N-(2-hydroxyethyl)benzenesulfonamide $^1$H NMR (DMSO-d$_6$, 400 MHz) δ 12.71 (brs, 1H), 9.14 (s, 1H), 9.00 (d, 1H), 8.50 (t, 1H), 8.32 (s, 2H), 7.89 (s, 1H), 7.72 (s, 1H), 4.70 (brs, 1H), 4.00 (t, 2H), 3.00 (t, 2H); (yield: 49%)

Example 298

(Z)-4-[2-{(2,4-Dioxothiazolidin-5-ylidene)methyl}furo[3,2-c]pyridin-7-yl]-N,N,3-trimethylbenzenesulfonamide $^1$H NMR (DMSO-d$_6$, 400 MHz) δ 12.63 (brs, 1H), 9.14 (s, 1H), 8.60 (s, 1H), 7.83 (d, 2H), 7.75-7.70 (m, 3H), 2.67 (s, 6H), 2.32 (s, 3H); (yield: 53%)

Example 299

(Z)-Methyl 4-[2-{(2,4-dioxothiazolidin-5-ylidene)methyl}furo[3,2-c]pyridin-7-yl]-2-methoxybenzoate $^1$H NMR (DMSO-d$_6$, 400 MHz) δ 9.10 (s, 1H), 8.86 (s, 1H), 7.86 (d, 2H), 7.71 (s, 1H), 7.64 (s, 1H), 7.59 (d, 1H), 3.97 (s, 3H), 3.85 (s, 3H); (yield: 56%)

Example 300

(Z)-Methyl 4-[2-{(2,4-dioxothiazolidin-5-ylidene)methyl}furo[3,2-c]pyridin-7-yl]-2-fluorobenzoate $^1$H NMR (DMSO-d$_6$, 400 MHz) δ 12.66 (brs, 1H), 9.12 (s, 1H), 8.92 (s, 1H), 8.10 (t, 1H), 8.03 (d, 1H), 7.97 (d, 1H), 7.87 (s, 1H), 7.71 (s, 1H), 3.92 (s, 3H); (yield: 54%)

Example 301

(Z)-Methyl 3-[2-{(2,4-dioxothiazolidin-5-ylidene)methyl}furo[3,2-c]pyridin-7-yl]-5-fluorobenzoate $^1$H NMR (DMSO-d$_6$, 400 MHz) δ 12.65 (brs, 1H), 9.10 (s, 1H), 8.90 (s, 1H), 8.44 (s, 1H), 8.13 (d, 1H), 7.85-7.83 (m, 2H), 7.71 (s, 1H), 3.93 (s, 3H); (yield: 57%)

Example 302

(Z)-Methyl 2-chloro-5-[2-{(2,4-dioxothiazolidin-5-ylidene)methyl}furo[3,2-c]pyridin-7-yl]benzoate $^1$H NMR (DMSO-d$_6$, 400 MHz) δ 12.65 (brs, 1H), 9.08 (s, 1H), 8.86 (s, 1H), 8.44 (s, 1H), 8.12 (d, 1H), 7.86 (s, 1H), 7.82 (d, 1H), 7.71 (s, 1H), 3.93 (s, 3H); (yield: 52%)

Example 303

(Z)—N-(4-[2-{(2,4-Dioxothiazolidin-5-ylidene)methyl}furo[3,2-c]pyridin-7-yl]phenyl)methanesulfonamide $^1$H NMR (DMSO-d$_6$, 400 MHz) δ 12.65 (brs, 1H), 10.02 (s, 1H), 9.02 (s, 1H), 8.78 (s, 1H), 7.96 (d, 2H), 7.86 (s, 1H), 7.68 (s, 1H), 7.42 (d, 2H), 3.09 (s, 3H); (yield: 57%)

Example 304

(Z)-3-[2-{(2,4-Dioxothiazolidin-5-ylidene)methyl}furo[3,2-c]pyridin-7-yl]-N,N-dimethylbenzamide $^1$H NMR (DMSO-d$_6$, 400 MHz) δ 12.60 (brs, 1H), 9.05 (s, 1H), 8.86 (s, 1H), 8.03-8.01 (m, 2H), 7.84 (s, 1H), 7.68-7.64 (m, 2H), 7.52 (d, 1H), 3.01 (brs, 6H); (yield: 51%)

Example 305

(Z)—N-(4-[2-{(2,4-Dioxothiazolidin-5-ylidene)methyl}furo[3,2-c]pyridin-7-yl]-2,6-dimethylphenyl)methanesulfonamide $^1$H NMR (DMSO-d$_6$, 400 MHz) δ 9.02 (s, 1H), 8.91 (brs, 1H), 8.81 (s, 1H), 7.85 (s, 1H), 7.75 (s, 2H), 7.67 (s, 1H), 3.11 (s, 3H), 2.45 (s, 6H); (yield: 51%)

Example 306

(Z)-4-[2-{(2,4-Dioxothiazolidin-5-ylidene)methyl}furo[3,2-c]pyridin-7-yl]-N,2-dimethylbenzenesulfonamide $^1$H NMR (DMSO-d$_6$, 400 MHz) δ 12.71 (brs, 1H), 9.11 (s, 1H), 8.89 (s, 1H), 8.09 (s, 1H), 7.99 (s, 2H), 7.89 (s, 1H), 7.72 (s, 1H), 7.66 (t, 1H), 2.71 (s, 3H), 2.50 (s, 3H); (yield: 51%)

Example 307

(Z)-5-([7-{3-Methyl-4-(morpholinosulfonyl)phenyl}furo[3,2-c]pyridin-2-yl]methylene)thiazolidine-2,4-dione $^1$H NMR (DMSO-d$_6$, 400 MHz) δ 12.71 (brs, 1H), 9.12 (s, 1H), 8.89 (s, 1H), 8.12 (s, 1H), 8.00 (s, 2H), 7.89 (s, 1H), 7.71 (s, 1H), 3.65 (t, 4H), 3.09 (t, 3H), 2.73 (s, 3H); (yield: 53%)

Example 308

(Z)-4-[2-{(2,4-Dioxothiazolidin-5-ylidene)methyl}furo[3,2-c]pyridin-7-yl]-N-ethyl-2-methyl-benzenesulfonamide $^1$H NMR (DMSO-d$_6$, 400 MHz) δ 12.71 (brs, 1H), 9.10 (s, 1H), 8.87 (s, 1H), 8.06 (s, 1H), 8.00 (d, 1H), 7.95 (d, 1H), 7.88 (s, 1H), 7.80 (t, 1H), 7.71 (s, 1H), 2.87 (q, 2H), 2.72 (s, 3H), 1.00 (t, 3H); (yield: 56%)

Example 309

(Z)-4-[2-{(2,4-Dioxothiazolidin-5-ylidene)methyl}furo[3,2-c]pyridin-7-yl]-N-isopropyl-2-methylbenzenesulfonamide $^1$H NMR (DMSO-d$_6$, 400 MHz) δ 12.70 (brs, 1H), 9.10 (s, 1H), 8.86 (s, 1H), 8.04 (t, 1H), 7.94 (d, 1H), 7.88 (s, 1H), 7.78 (d, 1H), 7.71 (s, 1H), 2.72 (s, 3H), 1.00 (d, 6H); (yield: 50%)

Example 310

(Z)—N-tert-Butyl-4-[2-{(2,4-dioxothiazolidin-5-ylidene)methyl}furo[3,2-c]pyridin-7-yl]-2-methyl-benzenesulfonamide $^1$H NMR (DMSO-d$_6$, 400 MHz) δ 12.69 (brs, 1H), 9.09 (s, 1H), 8.85 (s, 1H), 8.06 (d, 1H), 8.00 (s, 1H), 7.91 (d, 1H), 7.90 (s, 1H), 7.70 (s, 1H), 7.65 (s, 1H), 2.73 (s, 3H), 1.15 (s, 9H); (yield: 55%)

Example 311

(Z)-2-Amino-5-[2-{(2,4-dioxothiazolidin-5-ylidene)methyl}furo[3,2-c]pyridin-7-yl]benzonitrile $^1$H NMR (DMSO-d$_6$, 400 MHz) δ 12.70 (brs, 1H), 9.02 (s, 1H), 8.80 (s, 1H), 8.08 (s, 1H), 7.96 (d, 1H), 7.89 (s, 1H), 7.70 (s, 1H), 7.01 (d, 1H), 6.51 (brs, 2H)

Example 312

(Z)-5-([7-{4-Amino-3-(trifluoromethyl)phenyl}furo[3,2-c]pyridin-2-yl]methylene)thiazolidine-2,4-dione $^1$H NMR (DMSO-d$_6$, 400 MHz) δ 12.68 (brs, 1H), 9.01 (s, 1H), 8.77 (s, 1H), 7.98 (s, 1H), 7.90-7.85 (m, 2H), 7.71 (s, 1H), 7.05 (d, 1H), 6.05 (brs, 2H)

Example 313

(Z)-5-[{7-(6-Amino-5-methylpyridin-3-yl)furo[3,2-c]pyridin-2-yl}methylene]thiazolidine-2,4-dione $^1$H NMR (DMSO-d$_6$, 400 MHz) δ 11.96 (brs, 1H), 8.95 (s, 1H), 8.77 (s, 1H), 8.51 (s, 1H), 7.97 (s, 1H), 7.87 (s, 1H), 7.67 (s, 1H), 6.41 (brs, 1H), 1.91 (s, 3H)

Example 314

(Z)-5-([7-{4-(1-Methyl-5-oxo-1H-1,2,4-trizol-4(5H)-yl)phenyl}furo[3,2-c]pyridin-2-yl]methylene)thiazolidine-2,4-dione $^1$H NMR (DMSO-d$_6$, 400 MHz) δ 12.71 (brs, 1H), 9.07 (s, 1H), 8.85 (s, 1H), 8.64 (s, 1H), 8.13 (d, 1H), 8.00 (d, 1H), 7.88 (s, 1H), 7.72 (s, 1H), 3.43 (s, 3H)

Example 315

(Z)-5-([7-{4-(1-Isopropyl-5-oxo-1H-1,2,4-triazol-4(5H)-yl)phenyl}furo[3,2-c]pyridin-2-yl]methylene)thiazolidine-2,4-dione $^1$H NMR (DMSO-d$_6$, 400 MHz) δ 12.71 (brs, 1H), 9.07 (s, 1H), 8.85 (s, 1H), 8.64 (s, 1H), 8.13 (d, 1H), 8.01 (d, 1H), 7.88 (s, 1H), 7.72 (s, 1H), 4.43 (q, 1H), 1.34 (d, 6H)

Example 316

(Z)-5-([7-{2-Methoxy-5-(pyrrolidin-1-ylmethyl)phenyl}furo[3,2-c]pyridin-2-yl]methylene)thiazolidine-2,4-dione Step 1: Synthesis of 3-{2-(diethoxymethyl)furo[3,2-c]pyridin-7-yl}-4-methoxybenzaldehyde A solution prepared by dissolving 2-(diethoxymethyl)-7-(4,4,5,5-tetramethyl-1,3-dioxaborolan-2-yl)furo[3,2-c]pyridine (1.0 mmol) prepared in Reference Example 2 in toluene/water (2/1, v/v, 5 ml) was added with 3-bromo-4-methoxybenzaldehyde (1.2 mmol), sodium carbonate (2.2 mmol), tetrakis(triphenylphosphine)palladium(0) (5.0 mol %), and stirred under reflux for 12 hours under a nitrogen atmosphere. The organic layer was separated and concentrated under reduced pressure. The residue thus obtained was purified by silica gel column chromatography (n-hexane/ethyl acetate=4/1, v/v) to obtain the title compound as light brown oil (yield: 61%).

Step 2: Synthesis of 2-(diethoxymethyl)-7-{2-methoxy-5-(pyrrolidin-1-ylmethyl)phenyl}furo[3,2-c]pyridine A solution prepared by dissolving 3-{2-(diethoxymethyl)furo[3,2-c]pyridin-7-yl}-4-methoxybenzaldehyde (1.0 mmol) obtained in Step 1, pyrrolidine (3.0 mmol) and acetic acid (catalytic amount) in tetrahydrofuran (5 ml) was stirred at room temperature for 30 minutes, which was further added with sodium triacetoxyborohydride (4 mmol). The reaction solution was stirred at room temperature overnight. The reaction was terminated by adding a saturated sodium bicarbonate solution. The reaction was added with dichloromethane, extracted, and the extract was dried over anhydrous magnesium sulfate, filtered, and concentrated under reduced pressure. The residue thus obtained was purified by silica gel column chromatography (n-hexane/ethyl acetate=2/1, v/v) to obtain the title compound as a white solid (yield: 91%).

Step 3: Synthesis of 7-{2-methoxy-5-(pyrrolidin-1-ylmethyl)phenyl}furo[3,2-c]pyridine-2-carbaldehyde A solution prepared by dissolving 2-(diethoxymethyl)-7-{2-methoxy-5-(pyrrolidin-1-ylmethyl)phenyl}furo[3,2-c]pyridine (0.5 mmol) obtained in Step 2 in tetrahydrofuran (5 ml) was added with a 3N aqueous hydrochloric acid solution (5 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract was washed with brine, dried over anhydrous magnesium sulfate, filtered, and the filtrate was concentrated under reduced pressure. The residue thus obtained was purified by silica gel column chromatography (n-hexane/ethyl acetate=2/1, v/v) to obtain the title compound as a white solid (yield: 84%).

Step 4: Synthesis of (Z)-5-([7-{2-methoxy-5-(pyrrolidin-1-ylmethyl)phenyl}furo[3,2-c]pyridin-2-yl]methylene)thiazolidine-2,4-dione A solution prepared by dissolving 7-{2-methoxy-5-(piperidin-1-ylmethyl)phenyl}furo[3,2-c]pyridine-2-carbaldehyde (0.4 mmol) obtained in Step 3 in acetic acid (3 ml) was added thiazolidinedione (0.5 mmol) and β-alanine (0.4 mmol), and stirred under reflux for 4 hours. After cooled to room temperature, the resulting solid was filtered, washed with acetic acid and water, and dried to obtain the title compound as a light yellow solid (yield: 69%).

$^1$H NMR (DMSO-$d_6$, 300 MHz) δ 8.95 (s, 1H), 8.49 (s, 1H), 7.60 (m, 2H), 7.30 (m, 3H), 4.18 (brs, 2H), 3.82 (brs, 3H), 3.07 (brs, 4H), 1.88 (brs, 4H)

Example 317

(Z)-5-([7-{2-Methoxy-5-(morpholinomethyl)phenyl}furo[3,2-c]pyridin-2-yl]methylene)thiazolidine-2,4-dione The title compound of Example 316 was prepared in the same manner as described in Example 316 above, except for using morpholine instead of pyrrolidine in Step 2 of Example 316.

$^1$H NMR (DMSO-$d_6$, 300 MHz) δ 8.99 (s, 1H), 8.55 (s, 1H), 7.69 (s, 1H), 7.56 (s, 1H), 7.47 (m, 2H), 7.23 (d, 1H), 3.79 (s, 3H), 3.58 (m, 6H), 2.50 (brs, 4H); (yield: 23%)

Example 318

(Z)-5-([7-{2-Methoxy-5-(piperidin-1-ylmethyl)phenyl}furo[3,2-c]pyridin-2-yl]methylene)thiazolidine-2,4-dione The title compound of Example 316 was prepared in the same manner as described in Example 316 above, except for using piperidine instead of pyrrolidine in Step 2 of Example 316.

$^1$H NMR (DMSO-$d_6$, 300 MHz) δ 8.96 (s, 1H), 8.52 (s, 1H), 7.57 (m, 2H), 7.41 (s, 1H), 7.36 (s, 1H), 7.30 (d, 1H), 4.03 (brs, 2H), 3.82 (s, 3H), 2.89 (brs, 4H), 1.65 (brs, 4H), 1.48 (brs, 2H)

Example 319

(Z)-5-([7-{6-(Methylsulfonyl)pyridin-3-yl}furo[3,2-c]pyridin-2-yl]methylene)-2-thioxothiazolidin-4-one Step 1: Synthesis of 2-(diethoxymethyl)-7-{6-(methylsulfonyl)pyridin-3-yl}furo[3,2-c]pyridine A solution prepared by 2-(diethoxymethyl)-7-(4,4,5,5-tetramethyl-1,3-dioxaborolan-2-yl)furo[3,2-c]pyridine (1.0 mmol) obtained in Reference Example 2 in tetrahydrofuran/water (4/1, v/v, 5 ml) was added with 5-bromo-2-(methylsulfonyl)pyridine (1.2 mmol), sodium carbonate (2.2 mmol) and tetrakis(triphenylphosphine)palladium(0) (5.0 mol %), and stirred under reflux for 12 hours under a nitrogen atmosphere. The organic layer was separated and concentrated under reduced pressure. The residue thus obtained was purified by silica gel column chromatography (n-hexane/ethyl acetate=4/1, v/v) to obtain the title compound as light brown oil (yield: 51%).

Step 2: Synthesis of 7-{6-(methylsulfonyl)pyridin-3-yl}furo[3,2-c]pyridine-2-carbaldehyde A solution prepared by dissolving 2-(diethoxymethyl)-7-{6-(methylsulfonyl)pyridin-3-yl}furo[3,2-c]pyridine (0.5 mmol) obtained in Step 1 in tetrahydrofuran (5 ml) was a 3N aqueous hydrochloric acid solution (5 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract washed with brine, dried over anhydrous magnesium sulfate, filtered, and concentrated under reduced pressure. The residue thus obtained was purified by silica gel column chromatography (n-hexane/ethyl acetate=4/1, v/v) to obtain the title compound as light brown oil (yield: 80%).

Step 3: Synthesis of (Z)-2-thioxo-5-([7-{4-(trifluoromethoxy)phenyl}furo[3,2-c]pyridin-2-yl]methylene)thiazolidin-4-one A solution prepared by dissolving 7-{6-(methylsulfonyl)pyridin-3-yl}furo[3,2-c]pyridine-2-carbaldehyde (0.1 mmol) obtained in Step 2 in acetic acid (3 ml) was added with rhodanine (0.11 mmol) and sodium acetate (0.12 mmol), and stirred under reflux for 5 hours. After cooled to room temperature, the resulting solid was filtered, washed with acetic acid and water, and dried to obtain the title compound as a yellow solid (yield: 82%).

$^1$H NMR (DMSO-$d_6$, 400 MHz) δ 9.40 (s, 1H), 9.19 (s, 1H), 8.97 (s, 1H), 8.75 (d, 1H), 8.25 (d, 1H), 7.80 (s, 1H), 7.76 (s, 1H), 3.40 (s, 3H)

Examples 320 to 363

The title compounds of Examples 320 to 363 were prepared in the same manner as described in Example 319 above, except for using each of the following compounds: 3-bromo-N,N-dimethylbenzenesulfonamide, 4-bromo-N,N-dimethylbenzenesulfonamide, 4-bromo-2-chlorophenol, 4-bromo-o-cresol, 5-bromo-2-hydroxybenzonitrile, 1-(5- bromo-2-hydroxyphenyl)propan-1-one, 1-(5-bromo-2-hydroxyphenyl)ethanone, 4-bromo-2-fluorophenol, 5-bromo-2-methoxypyridine-3-carbonitrile, 4-bromo-2-fluoro-N-methylbenzenesulfonamide, 4-bromo-2-fluoro-N,N-dimethylbenzenesulfonamide, 4-(4-bromo-2-fluorophenylsulfonyl)morpholine, 5-bromo-1,3-difluoro-2-(methylsulfonyl)benzene, 4-bromo-2-fluoro-1-(methylsulfonyl)benzene, methyl 4-bromo-2,6-difluorobenzoate, 4-bromo-2,6-difluoroaniline, 4-bromo-2,6-dimethylaniline, 4-bromo-2-methylaniline, 4-bromo-N-methyl-2-(trifluoromethoxy)benzenesulfonamide, 4-bromo-N,N-dimethyl-2-(trifluoromethoxy)benzenesulfonamide, 4-{4-bromo-2-(trifluoromethoxy)phenylsulfonyl}morpholine, 4-bromo-2,6-dichloro-N-methylbenzenesulfonamide, 4-bromo-2,6-dichloro-N,N-dimethylbenzenesulfonamide, 4-(4-bromo-2,6-dichlorophenylsulfonyl)morpholine, 4-bromo-2,6-dichloro-N-ethylbenzenesulfonamide, 4-bromo-2,6-dichloro-N-isopropylbenzenesulfonamide, 4-bromo-N-tert-butyl-2,6-dichlorobenzenesulfonamide, 4-bromo-2,6-dichloro-N-(2-hydroxyethyl)benzenesulfonamide, 4-bromo-N,N,3-trimethylbenzenesulfonamide, methyl 4-bromo-2-methoxybenzoate, methyl 4-bromo-2-fluorobenzoate, methyl 3-bromo-5-fluorobenzoate, methyl 5-bromo-2-chlorobenzoate, N-(4-bromophenyl)methanesulfonamide, 3-bromo-N,N-dimethylbenzamide, N-(4-bromo-2,6-dimethylphenyl)methanesulfonamide, 4-bromo-N-ethyl-2-methylbenzenesulfonamide, 4-bromo-N-isopropyl-2-methylbenzenesulfonamide, 4-bromo-N-tert-butyl-2-methylbenzenesulfonamide, 4-bromo-N-(2-hydroxyethyl)-2-methylbenzenesulfonamide, 2-amino-5-bromobenzonitrile, 4-bromo-2-(trifluoromethyl)aniline, 4-(4-bromophenyl)-1-methyl-1H-1,2,4-triazol-5(4H)-one and 4-(4-bromophenyl)-1-isopropyl-1H-1,2,4-triazol-5(4H)-one, instead of 5-bromo-2-(methylsulfonyl)pyridine in Step 1 of Example 319.

Example 320

(Z)—N,N-Dimethyl-3-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.13 (s, 1H), 8.83 (s, 1H), 7.31 (m, 1H), 8.19 (s, 1H), 7.95~7.87 (m, 2H), 7.78 (s, 1H), 7.72 (s, 1H), 2.72 (s, 6H); (yield: 56%)

Example 321

(Z)—N,N-Dimethyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 13.90 (brs, 1H), 9.14 (s, 1H), 8.87 (s, 1H), 8.22 (d, 2H), 7.94 (d, 2H), 7.76 (s, 1H), 7.73 (s, 1H), 2.69 (s, 6H); (yield: 52%)

Example 322

(Z)-5-[{7-(3-Chloro-4-hydroxyphenyl)furo[3,2-c]pyridin-2-yl}methylene]-2-thioxothiazolidin-4-one $^1$H NMR (DMSO-d$_6$, 400 MHz) δ 10.67 (s, 1H), 9.01 (s, 1H), 8.79 (s, 1H), 8.09 (s, 1H), 7.79 (s, 1H), 7.77 (m, 2H), 7.18 (d, 1H); (yield: 50%)

Example 323

(Z)-5-[{7-(4-Hydroxy-3-methylphenyl)furo[3,2-c]pyridin-2-yl}methylene]-2-thioxothiazolidin-4-one $^1$H NMR (DMSO-d$_6$, 400 MHz) δ 9.80 (s, 1H), 8.97 (s, 1H), 8.74 (s, 1H), 7.82 (m, 1H), 7.73 (m, 2H), 7.61 (d, 1H), 7.00 (d, 1H), 2.29 (s, 3H); (yield: 40%)

Example 324

(Z)-2-Hydroxy-5-[2-{(4-oxo-2-thioxothiazolidin-5-ylidene)methyl}furo[3,2-c]pyridin-7-yl]benzonitrile $^1$H NMR (DMSO-d$_6$, 400 MHz) δ 11.57 (s, 1H), 9.04 (s, 1H), 8.79 (s, 1H), 8.24 (m, 1H), 8.12 (d, 1H), 7.73 (m, 2H), 7.24 (d, 1H); (yield: 36%)

Example 325

(Z)-5-[{7-(4-Hydroxy-3-propionylphenyl)furo[3,2-c]pyridin-2-yl}methylene]-2-thioxothiazolidin-4-one $^1$H NMR (DMSO-d$_6$, 400 MHz) δ 12.06 (brs, 1H), 9.05 (s, 1H), 8.78 (s, 1H), 8.39 (s, 1H), 8.07 (d, 1H), 7.75 (d, 2H), 7.20 (d, 1H), 3.30 (m, 2H), 1.14 (t, 3H); (yield: 48%)

Example 326

(Z)-5-[{7-(3-Acetyl-4-hydroxyphenyl)furo[3,2-c]pyridin-2-yl}methylene]-2-thioxothiazolidin-4-one $^1$H NMR (DMSO-d$_6$, 400 MHz) δ 12.01 (brs, 1H), 9.05 (s, 1H), 8.79 (s, 1H), 8.41 (s, 1H), 8.09 (m, 1H), 7.72 (m, 2H), 7.19 (m, 1H), 2.78 (s, 3H); (yield: 47%)

Example 327

(Z)-5-[{7-(3-Fluoro-4-hydroxyphenyl)furo[3,2-c]pyridin-2-yl}methylene]-2-thioxothiazolidin-4-one $^1$H NMR (DMSO-d$_6$, 400 MHz) δ 10.37 (s, 1H), 9.01 (s, 1H), 8.79 (s, 1H), 7.85 (d, 1H), 7.74 (m, 2H), 7.67 (m, 1H), 7.15 (m, 1H); (yield: 50%)

Example 328

(Z)-2-Methoxy-5-[2-{(4-oxo-2-thioxothiazolidin-5-ylidene)methyl}furo[3,2-c]pyridin-7-yl]nicotinonitrile $^1$H NMR (DMSO-d$_6$, 400 MHz) δ 9.09 (d, 2H), 8.88 (s, 2H), 7.75 (d, 2H), 4.12 (s, 3H); (yield: 40%)

Example 329

(Z)-2-Fluoro-N-methyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.15 (s, 1H), 8.93 (s, 1H), 8.15 (d, 1H), 8.05-7.92 (m, 3H), 7.76 (d, 2H), 2.60 (d, 3H); (yield: 52%)

Example 330

(Z)-2-Fluoro-N,N-dimethyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.15 (s, 1H), 8.93 (s, 1H), 8.20 (d, 1H), 8.04 (d, 1H), 7.98 (t, 1H), 7.76 (d, 2H), 2.80 (s, 6H) (yield: 57%)

Example 331

(Z)-5-([7-{3-Fluoro-4-(morpholinosulfonyl)phenyl}furo[3,2-c]pyridin-2-yl]methylene)-2-thioxothiazolidin-4-one $^1$H NMR (400 MHz, DMSO-d$_6$) δ 9.16 (s, 1H), 8.93 (s, 1H), 8.19 (d, 1H), 8.05 (d, 1H), 7.96 (t, 1H), 7.76 (d, 2H), 3.68 (t, 4H), 3.11 (t, 4H); (yield: 51%)

Example 332

(Z)-5-([7-{3,5-Difluoro-4-(methylsulfonyl)phenyl}furo[3,2-c]pyridin-2-yl]methylene)-2-thioxothiazolidin-4-one $^1$H NMR (DMSO-d$_6$, 400 MHz) δ 9.17 (s, 1H), 9.01 (s, 1H), 8.09 (d, 2H), 7.77 (d, 2H), 3.53 (s, 3H); (yield: 41%)

Example 333

(Z)-5-([7-{3-Fluoro-4-(methylsulfonyl)phenyl}furo[3,2-c]pyridin-2-yl]methylene)-2-thioxothiazolidin-4-one $^1$H NMR (400 MHz, DMSO-d$_6$) δ 9.16 (s, 1H), 8.95 (s, 1H), 8.22 (d, 1H), 8.13 (d, 1H), 8.04 (t, 1H), 7.77 (d, 2H), 3.44 (s, 3H); (yield: 53%)

Example 334

(Z)-Methyl 2,6-difluoro-4-[2-{(4-oxo-2-thioxothiazolidin-5-ylidene)methyl}furo[3,2-c]pyridin-7-yl]benzoate $^1$H NMR (DMSO-d$_6$, 400 MHz) δ 9.13 (s, 1H), 8.95 (s, 1H), 7.97 (m, 2H), 7.72 (s, 1H), 7.63 (s, 1H), 3.94 (s, 3H); (yield: 56%)

Example 335

(Z)-5-[{7-(4-Amino-3,5-difluorophenyl)furo[3,2-c]pyridin-2-yl}methylene]-2-thioxothiazolidin-4-one $^1$H NMR (DMSO-d$_6$, 400 MHz) δ 8.98 (s, 1H), 8.81 (s, 1H), 7.72-7.66 (m, 4H), 5.68 (brs, 2H); (yield: 54%)

Example 336

(Z)-5-[{7-(4-Amino-3,5-dimethylphenyl)furo[3,2-c]pyridin-2-yl}methylene]-2-thioxothiazolidin-4-one $^1$H NMR (DMSO-d$_6$, 400 MHz) δ 8.91 (s, 1H), 8.72 (s, 1H), 7.71 (d, 2H), 7.56 (s, 2H), 2.24 (s, 6H) (yield: 54%)

Example 337

(Z)-5-[{7-(4-Amino-3-methylphenyl)furo[3,2-c]pyridin-2-yl}methylene]-2-thioxothiazolidin-4-one $^1$H NMR (DMSO-d$_6$, 400 MHz) δ 8.97 (s, 1H), 8.74 (s, 1H), 7.80-7.72 (m, 4H), 7.01 (d, 1H), 5.90 (brs, 2H); (yield: 52%)

Example 338

(Z)—N-Methyl-4-[2-{(4-oxo-2-thioxothiazolidin-5-ylidene)methyl}furo[3,2-c]pyridin-7-yl]-2-(trifluoromethoxy)benzenesulfonamide $^1$H NMR (DMSO-d$_6$, 400 MHz) δ 13.90 (brs, 1H), 9.16 (s, 1H), 8.88 (s, 1H), 8.17-8.08 (m, 3H), 7.90 (t, 1H), 7.78 (s, 1H), 7.74 (s, 1H), 2.62 (d, 3H); (yield: 57%)

Example 339

(Z)—N,N-Dimethyl-4-[2-{(4-oxo-2-thioxothiazolidin-5-ylidene)methyl}furo[3,2-c]pyridin-7-yl]-2-(trifluoromethoxy)benzenesulfonamide $^1$H NMR (DMSO-d$_6$, 400 MHz) δ 13.89 (brs, 1H), 9.16 (s, 1H), 8.89 (s, 1H), 8.17-8.10 (m, 3H), 7.78 (s, 1H), 7.74 (s, 1H), 2.83 (s, 6H); (yield: 54%)

Example 340

(Z)-5-([7-{4-(Morpholinosulfonyl)-3-(trifluoromethoxy)phenyl}furo[3,2-c]pyridin-2-yl]methylene)-2-thioxothiazolidin-4-one $^1$H NMR (DMSO-d$_6$, 400 MHz) δ 13.85 (brs, 1H), 9.21 (s, 1H), 8.89 (s, 1H), 8.28-8.09 (m, 3H), 7.77 (s, 1H), 7.73 (s, 1H), 3.66 (t, 4H), 3.14 (t, 4H); (yield: 51%)

Example 341

(Z)-2,6-Dichloro-N-methyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.09 (s, 1H), 8.96 (s, 1H), 8.29 (s, 2H), 8.03 (m, 1H), 7.69 (d, 1H), 2.55 (d, 3H); (yield: 53%)

Example 342

(Z)-2,6-Dichloro-N,N-dimethyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.16 (s, 1H), 9.02 (s, 1H), 8.37 (s, 2H), 7.75 (d, 2H), 2.95 (s, 6H); (yield: 56%)

Example 343

(Z)-5-([7-{3,5-Dichloro-4-(morpholinosulfonyl)phenyl}furo[3,2-c]pyridin-2-yl]methylene)-2-thioxothiazolidin-4-one $^1$H NMR (DMSO-d$_6$, 400 MHz) δ 9.09 (s, 1H), 8.95 (s, 1H), 8.31 (s, 2H), 7.69 (d, 2H), 3.59 (t, 4H), 3.30 (t, 4H); (yield: 54%)

Example 344

(Z)-2,6-Dichloro-N-ethyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.08 (s, 1H), 8.95 (s, 1H), 8.27 (s, 2H), 8.17 (m, 1H), 7.69 (d, 2H), 2.90 (m, 2H), 0.98 (t, 3H); (yield: 44%)

Example 345

(Z)-2,6-Dichloro-N-isopropyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.08 (s, 1H), 8.95 (s, 1H), 8.26 (s, 2H), 8.12 (d, 1H), 7.69 (d, 2H), 3.41 (m, 1H), 1.00 (d, 6H); (yield: 52%)

Example 346

(Z)—N-tert-Butyl-2,6-dichloro-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.08 (s, 1H), 8.94 (s, 1H), 8.24 (s, 2H), 7.99 (s, 1H), 7.68 (d, 2H), 3.40 (m, 1H), 1.15 (s, 9H) (yield: 57%)

Example 347

(Z)-2,6-Dichloro-N-(2-hydroxyethyl)-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.08 (s, 1H), 8.97 (s, 1H), 8.28 (s, 2H), 8.11 (t, 1H), 7.69 (d, 2H), 3.37 (t, 2H), 2.28 (t, 2H); (yield: 51%)

Example 348

(Z)—N,N,3-Trimethyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.16 (s, 1H), 8.62 (s, 1H), 7.86 (s, 1H), 7.76 (s, 1H), 7.74 (s, 2H), 7.66 (s, 1H), 2.69 (s, 6H), 2.33 (s, 3H); (yield: 49%)

Example 349

(Z)-Methyl 2-methoxy-4-[2-{(4-oxo-2-thioxothiazolidin-5-ylidene)methyl}furo[3,2-c]pyridin-7-yl]benzoate $^1$H NMR (DMSO-d$_6$, 400 MHz) δ 9.11 (s, 1H), 8.86 (s, 1H), 7.84 (d, 1H), 7.77 (s, 1H), 7.73 (s, 1H), 7.68 (s, 1H), 7.58 (d, 1H), 4.00 (s, 3H), 3.85 (s, 3H); (yield: 53%)

Example 350

(Z)-Methyl 2-fluoro-4-[2-{(4-oxo-2-thioxothiazolidin-5-ylidene)methyl}furo[3,2-c]pyridin-7-yl]benzoate $^1$H NMR (DMSO-d$_6$, 400 MHz) δ 9.13 (s, 1H), 8.23 (s, 1H), 8.10-8.04 (m, 2H), 7.97 (d, 1H), 7.75 (d, 2H), 3.93 (s, 3H); (yield: 56%)

Example 351

(Z)-Methyl 3-fluoro-5-[2-{(4-oxo-2-thioxothiazolidin-5-ylidene)methyl}furo[3,2-c]pyridin-7-yl]benzoate $^1$H NMR (DMSO-d$_6$, 400 MHz) δ 9.12 (s, 1H), 8.90 (s, 1H), 8.44 (s, 1H), 8.14 (d, 1H), 7.86 (d, 1H), 7.79 (s, 1H), 7.73 (s, 1H), 3.94 (s, 3H); (yield: 54%)

Example 352

(Z)-Methyl 2-chloro-5-[2-{(4-oxo-2-thioxothiazolidin-5-ylidene)methyl}furo[3,2-c]pyridin-7-yl]benzoate $^1$H NMR (DMSO-d$_6$, 400 MHz) δ 9.11 (s, 1H), 8.85 (s, 1H), 8.47 (s, 1H), 8.14 (d, 1H), 7.81 (d, 1H), 7.78 (s, 1H), 7.73 (s, 1H); (yield: 57%)

Example 353

(Z)—N-(4-[2-{(4-Oxo-2-thioxothiazolidin-5-ylidene)methyl}furo[3,2-c]pyridin-7-yl]phenyl)methanesulfonamide $^1$H NMR (DMSO-d$_6$, 400 MHz) δ 9.03 (s, 1H), 8.78 (s, 1H), 7.97 (d, 2H), 7.72 (d, 2H), 7.43 (d, 2H), 3.10 (s, 3H); (yield: 52%)

Example 354

(Z)—N,N-Dimethyl-3-[2-{(4-oxo-2-thioxothiazolidin-5-ylidene)methyl}furo[3,2-c]pyridin-7-yl]benzamide $^1$H NMR (DMSO-d$_6$, 400 MHz) δ 9.08 (s, 1H), 8.84 (s, 1H), 8.04-8.00 (m, 2H), 7.76 (s, 1H), 7.72 (s, 1H), 7.65 (t, 1H), 7.55 (d, 1H), 3.06 (s, 6H); (yield: 57%)

Example 355

(Z)—N-(2,6-Dimethyl-4-[2-{(4-oxo-2-thioxothiazolidin-5-ylidene)methyl}furo[3,2-c]pyridin-7-yl]phenyl)methanesulfonamide $^1$H NMR (DMSO-d$_6$, 400 MHz) δ 9.05 (s, 1H), 8.99 (brs, 1H), 8.83 (s, 1H), 7.79 (s, 2H), 7.72 (d, 2H), 3.12 (s, 3H); (yield: 51%)

Example 356

(Z)—N-Ethyl-2-methyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.12 (s, 1H), 8.89 (s, 1H), 8.45 (s, 1H), 8.00 (d, 1H), 7.95 (d, 1H), 7.81 (t, 1H), 7.75 (d, 2H), 2.90 (q, 2H), 2.76 (s, 3H), 1.02 (t, 3H); (yield: 51%)

Example 357

(Z)—N-Isopropyl-2-methyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 8.96 (s, 1H), 8.73 (s, 1H), 7.94 (s, 1H), 7.87 (d, 1H), 7.77 (d, 1H), 7.64-7.59 (m, 3H), 2.61 (s, 3H), 0.86 (d, 6H); (yield: 53%)

Example 358

(Z)—N-tert-Butyl-2-methyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.11 (s, 1H), 8.87 (s, 1H), 8.06 (d, 2H), 7.92 (d, 1H), 7.74 (d, 2H), 7.64 (s, 1H), 2.78 (s, 3H), 1.16 (s, 9H); (yield: 56%)

Example 359

(Z)—N-(2-Hydroxyethyl)-2-methyl-4-[2-{(4-oxo-2-thioxothiazolidin-5-ylidene)methyl}furo[3,2-c]pyridin-7-yl]benzenesulfonamide $^1$H NMR (DMSO-d$_6$, 400 MHz) δ 9.13 (s, 1H), 8.91 (s, 1H), 8.14 (s, 1H), 8.03-7.96 (m, 2H), 7.75 (d, 2H), 3.98 (t, 2H), 3.20 (m, 2H), 2.85 (m, 1H), 2.73 (s, 3H); (yield: 50%)

Example 360

(Z)-2-Amino-5-[2-{(4-oxo-2-thioxothiazolidin-5-ylidene)methyl}furo[3,2-c]pyridin-7-yl]benzonitrile $^1$H NMR (DMSO-d$_6$, 400 MHz) δ 9.01 (s, 1H), 8.78 (s, 1H), 8.05 (s, 1H), 7.97 (d, 1H), 7.80-7.70 (m, 2H), 7.01 (d, 1H), 6.52 (brs, 2H)

Example 361

(Z)-5-([7-{4-Amino-3-(trifluoromethyl)phenyl}furo[3,2-c]pyridin-2-yl]methylene)-2-thioxothiazolidin-4-one $^1$H NMR (DMSO-d$_6$, 400 MHz) δ 9.04 (s, 1H), 8.79 (s, 1H), 7.98 (s, 1H), 7.89 (d, 1H), 7.80-7.70 (m, 2H), 7.06 (d, 1H), 6.04 (brs, 2H)

Example 362

(Z)-5-([7-{4-(1-Methyl-5-oxo-1H-1,2,4-triazol-4(5H)-yl)phenyl}furo[3,2-c]pyridin-2-yl]methylene)-2-thioxothiazolidin-4-one $^1$H NMR (DMSO-d$_6$, 400 MHz) δ 9.08 (s, 1H), 8.86 (s, 1H), 8.64 (s, 1H), 8.15 (d, 1H), 8.00 (d, 1H), 7.80-7.70 (m, 2H), 3.44 (s, 3H)

Example 363

(Z)-5-([7-{4-(1-Isopropyl-5-oxo-1H-1,2,4-triazol-4(5H)-yl)phenyl}furo[3,2-c]pyridin-2-yl]methylene)-2-thioxothiazolidin-4-one $^1$H NMR (DMSO-d$_6$, 400 MHz) δ 9.09 (s, 1H), 8.86 (s, 1H), 8.63 (s, 1H), 8.15 (d, 1H), 8.01 (d, 1H), 7.78 (s, 1H), 7.75 (s, 1H), 4.50-4.40 (m, 1H), 1.35 (d, 6H)

Example 364

(Z)-5-([7-{4-(Isopropylsulfonyl)piperazin-1-yl}furo[3,2-c]pyridin-2-yl]methylene)thiazolidine-2,4-dione Step 1: Synthesis of 2-(diethoxymethyl)-7-(piperazin-1-yl)furo[3,2-c]pyridine A solution prepared by dissolving 2-(diethoxymethyl)-7-iodofuro[3,2-c]pyridine (1.0 mmol) obtained in Reference Example 1 in toluene (5 ml) was added with piperazine (1.2 mmol), BINAP (4 mole %), sodium t-butoxide (2.2 mmol) and tris(dibenzylideneacetone)dipalladium(0) (5.0 mol %), and stirred under reflux for 12 hours under a nitrogen atmosphere. The organic layer was separated and concentrated under reduced pressure. The residue thus obtained was purified by silica gel column chromatography (n-hexane/ethyl acetate=1/1, v/v) to obtain the title compound as a light yellow solid (yield: 89%).

Step 2: Synthesis of 2-(diethoxymethyl)-7-{4-(isopropylsulfonyl)piperazin-1-yl}furo[3,2-c]pyridine A solution prepared by dissolving 2-(diethoxymethyl)-7-(piperazin-1-yl)furo[3,2-c]pyridine (0.8 mmol) obtained in Step 1 in N,N-dimethylformamide (4 ml) was added with triethylamine (2.4 mmol) at 0° C., and stirred for 10 minutes. The reaction solution was added with isopropylsulfonylchloride (1.0 mmol), and stirred at room temperature for 30 minutes. The reaction was terminated by adding water, and the reaction solution was extracted with ethyl acetate. The extract was washed with brine, dried over anhydrous magnesium sulfate, filtered, and the filtrate was concentrated under reduced pressure. The residue thus obtained was purified by silica gel column chromatography (n-hexane/ethyl acetate=1/1, v/v) to obtain the title compound as light brown oil (yield: 80%).

Step 3: Synthesis of 7-{4-(isopropylsulfonyl)piperazin-1-yl}furo[3,2-c]pyridine-2-carbaldehyde A solution prepared by dissolving 2-(diethoxymethyl)-7-{4-(isopropylsulfonyl)piperazin-1-yl}furo[3,2-c]pyridine (0.5 mmol) obtained in Step 2 tetrahydrofuran (5 ml) added with a 3N aqueous hydrochloric acid solution (5 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract was washed with brine, dried over anhydrous magnesium sulfate, filtered, and the filtrate was concentrated under reduced pressure. The residue thus obtained was purified by silica gel column chromatography (n-hexane/ethyl acetate=1/1, v/v) to obtain the title compound as light brown oil (yield: 91%).

Step 4: Synthesis of (Z)-5-([7-{4-(isopropylsulfonyl)piperazin-1-yl}furo[3,2-c]pyridin-2-yl]methylene)thiazolidine-2,4-dione A solution prepared by dissolving 7-{4-(isopropylsulfonyl)piperazin-1-yl}furo[3,2-c]pyridine-2-carbaldehyde (0.4 mmol) obtained in Step 3 in acetic acid (3 ml) was added with thiazolidinedione (0.5 mmol) and β-alanine (0.4 mmol), and stirred under reflux for 4 hours. After the reaction solution was cooled to room temperature, the solid thus obtained was filtered, washed with acetic acid and water, and dried to obtain the title compound as a light yellow solid (yield: 80%).

$^1$H NMR (DMSO-d$_6$, 300 MHz) δ 8.66 (s, 1H), 8.16 (s, 1H), 7.85 (s, 1H), 7.60 (s, 1H), 3.51 (m, 4H), 3.43 (m, 5H), 1.28 (d, 6H)

Examples 365 to 381

The title compounds of Examples 365 to 381 were prepared in the same manner as described in Example 364 above, except for using each of the following compounds: morpholine, piperidine, 1-methylpiperazine, aniline, benzylamine, ethyl p-aminobenzoate, 4-chloroaniline, 3-aminobenzonitrile, 5-amino-2-(trifluoromethyl)pyridine, 4-amino-2-chloropyridine, 5-amino-2-chloropyridine, 2-thiophenethylamine, 3-methoxyphenylethylamine, 3-phenyl-1-propylamine, 3-(trifluoromethyl)benzylamine, 2,4-dichlorophenethylamine and 2-thiophenemethylamine, instead of piperazine in Step 1 of Example 364.

Example 365

(Z)-5-{(7-Morpholinofuro[3,2-c]pyridin-2-yl)methylene}thiazolidine-2,4-dione $^1$H NMR (DMSO-d$_6$, 300 MHz) δ 8.64 (s, 1H), 8.12 (s, 1H), 7.83 (s, 1H), 7.58 (s, 1H), 3.87 (brs, 4H), 3.35 (brs, 4H); (yield: 53%)

Example 366

(Z)-5-[{7-(Piperidin-1-yl)furo[3,2-c]pyridin-2-yl}methylene]thiazolidine-2,4-dione $^1$H NMR (DMSO-d$_6$, 300 MHz) δ 8.59 (s, 1H), 8.09 (s, 1H), 7.83 (s, 1H), 7.57 (s, 1H), 3.35 (brs, 4H), 1.76 (brs, 4H), 1.64 (brs, 2H); (yield: 57%)

Example 367

(Z)-5-[{7-(4-Methylpiperazin-1-yl)furo[3,2-c]pyridin-2-yl}methylene]thiazolidine-2,4-dione $^1$H NMR (DMSO-d$_6$, 300 MHz) δ 8.58 (s, 1H), 8.05 (s, 1H), 7.62 (s, 1H), 7.42 (s, 1H), 3.56 (brs, 4H), 2.89 (brs, 4H), 2.47 (s, 3H); (yield: 57%)

Example 368

(Z)-5-[{7-(Phenylamino)furo[3,2-c]pyridin-2-yl}methylene]thiazolidine-2,4-dione $^1$H NMR (DMSO-d$_6$, 400 MHz) δ 12.27 (brs, 1H), 8.66 (s, 1H), 8.50 (s, 1H), 8.33 (s, 1H), 7.74 (s, 1H), 7.59 (s, 1H), 6.89 (m, 3H), 7.26 (t, 2H); (yield: 57%)

Example 369

(Z)-5-[{7-(Benzylamino)furo[3,2-c]pyridin-2-yl}methylene]thiazolidine-2,4-dione $^1$H NMR (DMSO-d$_6$, 300 MHz) δ 8.29 (s, 1H), 7.83 (s, 1H), 7.77 (s, 1H), 7.50 (s, 1H), 7.41 (d, 2H), 7.32 (t, 2H), 7.22 (t, 1H), 6.65 (t, 1H), 4.62 (d, 2H); (yield: 57%)

Example 370

(Z)-Ethyl 4-[2-{(2,4-dioxothiazolidin-5-ylidene)methyl}furo[3,2-c]pyridin-7-ylamino]benzoate $^1$H NMR (DMSO-d$_6$, 400 MHz) δ 12.53 (brs, 1H), 9.10 (s, 1H), 8.81 (s, 1H), 8.43 (s, 1H), 7.84 (d, 2H), 7.76 (s, 1H), 7.63 (s, 1H), 6.99 (d, 2H), 2.25 (dd, 2H), 1.30 (t, 3H); (yield: 57%)

Example 371

(Z)-5-[{7-(4-Chlorophenylamino)furo[3,2-c]pyridin-2-yl}methylene]thiazolidine-2,4-dione $^1$H NMR (DMSO-d$_6$, 400 MHz) δ 12.59 (brs, 1H), 8.70 (s, 1H), 8.66 (s, 1H), 7.75 (s, 1H), 7.60 (s, 1H), 7.28 (d, 2H), 6.90 (d, 2H); (yield: 57%)

Example 372

(Z)-3-[2-{(2,4-Dioxothiazolidin-5-ylidene)methyl}furo[3,2-c]pyridin-7-ylamino]benzonitrile $^1$H NMR (DMSO-d$_6$, 400 MHz) δ 12.58 (brs, 1H), 8.96 (s, 1H), 8.78 (s, 1H), 8.39 (s, 1H), 7.77 (s, 1H), 7.63 (s, 1H), 7.43 (dd, 1H), 7.28 (d, 1H), 7.19 (s, 1H); (yield: 57%)

Example 373

(Z)-5-([7-{6-(Trifluoromethyl)pyridin-3-ylamino}furo[3,2-c]pyridin-2-yl]methylene)thiazolidine-2,4-dione $^1$H NMR (DMSO-d$_6$, 400 MHz) δ 12.57 (brs, 1H), 9.35 (s, 1H), 8.84 (s, 1H), 8.45 (s, 1H), 8.32 (s, 1H), 7.77 (s, 1H), 7.70 (d, 1H), 7.65 (s, 1H), 7.30 (d, 1H); (yield: 57%)

Example 374

(Z)-5-[{7-(2-Chloropyridin-4-ylamino)furo[3,2-c]pyridin-2-yl}methylene]thiazolidine-2,4-dione $^1$H NMR (DMSO-d$_6$, 400 MHz) δ 12.56 (brs, 1H), 9.41 (s, 1H), 8.83 (s, 1H), 8.38 (s, 1H), 7.99 (s, 1H), 7.75 (s, 1H), 7.61 (d, 1H), 6.68 (s, 1H), 6.63 (s, 1H); (yield: 57%)

Example 375

(Z)-5-[{7-(6-Chloropyridin-3-ylamino)furo[3,2-c]pyridin-2-yl}methylene]thiazolidine-2,4-dione $^1$H NMR (DMSO-d$_6$, 400 MHz) δ 12.59 (brs, 1H), 8.92 (s, 1H), 8.75 (s, 1H), 8.38 (s, 1H), 8.02 (s, 1H), 7.76 (s, 1H), 7.62 (s, 1H), 7.30-7.37 (m, 2H); (yield: 57%)

Example 376

(Z)-5-([7-{2-(Thiophen-2-yl)ethylamino}furo[3,2-c]pyridin-2-yl]methylene)thiazolidine-2,4-dione $^1$H NMR (DMSO-d$_6$, 400 MHz) δ 8.32 (s, 1H), 7.98 (s, 1H), 7.73 (s, 1H), 7.48 (s, 1H), 7.34 (s, 1H), 6.97 (s, 2H), 5.94 (brs, 1H), 3.66 (m, 2H), 3.16 (m, 2H); (yield: 57%)

Example 377

(Z)-5-[{7-(3-Methoxyphenethylamino)furo[3,2-c]
pyridin-2-yl}methylene]thiazolidine-2,4-dione $^1$H NMR (DMSO-d$_6$, 400 MHz) δ 11.95 (brs, 1H), 8.32 (s, 1H), 8.00 (s, 1H), 7.75 (s, 1H), 7.50 (s, 1H), 7.18 (t, 1H), 6.86 (m, 2H), 6.77 (d, 1H), 5.83 (brs, 1H), 3.72 (s, 3H), 3.64 (m, 2H), 2.90 (m, 2H); (yield: 57%)

Example 378

(Z)-5-[{7-(3-Phenylpropylamino)furo[3,2-c]pyridin-
2-yl}methylene]thiazolidine-2,4-dione $^1$H NMR (DMSO-d$_6$, 400 MHz) δ 8.29 (s, 1H), 7.92 (s, 1H), 7.74 (s, 1H), 7.48 (s, 1H), 7.16-7.28 (m, 5H), 5.97 (brs, 1H), 3.58 (m, 2H), 2.72 (m, 2H), 1.83 (m, 2H); (yield: 57%)

Example 379

(Z)-5-([7-{3-(Trifluoromethyl)benzylamino}furo[3,
2-c]pyridin-2-yl]methylene)thiazolidine-2,4-dione $^1$H NMR (DMSO-d$_6$, 400 MHz) δ 8.31 (s, 1H), 7.71-7.84 (m, 4H), 7.56-7.59 (m, 2H), 7.50 (s, 1H), 6.72 brs, 1H), 4.70 (d, 2H); (yield: 57%)

Example 380

(Z)-5-[{7-(2,4-Dichlorophenethylamino)furo[3,2-c]
pyridin-2-yl}methylene]thiazolidine-2,4-dione $^1$H NMR (DMSO-d$_6$, 400 MHz) δ 8.54 (s, 1H), 8.06 (s, 1H), 7.83 (s, 1H), 7.64 (s, 1H), 7.56 (s, 1H), 7.46 (d, 1H), 7.36 (d, 1H), 6.31 (brs, 1H), 3.69 (m, 2H), 3.06 (m, 2H); (yield: 57%)

Example 381

(Z)-5-[{7-(Thiophen-2-ylmethylamino)furo[3,2-c]
pyridin-2-yl}methylene]thiazolidine-2,4-dione $^1$H NMR (DMSO-d$_6$, 400 MHz) δ 8.30 (s, 1H), 7.75-7.83 (m, 2H), 7.49 (s, 1H), 7.36 (m, 1H), 7.25 (m, 1H), 7.05 (m, 1H), 6.66 (brs, 1H), 4.64 (s, 2H); (yield: 57%)

Example 382

(Z)-4-[2-{(2,4-Dioxothiazolidin-5-ylidene)
methyl}furo[3,2-c]pyridin-7-yl]piperazine-1-sulfo-
namide Step 1: Synthesis of 4-{2-(diethoxymethyl)furo[3,2-
c]pyridin-7-yl}piperazine-1-sulfonamide A solution prepared by dissolving 2-(diethoxymethyl)-7-(piperazin-1-yl)furo[3,2-c]pyridine (1.0 mmol) obtained in Step 1 of Example 364 in 1,4-dioxane (5 ml) was added with sulfuric diamide (2.0 mmol), and stirred under reflux for 12 hours. The reaction solution was cooled to room temperature, added with water, which was then extracted with ethyl acetate. The extract was washed with brine, dried over anhydrous magnesium sulfate, which was then filtered. The filtrate was concentrated under reduced pressure, and the residue thus obtained was purified by silica gel column chromatography (n-hexane/ethyl acetate=1/1, v/v) to obtain the title compound as a light yellow solid (yield: 51%).

Step 2: Synthesis of 4-(2-formylfuro[3,2-c]pyridin-
7-yl)piperazine-1-sulfonamide A solution prepared by dissolving 4-{2-(diethoxymethyl)furo[3,2-c]pyridin-7-yl}piperazine-1-sulfonamide (0.5 mmol) obtained in Step 1 in tetrahydrofuran (5 ml) was added with a 3N aqueous hydrochloric acid solution (5 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, which was then concentrated under reduced pressure. The resulting residue was purified by silica gel column chromatography (n-hexane/ethyl acetate=4/1, v/v) to obtain the title compound as light brown oil (yield: 91%).

Step 3: Synthesis of (Z)-4-[2-{(2,4-dioxothiazoli-
din-5-ylidene)methyl}furo[3,2-c]pyridin-7-yl]pipera-
zine-1-sulfonamide A solution prepared by dissolving 4-(2-formylfuro[3,2-c]pyridin-7-yl)piperazine-1-sulfonamide (0.4 mmol) obtained in Step 2 in acetic acid (3 ml) was added with thiazolidinedione (0.5 mmol) and β-alanine (0.4 mmol), and stirred under reflux for 4 hours. After the reaction solution was cooled to room temperature, the solid thus obtained was filtered, washed with acetic acid and water, and dried to obtain the title compound as a light yellow solid (yield: 85%).

$^1$H NMR (DMSO-d$_6$, 300 MHz) δ 8.67 (s, 1H), 8.16 (s, 1H), 7.86 (s, 1H), 7.62 (s, 1H), 7.02 (s, 2H), 3.48 (brs, 4H), 3.23 (brs, 4H)

Example 383

(E)-3-Methyl-4-([7-{3-(trifluoromethoxy)
phenyl}furo[3,2-c]pyridin-2-yl]-methylene)-1H-
pyrazol-5(4H)-one Step 1: Synthesis 2-(diethoxymethyl)-7-{3-(trifluo-
romethoxy)phenyl}furo[3,2-c]pyridine A solution prepared by dissolving 2-(diethoxymethyl)-7-(4,4,5,5-tetramethyl-1,3-dioxaborolan-2-yl)furo[3,2-c]pyridine (1.0 mmol) obtained in Reference Example 2 in tetrahydrofuran/water (4/1, v/v, 5 ml) was added with 1-iodo-3-(trifluoromethoxy)benzene (1.2 mmol), sodium carbonate (2.2 mmol) and tetrakis(triphenylphosphine)palladium(0) (5.0 mol %), and stirred under reflux for 12 hours under a nitrogen atmosphere. The organic layer was separated and concentrated under reduced pressure. The residue thus obtained was purified by silica gel column chromatography (n-hexane/ethyl acetate=4/1, v/v) to obtain the title compound as light brown oil (yield: 89%).

$^1$H NMR (CDCl$_3$, 300 MHz) δ 8.90 (s, 1H), 8.67 (s, 1H), 7.82-7.72 (m, 2H), 7.56 (dd, 1H), 7.30 (d, 1H), 6.97 (s, 1H), 5.71 (s, 1H), 3.76-3.66 (m, 4H), 1.29 (t, 6H)

Step 2: Synthesis of 7-{3-(trifluoromethoxy)
phenyl}furo[3,2-c]pyridine-2-carbaldehyde A solution prepared by dissolving 2-(diethoxymethyl)-7-{3-(trifluoromethoxy)phenyl}furo[3,2-c]pyridine (0.5 mmol) obtained in Step 1 in tetrahydrofuran (5 ml) was added with a 3N aqueous hydrochloric acid solution (5 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, which was then concentrated under reduced pressure. The resulting residue was purified by silica gel column chromatography (n-hexane/ethyl acetate=4/1, v/v) to obtain the title compound as light brown oil (yield: 91%).

$^1$H NMR (CDCl$_3$, 300 MHz) δ 10.00 (s, 1H), 9.13 (brs, 1H), 8.85 (brs, 1H), 7.85 (d, 1H), 7.74-7.72 (m, 2H), 7.60 (dd, 1H), 7.36 (d, 1H)

Step 3: Synthesis of (E)-3-methyl-4-([7-{3-(trifluoromethoxy)phenyl}furo[3,2-c]pyridin-2-yl]-methylene)-1H-pyrazol-5(4H)-one A solution prepared by dissolving 7-{3-(trifluoromethoxy)phenyl}furo[3,2-c]pyridine-2-carbaldehyde (0.4 mmol) obtained in Step 2 in acetic acid (3 ml) was added with 3-methyl-1H-pyrazol-5(4H)-one (0.5 mmol) and β-alanine (0.4 mmol), and stirred under reflux for 4 hours. After cooled to room temperature, the resulting solid was filtered, washed with acetic acid and water, and dried to obtain the title compound as a light yellow solid (yield: 85%).

$^1$H NMR (DMSO-d$_6$, 300 MHz) δ 8.85 (s, 1H), 8.71 (s, 1H), 7.94 (d, 1H), 7.87 (s, 1H), 7.66 (dd, 1H), 7.46 (d, 1H), 6.66 (s, 1H), 5.13 (s, 1H), 2.11 (s, 3H)

Example 384

(Z)-1-Methyl-5-([7-{3-(trifluoromethoxy)phenyl}furo[3,2-c]pyridin-2-yl]methylene)imidazolidine-2,4-dione A solution prepared by dissolving 7-{3-(trifluoromethoxy)phenyl}furo[3,2-c]pyridine-2-carbaldehyde (0.4 mmol) obtained in Step 2 of Example 383 in acetic acid (3 ml) was added with 1-methylimidazolidine-2,4-dione (0.5 mmol) and β-alanine (0.4 mmol), and stirred under reflux for 4 hours. After cooled to room temperature, the resulting solid was filtered, washed with acetic acid and water, and dried to obtain the title compound as a light yellow solid (yield: 85%).

$^1$H NMR (DMSO-d$_6$, 300 MHz) δ 11.99 (brs, 1H), 9.05 (s, 1H), 8.75 (s, 1H), 8.13 (s, 1H), 8.06 (d, 1H), 7.97 (s, 1H), 7.73 (t, 1H), 7.52 (d, 1H), 6.47 (s, 1H), 3.15 (s, 3H)

Example 385

(Z)-4-[2-{(2,4-Dioxothiazolidin-5-ylidene)methyl}furo[3,2-c]pyridin-7-yl]-N,N-dimethyl-5,6-dihydropyridine-1(2H)-sulfonamide Step 1: Synthesis of 4-(2-formylfuro[3,2-c]pyridin-7-yl)-N,N-dimethyl-5,6-dihydropyridine-1(2H)-sulfonamide A solution prepared by dissolving 7-(1,2,3,6-tetrahydropyridin-4-yl)furo[3,2-c]pyridine-2-carbaldehyde (0.35 mmol) obtained in Reference Example 4 in tetrahydrofuran (1 ml) was added with triethylamine (1.75 mmol) at room temperature, which was then slowly added with dimethylsulfamoyl chloride (0.53 mmol). The reaction mixture stirred at room temperature for 12 hours. The reaction solution was neutralized by adding an aqueous sodium bicarbonate solution thereto, and the organic solvent was removed therefrom under reduced pressure, which was then extracted with ethyl acetate. The extract was washed with brine, dried over anhydrous magnesium sulfate, filtered, and the filtrate was concentrated under reduced pressure. The residue thus obtained was purified by silica gel column chromatography (n-hexane/ethyl acetate=4/1, v/v) to obtain the title compound as light brown oil.

$^1$H NMR (400 MHz, CDCl$_3$) δ 9.88 (s, 1H), 9.01 (brs, 1H), 8.60 (brs, 1H), 7.59 (s, 1H), 6.63 (brs, 1H), 3.98 (brs, 2H), 3.49 (t, 2H), 2.86 (s, 6H), 2.75 (brs, 2H); (yield: 46%)

Step 2: Synthesis of (Z)-4-[2-{(2,4-dioxothiazolidin-5-ylidene)methyl}furo[3,2-c]pyridin-7-yl]-N,N-dimethyl-5,6-dihydropyridine-1(2H)-sulfonamide A solution prepared by dissolving 4-(2-formylfuro[3,2-c]pyridin-7-yl)-N,N-dimethyl-5,6-dihydropyridine-1(2H)-sulfonamide obtained in Step 1 in acetic acid (3 ml) was added with thiazolidinedione (0.5 mmol) and β-alanine (0.4 mmol), and stirred under reflux for 4 hours. After the reaction solution was cooled to room temperature, the solid thus obtained was filtered, washed with acetic acid and water, and dried to obtain the title compound as a solid.

$^1$H NMR (DMSO-d$_6$, 400 MHz) δ 8.98 (s, 1H), 8.56 (s, 1H), 7.86 (s, 1H), 7.65 (s, 1H), 6.63 (s, 1H), 4.02 (t, 2H), 3.52 (t, 2H), 2.79 (s, 6H), 2.74 (t, 2H); (yield: 46%)

Example 386

(Z)-5-([7-{1-(Cyclopropylsulfonyl)-1,2,3,6-tetrahydropyridin-4-yl}furo[3,2-c]pyridin-2-yl]methylene)thiazolidine-2,4-dione Step 1: Synthesis of 7-(1-(cyclopropylsulfonyl)-1,2,3,6-tetrahydropyridin-4-yl)furo[3,2-c]pyridine-2-carbaldehyde A solution prepared by dissolving 7-(1,2,3,6-tetrahydropyridin-4-yl)furo[3,2-c]pyridine-2-carbaldehyde (0.35 mmol) obtained in Reference Example 4 in tetrahydrofuran (1 ml) was added with triethylamine (1.75 mmol) at room temperature, which was then slowly added with cyclopropylsulfonyl chloride (0.53 mmol). The reaction mixture stirred at room temperature for 12 hours. The reaction solution was neutralized by adding an aqueous sodium bicarbonate solution thereto, and the organic solvent was removed therefrom under reduced pressure, which was then extracted with ethyl acetate. The extract was washed with brine, dried over anhydrous magnesium sulfate, filtered, and the filtrate was concentrated under reduced pressure. The residue thus obtained was purified by silica gel column chromatography (n-hexane/ethyl acetate=4/1, v/v) to obtain the title compound as light brown oil.

$^1$H NMR (CDCl$_3$, 400 MHz) δ 9.95 (s, 1H), 9.03 (s, 1H), 8.62 (s, 1H), 7.66 (s, 1H), 6.69 (brs, 1H), 4.17 (brs, 2H), 3.66 (t, 2H), 2.86 (brs, 2H), 2.38 (m, 1H), 1.26 (m, 2H), 1.02 (m, 2H); (yield: 56%)

Step 2: Synthesis of (Z)-5-([7-{1-(cyclopropylsulfonyl)-1,2,3,6-tetrahydropyridin-4-yl}furo[3,2-c]pyridin-2-yl]methylene)thiazolidine-2,4-dione A solution prepared by dissolving 7-{1-(cyclopropylsulfonyl)-1,2,3,6-tetrahydropyridin-4-yl}furo[3,2-c]pyridine-2-carbaldehyde obtained in Step 1 in acetic acid (3 ml) was added with thiazolidinedione (0.5 mmol) and β-alanine (0.4 mmol), and stirred under reflux for 4 hours. After the reaction solution was cooled to room temperature, the solid thus obtained was filtered, washed with acetic acid and water, and dried to obtain the title compound as a solid.

$^1$H NMR (DMSO-d$_6$, 400 MHz) δ 12.71 (brs, 1H), 8.98 (s, 1H), 8.58 (s, 1H), 7.85 (s, 1H), 7.65 (s, 1H), 6.70 (s, 1H), 4.09 (t, 2H), 3.55 (t, 2H), 2.83 (brs, 2H), 2.76 (m, 1H), 1.02 (m, 4H); (yield: 49%)

Example 387

(Z)—N,N-Dimethyl-4-[2-{(4-oxo-2-thioxothiazolidin-5-ylidene)methyl}furo[3,2-c]pyridin-7-yl]-5,6-dihydropyridine-1(2H)-sulfonamide Step 1: Synthesis of 4-(2-formylfuro[3,2-c]pyridin-7-yl)-N,N-dimethyl-5,6-dihydropyridine-1(2H)-sulfonamide A solution prepared by dissolving 7-(1,2,3,6-tetrahydropyridin-4-yl)furo[3,2-c]pyridine-2-carbaldehyde (0.35 mmol) obtained in Reference Example 4 in tetrahydrofuran (1 ml) was added with triethylamine (1.75 mmol) at room temperature, which was then slowly added with dimethylsulfamoyl chloride (0.53 mmol). The reaction mixture stirred at room temperature for 12 hours. The reaction solution was neutralized by adding an aqueous sodium bicarbonate solution thereto, and the organic solvent was removed therefrom under reduced pressure, which was then extracted with ethyl acetate. The extract was washed with brine, dried over anhydrous magnesium sulfate, filtered, and the filtrate was concentrated under reduced pressure. The residue thus obtained was purified by silica gel column chromatography (n-hexane/ethyl acetate=4/1, v/v) to obtain the title compound as light brown oil.

$^1$H NMR (CDCl$_3$, 400 MHz) δ 9.88 (s, 1H), 9.01 (brs, 1H), 8.60 (brs, 1H), 7.59 (s, 1H), 6.63 (brs, 1H), 3.98 (brs, 2H), 3.49 (t, 2H), 2.86 (s, 6H), 2.75 (brs, 2H); (yield: 46%)

Step 2: Synthesis of (Z)-4-[2-{(2,4-dioxothiazolidin-5-ylidene)methyl}furo[3,2-c]pyridin-7-yl]-N,N-dimethyl-5,6-dihydropyridine-1(2H)-sulfonamide A solution prepared by dissolving 4-(2-formylfuro[3,2-c]pyridin-7-yl)-N,N-dimethyl-5,6-dihydropyridine-1(2H)-sulfonamide obtained in Step 1 in acetic acid (3 ml) was added with rhodanine (0.5 mmol) and sodium acetate (0.4 mmol), and stirred under reflux for 4 hours. After cooled to room temperature, the resulting solid was filtered, washed with acetic acid and water, and dried to obtain the title compound as a solid.

$^1$H NMR (DMSO-d$_6$, 400 MHz) δ 9.00 (s, 1H), 8.58 (s, 1H), 7.71 (d, 2H), 6.63 (s, 1H), 4.02 (t, 2H), 3.51 (t, 2H), 2.83 (s, 6H), 2.80 (brs, 2H); (yield: 50%)

Example 388

(Z)-5-([7-{1-(Cyclopropylsulfonyl)-1,2,3,6-tetrahydropyridin-4-yl}furo[3,2-c]pyridin-2-yl]methylene)-2-thioxothiazolidin-4-one Step 1: Synthesis of 7-{1-(cyclopropylsulfonyl)-1,2,3,6-tetrahydropyridin-4-yl}furo[3,2-c]pyridine-2-carbaldehyde A solution prepared by dissolving 7-(1,2,3,6-tetrahydropyridin-4-yl)furo[3,2-c]pyridine-2-carbaldehyde (0.35 mmol) obtained in Reference Example 4 in tetrahydrofuran (1 ml) was added with triethylamine (1.75 mmol) at room temperature, which was then slowly added with cyclopropylsulfonyl chloride (0.53 mmol). The reaction mixture stirred at room temperature for 12 hours. The reaction solution was neutralized by adding an aqueous sodium bicarbonate solution thereto, and the organic solvent was removed therefrom under reduced pressure, which was then extracted with ethyl acetate. The extract was washed with brine, dried over anhydrous magnesium sulfate, filtered, and the filtrate was concentrated under reduced pressure. The residue thus obtained was purified by silica gel column chromatography (n-hexane/ethyl acetate=4/1, v/v) to obtain the title compound as light brown oil.

$^1$H NMR (CDCl$_3$, 400 MHz) δ 9.95 (s, 1H), 9.03 (s, 1H), 8.62 (s, 1H), 7.66 (s, 1H), 6.69 (brs, 1H), 4.17 (brs, 2H), 3.66 (t, 2H), 2.86 (brs, 2H), 2.38 (m, 1H), 1.26 (m, 2H), 1.02 (m, 2H); (yield: 56%)

Step 2: Synthesis of (Z)-5-([7-{1-(cyclopropylsulfonyl)-1,2,3,6-tetrahydropyridin-4-yl}furo[3,2-c]pyridin-2-yl]methylene)thiazolidine-2,4-dione A solution prepared by dissolving 7-[1-(cyclopropylsulfonyl)-1,2,3,6-tetrahydropyridin-4-yl}furo[3,2-c]pyridine-2-carbaldehyde obtained in Step 1 in acetic acid (3 me was added with rhodanine (0.5 mmol) and sodium acetate (0.4 mmol), and stirred under reflux for 4 hours. After cooled to room temperature, the resulting solid was filtered, washed with acetic acid and water, and dried to obtain the title compound as a solid.

$^1$H NMR (DMSO-d$_6$, 400 MHz) δ 12.71 (brs, 1H), 8.98 (s, 1H), 8.58 (s, 1H), 7.85 (s, 1H), 7.65 (s, 1H), 6.70 (s, 1H), 4.09 (t, 2H), 3.55 (t, 2H), 2.83 (brs, 2H), 2.76 (m, 1H), 1.02 (m, 4H); (yield: 49%)

$^1$H NMR (400 MHz, DMSO-d$_6$) δ 9.00 (s, 1H), 8.60 (s, 1H), 7.72 (d, 2H), 6.69 (s, 1H), 4.11 (t, 2H), 3.56 (t, 2H), 2.84 (brs, 2H), 2.75 (m, 1H), 1.02 (m, 4H); (yield: 55%)

Example 389

(Z)-2-(Benzylamino)-5-[{7-(4-methoxyphenyl)furo[3,2-c]pyridin-2-yl}methylene]thiazol-4(5H)-one Step 1: Synthesis of (Z)-5-[{7-(4-methoxyphenyl)furo[3,2-c]pyridin-2-yl}methylene]-2-(methylthio)thiazol-4(5H)-one A solution prepared by dissolving (Z)-5-[{7-(4-methoxyphenyl)furo[3,2-c]pyridin-2-yl}methylene]-2-thioxothiazolidin-4-one (5.02 mmol) obtained in Example 152 in ethanol/dichloromethane (1/1, v/v, 50 ml) was added with iodomethane (6.53 mmol) and diisopropylethylamine (15.06 mmol), and stirred for 24 hours at room temperature. The reaction was terminated by adding water, and the reaction solution was extracted with dichloromethane. The extract was washed with brine, dried over anhydrous magnesium sulfate and filtered. The filtrate was concentrated under reduced pressure, and the residue thus obtained was purified by silica gel column chromatography (dichloromethane/methanol=50/1, v/v) to obtain the title compound as a yellow solid (yield: 57%).

$^1$H NMR (DMSO-d$_6$, 300 MHz) δ 8.99 (s, 1H), 8.76 (s, 1H), 7.94 (d, 2H), 7.92 (s, 1H), 7.75 (s, 1H), 7.18 (d, 2H), 3.86 (s, 3H), 2.86 (s, 3H)

Step 2: Synthesis of (Z)-2-(benzylamino)-5-((7-(4-methoxyphenyl)furo[3,2-c]pyridin-2-yl)methylene)thiazol-4(5H)-one A solution prepared by dissolving (Z)-5-[{7-(4-methoxyphenyl)furo[3,2-c]pyridin-2-yl}methylene]-2-(methylthio)thiazol-4(5H)-one (0.131 mmol) obtained in Step 1 in acetonitrile (1.0 ml) was added with diisopropylethylamine (0.261 mmol) and benzylamine (0.261 mmol) was subjected to a reaction at 145° C. for 20 minutes by using a microwave reactor. The reaction solution was cooled to room temperature and filtered. The resulting solid was washed with acetonitrile and dried to obtain the title compound as a yellow solid (yield: 38%).

$^1$H NMR (DMSO-$d_6$, 400 MHz) δ 8.95 (s, 1H), 8.75 (s, 1H), 7.99 (d, 2H), 7.67 (s, 1H), 7.57 (s, 1H), 7.31-7.95 (m, 5H), 7.20 (d, 2H), 4.78 (s, 2H), 3.85 (s, 3H)

Examples 390 to 393

The title compounds of Examples 390 to 393 were prepared in the same manner as described in Example 389 above, except for using each of the following compounds: morpholine, phenethylamine, p-anisidine and ammonia (7N, in methanol), instead of benzylamine in Step 2 of Example 389.

Example 390

(Z)-5-[{7-(4-Methoxyphenyl)furo[3,2-c]pyridin-2-yl}methylene]-2-morpholinothiazol-4(5H)-one $^1$H NMR (DMSO-$d_6$, 400 MHz) δ 8.89 (s, 1H), 8.69 (s, 1H), 7.88 (d, 2H), 7.71 (s, 1H), 7.13 (s, 1H), 7.05 (d, 2H), 4.11 (s, 2H), 3.89 (s, 5H), 3.83 (s, 2H), 3.62 (s, 2H); (yield: 57%)

Example 391

(Z)-5-[{7-(4-Methoxyphenyl)furo[3,2-c]pyridin-2-yl}methylene]-2-(phenethylamino)thiazol-4(5H)-one $^1$H NMR (DMSO-$d_6$, 400 MHz) δ 8.94 (s, 1H), 8.74 (s, 1H), 7.98 (d, 2H), 7.64 (s, 1H), 7.54 (s, 1H), 7.19-7.33 (m, 8H), 3.88 (s, 3H), 3.77 (dd, 2H), 2.95 (brs, 2H); (yield: 57%)

Example 392

(Z)-2-{(4-Methoxyphenyl)amino}-5-[{7-(4-methoxyphenyl)furo[3,2-c]pyridin-2-yl}methylene]thiazol-4(5H)-one $^1$H NMR (DMSO-$d_6$, 400 MHz) δ 8.95 (d, 1H), 8.75 (d, 1H), 8.05-7.95 (m, 2H), 7.86 (d, 1H), 7.75-7.70 (m, 1H), 7.59 (d, 1H), 7.30-6.95 (m, 4H), 6.87 (d, 1H), 3.83 (d, 6H); (yield: 42%)

Example 393

(Z)-2-Amino-5-[{7-(4-methoxyphenyl)furo[3,2-c]pyridin-2-yl}methylene]thiazol-4(5H)-one $^1$H NMR (DMSO-$d_6$, 400 MHz) δ 8.85 (s, 1H), 8.63 (s, 1H), 7.93 (d, 1H), 7.68 (s, 1H), 7.42 (s, 1H), 7.20 (d, 1H); (yield: 61%)

Example 394

(Z)-5-[{7-(3-Fluoro-4-isopropoxyphenyl)furo[3,2-c]pyridin-2-yl}methylene]-2-(methylamino)thiazol-4(5H)-one

Step 1: Synthesis of (Z)-5-[{7-(3-fluoro-4-isopropoxyphenyl)furo[3,2-c]pyridin-2-yl}methylene]-2-(methylthio)thiazol-4(5H)-one A solution prepared by dissolving (Z)-5-[{7-(3-fluoro-4-isopropoxyphenyl)furo[3,2-c]pyridin-2-yl}methylene]-2-thioxothiazolidin-4-one (1.2 mmol) obtained in Example 164 in ethanol/dichloromethane (1/1, v/v, 20 ml) was added with iodomethane (1.57 mmol) and diisopropylethylamine (3.6 mmol), and stirred at room temperature for 6 hours. The reaction was terminated by adding water, and the reaction solution was extracted with dichloromethane. The extract was washed with brine, dried over anhydrous magnesium sulfate and filtered. The filtrate was concentrated under reduced pressure, and the residue thus obtained was purified by silica gel column chromatography (dichloromethane/methanol=50/1, v/v) to obtain the title compound as a yellow solid (yield: 93%).

$^1$H NMR (DMSO-$d_6$, 400 MHz) δ 9.01 (s, 1H), 8.81 (s, 1H), 7.90 (d, 2H), 7.76 (d, 2H), 7.41 (dd, 1H), 4.73-7.80 (m, 2H), 2.85 (s, 3H), 1.35 (d, 6H)

Step 2: Synthesis of (Z)-5-[{7-(3-fluoro-4-isopropoxyphenyl)furo[3,2-c]pyridin-2-yl}methylene]-2-(methylamino)thiazol-4(5H)-one A solution prepared by dissolving (Z)-5-[{7-(3-fluoro-4-isopropoxyphenyl)furo[3,2-c]pyridin-2-yl}methylene]-2-(methylthio)thiazol-4(5H)-one (0.093 mmol) obtained in Step 1 in isopropanol (1.5 ml) was added with potassium tert-butoxide (0.102 mmol) and methylamine hydrochloride (0.102 mmol), and stirred under reflux for 4 hours. The reaction solution was cooled to room temperature, added with water to terminate the reaction, which was then extracted with dichloromethane. The extract thus obtained was washed with brine, dried over anhydrous magnesium sulfate, filtered, and the filtrate was concentrated under reduced pressure. The resulting solid was purified by silica gel column chromatography (dichloromethane/methanol=40/1, v/v) to obtain the title compound as a yellow solid (yield: 30%).

$^1$H NMR (CD$_3$OD, 400 MHz) δ 8.85 (s, 1H), 8.61 (s, 1H), 7.66-7.75 (m, 2H), 7.59 (s, 1H), 7.29 (s, 1H), 7.22-7.27 (m, 1H), 4.71 (m, 1H), 3.20 (s, 3H), 1.44 (d, 6H).

Example 395

(Z)-5-[{7-(3-Fluoro-4-isopropoxyphenyl)furo[3,2-c]pyridin-2-yl}methylene]-2-(piperazin-1-yl)thiazol-4(5H)-one The title compound was prepared in the same manner as described in Example 394 above, except for using piperazine instead of methylamine hydrochloride in Step 2 of Example 394.

1H NMR (CD$_3$OD, 400 MHz) δ 8.85 (s, 1H), 8.61 (s, 1H), 7.66-7.75 (m, 2H), 7.59 (s, 1H), 7.29 (s, 1H), 7.22-7.27 (m, 1H), 4.71 (m, 1H), 3.20 (s, 3H), 1.44 (d, 6H).

Example 396

(Z)-3-(2-Hydroxyethyl)-5-[{7-(4-methoxyphenyl)furo[3,2-c]pyridin-2-yl}methylene]thiazolidine-2,4-dione Step 1: Synthesis of 3-(2-hydroxyethyl)thiazolidine-2,4-dione Thiazolidinedione (12.8 mmol), 2-iodoethanol (15.1 mmol), potassium carbonate (17.4 mmol) and tetrabutylammonium iodide (1.3 mmol) were placed in acetone (25 ml), and stirred at 40° C. for 10 hours. The reaction mixture was cooled to room temperature, filtered through Celite, and concentrated under reduced pressure to yield brown oil. The residue thus obtained was purified by silica gel column chromatography (n-hexane/ethyl acetate=4/1, v/v) to obtain the title compound as colorless oil (yield: 54%).

$^1$H NMR (CDCl$_3$, 400 MHz) δ 4.00 (s, 2H), 3.85 (brs, 4H), 1.94 (brs, 1H)

Step 2: Synthesis of 2-(diethoxymethyl)-7-(4-methoxyphenyl)furo[3,2-c]pyridine

A solution was prepared by dissolving 2-(diethoxymethyl)-7-iodofuro[3,2-c]pyridine (0.2 mmol) obtained in Reference Example 1, tetrakis(triphenylphosphine)palladium(0) (0.02 mmol), 4-methoxyphenylboronic acid (0.4 mmol) in dimethoxyethyne (2 ml) was added with ethanol (0.5 ml) and 2M sodium carbonate (0.5 ml), heated to 85° C., and stirred for 3 hours. The reaction mixture was cooled to room temperature, diluted with ethyl acetate, washed with water and brine, in sequence, which was then dried over anhydrous magnesium sulfate and filtered. After the filtrate was concentrated under reduced pressure, the residue thus obtained was purified by silica gel column chromatography (n-hexane/ethyl acetate=4/1, v/v) to obtain the title compound as yellow oil (yield: 55%).

Step 3: Synthesis of 7-(4-methoxyphenyl)furo[3,2-c]pyridine-2-carbaldehyde

A solution prepared by dissolving 2-(diethoxymethyl)-7-(4-methoxyphenyl)furo[3,2-c]pyridine (0.1 mmol) obtained in Step 2 in tetrahydrofuran (1 ml) was added with a 3N aqueous hydrochloric acid solution (1 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, which was then concentrated under reduced pressure to obtain the title compound as light brown oil (yield: 84%).

Step 4: Synthesis of (Z)-3-(2-hydroxyethyl)-5-((7-(4-methoxyphenyl)furo[3,2-c]pyridin-2-yl)methylene)thiazolidine-2,4-dione A solution prepared by dissolving 7-(4-methoxyphenyl)furo[3,2-c]pyridine-2-carbaldehyde (0.1 mmol) obtained in Step 3 in acetic acid (2 ml) was added with 3-(2-hydroxyethyl)thiazolidine-2,4-dione (0.2 mmol) obtained in Step 1 and β-alanine (0.2 mmol), and stirred under reflux for 4 hours. After cooled to room temperature, the reaction solution was added with water, and the resulting solid was filtered and dried. The residue thus obtained was purified by silica gel column chromatography (n-hexane/ethyl acetate=4/1, v/v) to obtain the title compound as colorless oil (yield: 30%).

$^1$H NMR (CDCl$_3$, 400 MHz) δ 8.92 (s, 1H), 8.72 (s, 1H), 7.84 (d, 2H), 7.81 (s, 1H), 7.24 (s, 1H) 7.13 (d, 2H), 4.33 (t, 2H), 4.04 (t, 2H), 3.93 (s, 3H)

Example 397

(Z)-5-[{7-(4-Methoxyphenyl)furo[3,2-c]pyridin-2-yl}methylene]-3-methyl-2-thioxothiazolidin-4-one A solution prepared by dissolving 7-(4-methoxyphenyl)furo[3,2-c]pyridine-2-carbaldehyde (0.08 mmol) obtained in Step 3 of Example 396 in acetic acid (5 ml) was added with N-methylrhodanine (0.08 mmol) and sodium acetate (0.08 mmol), and stirred under reflux for 4 hours. After cooled to room temperature, the resulting solid was filtered, washed with acetic acid and water, and dried to obtain the title compound as a light yellow solid (yield: 75%).

$^1$H NMR (DMSO-d$_6$, 400 MHz) δ 9.02 (s, 1H), 8.76 (s, 1H), 8.00-7.90 (m, 3H), 7.78 (s, 1H), 7.16 (d, 2H), 3.87 (s, 3H), 3.41 (s, 3H)

Example 398

(Z)-5-[{7-(4-(Methylthio)phenyl)furo[3,2-c]pyridin-2-yl}methylene]-2-thioxoimidazolidin-4-one A solution prepared by dissolving 7-{4-(methylthio)phenyl}furo[3,2-c]pyridine-2-carbaldehyde (0.11 mmol) obtained in Step 2 of Example 23 in acetic acid (1 ml) was added with 2-thiohydantoin (0.13 mmol) and sodium acetate (0.11 mmol), and stirred under reflux for 5 hours. After cooled to room temperature, the resulting solid was filtered, washed with acetic acid and water, and dried to obtain the title compound as a light yellow solid (yield: 87%).

$^1$H NMR (DMSO-d$_6$, 400 MHz) δ 12.61 (brs, 1H), 11.84 (brs, 1H), 8.97 (s, 1H), 7.75 (s, 1H), 7.97 (d, 2H), 7.88 (s, 1H), 7.44 (d, 2H), 6.53 (s, 1H), 2.56 (s, 3H)

Example 399

(Z)-5-[{7-(6-Fluoropyridin-3-yl)furo[3,2-c]pyridin-2-yl}methylene]-2-thioxoimidazolidin-4-one A solution prepared by dissolving 7-(6-fluoropyridin-3-yl)furo[3,2-c]pyridine-2-carbaldehyde (0.12 mmol) obtained in Step 2 of Example 153 in acetic acid (1 ml) was added with 2-thiohydantoin (0.14 mmol) and sodium acetate (10.12 mmol), and stirred under reflux for 5 hours. After cooled to room temperature, the resulting solid was filtered, washed with acetic acid and water, and dried to obtain the title compound as a light yellow solid (yield: 88%).

$^1$H NMR (DMSO-d$_6$, 400 MHz) δ 12.61 (brs, 1H), 11.97 (brs, 1H), 8.91 (s, 1H), 8.68 (s, 1H), 8.14 (d, 1H), 8.08 (s, 1H), 7.87 (s, 1H), 6.52 (s, 1H)

Example 400

(Z)-5-[{7-(3-Methoxyphenyl)furo[3,2-c]pyridin-2-yl}methylene]imidazolidine-2,4-dione A solution prepared by dissolving 7-(3-methoxyphenyl)furo[3,2-c]pyridin-2-carbaldehyde (0.12 mmol) Step 2 of Example 26 in acetic acid (1 ml) was added with 2-thiohydantoin (0.14 mmol) and sodium acetate (0.12 mmol), and stirred under reflux for 5 hours. After cooled to room temperature, the resulting solid was filtered, washed with acetic acid and water, and dried to obtain the title compound as a light yellow solid (yield: 21%).

$^1$H NMR (DMSO-d$_6$, 400 MHz) δ 9.96 (s, 1H), 9.19 (s, 1H), 8.91 (s, 1H), 8.18 (s, 1H), 7.51~7.49 (m, 3H), 7.10 (s, 1H), 3.86 (s, 3H)

Example 401

(Z)-4-[2-{(2,4-Dioxothiazolidin-5-ylidene)methyl}furo[3,2-c]pyridin-7-yl]-N-(2-hydroxyethyl)benzamide Step 1: Synthesis of methyl 4-{2-(diethoxymethyl)furo[3,2-c]pyridin-7-yl)benzoate A solution prepared by dissolving 2-(diethoxymethyl)-7-iodofuro[3,2-c]pyridine (1.0 mmol) obtained in Reference Example 1 in tetrahydrofuran/water (4/1, v/v, 5 ml) was added with 4-(methoxycarbonyl)phenylboronic acid (1.2 mmol), sodium carbonate (2.2 mmol) and tetrakis(triphenylphosphine)palladium(0) (5.0 mol %), and stirred overnight under reflux. The organic layer was separated and concentrated under reduced pressure. The residue thus obtained was purified by silica gel column chromatography (n-hexane/ethyl acetate=4/1, v/v) to obtain the title compound as light brown oil (yield: 84%).

Step 2: Synthesis of 4-{2-(diethoxymethyl)furo[3,2-c]pyridin-7-yl)benzoic acid

A solution prepared by dissolving methyl 4-{2-(diethoxymethyl)furo[3,2-c]pyridin-7-yl)benzoate (0.6 mmol) obtained in Step 1 in tetrahydrofuran/methanol (1/1, 6 ml) wad added with a 3N aqueous sodium hydroxide solution (3 ml), and stirred overnight at room temperature. The organic solvent was removed from the reaction solution under reduced pressure, and the remaining aqueous layer was diluted with water. The aqueous layer was added with 1N aqueous hydrochloric acid until the pH of the solution became 3-4, which was then extracted with dichloromethane. The extract was washed with brine, dried over anhydrous magnesium sulfate and filtered. The residue thus obtained was concentrated under reduced pressure to obtain the title compound as a light yellow solid (yield: 58%)

Step 3: Synthesis of 4-{2-(diethoxymethyl)furo[3,2-c]pyridin-7-yl}-N-(2-hydroxyethyl)benzamide A solution prepared by dissolving 4-{2-(diethoxymethyl)furo[3,2-c]pyridin-7-yl)benzoic acid (0.176 mmol) obtained in Step 2, ethanolamine (0.352 mmol), (benzotriazol-1-yloxy)tris-(dimethylamino)phosphonium hexafluorophosphate (0.176 mmol) and diisopropylethylamine (0.352 mmol) in N,N-dimethylformamide (1.5 ml) was stirred at room temperature for 1 hour. The reaction was terminated by adding water, and the reaction solution was extracted with ethyl acetate. The extract was dried over anhydrous magnesium sulfate, filtered, and the filtrate was concentrated. The residue thus obtained was purified by silica gel column chromatography (n-hexane/ethyl acetate=1/1, v/v) to obtain the title compound as a white solid (yield: 56%).

Step 4: Synthesis of 4-(2-formylfuro[3,2-c]pyridin-7-yl)-N-(2-hydroxyethyl)benzamide A solution prepared by dissolving 4-(2-(diethoxymethyl)furo[3,2-c]pyridin-7-yl)-N-(2-hydroxyethyl)benzamide (0.1 mmol) obtained in Step 3 in tetrahydrofuran (1.5 ml) was added with 3N hydrochloride (0.5 ml), and stirred overnight at 80° C. The reaction solution was neutralized by adding an aqueous sodium carbonate solution, and the organic solvent was removed therefrom under reduced pressure, which was then extracted with dichloromethane. The extract thus obtained was washed with brine, dried over anhydrous magnesium sulfate, filtered, and concentrated. The residue thus obtained was purified by silica gel column chromatography (dichloromethane/methanol=30/1, v/v) to obtain the title compound as a white solid (yield: 85%).

$^1$H NMR (CD$_3$OD, 400 MHz) δ 8.84 (s, 1H), 8.61 (s, 1H), 7.98 (s, 4H), 7.05 (s, 1H), 5.75 (s, 1H), 3.76 (s, 2H), 3.56 (s, 2H).

Step 5: Synthesis of (Z)-4-[2-{(2,4-dioxothiazolidin-5-ylidene)methyl}furo[3,2-c]pyridin-7-yl]-N-(2-hydroxyethyl)benzamide A solution prepared by dissolving 4-(2-formylfuro[3,2-c]pyridin-7-yl)-N-(2-hydroxyethyl)benzamide (0.081 mmol) obtained in Step 4 in acetic acid (2 ml) was added with thiazolidinedione (0.089 mmol), β-alanine (0.089 mmol), and stirred under reflux overnight. After cooled to room temperature, the resulting solid was filtered, washed with acetic acid and water, and dried to obtain the title compound as a yellow solid (yield: 73%).

$^1$H NMR (DMSO-d$_6$, 400 MHz) δ 9.08 (s, 1H), 8.87 (s, 1H), 8.66 (s, 1H), 8.10 (s, 3H), 7.84 (s, 1H), 7.69 (s, 1H), 4.79 (s, 1H), 3.57 (s, 2H), 3.36 (s, 2H).

Examples 402 and 403

The title compounds of Examples 402 and 403 were prepared in the same manner as described in Example 401 above, except for using propylamine and isopropylamine, respectively, instead of ethanolamine in Step 1 of Example 401.

Example 402

(Z)-4-[2-{(2,4-Dioxothiazolidin-5-ylidene)methyl}furo[3,2-c]pyridin-7-yl]-N-propylbenzamide $^1$H NMR (DMSO-d$_6$, 400 MHz) δ 9.08 (s, 1H), 8.87 (s, 1H), 8.67 (s, 1H), 8.09 (s, 3H), 7.87 (s, 1H), 7.71 (s, 1H), 3.29 (s, 2H), 1.56-1.60 (m, 2H), 0.9 (t, 3H); (yield: 88%)

Example 403

(Z)-4-[2-{(2,4-Dioxothiazolidin-5-ylidene)methyl}furo[3,2-c]pyridin-7-yl]-N-isopropylbenzamide $^1$H NMR (DMSO-d$_6$, 400 MHz) δ 9.08 (s, 1H), 8.87 (s, 1H), 8.43 (d, 1H), 8.09 (s, 3H), 7.88 (s, 1H), 7.72 (s, 1H), 4.13-4.18 (m, 1H), 1.22 (d, 6H); (yield: 80%)

Example 404

7-(4-tert-Butylphenyl)-2-(3-fluorophenyl)furo[3,2-c]pyridine

Step 1: Synthesis of 2-(3-fluorophenyl)-7-iodofuro[3,2-c]pyridine 3,5-Diiodopyridin-4-ol (5.0 mmol), 1-ethynyl-3-fluorobenzene (6.0 mmol) and copper(II) oxide (3.5 mmol) were added with anhydrous pyridine (30 ml) and stirred under reflux for 6 hours. The reaction mixture was cooled to room temperature, filtered through Celite, and concentrated under reduced pressure to yield brown oil. The residue was diluted with ethyl acetate, washed with aqueous ammonia, water and brine, in sequence, which was then dried over anhydrous magnesium sulfate and filtered. After the filtrate was concentrated under reduced pressure, the residue thus obtained was purified by silica gel column chromatography (n-hexane/ethyl acetate=10/1, v/v) to obtain the title compound as light brown oil (yield: 68%).

Step 2: Synthesis of 7-(4-tert-butylphenyl)-2-(3-fluorophenyl)furo[3,2-c]pyridine A solution prepared by dissolving 2-(3-fluorophenyl)-7-iodofuro[3,2-c]pyridine (1.0 mmol) obtained in Step 1 in tetrahydrofuran/water (4/1, v/v, 5 ml) was added with 4-tert-butylphenylboronic acid (1.2 mmol), sodium carbonate (2.2 mmol) and tetrakis(triphenylphosphine)palladium(0) (5.0 mol %), and stirred under reflux for 12 hours. The organic layer was separated and concentrated under reduced pressure. The residue thus obtained was purified by silica gel column chromatography (n-hexane/ethyl acetate=4/1, v/v) to obtain the title compound as light brown oil (yield: 82%).

$^1$H NMR (CDCl$_3$, 300 MHz) δ 8.91 (s, 1H), 8.72 (s, 1H), 7.88 (d, 2H), 7.63 (m, 3H), 7.46 (m, 2H), 7.17 (s, 1H), 7.11 (m, 1H), 1.42 (s, 9H)

Example 405

N-[5-{7-(4-tert-Butylphenyl)furo[3,2-c]pyridin-2-yl}pyridin-3-yl]acetamide

Step 1: Synthesis of N-{5-(7-iodofuro[3,2-c]pyridin-2-yl)pyridin-3-yl}acetamide

A solution prepared by dissolving 3,5-diiodopyridin-4-ol (5.0 mmol), N-(5-ethynylpyridin-3-yl)acetamide (6.0 mmol) and copper(II) oxide (3.5 mmol) in anhydrous pyridine (30 ml) was stirred under reflux for 6 hours. The reaction mixture was cooled to room temperature, filtered through Celite, and concentrated under reduced pressure to yield brown oil. The residue was diluted with ethyl acetate, washed with aqueous ammonia, water and brine, in sequence, which was then dried over anhydrous magnesium sulfate and filtered. After the filtrate was concentrated, the residue thus obtained was purified by silica gel column chromatography (n-hexane/ethyl acetate=10/1, v/v) to obtain the title compound as light brown oil (yield: 49%).

Step 2: Synthesis of N-[5-{7-(4-tert-butylphenyl)furo[3,2-c]pyridin-2-yl}pyridin-3-yl]acetamide A solution prepared by dissolving N-{5-(7-iodofuro[3,2-c]pyridin-2-yl)pyridin-3-yl}acetamide (1.0 mmol) obtained in Step 1 in tetrahydrofuran/water (4/1, v/v, 5 ml) was added with 4-tert-butylphenylboronic acid (1.2 mmol), sodium carbonate (2.2 mmol) and tetrakis(triphenylphosphine)palladium(0) (5.0 mol %), and stirred under reflux for 12 hours. The organic layer was separated and concentrated under reduced pressure. The residue thus obtained was purified by silica gel column chromatography (n-hexane/ethyl acetate=4/1, v/v) to obtain the title compound as light brown oil (yield: 80%)

$^1$H NMR (CDCl$_3$, 300 MHz) δ 8.93 (s, 1H), 8.89 (s, 1H), 8.75 (s, 1H), 8.63 (s, 1H), 8.18 (s, 1H), 7.87 (d, 2H), 7.61 (d, 2H), 7.23 (s, 1H), 2.25 (s, 3H), 1.41 (s, 9H)

Example 406

1-[5-{7-(4-tert-Butylphenyl)furo[3,2-c]pyridin-2-yl}pyridin-3-yl]-3-phenylurea

Step 1: Synthesis of 5-(7-iodofuro[3,2-c]pyridin-2-yl)pyridin-3-amine

A solution prepared by dissolving 3,5-diiodopyridin-4-ol (5.0 mmol), 5-ethynylpyridin-3-amine (6.0 mmol) and copper(II) oxide (3.5 mmol) in anhydrous pyridine (30 ml) and stirred under reflux for 6 hours. The reaction mixture was cooled to room temperature, filtered through Celite, and concentrated under reduced pressure to yield brown oil. The residue was diluted with ethyl acetate, washed with aqueous ammonia, water and brine, in sequence, which was then dried over anhydrous magnesium sulfate and filtered. After the filtrate was concentrated under reduced pressure, the residue thus obtained was purified by silica gel column chromatography (n-hexane/ethyl acetate=10/1, v/v) to obtain the title compound as light brown oil (yield: 56%).

Step 2: Synthesis of 5-{7-(4-tert-butylphenyl)furo[3,2-c]pyridin-2-yl}pyridin-3-amine A solution prepared by dissolving 5-(7-iodofuro[3,2-c]pyridin-2-yl)pyridin-3-amine (1.0 mmol) obtained in Step 1 in tetrahydrofuran/water (4/1, v/v, 5 ml) was added with 4-tert-butylphenylboronic acid (1.2 mmol), sodium carbonate (2.2 mmol) and tetrakis(triphenylphosphine)palladium(0) (5.0 mol %), and stirred under reflux for 12 hours. The organic layer was separated and concentrated under reduced pressure. The residue thus obtained was purified by silica gel column chromatography (n-hexane/ethyl acetate=4/1, v/v) to obtain the title compound as light brown oil (yield: 62%).

$^1$H NMR (CDCl$_3$, 300 MHz) δ 8.86 (s, 1H), 8.69 (s, 1H), 8.56 (s, 1H), 8.12 (s, 1H), 7.87 (d, 2H), 7.61 (d, 2H), 7.43 (s, 1H), 7.18 (s, 1H), 3.88 (s, 2H), 1.42 (s, 9H)

Step 3: Synthesis of 1-[5-{7-(4-tert-butylphenyl)furo[3,2-c]pyridin-2-yl}pyridin-3-yl]-3-phenylurea A solution prepared by dissolving 5-{7-(4-tert-butylphenyl)furo[3,2-c]pyridin-2-yl}pyridin-3-amine (0.1 mmol) obtained in Step 2 in tetrahydrofuran (1 ml) was added with isocyanatobenzene (0.12 mmol) and stirred overnight at room temperature. After the reaction was terminated by adding methanol, the solid thus obtained was filtered, washed with ethyl acetate and dried to obtain the title compound as a white solid (yield: 80%).

$^1$H NMR (acetone-d$_6$, 300 MHz) δ 8.95 (s, 1H), 8.91 (s, 1H), 8.85 (d, 1H), 8.67-8.74 (m, 2H), 8.48 (d, 1H), 8.38 (brs, 1H), 8.12 (d, 1H), 8.04-7.97 (m, 2H), 7.71-7.61 (m, 2H), 7.56-7.55 (m, 1H), 7.49 (s, 1H), 7.32 (t, 2H), 7.04 (t, 1H), 1.43 (s, 9H)

Example 407

2-Methoxy-5-{7-(4-methoxy-3,5-dimethylphenyl)furo[3,2-c]pyridin-2-yl}pyridin-3-amine Step 1: 5-(7-Iodofuro[3,2-c]pyridin-2-yl)-2-methoxypyridin-3-amine A solution prepared by dissolving 3,5-diiodopyridin-4-ol (8.77 mmol) in anhydrous pyridine (50 ml) was added with 5-ethynyl-2-methoxypyridin-3-amine (8.77 mmol) and copper(II) oxide (5.7 mmol), and stirred under reflux for 7 hours under a nitrogen atmosphere. The reaction solution was cooled to room temperature, filtered, and the filtrate was concentrated under reduced pressure. The residue was diluted with ethyl acetate, washed with aqueous ammonia, water and brine, in sequence, which was then dried over anhydrous magnesium sulfate and filtered. After the filtrate was concentrated under reduced pressure, the residue thus obtained was introduced to diethyl ether (30 ml) and stirred at room temperature for 2 hours. The resulting solid was filtered and dried to obtain the title compound as a light green solid (yield: 51%).

$^1$H NMR (CDCl$_3$, 400 MHz) δ 8.76 (s, 1H), 8.69 (s, 1H), 8.14 (s, 1H), 7.34 (s, 1H), 7.01 (s, 1H), 4.06 (s, 3H), 4.00-3.90 (m, 2H)

Step 2: 2-Methoxy-5-{7-(4-methoxy-3,5-dimethylphenyl)furo[3,2-c]pyridin-2-yl}pyridin-3-amine A solution prepared by dissolving 5-(7-iodofuro[3,2-c]pyridin-2-yl)-2-methoxypyridin-3-amine (0.27 mmol) obtained in Step 1 in toluene/ethanol/water (5/1/2, v/v, 2 ml) was added with 3,5-dimethyl-4-methoxyphenylboronic acid (0.32 mmol), sodium carbonate (0.68 mmol) and tetrakis(triphenylphosphine)palladium(0) (5.0 mol %) and stirred under reflux for 4 hours under a nitrogen atmosphere. The organic layer was separated and concentrated under reduced pressure. The residue thus obtained was washed with ethyl acetate to obtain the title compound as a light yellow solid (yield: 63%).

$^1$H NMR (CDCl$_3$, 400 MHz) δ 8.82 (s, 1H), 8.58 (s, 1H), 8.14 (s, 1H), 7.56 (s, 2H), 7.28 (s, 1H), 6.97 (s, 1H), 4.06 (s, 3H), 3.95 (brs, 2H), 3.82 (s, 3H), 2.42 (s, 6H)

Example 408

2,4-Difluoro-N-[2-methoxy-5-{7-(4-methoxy-3,5-dimethylphenyl)furo[3,2-c]pyridin-2-yl}pyridin-3-yl]benzenesulfonamide A solution prepared by dissolving 2-methoxy-5-{7-(4-methoxy-3,5-dimethylphenyl)furo[3,2-c]pyridin-2-yl}pyridin-3-amine (0.04 mmol) obtained in Example 407 in dichloromethane (1 ml) was added with diisopropylethylamine (0.12 mmol) and 2,4-difluorobenzenesulfonyl chloride (0.05 mmol), in sequence, and stirred overnight at room temperature. The reaction solution was added with water and extracted with ethyl acetate. The extract was washed with brine, dried over anhydrous magnesium sulfate and filtered. After the filtrate was concentrated under reduced pressure, the residue thus obtained was purified by silica gel column chromatography (n-hexane/ethyl acetate=2/1, v/v) to obtain the title compound as a light yellow solid (yield: 75%).

$^1$H NMR (CDCl$_3$, 400 MHz) δ 8.88 (s, 1H), 8.77 (s, 1H), 8.66 (s, 1H), 8.25-8.05 (m, 2H), 7.65-7.55 (m, 2H), 7.10 (t, 2H), 6.97 (t, 2H), 3.83 (s, 3H), 3.77 (s, 3H), 2.43 (s, 6H)

Example 409

N-[2-Methoxy-5-{7-(4-methoxy-3,5-dimethylphenyl)furo[3,2-c]pyridin-2-yl}pyridin-3-yl]methanesulfonamide In accordance with the same procedures as in Example 408, except for using 2-methoxy-5-{7-(4-methoxy-3,5-dim-ethylphenyl)furo[3,2-c]pyridin-2-yl}pyridin-3-amine obtained in Example 407 and methanesulfonyl chloride, the title compound was obtained as a light yellow solid (yield: 50%).

$^1$H NMR (CDCl$_3$, 400 MHz) δ 8.86 (s, 1H), 8.77 (s, 1H), 8.63 (s, 1H), 7.98 (s, 1H), 7.60-7.50 (m, 2H), 7.12 (s, 1H), 4.13 (s, 3H), 3.82 (s, 3H), 3.49 (s, 3H), 2.41 (s, 6H)

Example 410

(Z)-5-[1-{7-(4-Methoxyphenyl)furo[3,2-c]pyridin-2-yl}ethylidene]thiazolidine-2,4-dione Step 1: Synthesis of 1-(7-(4-methoxyphenyl)furo[3,2-c]pyridin-2-yl)ethanone A solution prepared by dissolving 1-(7-iodofuro[3,2-c]pyridin-2-yl)ethanone (1.0 mmol) obtained in Reference Example 5 in tetrahydrofuran/water (4/1, v/v, 5 ml) was added with 4-methoxyphenylboronic acid (1.2 mmol), sodium carbonate (2.2 mmol) and tetrakis(triphenylphosphine)palladium(0) (5.0 mol %), and stirred overnight under reflux. The organic layer was separated and concentrated under reduced pressure. The residue thus obtained was purified by silica gel column chromatography (n-hexane/ethyl acetate=4/1, v/v) to obtain the title compound as light brown oil (yield: 45%).

Step 2: Synthesis of (Z)-5-[1-{7-(4-methoxyphenyl)furo[3,2-c]pyridin-2-yl}ethylidene]thiazolidine-2,4-dione A solution prepared by dissolving 1-(7-(4-methoxyphenyl)furo[3,2-c]pyridin-2-yl)ethanone (0.4 mmol) obtained in Step 1 in acetic acid (3 ml) was added with thiazolidinedione (0.5 mmol) and β-alanine (0.4 mmol), and stirred under reflux for 4 hours. The reaction solution was cooled to room temperature, and the resulting solid was filtered, washed with acetic acid and water, and dried to obtain the title compound as a light yellow solid (yield: 45%).

$^1$H NMR (DMSO-d$_6$, 400 MHz) δ 12.45 (brs, 1H), 8.99 (s, 1H), 8.73 (s, 1H), 7.90 (d, 2H), 7.84 (s, 1H), 7.14 (d, 2H), 3.86 (s, 3H), 2.76 (s, 3H)

Example 411

(Z)-5-(1-[7-{6-Methoxy-5-(trifluoromethyl)pyridin-3-yl}furo[3,2-c]pyridin-2-yl]ethylidene)thiazolidine-2,4-dione The title compound was prepared in the same manner as described in Example 410 above, except for using 6-methoxy-5-(trifluoromethyl)pyridine-3-boronic acid instead of 4-methoxyphenylboronic acid in Step 1 of Example 410.

$^1$H NMR (DMSO-d$_6$, 400 MHz) δ 12.45 (brs, 1H), 8.99 (s, 1H), 8.73 (s, 1H), 7.90 (d, 2H), 7.84 (s, 1H), 7.14 (d, 2H), 3.86 (s, 3H), 2.76 (s, 3H); (yield: 40%)

Example 412

(Z)-2-{(2,4-Dioxothiazolidin-5-ylidene)methyl}-N-(2-methoxyphenyl)furo[3,2-c]pyridine-7-carboxamide Step 1: 2-(Diethoxymethyl)-N-(2-methoxyphenyl)furo[3,2-c]pyridine-7-carboxamide A solution prepared by dissolving 2-(diethoxymethyl)furo[3,2-c]pyridine-7-carboxylic acid (0.301 mmol) obtained in Reference Example 6 in N,N-dimethylformamide (3 ml) was added with o-anisidine (0.392 mmol), (benzotriazol-1-yloxy)-tris-(dimethylamino)phosphonium hexafluorophosphate (0.301 mmol) and diisopropylethylamine (0.905 mmol), and stirred overnight at room temperature. The reaction solution was added with water and extracted with diethyl ether. The extract was washed with brine, dried over anhydrous magnesium sulfate to remove water, filtered and concentrated under reduced pressure. The resulting residue was purified by silica gel column chromatography (n-hexane/ethyl acetate=1/1, v/v) to obtain the title compound as a light yellow solid (yield: 45%).

Step 2: Synthesis of 2-formyl-N-(2-methoxyphenyl)furo[3,2-c]pyridine-7-carboxamide A solution prepared by dissolving 2-(diethoxymethyl)-N-(2-methoxyphenyl)furo[3,2-c]pyridine-7-carboxamide (0.135 mmol) obtained in Step 1 in tetrahydrofuran (2 ml) was added with a 3N aqueous hydrochloric acid solution (0.6 ml), and stirred at 45° C. for 2 hours. The reaction solution was neutralized by adding an aqueous sodium bicarbonate solution thereto, and the organic solvent was removed therefrom under reduced pressure, which was then extracted with dichloromethane. The extract thus obtained was washed with brine, dried over anhydrous magnesium sulfate and filtered, and the filtrate was concentrated under reduced pressure. The residue thus obtained was purified by silica gel column chromatography (n-hexane/ethyl acetate=2/1, v/v) to obtain the title compound as a light yellow solid (yield: 80%).

$^1$H NMR (CDCl$_3$, 400 MHz) δ 10.00 (s, 1H), 9.91 (brs, 1H), 9.47 (s, 1H), 9.24 (s, 1H), 8.63 (dd, 1H), 7.75 (s, 1H), 7.12 (m, 1H), 6.99 (m, 2H), 4.12 (s, 3H)

Step 3: Synthesis of (Z)-2-{(2,4-dioxothiazolidin-5-ylidene)methyl}-N-(2-methoxyphenyl)furo[3,2-c]pyridine-7-carboxamide A solution prepared by dissolving 2-formyl-N-(2-methoxyphenyl)furo[3,2-c]pyridine-7-carboxamide (0.054 mmol) obtained in Step 2 in acetic acid (2 ml) was added with thiazolidinedione (0.0702 mmol) and β-alanine (0.0702 mmol), and stirred under reflux for 4 hours. After cooled to room temperature, the resulting solid was filtered, washed with acetic acid and water, and dried to obtain the title compound as a light yellow solid (yield: 57%).

$^1$H NMR (DMSO-d$_6$, 400 MHz) δ 12.68 (brs, 1H), 9.70 (s, 1H), 9.20 (s, 1H), 8.92 (s, 1H), 8.08 (d, 1H), 7.84 s, 1H), 7.69 (s, 1H), 7.19 (m, 2H), 7.02 (dd, 1H), 3.85 (s, 3H)

Examples 413 to 422

The title compounds of Examples 413 to 422 were prepared in the same manner as described in Example 412 above, except for using each of the following compounds: m-anisidine, p-anisidine, butylamine, 4-chlorobenzylamine, 4-methoxybenzylamine, piperidine, phenethylamine, methylamine hydrochloride, 3-phenyl-1-propylamine and cyclohexylamine, instead of o-anisidine in Step 1 of Example 412.

Example 413

(Z)-2-{(2,4-Dioxothiazolidin-5-ylidene)methyl}-N-(3-methoxyphenyl)furo[3,2-c]pyridine-7-carboxamide $^1$H NMR (DMSO-d$_6$, 400 MHz) δ 12.65 (brs, 1H), 10.53 (s, 1H), 9.20 (s, 1H), 8.56 (s, 1H), 7.86 (s, 1H), 7.70 (s, 1H), 7.44 (m, 2H), 7.30 (dd, 1H), 6.74 (dd, 1H), 3.78 (s, 3H); (yield: 16%)

Example 414

(Z)-2-{(2,4-Dioxothiazolidin-5-ylidene)methyl}-N-(4-methoxyphenyl)furo[3,2-c]pyridine-7-carboxamide $^1$H NMR (DMSO-d$_6$, 400 MHz) δ 12.65 (brs, 1H), 10.42 (s, 1H), 9.19 (s, 1H), 8.85 (s, 1H), 7.87 (s, 1H), 7.72 (m, 3H), 6.97 (d, 2H), 3.77 (s, 3H); (yield: 18%)

Example 415

(Z)—N-Butyl-2-{(2,4-dioxothiazolidin-5-ylidene)methyl}furo[3,2-c]pyridine-7-carboxamide $^1$H NMR (DMSO-d$_6$, 400 MHz) δ 12.69 (brs, 1H), 9.14 (s, 1H), 8.75 (s, 1H), 8.49 (brs, 1H), 7.85 (s, 1H), 7.66 (s, 1H), 3.37 (m, 2H), 1.62 (m, 2H), 1.42 (m, 2H), 0.94 (t, 3H); (yield: 27%)

Example 416

(Z)—N-(4-Chlorobenzyl)-2-{(2,4-dioxothiazolidin-5-ylidene)methyl}furo[3,2-c]pyridine-7-carboxamide $^1$H NMR (DMSO-d$_6$, 400 MHz) δ 12.67 (brs, 1H), 9.16 (s, 1H), 9.11 (brs, 1H), 7.84 (s, 1H), 7.66 (s, 1H), 7.41 (m, 4H), 4.58 (d, 2H); (yield: 27%)

Example 417

(Z)-2-{(2,4-Dioxothiazolidin-5-ylidene)methyl}-N-(4-methoxybenzyl)furo[3,2-c]pyridine-7-carboxamide $^1$H NMR (DMSO-d$_6$, 400 MHz) δ 12.66 (brs, 1H), 9.14 (s, 1H), 8.96 (brs, 1H), 7.79 (s, 1H), 7.82 (s, 1H), 7.65 (s, 1H), 7.35 (d, 2H), 6.92 (d, 2H), 4.51 (d, 2H), 3.74 (s, 3H); (yield: 24%)

Example 418

(Z)-5-{(7-(Piperidine-1-carbonyl)furo[3,2-c]pyridin-2-yl)methylene}thiazolidine-2,4-dione $^1$H NMR (DMSO-d$_6$, 400 MHz) δ 12.72 (brs, 1H), 9.11 (s, 1H), 8.53 (s, 1H), 7.84 (s, 1H), 7.67 (s, 1H), 3.73 (m, 2H), 3.25 (m, 2H), 1.65 (m, 4H) 1.46 (m, 2H); (yield: 34%)

Example 419

(Z)-2-{(2,4-Dioxothiazolidin-5-ylidene)methyl}-N-phenethylfuro[3,2-c]pyridine-7-carboxamide $^1$H NMR (DMSO-d$_6$, 400 MHz) δ 12.70 (brs, 1H), 9.14 (s, 1H), 8.74 (s, 1H), 8.64 (brs, 1H), 7.85 (s, 1H), 7.65 (s, 1H), 7.29 (m, 5H), 3.61 (m, 2H), 2.95 (m, 2H); (yield: 36%)

Example 420

(Z)-2-{(2,4-Dioxothiazolidin-5-ylidene)methyl}-N-methylfuro[3,2-c]pyridine-7-carboxamide $^1$H NMR (DMSO-d$_6$, 400 MHz) δ 12.70 (brs, 1H), 9.14 (s, 1H), 8.77 (s, 1H), 8.53 (brs, 1H), 7.85 (s, 1H), 7.64 (s, 1H), 2.91 (d, 3H); (yield: 19%)

Example 421

(Z)-2-{(2,4-Dioxothiazolidin-5-ylidene)methyl}-N-(3-phenylpropyl)furo[3,2-c]pyridine-7-carboxamide $^1$H NMR (DMSO-d$_6$, 400 MHz) δ 12.70 (brs, 1H), 9.14 (s, 1H), 8.76 (s, 1H), 8.57 (brs, 1H), 7.86 (s, 1H), 7.66 (s, 1H), 7.26 (m, 5H), 3.40 (m, 2H), 2.71 (m, 2H), 1.92 (m, 2H); (yield: 62%)

Example 422

(Z)—N-Cyclohexyl-2-{(2,4-dioxothiazolidin-5-ylidene)methyl}furo[3,2-c]pyridine-7-carboxamide $^1$H NMR (DMSO-d$_6$, 400 MHz) δ 12.69 (brs, 1H), 9.13 (s, 1H), 8.74 (s, 1H), 8.32 (d, 1H), 7.86 (s, 1H), 7.67 (s, 1H), 3.88 (m, 1H), 1.97 (m, 2H), 1.77 (m, 2H), 1.64 (d, 1H), 1.38 (m, 4H), 1.24 (m, 1H); (yield: 39%)

Example 423

(Z)—N-(2-Methoxyphenyl)-2-{(4-oxo-2-thioxothiazolidin-5-ylidene)methyl}furo[3,2-c]pyridine-7-carboxamide A solution prepared by dissolving 2-formyl-N-(2-methoxyphenyl)furo[3,2-c]pyridine-7-carboxamide (0.054 mmol) obtained in Step 2 of Example 412 in acetic acid (2 ml) was added with rhodanine (0.0702 mmol) and sodium acetate (0.0702 mmol), and stirred under reflux for 4 hours. After cooled to room temperature, the resulting solid was filtered, washed with acetic acid and water, and dried to obtain the title compound as a yellow solid (yield: 47%).

$^1$H NMR (DMSO-d$_6$, 400 MHz) δ 13.85 (brs, 1H), 9.73 (s, 1H), 9.22 (s, 1H), 8.92 (s, 1H), 8.08 (d, 1H), 7.77 (s, 1H), 7.72 (s, 1H), 7.20 (m, 2H), 7.02 (dd, 1H), 3.86 (s, 3H); (yield: 47%)

Examples 424 to 433

The title compounds of Examples 424 to 433 were prepared in the same manner as described in Example 423 above, except for using each of the following compounds: m-anisidine, p-anisidine, butylamine, 4-chlorobenzylamine, 4-methoxybenzylamine, piperidine, phenethylamine, methylamine hydrochloride, 3-phenyl-1-propylamine and cyclohexylamine, instead of o-anisidine in Step 1 of Example 412.

Example 424

(Z)—N-(3-Methoxyphenyl)-2-{(4-oxo-2-thioxothiazolidin-5-ylidene)methyl}furo[3,2-c]pyridine-7-carboxamide $^1$H NMR (DMSO-d$_6$, 400 MHz) δ 13.83 (brs, 1H), 10.57 (s, 1H), 9.22 (s, 1H), 8.88 (s, 1H), 7.76 (s, 1H), 7.73 (s, 1H), 7.49 (s, 1H), 7.44 (d, 1H), 7.30 (dd, 1H), 6.75 (dd, 1H), 3.78 (s, 3H); (yield: 19%)

Example 425

(Z)—N-(4-Methoxyphenyl)-2-{(4-oxo-2-thioxothiazolidin-5-ylidene)methyl}furo[3,2-c]pyridine-7-carboxamide $^1$H NMR (DMSO-d$_6$, 400 MHz) δ 13.84 (brs, 1H), 10.46 (s, 1H), 9.21 (s, 1H), 8.88 (s, 1H), 7.75 (m, 4H), 6.97 (d, 2H), 3.78 (s, 3H); (yield: 21%)

Example 426

(Z)—N-Butyl-2-{(4-oxo-2-thioxothiazolidin-5-ylidene)methyl}furo[3,2-c]pyridine-7-carboxamide $^1$H NMR (DMSO-d$_6$, 400 MHz) δ 13.77 (brs, 1H), 9.15 (s, 1H), 8.76 (s, 1H), 8.54 (brs, 1H), 7.73 (s, 2H), 3.40 (m, 2H), 1.65 (m, 2H), 1.43 (m, 2H), 0.96 (t, 3H); (yield: 23%)

Example 427

(Z)—N-(4-Chlorobenzyl)-2-{(4-oxo-2-thioxothiazolidin-5-ylidene)methyl}furo[3,2-c]pyridine-7-carboxamide $^1$H NMR (DMSO-d$_6$, 400 MHz) δ 13.83 (brs, 1H), 9.18 (m, 2H), 8.82 (s, 1H), 7.72 (d, 2H), 7.45 (m, 4H), 4.58 (d, 2H); (yield: 27%)

Example 428

(Z)—N-(4-Methoxybenzyl)-2-{(4-oxo-2-thioxothiazolidin-5-ylidene)methyl}furo[3,2-c]pyridine-7-carboxamide $^1$H NMR (DMSO-d$_6$, 400 MHz) δ 13.80 (brs, 1H), 9.16 (s, 1H), 9.06 (brs, 1H), 8.80 (s, 1H), 7.71 (d, 2H), 7.38 (d, 2H), 6.93 (d, 2H), 4.52 (d, 2H), 3.73 (s, 3H); (yield: 25%)

Example 429

(Z)-5-[{7-(Piperidine-1-carbonyl)furo[3,2-c]pyridin-2-yl}methylene]-2-thioxothiazolidin-4-one $^1$H NMR (DMSO-d$_6$, 400 MHz) δ 13.79 (brs, 1H), 9.12 (s, 1H), 8.55 (s, 1H), 7.73 (s, 1H), 7.71 (s, 1H), 3.74 (m, 2H), 3.25 (m, 2H), 1.65 (m, 4H) 1.47 (m, 2H); (yield: 25%)

Example 430

(Z)-2-{(4-Oxo-2-thioxothiazolidin-5-ylidene)methyl}-N-phenethylfuro[3,2-c]pyridine-7-carboxamide $^1$H NMR (DMSO-d$_6$, 400 MHz) δ 13.73 (brs, 1H), 9.16 (s, 1H), 8.75 (s, 1H), 8.72 (brs, 1H), 7.73 (s, 2H), 7.33 (m, 5H), 3.63 (m, 2H), 3.00 (m, 2H); (yield: 19%)

Example 431

(Z)—N-Methyl-2-{(4-oxo-2-thioxothiazolidin-5-ylidene)methyl}furo[3,2-c]pyridine-7-carboxamide $^1$H NMR (DMSO-d$_6$, 400 MHz) δ 13.68 (brs, 1H), 9.15 (s, 1H), 8.78 (s, 1H), 8.59 (brs, 1H), 7.71 (s, 1H), 7.70 (s, 1H), 2.92 (d, 3H); (yield: 38%)

Example 432

(Z)-2-{(4-Oxo-2-thioxothiazolidin-5-ylidene)methyl}-N-(3-phenylpropyl)furo[3,2-c]pyridine-7-carboxamide $^1$H NMR (DMSO-d$_6$, 400 MHz) δ 13.72 (brs, 1H), 9.16 (s, 1H), 8.77 (s, 1H), 8.61 (brs, 1H), 7.72 (s, 2H), 7.24 (m, 5H), 3.41 (m, 2H), 2.73 (m, 2H), 1.98 (m, 2H); (yield: 43%)

Example 433

(Z)—N-Cyclohexyl-2-{(4-oxo-2-thioxothiazolidin-5-ylidene)methyl}furo[3,2-c]pyridine-7-carboxamide $^1$H NMR (DMSO-d$_6$, 400 MHz) δ 13.84 (brs, 1H), 9.14 (s, 1H), 8.76 (s, 1H), 8.32 (d, 1H), 7.72 (s, 1H), 7.70 (s, 1H), 3.88 (m, 1H), 1.99 (m, 2H), 1.78 (m, 2H), 1.64 (d, 1H), 1.39 (m, 5H); (yield: 19%)

Example 434

(Z)-5-[{7-(Cyclopropylethynyl)furo[3,2-c]pyridin-2-yl}methylene]thiazolidine-2,4-dione

Step 1: Synthesis of 7-(cyclopropylethynyl)-2-(diethoxymethyl)furo[3,2-c]pyridine A solution prepared by dissolving 2-(diethoxymethyl)-7-iodofuro[3,2-c]pyridine (0.23 mmol) obtained in Reference Example 1, triphenylphosphine (0.08 mmol) and copper(I) iodide (0.10 mmol) in anhydrous triethylamine (3 ml) was added with bis(triphenylphosphine)palladium(II) dichloride (0.02 mmol), and stirred at room temperature for 20 minutes. The reaction mixture was slowly added with cyclopropylacetylene (0.69 mmol), heated to 60° C. and stirred for 12 hours. The reaction mixture was cooled to room temperature, diluted with ethyl acetate and washed with a saturated aqueous ammonium chloride solution, water and brine, in sequence, which was then dried over anhydrous magnesium sulfate and filtered. The filtrate was concentrated, and the residue thus obtained was purified by silica gel column chromatography (n-hexane/ethyl acetate=10/1, v/v) to obtain the title compound as light brown oil (yield: 66%).

$^1$H NMR (CDCl$_3$, 400 MHz) δ 8.80 (brs, 1H), 8.63 (brs, 1H), 6.87 (s, 1H), 5.69 (s, 1H), 3.68 (m, 4H), 1.54 (m, 1H), 1.28 (t, 6H), 0.93 (m, 4H)

Step 2: Synthesis of 7-(cyclopropylethynyl)furo[3,2-c]pyridine-2-carbaldehyde A solution prepared by dissolving 7-(cyclopropylethynyl)-2-(diethoxymethyl)furo[3,2-c]pyridine (0.15 mmol) obtained in Step 1 in tetrahydrofuran (1 ml) was added with a 3N aqueous hydrochloric acid solution (1 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, and the filtrate was concentrated under reduced pressure to obtain the title compound as light brown oil (yield: 84%).

Step 3: Synthesis of (Z)-5-[{7-(cyclopropylethynyl)furo[3,2-c]pyridin-2-yl}methylene]thiazolidine-2,4-dione A solution prepared by dissolving 7-(cyclopropylethynyl)furo[3,2-c]pyridine-2-carbaldehyde (0.1 mmol) obtained in Step 2 in acetic acid (1 ml) was added with thiazolidinedione (0.2 mmol) and β-alanine (0.2 mmol), and stirred under reflux for 4 hours. After cooled to room temperature, the resulting solid was filtered, washed with acetic acid and water, and dried to obtain the title compound as a light yellow solid (yield: 80%).

$^1$H NMR (DMSO-d$_6$, 400 MHz) δ 12.71 (brs, 1H), 8.98 (s, 1H), 8.55 (s, 1H), 7.84 (s, 1H), 7.62 (s, 1H), 1.74 (m, 1H), 1.04 (m, 2H), 0.95 (m, 2H)

Examples 435 to 474

The title compounds of Examples 435 to 474 were prepared in the same manner as described in Example 434 above, except for using each of the following compounds: cyclopentylacetylene, cyclohexylacetylene, 1-ethynyl-4-methoxybenzene, 3,3-dimethyl-1-butyne, 1-pentyne, 4-ethynyl-α,α,α-trifluorotoluene, 3-ethynyl-α,α,α-trifluorotoluene, 2-ethynylanisole, 3-ethynylanisole, 1-ethynyl-3-fluorobenzene, 1-ethynyl-4-fluorobenzene, 2-ethynylpyridine, 3-ethynylpyridine, 4-ethynyl-N,N-dimethylaniline, 1-ethynyl-4-methoxy-2-methylbenzene, 1-ethynyl-3,5-dimethoxybenzene, 3,4-difluorophenylacetylene, 1-ethynylnaphthalene, 4-ethynyl-1-fluoro-2-methylbenzene, 2-ethynyltoluene, 1-chloro-2-ethynylbenzene, 3-hydroxyphenylacetylene, 1-ethynyl-2,4,5-trimethylbenzene, 3,4-dichlorophenylacetylene, 1-butyl-4-ethynylbenzene, 4-ethynylphenylacetonitrile, 3-(trifluoromethoxy)phenylacetylene, N-(4-ethynylphenyl)methanesulfonamide, 3-ethynylbenzonitrile, 1-ethyn-1-yl-4-propylbenzene, 4-ethoxyphenylacetylene, 2-ethynyl-1,3,5-trimethylbenzene, 2-ethynylbenzyl alcohol, 2-ethynylaniline, 3',4'-dimethoxyphenyl acetylene, 2-ethynyl-benzonitrile, 4'-isopropylphenyl acetylene, 2-ethynyl-naphthalene, 1-(4-ethynylphenyl)-piperidine and 1-ethynyl-2-(trifluoromethoxy)benzene, instead of cyclopropylacetylene in Step 1 of Example 434.

Example 435

(Z)-5-[{7-(Cyclopentylethynyl)furo[3,2-c]pyridin-2-yl}methylene]thiazolidine-2,4-dione $^1$H NMR (DMSO-d$_6$, 400 MHz) δ 12.68 (brs, 1H), 8.98 (s, 1H), 8.54 (s, 1H), 7.83 (s, 1H), 7.62 (s, 1H), 3.05 (m, 1H), 2.04 (m, 2H), 1.80 (m, 4H), 1.66 (m, 2H); (yield: 56%)

Example 436

(Z)-5-[{7-(Cyclohexylethynyl)furo[3,2-c]pyridin-2-yl}methylene]thiazolidine-2,4-dione $^1$H NMR (DMSO-d$_6$, 400 MHz) δ 12.68 (brs, 1H), 8.98 (s, 1H), 8.54 (s, 1H), 7.83 (s, 1H), 7.63 (s, 1H), 2.88 (m, 1H), 1.91 (m, 2H), 1.78 (m, 2H), 1.63 (m, 2H), 1.45 (m, 4H); (yield: 49%)

Example 437

(Z)-5-([7-{(4-Methoxyphenyl)ethynyl}furo[3,2-c]pyridin-2-yl]methylene)thiazolidine-2,4-dione $^1$H NMR (DMSO-d$_6$, 400 MHz) δ 12.64 (brs, 1H), 8.97 (s, 1H), 8.63 (s, 1H), 7.80 (s, 1H), 7.60 (s, 1H), 7.54 (d, 2H), 7.00 (d, 2H), 3.77 (s, 3H); (yield: 54%)

Example 438

(Z)-5-[{7-(3,3-Dimethylbutyn-1-yl)furo[3,2-c]pyridin-2-yl}methylene]thiazolidine-2,4-dione $^1$H NMR (DMSO-d$_6$, 400 MHz) δ 12.62 (brs, 1H), 8.98 (s, 1H), 8.52 (s, 1H), 7.82 (s, 1H), 7.62 (s, 1H), 1.42 (s, 9H); (yield: 61%)

Example 439

(Z)-5-[{7-(Pentyn-1-yl)furo[3,2-c]pyridin-2-yl}methylene]thiazolidine-2,4-dione $^1$H NMR (DMSO-d$_6$, 400 MHz) δ 12.67 (brs, 1H), 8.99 (s, 1H), 8.56 (s, 1H), 7.81 (s, 1H), 7.61 (s, 1H), 2.59 (t, 2H), 1.69 (t, 2H), 1.11 (t, 3H); (yield: 55%)

Example 440

(Z)-5-{(7-[{4-(Trifluoromethyl)phenyl}ethynyl]furo[3,2-c]pyridin-2-yl)methylene}thiazolidine-2,4-dione $^1$H NMR (DMSO-d$_6$, 400 MHz) δ 12.73 (brs, 1H), 9.12 (s, 1H), 8.80 (s, 1H), 7.91~7.85 (s, 4H), 7.70 (m, 2H); (yield: 67%)

Example 441

(Z)-5-{(7-[{3-(Trifluoromethyl)phenyl}ethynyl]furo[3,2-c]pyridin-2-yl)methylene}thiazolidine-2,4-dione $^1$H NMR (DMSO-d$_6$, 400 MHz) δ 12.72 (brs, 1H), 9.10 (s, 1H), 8.77 (s, 1H), 8.00 (s, 1H), 7.95 (m, 1H), 7.90 (m, 2H), 7.77 (m, 1H), 7.69 (m, 1H); (yield: 45%)

Example 442

(Z)-5-([7-{(2-Methoxyphenyl)ethynyl}furo[3,2-c]pyridin-2-yl]methylene)thiazolidine-2,4-dione $^1$H NMR (DMSO-d$_6$, 400 MHz) δ 12.70 (brs, 1H), 9.06 (s, 1H), 8.70 (s, 1H), 7.87 (s, 1H), 7.68 (s, 1H), 7.59 (m, 1H), 7.48 (m, 1H), 7.18 (d, 1H), 7.05 (t, 1H), 3.93 (s, 3H); (yield: 42%)

Example 443

(Z)-5-([7-{(3-Methoxyphenyl)ethynyl}furo[3,2-c]pyridin-2-yl]methylene)thiazolidine-2,4-dione $^1$H NMR (DMSO-d$_6$, 400 MHz) δ 12.72 (brs, 1H), 9.08 (s, 1H), 8.74 (s, 1H), 7.89 (s, 1H), 7.69 (s, 1H), 7.43 (m, 1H), 7.24 (m, 1H), 7.21 (m, 1H), 7.10 (m, 1H), 3.83 (s, 3H); (yield: 45%)

Example 444

(Z)-5-([7-{(3-Fluorophenyl)ethynyl}furo[3,2-c]pyridin-2-yl]methylene)thiazolidine-2,4-dione $^1$H NMR (DMSO-d$_6$, 400 MHz) δ 12.72 (brs, 1H), 9.10 (s, 1H), 8.76 (s, 1H), 7.88 (s, 1H), 7.68 (s, 1H), 7.55 (m, 1H), 7.50 (m, 2H), 7.40 (t, 1H); (yield: 39%)

Example 445

(Z)-5-([7-{(4-Fluorophenyl)ethynyl}furo[3,2-c]pyridin-2-yl]methylene)thiazolidine-2,4-dione $^1$H NMR (DMSO-d$_6$, 400 MHz) δ 12.72 (brs, 1H), 9.12 (brs, 1H), 8.79 (brs, 1H), 7.89 (s, 1H), 7.73 (m, 2H), 7.67 (s, 1H), 7.38 (t, 2H); (yield: 41%)

Example 446

(Z)-5-[{7-(Pyridin-2-ylethynyl)furo[3,2-c]pyridin-2-yl}methylene]thiazolidine-2,4-dione $^1$H NMR (DMSO-d$_6$, 400 MHz) δ 12.72 (brs, 1H), 9.12 (s, 1H), 8.80 (s, 1H), 8.70 (m, 1H), 7.95 (m, 1H), 7.88 (s, 1H), 7.75 (m, 1H), 7.69 (s, 1H), 7.51 (m, 1H); (yield: 41%)

Example 447

(Z)-5-[{7-(Pyridin-3-ylethynyl)furo[3,2-c]pyridin-2-yl}methylene]thiazolidine-2,4-dione $^1$H NMR (DMSO-d$_6$, 400 MHz) δ 12.73 (brs, 1H), 9.10 (s, 1H), 8.87 (s, 1H), 8.77 (s, 1H), 8.68 (m, 1H), 8.07 (m, 1H), 7.88 (s, 1H), 7.69 (s, 1H), 7.56 (m, 1H); (yield: 47%)

Example 448

(Z)-5-([7-{(4-(Dimethylamino)phenyl)ethynyl}furo[3,2-c]pyridin-2-yl]methylene)thiazolidine-2,4-dione $^1$H NMR (DMSO-d$_6$, 400 MHz) δ 12.58 (brs, 1H), 8.96 (s, 1H), 8.44 (s, 1H), 7.98 (d, 2H), 7.77 (s, 1H), 7.62 (s, 1H), 6.77 (d, 2H), 3.05 (s, 6H); (yield: 38%)

Example 449

(Z)-5-([7-{(4-Methoxy-2-methylphenyl)ethynyl}furo[3,2-c]pyridin-2-yl]methylene)thiazolidine-2,4-dione $^1$H NMR (DMSO-d$_6$, 400 MHz) δ 12.70 (brs, 1H), 9.03 (s, 1H), 8.71 (s, 1H), 7.84 (m, 1H), 7.67 (s, 1H), 7.55 (d, 1H), 7.00 (s, 1H), 6.88 (m, 1H), 3.82 (s, 3H), 2.58 (s, 3H); (yield: 38%)

Example 450

(Z)-5-([7-{(3,5-Dimethoxyphenyl)ethynyl}furo[3,2-c]pyridin-2-yl]methylene)thiazolidine-2,4-dione $^1$H NMR (DMSO-d$_6$, 400 MHz) δ 12.71 (brs, 1H), 9.06 (s, 1H), 8.70 (s, 1H), 7.87 (s, 1H), 7.67 (s, 1H), 6.80 (s, 2H), 6.64 (m, 1H), 3.81 (s, 6H); (yield: 39%)

Example 451

(Z)-5-([7-{(3,4-Difluorophenyl)ethynyl}furo[3,2-c]pyridin-2-yl]methylene)thiazolidine-2,4-dione $^1$H NMR (DMSO-d$_6$, 400 MHz) δ 12.82 (brs, 1H), 9.09 (s, 1H), 8.74 (s, 1H), 7.85 (m, 1H), 7.78 (m, 1H), 7.71 (s, 1H), 7.67 (s, 1H), 7.63 (m, 1H), 7.55 (m, 1H); (yield: 41%)

Example 452

(Z)-5-[{7-(Naphthalen-1-ylethynyl)furo[3,2-c]pyridin-2-yl}methylene]thiazolidine-2,4-dione $^1$H NMR (DMSO-d$_6$, 400 MHz) δ 12.74 (brs, 1H), 9.10 (s, 1H), 8.86 (s, 1H), 8.63 (d, 1H), 8.09 (m, 2H), 7.95 (d, 1H), 7.91 (s, 1H), 7.79 (t, 1H), 7.77 (s, 1H), 7.70 (m, 1H), 7.64 (m, 2H); (yield: 42%)

Example 453

(Z)-5-([7-{(4-Fluoro-3-methylphenyl)ethynyl}furo[3,2-c]pyridin-2-yl]methylene)thiazolidine-2,4-dione $^1$H NMR (DMSO-d$_6$, 400 MHz) δ 12.71 (brs, 1H), 9.06 (s, 1H), 8.70 (s, 1H), 7.87 (s, 1H), 7.66 (s, 1H), 7.63 (m, 1H), 7.54 (m, 1H), 7.29 (m, 1H), 2.30 (s, 1H); (yield: 47%)

Example 454

(Z)-5-[{7-(o-Tolylethynyl)furo[3,2-c]pyridin-2-yl}methylene]thiazolidine-2,4-dione $^1$H NMR (DMSO-d$_6$, 400 MHz) δ 12.71 (brs, 1H), 9.07 (s, 1H), 8.75 (s, 1H), 7.89 (s, 1H), 7.69 (s, 1H), 7.62 (d, 1H), 7.41 (m, 2H), 7.33 (m, 1H), 2.61 (s, 3H); (yield: 42%)

Example 455

(Z)-5-([7-{(2-Chlorophenyl)ethynyl}furo[3,2-c]pyridin-2-yl]methylene)thiazolidine-2,4-dione $^1$H NMR (DMSO-d$_6$, 400 MHz) δ 12.71 (brs, 1H), 9.12 (brs, 1H), 8.80 (brs, 1H), 7.85 (s, 1H), 7.79 (d, 1H), 7.68 (m, 2H), 7.52 (m, 1H), 7.48 (m, 1H); (yield: 40%)

Example 456

(Z)-5-([7-{(3-Hydroxyphenyl)ethynyl}furo[3,2-c]pyridin-2-yl]methylene)thiazolidine-2,4-dione $^1$H NMR (DMSO-d$_6$, 400 MHz) δ 12.71 (brs, 1H), 9.85 (s, 1H), 8.00 (brs, 1H), 7.94 (s, 1H), 7.30 (m, 1H), 7.09 (m, 1H), 7.02 (s, 1H), 6.91 (m, 1H); (yield: 47%)

Example 457

(Z)-5-([7-{(2,4,5-Trimethylphenyl)ethynyl}furo[3,2-c]pyridin-2-yl]methylene)thiazolidine-2,4-dione $^1$H NMR (DMSO-d$_6$, 400 MHz) δ 12.68 (brs, 1H), 9.03 (s, 1H), 8.69 (s, 1H), 7.85 (s, 1H), 7.67 (s, 1H), 7.41 (s, 1H), 7.16 (s, 1H), 2.51 (s, 3H), 2.25 (s, 3H), 2.23 (s, 3H); (yield: 42%)

Example 458

(Z)-5-([7-{(3,4-Dichlorophenyl)ethynyl}furo[3,2-c]pyridin-2-yl]methylene)thiazolidine-2,4-dione $^1$H NMR (DMSO-d$_6$, 400 MHz) δ 12.72 (brs, 1H), 9.09 (s, 1H), 8.74 (s, 1H), 7.92 (m, 1H), 7.86 (s, 1H), 7.78 (m, 1H), 7.67 (s, 1H), 7.62 (m, 1H); (yield: 40%)

Example 459

(Z)-5-([7-{(4-Butylphenyl)ethynyl}furo[3,2-c]pyridin-2-yl]methylene)thiazolidine-2,4-dione $^1$H NMR (DMSO-d$_6$, 400 MHz) δ 12.71 (brs, 1H), 9.05 (s, 1H), 8.70 (s, 1H), 7.86 (s, 1H), 7.66 (s, 1H), 7.57 (m, 1H), 7.33 (m, 1H), 2.65 (m, 2H), 1.59 (m, 2H), 1.34 (m, 2H), 0.92 (t, 3H); (yield: 36%)

Example 460

(Z)-2-{4-([2-{(2,4-Dioxothiazolidin-5-ylidene)methyl}furo[3,2-c]pyridin-7-yl]ethynyl)phenyl}acetonitrile $^1$H NMR (DMSO-d$_6$, 400 MHz) δ 12.71 (brs, 1H), 9.07 (s, 1H), 8.74 (s, 1H), 7.87 (s, 1H), 7.69 (m, 3H), 7.49 (m, 2H), 4.16 (s, 2H); (yield: 45%)

Example 461

(Z)-5-{(7-[{3-(Trifluoromethoxy)phenyl}ethynyl]furo[3,2-c]pyridin-2-yl)methylene}thiazolidine-2,4-dione $^1$H NMR (DMSO-d$_6$, 400 MHz) δ 12.70 (brs, 1H), 9.09 (s, 1H), 8.76 (s, 1H), 7.86 (s, 1H), 7.69 (m, 2H), 7.61 (m, 2H), 7.53 (m, 1H); (yield: 47%)

Example 462

(Z)—N-{4-([2-{(2,4-Dioxothiazolidin-5-ylidene)methyl}furo[3,2-c]pyridin-7-yl]ethynyl)phenyl}methanesulfonamide $^1$H NMR (DMSO-d$_6$, 400 MHz) δ 12.70 (brs, 1H), 10.19 (s, 1H), 9.01 (s, 1H), 8.71 (s, 1H), 7.87 (s, 1H), 7.64 (m, 3H), 7.56 (d, 1H), 7.31 (d, 2H), 7.22 (d, 1H), 3.10 (s, 3H); (yield: 45%)

Example 463

(Z)-3-([2-{(2,4-Dioxothiazolidin-5-ylidene)methyl}furo[3,2-c]pyridin-7-yl]ethynyl)benzonitrile $^1$H NMR (DMSO-d$_6$, 400 MHz) δ 12.71 (brs, 1H), 9.09 (s, 1H), 8.75 (s, 1H), 8.13 (s, 1H), 7.92 (m, 2H), 7.86 (s, 1H), 7.73 (m, 1H), 7.67 (s, 1H); (yield: 42%)

Example 464

(Z)-5-([7-{(4-Propylphenyl)ethynyl}furo[3,2-c]pyridin-2-yl]methylene)thiazolidine-2,4-dione $^1$H NMR (DMSO-d$_6$, 400 MHz) δ 12.71 (brs, 1H), 9.05 (s, 1H), 8.71 (s, 1H), 7.87 (s, 1H), 7.66 (s, 1H), 7.57 (d, 2H), 7.33 (d, 2H), 2.63 (m, 2H), 1.62 (m, 2H), 0.92 (t, 3H); (yield: 45%)

Example 465

(Z)-5-([7-{(4-Ethoxyphenyl)ethynyl}furo[3,2-c]pyridin-2-yl]methylene)thiazolidine-2,4-dione $^1$H NMR (DMSO-d$_6$, 400 MHz) δ 12.69 (brs, 1H), 9.03 (s, 1H), 8.68 (s, 1H), 7.85 (s, 1H), 7.65 (s, 1H), 7.56 (d, 2H), 7.04 (d, 2H), 4.11 (m, 2H), 1.36 (t, 3H); (yield: 39%)

Example 466

(Z)-5-[{7-(Mesitylethynyl)furo[3,2-c]pyridin-2-yl}methylene]thiazolidine-2,4-dione $^1$H NMR (DMSO-d$_6$, 400 MHz) δ 12.67 (brs, 1H), 9.03 (s, 1H), 8.71 (s, 1H), 7.84 (s, 1H), 7.68 (s, 1H), 7.02 (s, 2H), 2.53 (s, 6H), 2.30 (s, 3H); (yield: 41%)

Example 467

(Z)-5-{(7-[{2-(Hydroxymethyl)phenyl}ethynyl]furo[3,2-c]pyridin-2-yl)methylene}thiazolidine-2,4-dione $^1$H NMR (DMSO-d$_6$, 400 MHz) δ 12.70 (brs, 1H), 9.07 (s, 1H), 8.75 (s, 1H), 7.86 (s, 1H), 7.68 (s, 1H), 7.62 (m, 1H), 7.53 (m, 2H), 7.37 (m, 1H), 5.45~4.85 (m, 1+2H); (yield: 41%)

Example 468

(Z)-5-([7-{(2-Aminophenyl)ethynyl}furo[3,2-c]pyridin-2-yl]methylene)thiazolidine-2,4-dione $^1$H NMR (DMSO-d$_6$, 400 MHz) δ 12.63 (brs, 1H), 8.99 (s, 1H), 8.46 (s, 1H), 8.28 (m, 2H), 7.77 (s, 1H), 7.65 (m, 1H), 7.60 (s, 1H), 7.29 (m, 1H), 4.81 (s, 2H); (yield: 47%)

Example 469

(Z)-5-([7-{(3,4-Dimethoxyphenyl)ethynyl}furo[3,2-c]pyridin-2-yl]methylene)thiazolidine-2,4-dione $^1$H NMR (DMSO-d$_6$, 400 MHz) δ 12.71 (brs, 1H), 9.04 (m, 1H), 8.68 (m, 1H), 7.87 (s, 1H), 7.66 (s, 1H), 7.23 (m, 1H), 7.18 (m, 1H), 7.07 (m, 1H), 3.83 (s, 6H); (yield: 38%)

Example 470

(Z)-2-([2-{(2,4-Dioxothiazolidin-5-ylidene)methyl}furo[3,2-c]pyridin-7-yl]ethynyl)benzonitrile $^1$H NMR (DMSO-d$_6$, 400 MHz) δ 12.68 (brs, 1H), 9.14 (s, 1H), 8.78 (s, 1H), 8.04 (m, 1H), 7.90~7.87 (m, 2H), 7.86 (m, 1H), 7.73~7.69 (m, 1H); (yield: 38%)

Example 471

(Z)-5-([7-{(4-Isopropylphenyl)ethynyl}furo[3,2-c]pyridin-2-yl]methylene)thiazolidine-2,4-dione $^1$H NMR (DMSO-d$_6$, 400 MHz) δ 12.70 (brs, 1H), 9.05 (s, 1H), 8.71 (s, 1H), 7.87 (m, 1H), 7.67 (m, 1H), 7.59 (d, 2H), 7.38 (m, 2H), 2.97 (m, 1H), 1.24 (d, 6H); (yield: 49%)

Example 472

(Z)-5-[{7-(Naphthalen-2-ylethynyl)furo[3,2-c]pyridin-2-yl}methylene]thiazolidine-2,4-dione $^1$H NMR (DMSO-d$_6$, 400 MHz) δ 12.73 (brs, 1H), 9.09 (s, 1H), 8.78 (s, 1H), 8.33 (s, 1H), 8.07 (m, 1H), 8.05 (m, 2H), 7.88 (s, 1H), 7.71 (m, 1H), 7.62 (m, 2H); (yield: 41%)

Example 473

(Z)-5-{(7-[{4-(Piperidin-1-yl)phenyl}ethynyl]furo[3,2-c]pyridin-2-yl)methylene}thiazolidine-2,4-dione $^1$H NMR (DMSO-d$_6$, 400 MHz) δ 12.57 (brs, 1H), 8.97 (s, 1H), 8.44 (s, 1H), 7.98 (m, 2H), 7.77 (m, 1H), 7.60 (m, 1H), 7.01 (m, 2H), 3.32 (m, 4H), 1.61 (m, 6H); (yield: 42%)

Example 474

(Z)-5-{(7-[{2-(Trifluoromethoxy)phenyl}ethynyl]furo[3,2-c]pyridin-2-yl)methylene}thiazolidine-2,4-dione $^1$H NMR (DMSO-d$_6$, 400 MHz) δ 12.70 (brs, 1H), 9.11 (s, 1H), 8.74 (s, 1H), 7.85 (m, 2H), 7.65 (m, 2H), 7.56 (m, 2H); (yield: 47%)

Example 475

(Z)-5-[{7-(Cyclopropylethynyl)furo[3,2-c]pyridin-2-yl}methylene]-2-thioxothiazolidin-4-one Step 1: Synthesis of 7-(cyclopropylethynyl)-2-(diethoxymethyl)furo[3,2-c]pyridine A solution prepared by dissolving 2-(diethoxymethyl)-7-iodofuro[3,2-c]pyridine (0.23 mmol) obtained in Reference Example 1, triphenylphosphine (0.08 mmol) and copper(I) iodide (0.10 mmol) in anhydrous triethylamine (3 ml) was added with bis(triphenylphosphine)palladium(II) dichloride (0.02 mmol), and stirred at room temperature for 20 minutes. The reaction mixture was slowly added with cyclopropylacetylene (0.69 mmol), heated to 60° C., and stirred for 12 hours. The reaction mixture was cooled to room temperature, diluted with ethyl acetate, washed with a saturated aqueous ammonium chloride solution, water and brine, in sequence, which was then dried over anhydrous magnesium sulfate and filtered. The filtrate was concentrated, and the residue thus obtained was purified by silica gel column chromatography (n-hexane/ethyl acetate=10/1, v/v) to obtain the title compound as light brown oil (yield: 66%).

$^1$H NMR (CDCl$_3$, 400 MHz) δ 8.80 (brs, 1H), 8.63 (brs, 1H), 6.87 (s, 1H), 5.69 (s, 1H), 3.68 (m, 4H), 1.54 (m, 1H), 1.28 (t, 6H), 0.93 (m, 4H)

Step 2: Synthesis of 7-(cyclopropylethynyl)furo[3,2-c]pyridine-2-carbaldehyde

A solution prepared by dissolving 7-(cyclopropylethynyl)-2-(diethoxymethyl)furo[3,2-c]pyridine (0.15 mmol) obtained in Step 1 in tetrahydrofuran (1 ml) was added with a 3N aqueous hydrochloric acid solution (1 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, and the filtrate was concentrated under reduced pressure to obtain the title compound as light brown oil (yield: 84%).

Step 3: Synthesis of (Z)-5-[{7-(cyclopropylethynyl) furo[3,2-c]pyridin-2-yl}methylene]-2-thioxothiazolidin-4-one A solution prepared by dissolving 7-(cyclopropylethynyl) furo[3,2-c]pyridin-2-carbaldehyde (0.1 mmol) obtained in Step 2 in acetic acid (1 ml) was added with rhodanine (0.2 mmol) and sodium acetate (0.2 mmol), and stirred under reflux for 4 hours. After cooled to room temperature, the resulting solid was filtered, washed with acetic acid and water, and dried to obtain the title compound as a yellow solid (yield: 80%).

$^1$H NMR (DMSO-$d_6$, 400 MHz) δ 8.99 (s, 1H), 8.56 (s, 1H), 7.67 (d, 2H), 1.72 (m, 1H), 1.04 (m, 2H), 0.93 (m, 2H)

Examples 476 to 518

The title compounds of Examples 476 to 518 were prepared in the same manner as described in Example 475 above, except for using each of the following compounds: 3-butyn-1-ol, 3-butyn-2-ol, methyl propiolate, cyclopentylacetylene, cyclohexylacetylene, 1-ethynyl-4-methoxybenzene, 3,3-dimethyl-1-butyne, 3,3-diethoxy-1-propyne, 4-ethynyl-α,α,α-trifluorotoluene, 3-ethynyl-α,α,α-trifluorotoluene, 2-ethynylanisole, 3-ethynylanisole, 1-ethynyl-3-fluorobenzene, 1-ethynyl-4-fluorobenzene, 2-ethynylpyridine, 3-ethynylpyridine, 4-ethynyl-N,N-dimethylaniline, 1-ethynyl-4-methoxy-2-methylbenzene, 1-ethynyl-3,5-dimethoxybenzene, 3,4-difluorophenylacetylene, 1-ethynylnaphthalene, 4-ethynyl-1-fluoro-2-methylbenzene, 2-ethynyltoluene, 1-chloro-2-ethynylbenzene, 3-hydroxyphenylacetylene, 1-ethynyl-2,4,5-trimethylbenzene, 3,4-dichlorophenylacetylene, 1-butyl-4-ethynylbenzene, 4-ethynylphenylacetonitrile, 3-(trifluoromethoxy)phenylacetylene, N-(4-ethynylphenyl)methanesulfonamide, 3-ethynylbenzonitrile, 1-ethyn-1-yl-4-propylbenzene, 4-ethoxyphenylacetylene, 2-ethynyl-1,3,5-trimethylbenzene, 2-ethynylbenzyl alcohol, 3',4'-dimethoxyphenyl acetylene, 2-ethynyl-benzonitrile, 4'-isopropylphenyl acetylene, 2-ethynyl-naphthalene, 1-(4-ethynyl-phenyl)-piperidine, 1-ethynyl-2-(trifluoromethoxy)benzene and 4'-diethylaminophenyl acetylene, instead of cyclopropylacetylene in Step 1 of Example 475.

Example 476

(Z)-5-[{7-(4-Hydroxybutyn-1-yl)furo[3,2-c]pyridin-2-yl}methylene]-2-thioxothiazolidin-4-one $^1$H NMR (DMSO-$d_6$, 400 MHz) δ 9.02 (d, 1H), 8.59 (d, 1H), 7.69 (s, 1H), 4.29 (t, 1H), 3.72 (t, 1H), 2.97 (t, 1H), 2.74 (t, 1H); (yield: 50%)

Example 477

(Z)-5-[{7-(3-Hydroxybutyn-1-yl)furo[3,2-c]pyridin-2-yl}methylene]-2-thioxothiazolidin-4-one $^1$H NMR (DMSO-$d_6$, 400 MHz) δ 9.04 (s, 1H), 8.60 (s, 1H), 7.70 (s, 2H), 5.73 (brs, 1H), 4.76 (m, 1H), 1.54 (d, 3H); (yield: 44%)

Example 478

(Z)-Methyl 3-[2-{(4-oxo-2-thioxothiazolidin-5-ylidene)methyl}furo[3,2-c]pyridin-7-yl]propiolate $^1$H NMR (DMSO-$d_6$, 400 MHz) δ 9.13 (s, 1H), 8.79 (s, 1H), 7.66 (d, 2H), 3.81 (s, 3H); (yield: 55%)

Example 479

(Z)-5-[{7-(Cyclopentylethynyl)furo[3,2-c]pyridin-2-yl}methylene]-2-thioxothiazolidin-4-one $^1$H NMR (DMSO-$d_6$, 400 MHz) δ 9.00 (s, 1H), 8.56 (s, 1H), 7.68 (d, 2H), 3.06 (m, 1H), 2.04 (brs, 2H), 1.84 (m, 4H), 1.66 (m, 2H); (yield: 46%)

Example 480

(Z)-5-[{7-(Cyclohexylethynyl)furo[3,2-c]pyridin-2-yl}methylene]-2-thioxothiazolidin-4-one $^1$H NMR (DMSO-$d_6$, 400 MHz) δ 8.98 (s, 1H), 8.54 (s, 1H), 7.66 (s, 2H), 2.86 (brs, 1H), 1.91 (brs, 2H), 1.78 (brs, 2H), 1.69 (d, 2H), 1.50 (brs, 4H); (yield: 56%)

Example 481

(Z)-5-([7-{(4-Methoxyphenyl)ethynyl}furo[3,2-c] pyridin-2-yl]methylene)-2-thioxothiazolidin-4-one $^1$H NMR (DMSO-$d_6$, 400 MHz) δ 9.02 (s, 1H), 8.67 (s, 1H), 7.69-7.64 (m, 4H), 7.04 (d, 2H), 3.84 (s, 3H); (yield: 51%)

Example 482

(Z)-5-[{7-(3,3-Dimethylbutyn-1-yl)furo[3,2-c]pyridin-2-yl}methylene]-2-thioxothiazolidin-4-one $^1$H NMR (DMSO-$d_6$, 400 MHz) δ 8.99 (s, 1H), 8.54 (s, 1H), 7.67 (d, 2H), 1.44 (s, 9H); (yield: 59%)

Example 483

(Z)-5-[{7-(3,3-Diethoxypropyn-1-yl)furo[3,2-c]pyridin-2-yl}methylene]-2-thioxothiazolidin-4-one $^1$H NMR (DMSO-$d_6$, 400 MHz) δ 13.72-14.04 (m, 1H), 9.10 (s, 1H), 8.69 (s, 1H), 7.72 (s, 2H), 5.71 (s, 1H), 3.81-3.85 (m, 2H), 3.69-3.73 (m, 2H), 1.25 (dd, 6H); (yield: 59%)

Example 484

(Z)-2-Thioxo-5-{(7-[{4-(trifluoromethyl) phenyl}ethynyl]furo[3,2-c]pyridin-2-yl) methylene}thiazolidin-4-one $^1$H NMR (DMSO-$d_6$, 400 MHz) δ 9.12 (s, 1H), 8.80 (s, 1H), 7.94-7.86 (m, 4H), 7.74 (m, 2H); (yield: 40%)

Example 485

(Z)-2-Thioxo-5-{(7-[{3-(trifluoromethyl)phenyl}ethynyl]furo[3,2-c]pyridin-2-yl)methylene}thiazolidin-4-one ¹H NMR (DMSO-d₆, 400 MHz) δ 9.10 (s, 1H), 8.77 (s, 1H), 8.00 (m, 3H), 7.89 (m, 1H), 7.77 (m, 1H), 7.72 (s, 2H); (yield: 44%)

Example 486

(Z)-5-([7-{(2-Methoxyphenyl)ethynyl}furo[3,2-c]pyridin-2-yl]methylene)-2-thioxothiazolidin-4-one ¹H NMR (DMSO-d₆, 400 MHz) δ 9.07 (s, 1H), 8.71 (s, 1H), 7.74 (s, 2H), 7.64 (d, 1H), 7.49 (t, 1H), 7.18 (d, 1H), 7.05 (t, 1H), 3.96 (s, 3H); (yield: 50%)

Example 487

(Z)-5-([7-{(3-Methoxyphenyl)ethynyl}furo[3,2-c]pyridin-2-yl]methylene)-2-thioxothiazolidin-4-one ¹H NMR (DMSO-d₆, 400 MHz) δ 9.09 (s, 1H), 8.75 (s, 1H), 7.74 (d, 2H), 7.42 (t, 1H), 7.31 (d, 1H), 7.21 (m, 1H), 7.09 (m, 1H), 3.85 (s, 3H); (yield: 52%)

Example 488

(Z)-5-([7-{(3-Fluorophenyl)ethynyl}furo[3,2-c]pyridin-2-yl]methylene)-2-thioxothiazolidin-4-one ¹H NMR (DMSO-d₆, 400 MHz) δ 9.09 (s, 1H), 8.74 (s, 1H), 7.72 (s, 2H), 7.56 (s, 2H), 7.50 (d, 1H), 7.37 (m, 1H); (yield: 53%)

Example 489

(Z)-5-([7-{(4-Fluorophenyl)ethynyl}furo[3,2-c]pyridin-2-yl]methylene)-2-thioxothiazolidin-4-one ¹H NMR (DMSO-d₆, 400 MHz) δ 9.09 (s, 1H), 8.75 (s, 1H), 7.77 (m, 2H), 7.74 (d, 2H), 7.36 (t, 2H); (yield: 49%)

Example 490

(Z)-5-[{7-(Pyridin-2-ylethynyl)furo[3,2-c]pyridin-2-yl}methylene]-2-thioxothiazolidin-4-one ¹H NMR (DMSO-d₆, 400 MHz) δ 9.10 (s, 1H), 8.79 (s, 1H), 8.71 (d, 1H), 7.94 (m, 1H), 7.82 (m, 1H), 7.63 (m, 2H), 7.52 (m, 1H); (yield: 47%)

Example 491

(Z)-5-[{7-(Pyridin-3-ylethynyl)furo[3,2-c]pyridin-2-yl}methylene]-2-thioxothiazolidin-4-one ¹H NMR (DMSO-d₆, 400 MHz) δ 9.12 (s, 1H), 8.90 (s, 1H), 8.79 (s, 1H), 8.70 (m, 1H), 8.11 (m, 1H), 7.74 (d, 2H), 7.57 (m, 1H); (yield: 50%)

Example 492

(Z)-5-{(7-[{4-(Dimethylamino)phenyl}ethynyl]furo[3,2-c]pyridin-2-yl)methylene}-2-thioxothiazolidin-4-one ¹H NMR (DMSO-d₆, 400 MHz) δ 9.03 (s, 1H), 8.51 (s, 1H), 8.00 (d, 1H), 7.67 (m, 2H), 7.60 (m, 2H), 6.79 (m, 1H), 3.36 (s, 6H); (yield: 55%)

Example 493

(Z)-5-([7-{(4-Methoxy-2-methylphenyl)ethynyl}furo[3,2-c]pyridin-2-yl]methylene)-2-thioxothiazolidin-4-one ¹H NMR (DMSO-d₆, 400 MHz) δ 9.05 (s, 1H), 8.72 (s, 1H), 7.73 (m, 2H), 7.59 (d, 1H), 7.01 (m, 1H), 6.87 (m, 1H), 3.82 (s, 3H), 2.62 (s, 3H); (yield: 57%)

Example 494

(Z)-5-([7-{(3,5-Dimethoxyphenyl)ethynyl}furo[3,2-c]pyridin-2-yl]methylene)-2-thioxothiazolidin-4-one ¹H NMR (DMSO-d₆, 400 MHz) δ 9.09 (s, 1H), 8.74 (s, 1H), 7.74 (d, 2H), 6.83 (m, 2H), 6.65 (m, 1H), 3.83 (s, 6H); (yield: 40%)

Example 495

(Z)-5-([7-{(3,4-Difluorophenyl)ethynyl}furo[3,2-c]pyridin-2-yl]methylene)-2-thioxothiazolidin-4-one ¹H NMR (DMSO-d₆, 400 MHz) δ 9.10 (s, 1H), 8.74 (s, 1H), 7.80 (m, 1H), 7.72 (m, 2H), 7.58 (m, 2H); (yield: 46%)

Example 496

(Z)-5-[{7-(Naphthalen-1-ylethynyl)furo[3,2-c]pyridin-2-yl}methylene]-2-thioxothiazolidin-4-one ¹H NMR (DMSO-d₆, 400 MHz) δ 9.10 (s, 1H), 8.87 (s, 1H), 8.58 (d, 1H), 8.09 (m, 2H), 7.98 (m, 1H), 7.89 (t, 1H), 7.77 (s, 1H), 7.75 (s, 1H), 7.69 (m, 2H), 7.62 (m, 2H); (yield: 87%)

Example 497

(Z)-5-([7-{(4-Fluoro-3-methylphenyl)ethynyl}furo[3,2-c]pyridin-2-yl]methylene)-2-thioxothiazolidin-4-one ¹H NMR (DMSO-d₆, 400 MHz) δ 9.07 (s, 1H), 8.71 (s, 1H), 7.72 (d, 2H), 7.65 (m, 1H), 7.56 (m, 1H), 7.29 (t, 1H), 2.33 (s, 3H); (yield: 46%)

Example 498

(Z)-2-Thioxo-5-[{7-(o-tolylethynyl)furo[3,2-c]pyridin-2-yl}methylene]thiazolidin-4-one ¹H NMR (DMSO-d₆, 400 MHz) δ 9.08 (s, 1H), 8.76 (s, 1H), 7.73 (d, 2H), 7.67 (d, 1H), 7.41 (m, 2H), 7.27 (m, 1H), 2.64 (s, 3H); (yield: 47%)

Example 499

(Z)-5-([7-{(2-Chlorophenyl)ethynyl}furo[3,2-c]pyridin-2-yl]methylene)-2-thioxothiazolidin-4-one ¹H NMR (DMSO-d₆, 400 MHz) δ 9.12 (s, 1H), 8.79 (s, 1H), 7.82 (d, 1H), 7.73 (m, 2H), 7.68 (d, 1H), 7.53 (m, 1H), 7.48 (m, 2H); (yield: 50%)

Example 500

(Z)-5-([7-{(3-Hydroxyphenyl)ethynyl}furo[3,2-c]pyridin-2-yl]methylene)-2-thioxothiazolidin-4-one ¹H NMR (DMSO-d₆, 400 MHz) δ 9.82 (s, 1H), 9.12 (s, 1H), 9.77 (s, 1H), 7.73 (d, 2H), 7.29 (m, 1H), 7.17 (m, 1H), 7.03 (s, 1H), 6.93 (d, 1H); (yield: 54%)

Example 501

(Z)-2-Thioxo-5-([7-{(2,4,5-trimethylphenyl)ethynyl}furo[3,2-c]pyridin-2-yl]methylene)thiazolidin-4-one ¹H NMR (DMSO-d₆, 400 MHz) δ 9.05 (s, 1H), 8.71 (s, 1H), 7.72 (m, 2H), 7.43 (s, 1H), 7.17 (s, 1H), 2.55 (s, 3H), 2.26 (s, 6H); (yield: 45%)

Example 502

(Z)-5-([7-{(3,4-Dichlorophenyl)ethynyl}furo[3,2-c]pyridin-2-yl]methylene)-2-thioxothiazolidin-4-one ¹H NMR (DMSO-d₆, 400 MHz) δ 9.08 (s, 1H), 8.73 (s, 1H), 7.90 (m, 1H), 7.75 (m, 1H), 7.70 (s, 2H), 7.65 (m, 1H); (yield: 51%)

Example 503

(Z)-5-([7-{(4-Butylphenyl)ethynyl}furo[3,2-c]pyridin-2-yl]methylene)-2-thioxothiazolidin-4-one ¹H NMR (DMSO-d₆, 400 MHz) δ 9.06 (s, 1H), 8.71 (s, 1H), 7.72 (d, 2H), 7.62 (d, 2H), 7.33 (d, 2H), 2.66 (m, 2H), 1.58 (m, 2H), 1.33 (m, 2H), 0.92 (t, 3H); (yield: 47%)

Example 504

(Z)-2-{4-([2-{(4-Oxo-2-thioxothiazolidin-5-ylidene)methyl}furo[3,2-c]pyridin-7-yl]ethynyl)phenyl}acetonitrile ¹H NMR (DMSO-d₆, 400 MHz) δ 9.07 (s, 1H), 8.73 (s, 1H), 7.73 (m, 4H), 7.48 (d, 2H), 4.16 (s, 2H); (yield: 39%)

Example 505

(Z)-2-Thioxo-5-{(7-[{3-(trifluoromethoxy)phenyl}ethynyl]furo[3,2-c]pyridin-2-yl)methylene}thiazolidin-4-one ¹H NMR (DMSO-d₆, 400 MHz) δ 9.09 (s, 1H), 8.75 (s, 1H), 7.73 (m, 1H), 7.71 (m, 2H), 7.65 (m, 1H), 7.53 (m, 1H); (yield: 47%)

Example 506

(Z)—N-{4-([2-{(4-Oxo-2-thioxothiazolidin-5-ylidene)methyl}furo[3,2-c]pyridin-7-yl]ethynyl)phenyl}methanesulfonamide ¹H NMR (DMSO-d₆, 400 MHz) δ 9.06 (s, 1H), 8.71 (s, 1H), 7.71 (d, 1H), 7.67 (d, 1H), 7.56 (d, 1H), 7.32 (d, 1H), 7.22 (d, 1H), 3.09 (s, 3H); (yield: 45%)

Example 507

(Z)-3-([2-{(4-Oxo-2-thioxothiazolidin-5-ylidene)methyl}furo[3,2-c]pyridin-7-yl]ethynyl)benzonitrile ¹H NMR (DMSO-d₆, 400 MHz) δ 9.08 (s, 1H), 8.73 (s, 1H), 8.08 (m, 1H), 7.98 (m, 2H), 7.70 (m, 3H); (yield: 42%)

Example 508

(Z)-5-([7-{(4-Propylphenyl)ethynyl}furo[3,2-c]pyridin-2-yl]methylene)-2-thioxothiazolidin-4-one ¹H NMR (DMSO-d₆, 400 MHz) δ 9.06 (s, 1H), 8.71 (s, 1H), 7.71 (m, 2H), 7.63 (m, 2H), 7.32 (d, 2H), 2.64 (m, 2H), 1.63 (m, 2H), 0.92 (t, 3H); (yield: 45%)

Example 509

(Z)-5-([7-{(4-Ethoxyphenyl)ethynyl}furo[3,2-c]pyridin-2-yl]methylene)-2-thioxothiazolidin-4-one ¹H NMR (DMSO-d₆, 400 MHz) δ 9.03 (s, 1H), 8.68 (s, 1H), 7.70 (m, 2H), 7.63 (m, 2H), 7.03 (d, 2H), 4.12 (m, 2H), 1.36 (t, 3H); (yield: 39%)

Example 510

(Z)-5-[{7-(Mesitylethynyl)furo[3,2-c]pyridin-2-yl}methylene]-2-thioxothiazolidin-4-one ¹H NMR (DMSO-d₆, 400 MHz) δ 9.05 (s, 1H), 8.74 (s, 1H), 7.72 (d, 2H), 7.03 (s, 2H), 2.57 (s, 6H), 2.30 (s, 3H); (yield: 41%)

Example 511

(Z)-5-{(7-[{2-(Hydroxymethyl)phenyl}ethynyl]furo[3,2-c]pyridin-2-yl)methylene}-2-thioxothiazolidin-4-one ¹H NMR (DMSO-d₆, 400 MHz) δ 9.08 (s, 1H), 8.76 (s, 1H), 7.73 (s, 2H), 7.69 (d, 1H), 7.63 (m, 1H), 7.54 (m, 1H), 7.51 (m, 1H), 7.37 (m, 1H), 4.85 (s, 2H); (yield: 41%)

Example 512

(Z)-5-([7-{(3,4-Dimethoxyphenyl)ethynyl}furo[3,2-c]pyridin-2-yl]methylene)-2-thioxothiazolidin-4-one ¹H NMR (DMSO-d₆, 400 MHz) δ 9.03 (s, 1H), 8.68 (s, 1H), 7.71 (m, 2H), 7.28 (m, 1H), 7.17 (s, 1H), 7.05 (m, 1H), 3.84 (d, 6H); (yield: 47%)

Example 513

(Z)-2-([2-{(4-Oxo-2-thioxothiazolidin-5-ylidene)methyl}furo[3,2-c]pyridin-7-yl]ethynyl)benzonitrile $^1$H NMR (DMSO-d$_6$, 400 MHz) δ 9.14 (s, 1H), 8.77 (s, 1H), 8.04 (d, 1H), 7.93 (m, 1H), 7.85 (t, 1H), 7.73 (m, 3H); (yield: 38%)

Example 514

(Z)-5-([7-{(4-Isopropylphenyl)ethynyl}furo[3,2-c]pyridin-2-yl]methylene)-2-thioxothiazolidin-4-one $^1$H NMR (DMSO-d$_6$, 400 MHz) δ 9.06 (s, 1H), 8.71 (s, 1H), 7.71 (m, 2H), 7.64 (m, 2H), 7.38 (d, 2H), 3.34 (m, 1H), 1.24 (d, 6H); (yield: 38%)

Example 515

(Z)-5-[{7-(Naphthalen-2-ylethynyl)furo[3,2-c]pyridin-2-yl}methylene]-2-thioxothiazolidin-4-one $^1$H NMR (DMSO-d$_6$, 400 MHz) δ 9.07 (s, 1H), 8.76 (s, 1H), 8.32 (s, 1H), 8.03 (m, 3H), 7.73 (m, 3H), 7.62 (m, 2H); (yield: 39%)

Example 516

(Z)-5-{(7-[{4-(Piperidin-1-yl)phenyl}ethynyl]furo[3,2-c]pyridin-2-yl}methylene)-2-thioxothiazolidin-4-one $^1$H NMR (DMSO-d$_6$, 400 MHz) δ 8.99 (s, 1H), 8.47 (s, 1H), 7.98 (d, 2H), 7.67 (s, 1H), 7.64 (s, 1H), 7.00 (d, 1H), 4.63 (s, 2H), 3.42 (m, 4H), 1.61 (m, 6H); (yield: 41%)

Example 517

(Z)-2-Thioxo-5-{(7-[{2-(trifluoromethoxy)phenyl}ethynyl]furo[3,2-c]pyridin-2-yl)methylene}thiazolidin-4-one $^1$H NMR (DMSO-d$_6$, 400 MHz) δ 9.11 (s, 1H), 8.73 (s, 1H), 7.87 (m, 1H), 7.71 (m, 2H), 7.65 (m, 1H), 7.60~7.57 (m, 2H); (yield: 42%)

Example 518

(Z)-5-{(7-[{4-(Diethylamino)phenyl}ethynyl]furo[3,2-c]pyridin-2-yl)methylene}-2-thioxothiazolidin-4-one $^1$H NMR (DMSO-d$_6$, 400 MHz) δ 8.98 (s, 1H), 8.49 (s, 1H), 7.96 (m, 2H), 7.66 (s, 1H), 7.64 (s, 1H), 6.75 (m, 2H), 4.60 (s, 2H), 3.45 (m, 4H), 1.15 (t, 6H); (yield: 47%)

Example 519

5-[{7-(m-Tolylethynyl)furo[3,2-c]pyridin-2-yl}methyl]thiazolidine-2,4-dione

Step 1: Synthesis of 2-(diethoxymethyl)-7-(m-totlylethynyl)furo[3,2-c]pyridine

A solution prepared by dissolving 3-iodotoluene (0.65 mmol), triphenylphosphine (0.11 mmol) and copper(I) iodide (0.15 mmol) in anhydrous triethylamine (3 ml) was added with bis(triphenylphosphine)palladium(II) dichloride (0.03 mmol) and stirred at room temperature for 20 minutes. The reaction mixture was slowly added with 2-(diethoxymethyl)-7-ethynylfuro[3,2-c]pyridine (0.33 mmol) obtained in Reference Example 3, heated to 60° C. and stirred for 12 hours. The reaction mixture was cooled to room temperature, diluted with ethyl acetate and washed with a saturated aqueous ammonium chloride solution, water and brine, in sequence, which was then dried over anhydrous magnesium sulfate and filtered. The filtrate was concentrated, and the residue thus obtained was purified by silica gel column chromatography (n-hexane/ethyl acetate=10/1, v/v) to obtain the title compound as light brown oil (yield: 78%).

$^1$H NMR (CDCl$_3$, 400 MHz) δ 8.83 (s, 1H), 8.64 (s, 1H), 7.46 (s, 1H), 7.43 (d, 1H), 7.29 (d, 1H), 7.20 (d, 1H), 6.92 (s, 1H), 5.72 (s, 1H), 3.70 (m, 4H), 2.39 (s, 3H), 1.28 (t, 6H)

Step 2: Synthesis of 7-(m-tolylethynyl)furo[3,2-c]pyridine-2-carbaldehyde

A solution prepared by dissolving 2-(diethoxymethyl)-7-(m-tolylethynyl)furo[3,2-c]pyridine (0.15 mmol) obtained in Step 1 in tetrahydrofuran (1 ml) was added with a 3N aqueous hydrochloric acid solution (1 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, and the filtrate was concentrated under reduced pressure to obtain the title compound as light brown oil (yield: 84%).

Step 3: Synthesis of 5-[{7-(m-tolylethynyl)furo[3,2-c]pyridin-2-yl}methyl]thiazolidine-2,4-dione A solution prepared by dissolving 7-(m-tolylethynyl)furo[3,2-c]pyridine-2-carbaldehyde (0.1 mmol) obtained in Step 2 in acetic acid (1 ml) was added with thiazolidinedione (0.2 mmol) and β-alanine (0.2 mmol), and stirred under reflux for 4 hours. The reaction solution was cooled to room temperature, and the resulting solid was filtered, washed with acetic acid and water, and dried to obtain the title compound as a light yellow solid.

$^1$H NMR (DMSO-d$_6$, 400 MHz) δ 12.64 (brs, 1H), 9.00 (s, 1H), 8.64 (s, 1H), 7.80 (s, 1H), 7.60 (s, 1H), 7.45 (s, 1H), 7.38 (d, 1H), 7.32 (t, 1H), 7.26 (d, 1H), 2.31 (s, 3H); (yield: 52%)

Examples 520 to 545

The title compounds of Examples 520 to 545 were prepared in the same manner as described in Example 519 above, except for using each of the following compounds: 4-iodotoluene, 4-iodobenzonitrile, 2-iodophenol, 4-iodophenol, 2'-iodoacetophenone, 4'-iodoacetophenone, 2-iodobenzotrifluoride, 2-iodocumene, 3-iodothiophene, 1-tert-butyl-4-iodobenzene, 1-ethyl-2-iodobenzene, methyl 2-iodobenzoate, methyl 4-iodobenzoate, 1-iodo-4-(trifluoromethoxy)benzene, 1-chloro-3-iodobenzene, 1,3-dichloro-2-iodobenzene, 4-iodo-N-methylbenzenesulfonamide, 4-(4-iodophenylsulfonyl)morpholine, 4-iodo-N-isopropylbenzenesulfonamide, N-tert-butyl-4-iodobenzenesulfonamide, N-(2-hydroxyethyl)-4-iodobenzenesulfonamide, 1-chloro-4-iodobenzene, methyl 3-iodobenzoate, 3'-iodoacetophenone, 4-iodo-N,N-dimethylbenzenesulfonamide and N-ethyl-4-iodobenzenesulfonamide, instead of 3-iodotoluene in Step 1 of Example 519.

Example 520

5-[{7-(p-Tolylethynyl)furo[3,2-c]pyridin-2-yl}methyl]thiazolidine-2,4-dione $^1$H NMR (DMSO-d$_6$, 400 MHz) δ 12.64 (brs, 1H), 9.00 (s, 1H), 8.64 (s, 1H), 7.80 (s, 1H), 7.60 (s, 1H), 7.45 (s, 1H), 7.38 (d, 1H), 7.32 (t, 1H), 7.26 (d, 1H), 2.31 (s, 3H); (yield: 46%)

Example 521

(Z)-4-([2-{(2,4-Dioxothiazolidin-5-ylidene)methyl}furo[3,2-c]pyridin-7-yl]ethynyl)benzonitrile $^1$H NMR (DMSO-d$_6$, 400 MHz) δ 12.72 (brs, 1H), 9.11 (s, 1H), 8.79 (s, 1H), 7.99 (d, 2H), 7.85 (m, 3H), 7.69 (s, 1H); (yield: 59%)

Example 522

(Z)-5-([7-{(2-Hydroxyphenyl)ethynyl}furo[3,2-c]pyridin-2-yl]methylene)thiazolidine-2,4-dione $^1$H NMR (DMSO-d$_6$, 400 MHz) δ 12.74 (brs, 1H), 9.09 (d, 2H), 7.94 (s, 1H), 7.82 (d, 1H), 7.77 (s, 1H), 7.71 (d, 2H), 7.45 (t, 1H), 7.36 (t, 1H); (yield: 55%)

Example 523

(Z)-5-([7-{(4-Hydroxyphenyl)ethynyl}furo[3,2-c]pyridin-2-yl]methylene)thiazolidine-2,4-dione $^1$H NMR (DMSO-d$_6$, 400 MHz) δ 12.68 (brs, 1H), 10.07 (s, 1H), 9.02 (s, 1H), 8.66 (s, 1H), 7.85 (s, 1H), 7.65 (s, 1H), 7.49 (d, 2H), 6.87 (d, 2H); (yield: 49%)

Example 524

(Z)-5-([7-{(2-Acetylphenyl)ethynyl}furo[3,2-c]pyridin-2-yl]methylene)thiazolidine-2,4-dione $^1$H NMR (DMSO-d$_6$, 400 MHz) δ 12.75 (brs, 1H), 9.08 (s, 1H), 8.50 (s, 1H), 7.83 (s, 1H), 7.67 (s, 1H), 7.60 (d, 1H), 7.55 (d, 2H), 7.47 (t, 1H), 2.36 (s, 3H); (yield: 61%)

Example 525

(Z)-5-([7-{(4-Acetylphenyl)ethynyl}furo[3,2-c]pyridin-2-yl]methylene)thiazolidine-2,4-dione $^1$H NMR (DMSO-d$_6$, 400 MHz) δ 12.64 (brs, 1H), 9.08 (s, 1H), 8.76 (s, 1H), 8.05 (d, 2H), 7.85 (s, 1H), 7.79 (d, 2H), 7.66 (s, 1H), 2.63 (s, 3H); (yield: 56%)

Example 526

(Z)-5-{(7-[{(2-(Trifluoromethyl)phenyl}ethynyl]furo[3,2-c]pyridin-2-yl)methylene}thiazolidine-2,4-dione $^1$H NMR (DMSO-d$_6$, 400 MHz) δ 12.63 (brs, 1H), 9.10 (s, 1H), 8.74 (s, 1H), 7.90 (dd, 2H), 7.83-7.78 (m, 2H), 7.73-7.68 (m, 2H); (yield: 53%)

Example 527

(Z)-5-([7-{(2-Isopropylphenyl)ethynyl}furo[3,2-c]pyridin-2-yl]methylene)-2-thioxothiazolidin-4-one $^1$H NMR (DMSO-d$_6$, 400 MHz) δ 12.61 (brs, 1H), 9.05 (s, 1H), 8.74 (s, 1H), 7.85 (s, 1H), 7.67 (s, 1H), 7.63 (d, 1H), 7.46 (d, 2H), 7.30 (m, 1H), 3.71 (m, 1H), 1.33 (d, 6H); (yield: 57%)

Example 528

(Z)-5-[{7-(Thiophen-3-ylethynyl)furo[3,2-c]pyridin-2-yl}methylene]thiazolidine-2,4-dione $^1$H NMR (DMSO-d$_6$, 400 MHz) δ 12.60 (brs, 1H), 9.04 (s, 1H), 8.68 (s, 1H), 8.00 (s, 1H), 7.83 (s, 1H), 7.73 (s, 1H), 7.63 (s, 1H), 7.34 (m, 1H); (yield: 58%)

Example 529

(Z)-5-([7-{(4-tert-Butylphenyl)ethynyl}furo[3,2-c]pyridin-2-yl]methylene)thiazolidine-2,4-dione $^1$H NMR (DMSO-d$_6$, 400 MHz) δ 12.71 (brs, 1H), 9.05 (s, 1H), 8.71 (s, 1H), 7.86 (s, 1H), 7.66 (s, 1H), 7.60 (d, 2H), 7.53 (d, 2H), 1.32 (s, 9H); (yield: 53%)

Example 530

(Z)-5-([7-{(2-Ethylphenyl)ethynyl}furo[3,2-c]pyridin-2-yl]methylene)thiazolidine-2,4-dione $^1$H NMR (DMSO-d$_6$, 400 MHz) δ 12.70 (brs, 1H), 9.06 (s, 1H), 8.74 (s, 1H), 7.86 (s, 1H), 7.68 (s, 1H), 7.64 (d, 1H), 7.47-7.41 (m, 2H), 7.32 (m, 1H), 3.00 (q, 2H), 1.32 (t, 3H); (yield: 57%)

Example 531

(Z)-Methyl 2-([2-{(2,4-dioxothiazolidin-5-ylidene)methyl}furo[3,2-c]pyridin-7-yl]ethynyl)benzoate $^1$H NMR (DMSO-d$_6$, 400 MHz) δ 12.70 (brs, 1H), 9.09 (s, 1H), 8.73 (s, 1H), 8.03 (d, 1H), 7.82 (d, 2H), 7.75-7.61 (m, 3H), 3.92 (s, 3H); (yield: 58%)

Example 532

(Z)-Methyl 4-([2-{(2,4-dioxothiazolidin-5-ylidene)methyl}furo[3,2-c]pyridin-7-yl]ethynyl)benzoate $^1$H NMR (DMSO-d$_6$, 400 MHz) δ 12.66 (brs, 1H), 9.07 (s, 1H), 8.74 (s, 1H), 8.04 (d, 2H), 7.84-7.77 (m, 3H), 7.65 (s, 1H), 3.91 (s, 3H); (yield: 59%)

Example 533

(Z)-5-{(7-[{(4-(Trifluoromethoxy)phenyl}ethynyl]furo[3,2-c]pyridin-2-yl)methylene}thiazolidine-2,4-dione $^1$H NMR (DMSO-d$_6$, 400 MHz) δ 12.63 (brs, 1H), 9.07 (s, 1H), 8.74 (s, 1H), 7.85 (s, 1H), 7.80 (d, 2H), 7.66 (s, 1H), 7.50 (d, 2H); (yield: 55%)

Example 534

(Z)-5-([7-{(3-Chlorophenyl)ethynyl}furo[3,2-c]pyridin-2-yl]methylene)thiazolidine-2,4-dione $^1$H NMR (DMSO-d$_6$, 400 MHz) δ 12.70 (brs, 1H), 9.08 (s, 1H), 8.73 (s, 1H), 7.86 (s, 1H), 7.72 (S, 1H), 7.66-7.54 (m, 4H); (yield: 56%)

Example 535

(Z)-5-([7-{(2,6-dichlorophenyl)ethynyl}furo[3,2-c]pyridin-2-yl]methylene)thiazolidine-2,4-dione $^1$H NMR (DMSO-d$_6$, 400 MHz) δ 12.68 (brs, 1H), 9.07 (s, 1H), 8.71 (s, 1H), 7.83 (s, 1H), 7.77 (s, 1H), 7.69 (s, 2H), 7.64 (s, 1H); (yield: 53%)

Example 536

(Z)-4-([2-{(2,4-Dioxothiazolidin-5-ylidene)methyl}furo[3,2-c]pyridin-7-yl]ethynyl)-N-methylbenzenesulfonamide $^1$H NMR (DMSO-d$_6$, 400 MHz) δ 12.68 (brs, 1H), 9.11 (s, 1H), 8.78 (s, 1H), 7.89-7.87 (m, 4H), 7.68 (s, 1H), 7.50 (s, 1H), 2.51 (s, 3H); (yield: 57%)

Example 537

(Z)-5-{(7-[{4-(Morpholinosulfonyl)phenyl}ethynyl]furo[3,2-c]pyridin-2-yl)methylene}thiazolidine-2,4-dione $^1$H NMR (DMSO-d$_6$, 400 MHz) δ 12.67 (brs, 1H), 9.11 (s, 1H), 8.79 (s, 1H), 7.93 (d, 2H), 7.87-7.85 (m, 3H), 7.68 (s, 1H), 3.65 (brs, 4H), 2.96 (brs, 4H); (yield: 58%)

Example 538

(Z)-4-([2-{(2,4-Dioxothiazolidin-5-ylidene)methyl}furo[3,2-c]pyridin-7-yl]ethynyl)-N-isopropylbenzenesulfonamide $^1$H NMR (DMSO-d$_6$, 400 MHz) δ 12.65 (brs, 1H), 9.10 (s, 1H), 8.77 (s, 1H), 7.92 (d, 2H), 7.87-7.85 (m, 3H), 7.67 (s, 2H), 3.24 (m, 1H), 1.00 (d, 6H); (yield: 53%)

Example 539

(Z)—N-tert-Butyl-4-([2-{(2,4-dioxothiazolidin-5-ylidene)methyl}furo[3,2-c]pyridin-7-yl]ethynyl)benzenesulfonamide $^1$H NMR (DMSO-d$_6$, 400 MHz) δ 12.69 (brs, 1H), 9.10 (s, 1H), 8.77 (s, 1H), 7.95 (d, 2H), 7.86-7.83 (m, 3H), 7.67 (s, 1H), 7.60 (brs, 1H), 1.15 (s, 9H); (yield: 57%)

Example 540

(Z)-4-([2-{(2,4-Dioxothiazolidin-5-ylidene)methyl}furo[3,2-c]pyridin-7-yl]ethynyl)-N-(2-hydroxyethyl)benzenesulfonamide $^1$H NMR (DMSO-d$_6$, 400 MHz) δ 12.70 (brs, 1H), 9.10 (s, 1H), 8.78 (s, 1H), 7.93-7.85 (m, 6H), 7.67 (s, 1H), 3.99 (brs, 1H), 3.36 (brs, 1H), 3.00 (brs, 1H), 2.87 (brs, 1H); (yield: 58%)

Example 541

(Z)-5-([7-{(4-Chlorophenyl)ethynyl}furo[3,2-c]pyridin-2-yl]methylene)thiazolidine-2,4-dione $^1$H NMR (DMSO-d$_6$, 400 MHz) δ 12.65 (brs, 1H), 9.07 (s, 1H), 8.73 (s, 1H), 7.85 (s, 1H), 7.69-7.66 (m, 3H), 7.58 (d, 2H); (yield: 61%)

Example 542

(Z)-Methyl 3-([2-{(2,4-dioxothiazolidin-5-ylidene)methyl}furo[3,2-c]pyridin-7-yl]ethynyl)benzoate $^1$H NMR (DMSO-d$_6$, 400 MHz) δ 12.66 (brs, 1H), 9.08 (s, 1H), 8.77 (s, 1H), 8.21 (s, 1H), 8.07 (d, 1H), 7.92 (d, 1H), 7.86 (s, 1H), 7.71-7.67 (m, 2H), 3.92 (s, 3H); (yield: 56%)

Example 543

(Z)-5-([7-{(3-Acetylphenyl)ethynyl}furo[3,2-c]pyridin-2-yl]methylene)thiazolidine-2,4-dione $^1$H NMR (DMSO-d$_6$, 400 MHz) δ 9.09 (s, 1H), 8.77 (s, 1H), 8.21 (s, 1H), 8.06 (d, 1H), 7.91 (d, 1H), 7.86 (s, 1H), 7.70 (m, 1H), 7.67 (s, 1H), 2.68 (s, 3H); (yield: 53%)

Example 544

(Z)-4-([2-{(2,4-Dioxothiazolidin-5-ylidene)methyl}furo[3,2-c]pyridin-7-yl]ethynyl)-N,N-dimethylbenzenesulfonamide $^1$H NMR (DMSO-d$_6$, 400 MHz) δ 12.57 (brs, 1H), 9.09 (s, 1H), 8.77 (s, 1H), 7.92-7.84 (m, 5H), 7.66 (s, 1H), 3.22 (s, 6H); (yield: 57%)

Example 545

(Z)-4-([2-{(2,4-Dioxothiazolidin-5-ylidene)methyl}furo[3,2-c]pyridin-7-yl]ethynyl)-N-ethylbenzenesulfonamide $^1$H NMR (DMSO-d$_6$, 400 MHz) δ 12.67 (brs, 1H), 9.10 (s, 1H), 8.77 (s, 1H), 7.92-7.86 (m, 5H), 7.67 (m, 2H), 2.87 (brs, 2H), 1.01 (t, 3H); (yield: 58%)

Example 546

2-Thioxo-5-[{7-(m-tolylethynyl)furo[3,2-c]pyridin-2-yl}methyl]thiazolidin-4-one

Step 1: Synthesis of 2-(diethoxymethyl)-7-(m-tolylethynyl)furo[3,2-c]pyridine

A solution prepared by dissolving 3-iodotoluene (0.65 mmol), triphenylphosphine (0.11 mmol) and copper(I) iodide (0.15 mmol) in anhydrous triethylamine (3 ml) was added with bis(triphenylphosphine)palladium(II) dichloride (0.03 mmol), and stirred at room temperature for 20 minutes. The reaction mixture was slowly added with 2-(diethoxymethyl)-7-ethynylfuro[3,2-c]pyridine (0.33 mmol) obtained in Reference Example 3, heated to 60° C. and stirred for 12 hours. The reaction mixture was cooled to room temperature, diluted with ethyl acetate and washed with a saturated aqueous ammonium chloride solution, water and brine, in sequence, which was then dried over anhydrous magnesium sulfate and filtered. The filtrate was concentrated, and the residue thus obtained was purified by silica gel column chromatography (n-hexane/ethyl acetate=10/1, v/v) to obtain the title compound as light brown oil (yield: 78%).

$^1$H NMR (CDCl$_3$, 400 MHz) δ 8.83 (s, 1H), 8.64 (s, 1H), 7.46 (s, 1H), 7.43 (d, 1H), 7.29 (d, 1H), 7.20 (d, 1H), 6.92 (s, 1H), 5.72 (s, 1H), 3.70 (m, 4H), 2.39 (s, 3H), 1.28 (t, 6H)

Step 2: Synthesis of 7-(m-tolylethynyl)furo[3,2-c] pyridine-2-carbaldehyde

A solution prepared by dissolving 2-(diethoxymethyl)-7-(m-tolylethynyl)furo[3,2-c]pyridine (0.15 mmol) obtained in Step 1 in tetrahydrofuran (1 ml) was added with a 3N aqueous hydrochloric acid solution (1 ml), and stirred at room temperature for 2 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, and the filtrate was concentrated under reduced pressure to obtain the title compound as light brown oil (yield: 84%).

Step 3: Synthesis of 2-thioxo-5-[{7-(m-tolylethynyl)furo[3,2-c]pyridin-2-yl}methyl]thiazolidin-4-one A solution prepared by dissolving 7-(m-tolylethynyl)furo[3,2-c]pyridine-2-carbaldehyde (0.1 mmol) obtained in Step 2 in acetic acid (1 ml) was added with rhodanine (0.2 mmol) and sodium acetate (0.2 mmol), and stirred under reflux for 4 hours. After cooled to room temperature, the resulting solid was filtered, washed with acetic acid and water, and dried to obtain the title compound as a light yellow solid.

$^1$H NMR (DMSO-d$_6$, 400 MHz) δ 9.05 (s, 1H), 8.70 (s, 1H), 7.69 (s, 2H), 5.53 (s, 1H), 7.49 (s, 1H), 7.40-7.31 (m, 2H), 2.40 (s, 3H); (yield: 53%)

Examples 547 to 572

The title compounds of Examples 547 to 572 were prepared in the same manner as described in Example 546 above, except for using each of the following compounds: 4-iodotoluene, 4-iodobenzonitrile, 2-iodophenol, 4-iodophenol, 2'-iodoacetophenone, 4'-iodoacetophenone, 2-iodobenzotrifluoride, 2-iodocumene, 3-iodothiophene, 1-tert-butyl-4-iodobenzene, 1-ethyl-2-iodobenzene, methyl 2-iodobenzoate, methyl 4-iodobenzoate, 1-iodo-4-(trifluoromethoxy)benzene, 1-chloro-3-iodobenzene, 1,3-dichloro-2-iodobenzene, 4-iodo-N-methylbenzenesulfonamide, 4-(4-iodophenylsulfonyl)morpholine, 4-iodo-N-isopropylbenzenesulfonamide, N-tert-butyl-4-iodobenzenesulfonamide, N-(2-hydroxyethyl)-4-iodobenzenesulfonamide, 1-chloro-4-iodobenzene, methyl 3-iodobenzoate, 3'-iodoacetophenone, 4-iodo-N,N-dimethylbenzenesulfonamide and N-ethyl-4-iodobenzenesulfonamide, instead of 3-iodotoluene in Step 1 of Example 546.

Example 547

2-Thioxo-5-[{7-(p-tolylethynyl)furo[3,2-c]pyridin-2-yl}methyl]thiazolidin-4-one $^1$H NMR (DMSO-d$_6$, 400 MHz) δ 9.03 (s, 1H), 8.68 (s, 1H), 7.68 (s, 2H), 7.59 (d, 2H), 7.30 (d, 2H), 2.39 (s, 3H); (yield: 57%)

Example 548

(Z)-4-([2-{(4-Oxo-2-thioxothiazolidin-5-ylidene)methyl}furo[3,2-c]pyridin-7-yl]ethynyl)benzonitrile $^1$H NMR (DMSO-d$_6$, 400 MHz) δ 9.11 (s, 1H), 8.78 (s, 1H), 7.96 (m, 2H), 7.87 (d, 2H), 7.71 (s, 2H); (yield: 62%)

Example 549

(Z)-5-([7-{(2-Hydroxyphenyl)ethynyl}furo[3,2-c]pyridin-2-yl]methylene)-2-thioxothiazolidin-4-one $^1$H NMR (DMSO-d$_6$, 400 MHz) δ 9.13 (s, 1H), 9.09 (s, 1H), 7.81 (s, 1H), 7.78-7.74 (m, 4H), 7.46 (t, 1H), 7.40 (t, 1H); (yield: 54%)

Example 550

(Z)-5-([7-{(4-Hydroxyphenyl)ethynyl}furo[3,2-c]pyridin-2-yl]methylene)-2-thioxothiazolidin-4-one $^1$H NMR (DMSO-d$_6$, 400 MHz) δ 10.03 (brs, 1H), 9.02 (s, 1H), 8.66 (s, 1H), 7.69 (s, 2H), 7.55 (d, 2H), 6.87 (d, 2H); (yield: 52%)

Example 551

(Z)-5-([7-{(2-Acetylphenyl)ethynyl}furo[3,2-c]pyridin-2-yl]methylene)-2-thioxothiazolidin-4-one $^1$H NMR (DMSO-d$_6$, 400 MHz) δ 9.09 (s, 1H), 8.51 (s, 1H), 7.74 (s, 1H), 7.69 (s, 1H), 7.63 (t, 1H), 7.54 (t, 2H), 7.47 (t, 1H), 2.36 (s, 3H); (yield: 58%)

Example 552

(Z)-5-([7-{(4-Acetylphenyl)ethynyl}furo[3,2-c]pyridin-2-yl]methylene)-2-thioxothiazolidin-4-one $^1$H NMR (DMSO-d$_6$, 400 MHz) δ 9.09 (s, 1H), 8.77 (s, 1H), 8.05 (d, 2H), 7.83 (d, 2H), 7.71 (s, 2H), 2.63 (s, 3H); (yield: 55%)

Example 553

(Z)-2-Thioxo-5-{(7-[{2-(trifluoromethyl)phenyl}ethynyl]furo[3,2-c]pyridin-2-yl)methylene}thiazolidin-4-one $^1$H NMR (DMSO-d$_6$, 400 MHz) δ 9.11 (s, 1H), 8.74 (s, 1H), 7.97 (d, 1H), 7.90 (d, 1H), 7.80 (t, 1H), 7.73-7.69 (m, 3H); (yield: 50%)

Example 554

(Z)-5-([7-{(2-Isopropylphenyl)ethynyl}furo[3,2-c]pyridin-2-yl]methylene)-2-thioxothiazolidin-4-one $^1$H NMR (DMSO-d$_6$, 400 MHz) δ 9.06 (s, 1H), 8.75 (s, 1H), 7.73-7.67 (m, 3H), 7.46 (s, 2H), 7.31 (m, 1H), 3.67 (q, 1H), 1.36 (d, 6H); (yield: 57%)

Example 555

(Z)-5-[{7-(Thiophen-3-ylethynyl)furo[3,2-c]pyridin-2-yl}methylene]-2-thioxothiazolidin-4-one $^1$H NMR (DMSO-d$_6$, 400 MHz) δ 9.05 (s, 1H), 8.70 (s, 1H), 8.02 (s, 1H), 7.75 (s, 1H), 7.69 (s, 2H), 7.38 (d, 1H); (yield: 51%)

Example 556

(Z)-5-([7-{(4-tert-Butylphenyl)ethynyl}furo[3,2-c]pyridin-2-yl]methylene)-2-thioxothiazolidin-4-one $^1$H NMR (DMSO-d$_6$, 400 MHz) δ 9.04 (s, 1H), 8.70 (s, 1H), 7.69 (s, 2H), 7.64 (d, 2H), 7.51 (d, 2H), 1.33 (s, 9H); (yield: 50%)

Example 557

(Z)-5-([7-{(2-Ethylphenyl)ethynyl}furo[3,2-c]pyridin-2-yl]methylene)-2-thioxothiazolidin-4-one $^1$H NMR (DMSO-d$_6$, 400 MHz) δ 13.89 (brs, 1H), 9.07 (s, 1H), 8.75 (s, 1H), 7.72 (d, 2H), 7.67 (d, 1H), 7.44-7.41 (m, 2H), 7.31 (m, 1H), 2.98 (q, 2H), 1.37 (t, 3H); (yield: 57%)

Example 558

(Z)-Methyl 2-([2-{(4-oxo-2-thioxothiazolidin-5-ylidene)methyl}furo[3,2-c]pyridin-7-yl]ethynyl)benzoate $^1$H NMR (DMSO-d$_6$, 400 MHz) δ 13.87 (brs, 1H), 9.08 (s, 1H), 8.71 (s, 1H), 8.02 (d, 1H), 7.88 (d, 1H), 7.73-7.69 (m, 3H), 7.62 (m, 1H), 3.93 (s, 3H); (yield: 58%)

Example 559

(Z)-Methyl 4-([2-{(4-oxo-2-thioxothiazolidin-5-ylidene)methyl}furo[3,2-c]pyridin-7-yl]ethynyl)benzoate $^1$H NMR (DMSO-d$_6$, 400 MHz) δ 13.83 (brs, 1H), 9.05 (s, 1H), 8.71 (s, 1H), 8.01 (d, 2H), 7.80 (d, 2H), 7.67 (s, 1H), 3.90 (s, 3H); (yield: 52%)

Example 560

(Z)-2-Thioxo-5-{(7-[{4-(trifluoromethoxy)phenyl}ethynyl]furo[3,2-c]pyridin-2-yl)methylene}thiazolidin-4-one $^1$H NMR (DMSO-d$_6$, 400 MHz) δ 9.07 (s, 1H), 8.72 (s, 1H), 7.82 (d, 2H), 7.69 (s, 2H), 7.48 (d, 2H); (yield: 54%)

Example 561

(Z)-5-([7-{(3-Chlorophenyl)ethynyl}furo[3,2-c]pyridin-2-yl]methylene)-2-thioxothiazolidin-4-one $^1$H NMR (DMSO-d$_6$, 400 MHz) δ 9.09 (s, 1H), 8.74 (s, 1H), 7.72-7.54 (m, 6H); (yield: 61%)

Example 562

(Z)-5-([7-{(2,6-Dichlorophenyl)ethynyl}furo[3,2-c]pyridin-2-yl]methylene)-2-thioxothiazolidin-4-one $^1$H NMR (DMSO-d$_6$, 400 MHz) δ 9.09 (s, 1H), 8.73 (s, 1H), 7.78-7.64 (m, 5H); (yield: 63%)

Example 563

(Z)—N-Methyl-4-([2-{(4-oxo-2-thioxothiazolidin-5-ylidene)methyl}furo[3,2-c]pyridin-7-yl]ethynyl)benzenesulfonamide $^1$H NMR (DMSO-d$_6$, 400 MHz) δ 9.03 (s, 1H), 8.70 (s, 1H), 7.83 (m, 4H), 7.65 (s, 2H), 7.49 (brs, 1H), 2.43 (s, 3H); (yield: 55%)

Example 564

(Z)-5-{(7-[{4-(Morpholinosulfonyl)phenyl}ethynyl]furo[3,2-c]pyridin-2-yl)methylene}-2-thioxothiazolidin-4-one $^1$H NMR (DMSO-d$_6$, 400 MHz) δ 9.12 (s, 1H), 8.79 (s, 1H), 7.97 (d, 2H), 7.85 (d, 2H), 7.72 (s, 2H), 3.66 (brs, 4H), 2.98 (brs, 4H); (yield: 66%)

Example 565

(Z)—N-Isopropyl-4-([2-{(4-oxo-2-thioxothiazolidin-5-ylidene)methyl}furo[3,2-c]pyridin-7-yl]ethynyl)benzenesulfonamide $^1$H NMR (DMSO-d$_6$, 400 MHz) δ 9.11 (s, 1H), 8.78 (s, 1H), 7.92 (m, 4H), 7.71 (s, 2H), 7.70 (brs, 1H), 3.26 (m, 1H), 1.01 (d, 6H); (yield: 55%)

Example 566

(Z)—N-tert-Butyl-4-([2-{(4-oxo-2-thioxothiazolidin-5-ylidene)methyl}furo[3,2-c]pyridin-7-yl]ethynyl)benzenesulfonamide $^1$H NMR (DMSO-d$_6$, 400 MHz) δ 9.11 (s, 1H), 8.78 (s, 1H), 7.95 (d, 2H), 7.89 (d, 2H), 7.72 (s, 2H), 7.65 (brs, 1H), 1.15 (s, 9H); (yield: 49%)

Example 567

(Z)—N-(2-Hydroxyethyl)-4-([2-{(4-oxo-2-thioxothiazolidin-5-ylidene)methyl}furo[3,2-c]pyridin-7-yl]ethynyl)benzenesulfonamide $^1$H NMR (DMSO-d$_6$, 400 MHz) δ 9.11 (s, 1H), 8.78 (s, 1H), 7.92 (s, 4H), 7.72 (s, 1H), 7.70 (brs, 1H), 3.42 (brs, 2H), 2.90 (brs, 2H); (yield: 50%)

Example 568

(Z)-5-([7-{(4-Chlorophenyl)ethynyl}furo[3,2-c]pyridin-2-yl]methylene)-2-thioxothiazolidin-4-one $^1$H NMR (DMSO-d$_6$, 400 MHz) δ 9.08 (s, 1H), 8.73 (s, 1H), 7.74-7.70 (m, 4H), 7.56 (d, 2H); (yield: 55%)

Example 569

(Z)-Methyl 3-([2-{(4-oxo-2-thioxothiazolidin-5-ylidene)methyl}furo[3,2-c]pyridin-7-yl]ethynyl)benzoate $^1$H NMR (DMSO-$d_6$, 400 MHz) δ 9.09 (s, 1H), 8.78 (s, 1H), 8.21 (s, 1H), 8.07 (d, 1H), 7.97 (d, 1H), 7.71-7.66 (m, 3H); (yield: 56%)

Example 570

(Z)-5-([7-{(3-Acetylphenyl)ethynyl}furo[3,2-c]pyridin-2-yl]methylene)-2-thioxothiazolidin-4-one $^1$H NMR (DMSO-$d_6$, 400 MHz) δ 9.09 (s, 1H), 8.76 (s, 1H), 8.20 (s, 1H), 8.05 (d, 1H), 7.95 (d, 1H), 7.70 (s, 2H), 7.67 (m, 1H), 3.24 (s, 3H); (yield: 56%)

Example 571

(Z)—N,N-Dimethyl-4-([2-{(4-oxo-2-thioxothiazolidin-5-ylidene)methyl}furo[3,2-c]pyridin-7-yl]ethynyl)benzenesulfonamide $^1$H NMR (DMSO-$d_6$, 400 MHz) δ 9.10 (s, 1H), 8.77 (s, 1H), 7.94 (d, 2H), 7.85 (d, 2H), 7.70 (s, 2H), 2.69 (s, 6H); (yield: 54%)

Example 572

(Z)—N-Ethyl-4-([2-{(4-oxo-2-thioxothiazolidin-5-ylidene)methyl}furo[3,2-c]pyridin-7-yl)ethynyl)benzenesulfonamide $^1$H NMR (DMSO-$d_6$, 400 MHz) δ 9.10 (s, 1H), 8.77 (s, 1H), 7.90 (s, 3H), 7.87 (m, 1H), 7.70 (s, 2H), 7.65 (brs, 1H), 2.86 (brs, 2H), 1.01 (t, 3H); (yield: 62%)

Example 573

(Z)-5-[{6-(4-Methoxyphenyl)furo[3,2-c]pyridin-2-yl}methylene]thiazolidine-2,4-dione Step 1: Synthesis of 2-(diethoxymethyl)-6-(4-methoxyphenyl)furo[3,2-c]pyridine A solution prepared by dissolving 6-chloro-2-(diethoxymethyl)furo[3,2-c]pyridine (0.39 mmol) obtained in Reference Example 7 in toluene/ethanol/water (5/1/2, v/v, 4 ml) was added with 4-methoxyphenylboronic acid (0.47 mmol), sodium carbonate (0.98 mmol) and tetrakis(triphenylphosphine)palladium(0) (5.0 mol %), and stirred under reflux for 12 hours. The organic layer was separated and concentrated under reduced pressure. The residue thus obtained was purified by silica gel column chromatography (n-hexane/ethyl acetate=4/1, v/v) to obtain the title compound as light brown oil (yield: 80%).

$^1$H NMR (CDCl$_3$, 400 MHz) δ 8.91 (s, 1H), 8.00-7.95 (m, 2H), 7.77 (s, 1H), 7.05-7.00 (m, 2H), 6.87 (s, 1H), 5.68 (s, 1H), 3.87 (s, 3H), 3.70 (q, 4H), 1.29 (t, 6H)

Step 2: Synthesis of 6-(4-methoxyphenyl)furo[3,2-c]pyridine-2-carbaldehyde

A solution prepared by dissolving 2-(diethoxymethyl)-6-(4-methoxyphenyl)furo[3,2-c]pyridine (0.2 mmol) obtained in Step 1 in tetrahydrofuran (3 ml) was added with a 3N aqueous hydrochloric acid solution (3 ml), and stirred at room temperature for 12 hours. The reaction solution was neutralized by adding an aqueous sodium bicarbonate solution thereto, and the organic solvent was removed therefrom under reduced pressure, which was then extracted with ethyl acetate. The extract thus obtained was washed with brine, dried over anhydrous magnesium sulfate and filtered, and the filtrate was concentrated under reduced pressure to obtain the title compound as a yellow solid (yield: 90%).

$^1$H NMR (CDCl$_3$, 400 MHz) δ 9.91 (s, 1H), 9.13 (s, 1H), 8.04 (d, 2H), 7.86 (s, 1H), 7.62 (s, 1H), 7.04 (d, 2H), 3.89 (s, 3H)

Step 3: Synthesis of (Z)-5-[{6-(4-methoxyphenyl)furo[3,2-c]pyridin-2-yl}methylene]thiazolidine-2,4-dione A solution prepared by dissolving 6-(4-methoxyphenyl)furo[3,2-c]pyridine-2-carbaldehyde (0.1 mmol) obtained in Step 2 in acetic acid (2 ml) was added with thiazolidinedione (0.1 mmol) and β-alanine (0.1 mmol), and stirred under reflux for 4 hours. After cooled to room temperature, the resulting solid was filtered, washed with acetic acid and water, and dried to obtain the title compound as a light yellow solid (yield: 71%).

$^1$H NMR (DMSO-$d_6$, 400 MHz) δ 12.59 (brs, 1H), 9.00 (s, 1H), 8.18 (s, 1H), 8.11 (d, 2H), 7.74 (s, 1H), 7.53 (s, 1H), 6.99 (d, 2H), 3.76 (s, 3H)

Example 574

(Z)-5-([6-{4-(Trifluoromethoxy)benzyl}furo[3,2-c]pyridin-2-yl]methylene)thiazolidine-2,4-dione The title compound was prepared in the same manner as described in Example 573, except for using 4-(trifluoromethoxy)benzylboronic acid pinacol ester instead of 4-methoxyphenylboronic acid in Step 1 of Example 573.

$^1$H NMR (DMSO-$d_6$, 400 MHz) δ 12.65 (brs, 1H), 8.96 (s, 1H), 7.78 (s, 1H), 7.74 (s, 1H), 7.56 (s, 1H), 7.44 (d, 2H), 7.28 (d, 2H), 4.24 (s, 2H); (yield: 20%)

Example 575

(Z)-5-[{6-(2-Methoxyphenyl)furo[3,2-c]pyridin-2-yl}methylene]-2-thioxothiazolidin-4-one Step 1: Synthesis of 2-(diethoxymethyl)-6-(2-methoxyphenyl)furo[3,2-c]pyridine The title compound was prepared in the same manner as described in Step 1 of Example 573, except for using 6-chloro-2-(diethoxymethyl)furo[3,2-c]pyridine obtained in Reference Example 7 and 2-methoxyphenylboronic acid (yield: 55%).

Step 2: Synthesis of 6-(2-methoxyphenyl)furo[3,2-c]pyridine-2-carbaldehyde

The title compound was prepared in the same manner as described in Step 2 of Example 573, except for using 2-(diethoxymethyl)-6-(2-methoxyphenyl)furo[3,2-c]pyridine obtained in Step 1 (yield: 90%).

Step 3: Synthesis of (Z)-5-[{6-(2-methoxyphenyl)furo[3,2-c]pyridin-2-yl}methylene]-2-thioxothiazolidin-4-one A solution prepared by dissolving 6-(2-methoxyphenyl)furo[3,2-c]pyridine-2-carbaldehyde (0.1 mmol) obtained in Step 2 in acetic acid (2 ml) was added with rhodanine (0.1 mmol) and sodium acetate (0.1 mmol), and stirred under reflux for 5 hours. After cooled to room temperature, the resulting solid was filtered, washed with acetic acid and water, and dried to obtain the title compound as a yellow solid (yield: 78%).

$^1$H NMR (DMSO-$d_6$, 400 MHz) δ 9.13 (s, 1H), 8.20 (s, 1H), 7.91 (d, 1H), 7.69 (s, 2H), 7.43 (t, 1H), 7.20 (d, 1H), 7.09 (t, 1H), 3.91 (s, 3H)

Experimental Example 1

Assay for Phosphatidylinositol 3-Kinase Gamma (PI3Kγ) Activity

The compounds of the present invention were assayed for the activity of phosphatidylinositol 3-kinase gamma (PI3Kγ) by using a PI3K enzyme-homogenous time resolved fluorescence (PI3K-HTRF) kit, which is available from Upstate (Millipore Co, Billerica, Mass., USA).

Three kinds of buffer solutions including a phosphorylation reaction solution (a reaction buffer containing 40 mM MgCl$_2$ which is available from Upstate was diluted 4 times and added with 5 mM DTT), a stop solution (STOP A and B solutions which are available from Upstate were mixed at a ratio of 3:1) and a fluorescence detection solution (Detection solutions A, B and C which are available from Upstate were mixed at a ratio of 1:1:18) were prepared. 1 mM of PIP2 substrate (phosphatidylinositol 4,5 biphosphate; Upstate), PI3Kγ (#14-558; Upstate) enzyme and 10 mM ATP (Sigma Aldrich Co., St. Louis, Mo., USA) were prepared. Each of PI3Kγ, 1 mM PIP2 and 10 mM ATP was diluted to 2.9 μg/ml (final reaction concentration: 1.45 μg/ml), 20 μM (final reaction concentration: 10 μM) and 40 μM (final reaction concentration: 10 μM), respectively. The buffer solution used for dilution and preparation process was the phosphorylation reaction solution. The stop solution was used for the termination of phosphorylation reaction, and the fluorescence detection solution was used for the detection of time-resolved fluorescence signals.

Each test sample was transferred to a 384 well low flange white flat bottom microplate (#3572, Corning Life Sciences, Lowell, Mass., USA) by using a multi 8-channel (Pipetman Neo multi 8×20, Gilson, Middleton, Wis., USA) to make a final phosphorylation reaction volume of 20 μl per each well. For the negative control, 5 μl of 14.4% DMSO and 10 μl of PIP2 substration solution were used, and 5 μl of 14.4% DMSO and 10 μl of PIP2/PI3Kγ mixed solution were used as the positive control. For the test group, 5 μl of a solution prepared by dissolving the compound obtained in Example in DMSO and 10 μl of PIP2/PI3Kγ mixed solution were used. Before the initiation of the phosphorylation reaction, sample compounds were pretreated with the enzyme for approximately 10 minutes, and then the phosphorylation reaction was induced by adding 5 μl of ATP. Since each of the test compound and ATP takes up 25% of the total volume, and PIP2 and PI3Kγ take up 50% of the total volume during the reaction, each solution was concentrated 4 and 2 times, respectively, before mixing the solutions. Subsequently, the test sample was gently shook for 3 minutes and subjected to a phosphorylation reaction for 90 minutes at room temperature, which was then added with 5 μl of the stop solution to terminate the phosphorylation reaction. In order to induce a time-resolved fluorescence reaction, 5 μl of the fluorescence detection solution was added to the sample. The fluorescence detection solution contains biotin-phosphatidylinositol 3,4,5-triphosphate (PIP3), streptavidin-labeled Allopycocyanin (APC) and europium-labeled Pleckstrin homology domain (the PIP3 binds to PH domain), and the time-resolved fluorescence reaction is induced by a series of reaction of PH domain and PIP3, and biotin and streptavidin. The sample was left to stand for 6 hours at room temperature, and the time-resolved fluorescence resonance energy transfer (TR-FRET) rate was measured (emission wavelength: 665 nm, 620 nm, excitation wavelength: 340 nm) by using a Flexstation3 Micro plate reader (Molecular Devices, USA). TR-FRET Rate and TR-Inhibition Rate were calculated based on Equations 1 and 2 below, and the results are expressed in IC$_{50}$, which is the concentration of a compound that inhibits 50% of PI3Kγ activity in vitro. The results are shown in Table 1 below.

TR-FRET Rate=(665 nm emission wavelength/620 nm emission wavelength)×10000  <Equation 1>

TR-FRET Inhibition Rate=[(TR-FRET Rate of Sample−TR-FRET Rate of Negative Control)/(TR-FRET Rate of Positive Control−TR-FRET Rate of Negative Control)]×100  <Equation 2>

Experimental Example 2

Assay for Phosphatidylinositol 3-Kinase Alpha, Beta and Delta (PI3Kα, PI3Kβ and PI3Kδ) Activity The compounds of the present invention were assayed for the activity of PI3K subtypes, i.e., PI3Kα, PI3Kβ and PI3Kδ, using the same procedures as in Experimental Example 1. In order to test the sensitivity of each enzyme, the concentration of enzymes were measured at EC$_{75}$. However, PI3Kα (phosphatidylinositol 3-kinase alpha, #14-602; Upstate), PI3Kβ (phosphatidylinositol 3-kinase beta, #14-603; Upstate) and PI3Kδ (phosphatidylinositol 3-kinase delta, #14-604; Upstate) were used for the test instead of PI3Kγ. After obtaining EC$_{75}$ values, TR-FRET Inhibition Rates and IC$_{50}$, which is the concentration of a compound that inhibits 50% of PI3Kγ activity in vitro, at each final reaction concentration 0.3625 μg/ml (PI3Kα), 0.725 μg/ml (PI3Kβ) and 0.725 μg/ml (PI3Kδ) were calculated. The results are expressed in IC$_{50}$, which is the concentration of a compound that inhibits 50% of PI3Kγ activity in vitro. The results are shown in Table 1 below.

TABLE 1

| | IC$_{50}$ (nM) | | | |
| --- | --- | --- | --- | --- |
| Compound | PI3Kα (p110α/p85α)(h) | PI3K β (p110β/p85α)(h) | PI3Kδ (p110δ/p85α)(h) | PI3Kγ (p120γ)(h) |
| Example 2 | 35 | 208 | 117 | 654 |
| Example 6 | 2 | 3 | 2355 | 14 |
| Example 11 | 8 | 48 | 168 | 15 |
| Example 12 | 7 | 572 | >10000 | 28 |
| Example 14 | 6 | >10000 | 149 | 29 |

TABLE 1-continued

| Compound | PI3Kα (p110α/ p85α)(h) | PI3K β (p110β/ p85α)(h) | PI3Kδ (p110δ/ p85α)(h) | PI3Kγ (p120γ)(h) |
|---|---|---|---|---|
| Example 23 | 43 | >10000 | >10000 | 9 |
| Example 25 | 6 | >10000 | >10000 | 5 |
| Example 30 | 40 | 1370 | 460 | 6 |
| Example 33 | 8 | 77 | 37 | 9 |
| Example 36 | 86 | 14 | >10000 | 154 |
| Example 40 | 8 | 177 | 590 | 28 |
| Example 41 | 12 | 100 | 322 | 13 |
| Example 51 | 5 | >10000 | >10000 | 12 |
| Example 73 | 10 | >10000 | >10000 | 10 |
| Example 90 | 3 | 3574 | 6247 | 5 |
| Example 94 | 6 | >10000 | >10000 | 8 |
| Example 110 | 13 | 293 | 4235 | 96 |
| Example 125 | 58 | >10000 | >10000 | 12 |
| Example 132 | 22 | 337 | 98 | 95 |
| Example 134 | 95 | >1000 | 54 | 344 |
| Example 141 | 21 | 23 | 51 | 108 |
| Example 153 | 10 | 115 | 246 | 16 |
| Example 161 | 13 | >10000 | 191 | 17 |
| Example 187 | 5 | >10000 | >10000 | 10 |
| Example 195 | 2 | 156 | 1896 | 3 |
| Example 196 | 10 | >10000 | >10000 | 7 |
| Example 197 | 121 | >10000 | >10000 | 5 |
| Example 217 | 1 | 77 | 563 | 3 |
| Example 225 | 4 | >10000 | >10000 | 43 |
| Example 262 | 33 | >10000 | >10000 | 38 |
| Example 263 | 16 | 1400 | 2500 | 28 |
| Example 279 | 40 | 480 | 747 | 17 |
| Example 280 | 46 | 1109 | 3000 | 22 |
| Example 307 | 14 | 1941 | 52 | 15 |
| Example 310 | 11 | 1945 | 220 | 12 |
| Example 328 | 15 | 630 | >10000 | 56 |
| Example 330 | 24 | >10000 | >10000 | 12 |
| Example 332 | 10 | >10000 | 9300 | 19 |
| Example 339 | 8 | 443 | 188 | 16 |
| Example 343 | 19 | >10000 | 53 | 4 |
| Example 345 | 11 | 3857 | 89 | 4 |
| Example 351 | 4 | >10000 | >10000 | 9 |
| Example 361 | 41 | 1430 | 924 | 10 |
| Example 412 | 17 | 869 | 205 | 182 |
| Example 422 | 31 | 1231 | 1140 | 204 |
| Example 425 | 11 | 1141 | 8333 | 51 |
| Example 427 | 62 | 250 | 1167 | 134 |
| Example 435 | 58 | 4339 | 4283 | 48 |
| Example 437 | 8 | >10000 | >10000 | 9 |
| Example 441 | 2 | >10000 | >10000 | 10 |
| Example 450 | 8 | 4646 | >10000 | 13 |
| Example 453 | 25 | 5068 | 801 | 12 |
| Example 454 | 1 | 466 | 143 | 7 |
| Example 469 | 2 | 5085 | 37 | 17 |
| Example 475 | 68 | >10000 | >10000 | 10 |
| Example 483 | 23 | 184 | 113 | 33 |
| Example 486 | 4 | >10000 | >10000 | 14 |
| Example 498 | 2 | 2271 | 618 | 7 |
| Example 512 | 2 | 82 | 73 | 17 |
| Example 513 | 4 | 715 | 74 | 11 |
| Example 520 | 15 | 9739 | >10000 | 11 |
| Example 526 | 6 | 1211 | 33 | 23 |
| Example 528 | 8 | 638 | 92 | 24 |
| Example 532 | 5 | 1394 | 137 | 33 |
| Example 533 | 14 | 3717 | 2227 | 37 |
| Example 541 | 5 | 104 | 136 | 27 |
| Example 542 | 3 | >10000 | 1267 | 24 |
| Example 546 | 360 | 5499 | >10000 | 3 |
| Example 548 | 8 | 138 | 250 | 25 |
| Example 554 | 67 | 8623 | >10000 | 78 |
| Example 555 | 5 | 3474 | 120 | 18 |
| Example 558 | 3 | 468 | 41 | 10 |
| Example 569 | 1 | 5925 | 493 | 16 |
| Example 571 | 1 | 2410 | 78 | 15 |

As shown in Table 1 above, the results confirm that the compounds of the present invention exhibit an excellent inhibitory activity against PI3K.

What is claimed is:

1. A compound of formula (I) or a pharmaceutically acceptable salt thereof:

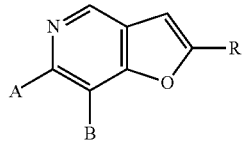

wherein,

A is hydrogen or —(CH$_2$)$_m$Q,

B is hydrogen; —(C≡C)R$_1$; —(CH$_2$)$_m$Q; —(CH═CH)(CH$_2$)$_m$Q; —(C≡C)(CH$_2$)$_m$Q; —NH(CH$_2$)$_p$Q; —(CONH)(CH$_2$)$_m$Q; or —CONR$_1$R$_2$, wherein, one of A and B is hydrogen, and A and B cannot be hydrogen at the same time, m is an integer from 0 to 3, p is an integer from 0 to 3, Q is phenyl; pyridyl; pyrazolyl; thiophenyl; pyrimidinyl; thiazolyl; pyridazinyl; piperazinyl; morpholinyl; piperidinyl; tetrahydropyridyl; naphthyl; benzothiophenyl; benzodioxolyl; dihydrobenzofuranyl; dihydrobenzoxazinyl; benzodioxinyl; benzothiadiazolyl; quinolyl; indazolyl; benzoimidazolyl; dihydrobenzodioxinyl; benzothiazolyl; or indolyl, wherein Q is optionally substituted with one or more substituents selected from the group consisting of hydroxy; amino; halogen; cyano; C$_1$-C$_{10}$alkyl optionally substituted with one or more substituents selected from the group consisting of halogen, hydroxy, cyano, C$_1$-C$_6$alkoxy and C$_1$-C$_6$alkylcarbonyloxy; C$_2$-C$_{10}$alkenyl; 4-oxo-2-thioxothiazolidin-5-ylidenyl; C$_2$-C$_{10}$alkynyl; C$_3$-C$_{10}$cycloalkyl; 5- to 7-membered heterocycloalkyl-C$_1$-C$_4$alkyl, wherein, said heterocycloalkyl is optionally substituted with C$_1$-C$_4$alkyl; C$_6$-C$_{12}$aryl; 5- to 12-membered heteroaryl optionally substituted with C$_1$-C$_4$alkyl; 3- to 12-membered heterocycloalkyl optionally substituted with C$_1$-C$_6$alkyl; C$_1$-C$_{10}$alkoxy optionally substituted with one or more substituents selected from halogen and cyano; C$_3$-C$_{10}$cycloalkyloxy; C$_6$-C$_{12}$aryl-C$_1$-C$_{10}$alkyloxy, wherein, said aryl is optionally substituted with C$_1$-C$_3$alkoxy; C$_6$-C$_{12}$aryloxy optionally substituted with one or more substituents selected from the group consisting of hydroxy, amino, halogen, hydroxycarbonyl, cyano and nitro; 5- to 12-membered heteroaryloxy optionally substituted with one or more substituents selected from the group consisting of hydroxy, amino, halogen, hydroxycarbonyl, cyano and nitro; C$_1$-C$_{10}$alkylcarbonyloxy; C$_1$-C$_{10}$alkylthio; mono- or di-C$_1$-C$_{10}$alkylamino; mono- or di-C$_3$-C$_7$cycloalkylamino; C$_6$-C$_{12}$arylamino; 5- to 12-membered heteroarylamino; C$_1$-C$_{10}$alkylsulfonylamino; C$_6$-C$_{12}$arylsulfonylamino; 5- to 12-membered heteroarylsulfonylamino; C$_1$-C$_{10}$alkylcarbonylamino; C$_6$-C$_{12}$arylcarbonylamino; 5- to 12-membered heteroarylcarbonylamino; formyl; C$_1$-C$_{10}$alkylcarbonyl; C$_6$-C$_{12}$arylcarbonyl; 5- to 12-membered heteroarylcarbonyl; C$_1$-C$_{10}$alkoxycarbonyl; hydroxycarbonyl; C$_6$-C$_{12}$aryloxycarbonyl; 5- to 12-membered heteroaryloxycarbonyl; aminocarbonyl; mono- or di-C$_1$-C$_{10}$alkylaminocarbonyl, wherein said alkyl is optionally substituted with hydroxy;

$C_6$-$C_{12}$arylaminocarbonyl; 5- to 12-membered heteroarylaminocarbonyl; aminosulfonyl; mono- or di-$C_1$-$C_{10}$alkylaminosulfonyl, wherein, said alkyl is optionally substituted with hydroxy; $C_3$-$C_7$cycloalkylaminosulfonyl; $C_1$-$C_{10}$alkylsulfonyl optionally substituted with hydroxy; 5- to 7-membered heterocycloalkyl-sulfonyl, wherein, said heterocycloalkyl is optionally substituted with $C_1$-$C_4$alkyl; $C_6$-$C_{12}$arylaminosulfonyl; 5- to 12-membered heteroarylaminosulfonyl; $C_1$-$C_{10}$alkylsulfinyl; $C_1$-$C_{10}$alkylcarbamoyloxy; and $C_1$-$C_{10}$alkylureido, $R_1$ and $R_2$ are each independently hydrogen; $C_1$-$C_{10}$alkyl optionally substituted with one or more substituents selected from hydroxy and $C_1$-$C_6$alkoxy; $C_3$-$C_{10}$cycloalkyl optionally substituted with one or more substituents selected from the group consisting of halogen, hydroxy, $C_1$-$C_6$alkoxy and $C_1$-$C_6$alkylcarbonyloxy; $C_1$-$C_{10}$alkoxycarbonyl; $C_1$-$C_{10}$alkylcarbonyl; or $R_1$ and $R_2$ join together to form a 5- to 12-membered ring optionally containing a heteroatom selected from N and O, R is a substituent selected from the group consisting of the following chemical formulae,

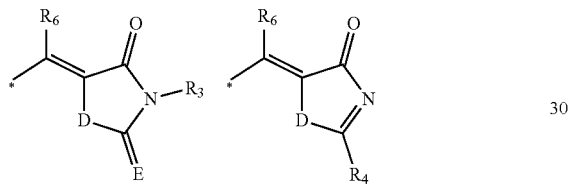

* indicates the binding site in which the compound of formula (I) is connected to, D is $NR_7$, O or S, E is O or S, $R_3$ is hydrogen; or $C_1$-$C_{10}$alkyl optionally substituted with hydroxy, $R_4$ is 3- to 12-membered heterocycloalkyl (said heterocycloalkyl is optionally substituted with $C_1$-$C_{10}$alkyl or halogen); $C_1$-$C_{10}$alkoxy; $C_1$-$C_{10}$alkylthio; or $NR_8R_9$, $R_6$ is hydrogen or $C_1$-$C_{10}$alkyl, $R_7$ is hydrogen or $C_1$-$C_{10}$alkyl, $R_8$ and $R_9$ are each independently hydrogen; $C_1$-$C_6$alkyl optionally substituted with one or more substituents selected from $C_1$-$C_6$alkoxycarbonyl and $C_6$-$C_{12}$aryl, wherein said aryl is optionally substituted with halogen or $C_1$-$C_6$alkoxy; $C_6$-$C_{12}$aryl optionally substituted with one or more substituents selected from the group consisting of halogen, $C_1$-$C_6$alkyl and $C_1$-$C_6$alkoxy; or 5- to 12-membered heteroaryl optionally substituted with one or more substituents selected from the group consisting of halogen, $C_1$-$C_6$alkyl and $C_1$-$C_6$alkoxy.

2. The compound of claim 1, wherein

A is hydrogen or —$(CH_2)_mQ$,

B is hydrogen; —(C≡C)$R_1$; —$(CH_2)_mQ$; —(CH═CH)$(CH_2)_mQ$; —(C≡C)$(CH_2)_mQ$; —$NH(CH_2)_pQ$; —$(CONH)(CH_2)_mQ$; or —$CONR_1R_2$, wherein, one of A and B is hydrogen, and A and B cannot be hydrogen at the same time, m is an integer from 0 to 3, p is an integer from 0 to 3, Q is phenyl; pyridyl; pyrazolyl; thiophenyl; pyrimidinyl; thiazolyl; pyridazinyl; piperazinyl; morpholinyl; piperidinyl; tetrahydropyridyl; naphthyl; benzothiophenyl; benzodioxolyl; dihydrobenzofuranyl; dihydrobenzoxazinyl; benzodioxinyl; benzothiadiazolyl; quinolyl; indazolyl; benzoimidazolyl; dihydrobenzodioxinyl; benzothiazolyl; or indolyl, wherein Q is optionally substituted with one or more substituents selected from the group consisting of hydroxy; amino; halogen; cyano; $C_1$-$C_6$alkyl optionally substituted with one or more substituents selected from the group consisting of halogen, hydroxy, cyano, $C_1$-$C_6$alkoxy and $C_1$-$C_6$alkylcarbonyloxy; $C_2$-$C_6$alkenyl; 4-oxo-2-thioxothiazolidin-5-ylidenyl; $C_2$-$C_6$alkynyl; $C_3$-$C_7$cycloalkyl; 5- to 7-membered heterocycloalkyl-$C_1$-$C_4$alkyl, wherein, said heterocycloalkyl is optionally substituted with $C_1$-$C_4$alkyl; $C_6$-$C_{12}$aryl; 5- to 12-membered heteroaryl optionally substituted with $C_1$-$C_4$alkyl; 3- to 12-membered heterocycloalkyl optionally substituted with $C_1$-$C_3$alkyl; $C_1$-$C_6$alkoxy optionally substituted with one or more of halogen and cyano; $C_3$-$C_7$cycloalkyloxy; $C_6$-$C_{12}$aryl-$C_1$-$C_6$alkyloxy, wherein, said aryl is optionally substituted with $C_1$-$C_3$alkoxy; $C_6$-$C_{12}$aryloxy optionally substituted with one or more substituents selected from the group consisting of hydroxy, amino, halogen, hydroxycarbonyl, cyano and nitro; 5- to 12-membered heteroaryloxy, wherein, said heteroaryl is optionally substituted with one or more substituents selected from the group consisting of hydroxy, amino, halogen, hydroxycarbonyl, cyano and nitro; $C_1$-$C_6$alkylcarbonyloxy; $C_1$-$C_6$alkylthio; mono- or di-$C_1$-$C_6$alkylamino; mono- or di-$C_3$-$C_7$cycloalkylamino; $C_6$-$C_{12}$arylamino; 5- to 12-membered heteroarylamino; $C_1$-$C_6$alkylsulfonylamino; $C_6$-$C_{12}$arylsulfonylamino; 5- to 12-membered heteroarylsulfonylamino; $C_1$-$C_6$alkylcarbonylamino; $C_6$-$C_{12}$arylcarbonylamino; 5- to 12-membered heteroarylcarbonylamino; formyl; $C_1$-$C_6$alkylcarbonyl; $C_6$-$C_{12}$arylcarbonyl; 5- to 12-membered heteroarylcarbonyl; $C_1$-$C_6$alkoxycarbonyl; hydroxycarbonyl; $C_6$-$C_{12}$aryloxycarbonyl; 5- to 12-membered heteroaryloxycarbonyl; aminocarbonyl; mono- or di-$C_1$-$C_6$alkylaminocarbonyl, wherein, said alkyl is optionally substituted with hydroxy; $C_6$-$C_{12}$arylaminocarbonyl; 5- to 12-membered heteroarylaminocarbonyl; aminosulfonyl; mono- or di-$C_1$-$C_6$alkylaminosulfonyl, wherein, said alkyl is optionally substituted with hydroxy; $C_3$-$C_7$cycloalkylaminosulfonyl; $C_1$-$C_6$alkylsulfonyl optionally substituted with hydroxy; 5- to 7-membered heterocycloalkyl-sulfonyl, wherein, said heterocycloalkyl is optionally substituted with $C_1$-$C_4$alkyl; $C_6$-$C_{12}$arylaminosulfonyl; 5- to 12-membered heteroarylaminosulfonyl; $C_1$-$C_6$alkylsulfinyl; $C_1$-$C_6$alkylcarbamoyloxy; and $C_1$-$C_6$alkylureido, $R_1$ and $R_2$ are each independently hydrogen; $C_1$-$C_6$alkyl optionally substituted with one or more substituents selected from hydroxy and $C_1$-$C_6$alkoxy; $C_3$-$C_7$cycloalkyl optionally substituted with one or more substituents selected from the group consisting of halogen, hydroxy, $C_1$-$C_6$alkoxy and $C_1$-$C_6$alkylcarbonyloxy; $C_1$-$C_6$alkoxycarbonyl; $C_1$-$C_6$alkylcarbonyl; or $R_1$ and $R_2$ join together to form a 5- to 12-membered ring optionally containing a heteroatom selected from N and O, R is a substituent selected from the group consisting of the following chemical formulae,

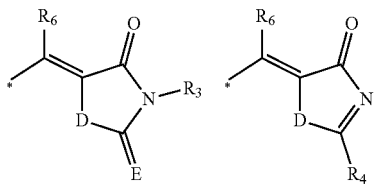

* indicates the binding site in which the compound of formula (I) is connected to,
D is $NR_7$, O or S,
E is O or S,
$R_3$ is hydrogen; or $C_1$-$C_6$alkyl optionally substituted with hydroxy,
$R_4$ is 3- to 12-membered heterocycloalkyl optionally substituted with $C_1$-$C_6$alkyl or halogen; $C_1$-$C_6$alkoxy; $C_1$-$C_6$alkylthio; or $NR_8R_9$,
$R_6$ is hydrogen or $C_1$-$C_6$alkyl,
$R_7$ is hydrogen or $C_1$-$C_6$alkyl,
$R_8$ and $R_9$ are each independently hydrogen; $C_1$-$C_6$alkyl optionally substituted with one or more substituents selected from $C_1$-$C_6$alkoxycarbonyl and $C_6$-$C_{12}$aryl optionally substituted with halogen or $C_1$-$C_6$alkoxy; $C_6$-$C_{12}$aryl optionally substituted with one or more substituents selected from the group consisting of halogen, $C_1$-$C_6$alkyl and $C_1$-$C_6$alkoxy; or 5- to 12-membered heteroaryl optionally substituted with one or more substituents selected from the group consisting of halogen, $C_1$-$C_6$alkyl and $C_1$-$C_6$alkoxy,
or a pharmaceutically acceptable salt thereof.

3. The compound of claim 1, wherein
A is hydrogen or —$(CH_2)_mQ$; B is hydrogen; —(C≡C)$R_1$; —$(CH_2)_mQ$; —(CH=CH)$(CH_2)_mQ$; —(C≡C)$(CH_2)_mQ$; —$NH(CH_2)_pQ$; —(CONH)$(CH_2)_mQ$; or —$CONR_1R_2$, wherein, one of A and B is hydrogen, and A and B cannot be hydrogen at the same time,
m is an integer from 0 to 3,
p is an integer from 0 to 3,
Q is phenyl; pyridyl; pyrazolyl; thiophenyl; pyrimidinyl; thiazolyl; pyridazinyl; piperazinyl; morpholinyl; piperidinyl; tetrahydropyridyl; naphthyl; benzothiophenyl; benzodioxolyl; dihydrobenzofuranyl; dihydrobenzoxazinyl; benzodioxinyl; benzothiadiazolyl; quinolyl; indazolyl; benzoimidazolyl; dihydrobenzodioxinyl; benzothiazolyl; or indolyl,
wherein Q is optionally substituted with one or more substituents selected from the group consisting of hydroxy; amino; halogen; cyano; $C_1$-$C_6$alkyl optionally substituted with one or more substituents selected from the group consisting of halogen, hydroxy, cyano, $C_1$-$C_6$alkoxy and $C_1$-$C_6$alkylcarbonyloxy; $C_2$-$C_6$alkenyl; 4-oxo-2-thioxothiazolidin-5-ylidenyl; $C_3$-$C_7$cycloalkyl; 5- to 7-membered heterocycloalkyl-$C_1$-$C_4$alkyl, wherein, said heterocycloalkyl is optionally substituted with $C_1$-$C_4$alkyl; $C_6$-$C_{12}$aryl; 5- to 12-membered heteroaryl heteroaryl is optionally substituted with $C_1$-$C_4$alkyl; 3- to 12-membered heterocycloalkyl optionally substituted with $C_1$-$C_3$alkyl; $C_1$-$C_6$alkoxy optionally substituted with one or more of halogen and cyano; $C_6$-$C_{12}$aryl-$C_1$-$C_6$alkyloxy, wherein, said aryl is optionally substituted with $C_1$-$C_3$alkoxy; $C_6$-$C_{12}$aryloxy optionally substituted with one or more cyanos; 5- to 12-membered heteroaryloxy; $C_1$-$C_6$alkylthio; mono- or di-$C_1$-$C_6$alkylamino; mono- or di-$C_3$-$C_7$cycloalkylamino; $C_1$-$C_6$alkylsulfonylamino; $C_6$-$C_{12}$arylsulfonylamino; $C_1$-$C_6$alkylcarbonylamino; formyl; $C_1$-$C_6$alkylcarbonyl; $C_1$-$C_6$alkoxycarbonyl; hydroxycarbonyl; aminocarbonyl; mono- or di-$C_1$-$C_6$alkylaminocarbonyl, wherein, said alkyl is optionally substituted with hydroxy; aminosulfonyl; mono- or di-$C_1$-$C_6$alkylaminosulfonyl, wherein, said alkyl is optionally substituted with hydroxy; $C_3$-$C_7$cycloalkylaminosulfonyl; $C_1$-$C_6$alkylsulfonyl; 5- to 7-membered heterocycloalkyl-sulfonyl, wherein, said heterocycloalkyl is optionally substituted with $C_1$-$C_4$alkyl; and $C_1$-$C_6$alkylsulfinyl,
$R_1$ and $R_2$ are each independently hydrogen; $C_1$-$C_6$alkyl optionally substituted with one or more of hydroxy and $C_1$-$C_6$alkoxy; $C_3$-$C_7$cycloalkyl; $C_1$-$C_6$alkoxycarbonyl; or $R_1$ and $R_2$ join together to form a 5- to 12-membered ring optionally containing a heteroatom selected from N and O,
R is a substituent selected from the group consisting of the following chemical formulae,

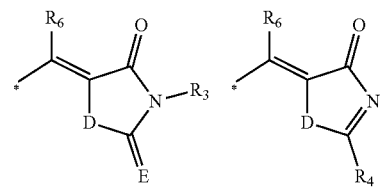

* indicates the binding site in which the compound of formula (I) is connected to,
D is $NR_7$, O or S,
E is O or S,
$R_3$ is hydrogen; or $C_1$-$C_6$alkyl optionally substituted with hydroxy,
$R_4$ is 3- to 12-membered heterocycloalkyl or $NR_8R_9$,
$R_6$ is hydrogen or $C_1$-$C_6$alkyl,
$R_7$ is hydrogen or $C_1$-$C_6$alkyl,
$R_8$ and $R_9$ are each independently hydrogen; $C_1$-$C_6$alkyl optionally substituted with one or more of $C_6$-$C_{12}$aryl, wherein said aryl is optionally substituted with halogen or $C_1$-$C_6$alkoxy; or $C_6$-$C_{12}$aryl optionally substituted with one or more substituents selected from the group consisting of halogen, $C_1$-$C_6$alkyl and $C_1$-$C_6$alkoxy,
or a pharmaceutically acceptable salt thereof.

4. The compound of claim 3, wherein
R is

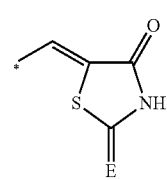

wherein, * indicates the binding site in which the compound of formula (I) is connected to; and E is O or S, or a pharmaceutically acceptable salt thereof.

5. The compound of claim 4, wherein
A is hydrogen,
B is —(C≡C)R$_1$; —(CH$_2$)$_m$Q; —(C≡C)(CH$_2$)$_m$Q; or —(CONH)(CH$_2$)$_m$Q,
m is 0,
Q is phenyl; pyridyl; pyrazolyl; thiophenyl; pyrimidinyl; thiazolyl; pyridazinyl; piperazinyl; morpholinyl; piperidinyl; tetrahydropyridyl; naphthyl; benzothiophenyl; benzodioxolyl; dihydrobenzofuranyl; dihydrobenzoxazinyl; benzodioxinyl; benzothiadiazolyl; quinolyl; indazolyl; benzoimidazolyl; dihydrobenzodioxinyl; benzothiazolyl; or indolyl,
wherein Q is optionally substituted with one or more substituents selected from the group consisting of hydroxy; amino; halogen; cyano; C$_1$-C$_6$alkyl optionally substituted with one or more substituents selected from the group consisting of halogen, hydroxy, cyano, C$_1$-C$_6$alkoxy and C$_1$-C$_6$alkylcarbonyloxy; C$_2$-C$_6$alkenyl; 4-oxo-2-thioxothiazolidin-5-ylidenyl; C$_3$-C$_7$cycloalkyl; 5- to 7-membered heterocycloalkyl-C$_1$-C$_4$alkyl, wherein, said heterocycloalkyl is optionally substituted with C$_1$-C$_4$alkyl; C$_6$-C$_{12}$aryl; 5- to 12-membered heteroaryl optionally substituted with C$_1$-C$_4$alkyl; 3- to 12-membered heterocycloalkyl optionally substituted with C$_1$-C$_3$alkyl; C$_1$-C$_6$alkoxy optionally substituted with one or more of halogen and cyano; C$_6$-C$_{12}$aryl-C$_1$-C$_6$alkyloxy, wherein, said aryl is optionally substituted with C$_1$-C$_3$alkoxy; C$_6$-C$_{12}$aryloxy optionally substituted with one or more cyanos; 5- to 12-membered heteroaryloxy; C$_1$-C$_6$alkylthio; mono- or di-C$_1$-C$_6$alkylamino; mono- or di-C$_3$-C$_7$cycloalkylamino; C$_1$-C$_6$alkylsulfonylamino; C$_6$-C$_{12}$arylsulfonylamino; C$_1$-C$_6$alkylcarbonylamino; formyl; C$_1$-C$_6$alkylcarbonyl; C$_1$-C$_6$alkoxycarbonyl; hydroxycarbonyl; aminocarbonyl; mono- or di-C$_1$-C$_6$alkylaminocarbonyl, wherein, said alkyl is optionally substituted with hydroxy; aminosulfonyl; mono- or di-C$_1$-C$_6$alkylaminosulfonyl, wherein, said alkyl is optionally substituted with hydroxy; C$_3$-C$_7$cycloalkylaminosulfonyl; C$_1$-C$_6$alkylsulfonyl; 5- to 7-membered heterocycloalkyl-sulfonyl, wherein, said heterocycloalkyl is optionally substituted with C$_1$-C$_4$alkyl; and C$_1$-C$_6$alkylsulfinyl,
R$_1$ is hydrogen; C$_1$-C$_6$alkyl optionally substituted with one or more substituents selected from hydroxy and C$_1$-C$_6$alkoxy; C$_3$-C$_7$cycloalkyl; or C$_1$-C$_6$alkoxycarbonyl,
or a pharmaceutically acceptable salt thereof.

6. The compound of claim 1, wherein the compound is selected from the group consisting of:
1) (Z)-5-([7-{4-(trifluoromethoxy)phenyl}furo[3,2-c]pyridin-2-yl]methylene)-thiazolidine-2,4-dione;
2) (Z)-5-[{7-(2,4-difluorophenyl)furo[3,2-c]pyridin-2-yl}methylene]thiazolidine-2,4-dione;
3) (Z)-methyl 4-[2-{(2,4-dioxothiazolidin-5-ylidene)methyl}furo[3,2-c]pyridin-7-yl]benzoate;
4) (Z)-4-[2-{(2,4-dioxothiazolidin-5-ylidene)methyl}furo[3,2-c]pyridin-7-yl]benzonitrile;
5) (Z)-3-[2-{(2,4-dioxothiazolidin-5-ylidene)methyl}furo[3,2-c]pyridin-7-yl]benzonitrile;
6) (Z)-5-([7-{3-(benzyloxy)phenyl}furo[3,2-c]pyridin-2-yl]methylene)thiazolidine-2,4-dione;
7) (Z)-5-([7-{4-(benzyloxy)phenyl}furo[3,2-c]pyridin-2-yl]methylene)thiazolidine-2,4-dione;
8) (Z)—N-(4-[2-{(2,4-dioxothiazolidin-5-ylidene)methyl}furo[3,2-c]pyridin-7-yl]phenyl)acetamide;
9) (Z)-5-{(7-phenylfuro[3,2-c]pyridin-2-yl)methylene}thiazolidine-2,4-dione;
10) (Z)-5-[{7-(4-tert-butylphenyl)furo[3,2-c]pyridin-2-yl}methylene]thiazolidine-2,4-dione;
11) (Z)-5-[{7-(6-hydroxypyridin-3-yl)furo[3,2-c]pyridin-2-yl}methylene]thiazolidine-2,4-dione;
12) (Z)-5-[{7-(1-methyl-1H-pyrazol-4-yl)furo[3,2-c]pyridin-2-yl}methylene]thiazolidine-2,4-dione;
13) (Z)-5-[{7-(thiophen-3-yl)furo[3,2-c]pyridin-2-yl}methylene]thiazolidine-2,4-dione;
14) (Z)-5-[{7-(benzo[b]thiophen-2-yl)furo[3,2-c]pyridin-2-yl}methylene]thiazolidine-2,4-dione;
15) (Z)-5-[{7-(4-aminophenyl)furo[3,2-c]pyridin-2-yl}methylene]thiazolidine-2,4-dione;
16) (Z)-5-[{7-(5-chlorothiophen-2-yl)furo[3,2-c]pyridin-2-yl}methylene]thiazolidine-2,4-dione;
17) (Z)-5-[{7-(3-chloro-4-methylphenyl)furo[3,2-c]pyridin-2-yl}methylene]thiazolidine-2,4-dione;
18) (Z)-5-[{7-(3,4-dichlorophenyl)furo[3,2-c]pyridin-2-yl}methylene]thiazolidine-2,4-dione;
19) (Z)-5-[{7-(4-(dimethylamino)phenyl}furo[3,2-c]pyridin-2-yl]methylene)thiazolidine-2,4-dione;
20) (Z)-5-[{7-(4-fluoro-3-methylphenyl)furo[3,2-c]pyridin-2-yl}methylene]thiazolidine-2,4-dione;
21) (Z)-5-([7-{4-fluoro-3-(trifluoromethyl)phenyl}furo[3,2-c]pyridin-2-yl]methylene)thiazolidine-2,4-dione;
22) (Z)-5-([7-{(E)-3,5-bis(trifluoromethyl)styryl}furo[3,2-c]pyridin-2-yl]methylene)thiazolidine-2,4-dione;
23) (Z)-5-([7-{4-(methylthio)phenyl}furo[3,2-c]pyridin-2-yl]methylene)thiazolidine-2,4-dione;
24) (Z)-5-([7-{3-(methylthio)phenyl}furo[3,2-c]pyridin-2-yl]methylene)thiazolidine-2,4-dione;
25) (Z)-5-[{7-(4-methoxyphenyl)furo[3,2-c]pyridin-2-yl}methylene]thiazolidine-2,4-dione;
26) (Z)-5-[{7-(3-methoxyphenyl)furo[3,2-c]pyridin-2-yl}methylene]thiazolidine-2,4-dione;
27) (Z)-5-[{7-(2-methoxyphenyl)furo[3,2-c]pyridin-2-yl}methylene]thiazolidine-2,4-dione;
28) (Z)-5-[{7-(4-chlorophenyl)furo[3,2-c]pyridin-2-yl}methylene]thiazolidine-2,4-dione;
29) (Z)-5-[{7-(4-acetylphenyl)furo[3,2-c]pyridin-2-yl}methylene]thiazolidine-2,4-dione;
30) (Z)-5-[{7-(6-methoxypyridin-3-yl)furo[3,2-c]pyridin-2-yl}methylene]thiazolidine-2,4-dione;
31) (Z)-5-[{7-(4-ethoxyphenyl)furo[3,2-c]pyridin-2-yl}methylene]thiazolidine-2,4-dione;
32) (Z)-5-[{7-(3,5-dimethoxyphenyl)furo[3,2-c]pyridin-2-yl}methylene]thiazolidine-2,4-dione;
33) (Z)-5-[{7-(3,4-dimethoxyphenyl)furo[3,2-c]pyridin-2-yl}methylene]thiazolidine-2,4-dione;
34) (Z)-5-[{7-(p-tolyl)furo[3,2-c]pyridin-2-yl}methylene]thiazolidine-2,4-dione;
35) (Z)-5-[{7-(4-vinylphenyl)furo[3,2-c]pyridin-2-yl}methylene]thiazolidine-2,4-dione;
36) (Z)-5-[{7-(benzo[d][1,3]dioxol-5-yl)furo[3,2-c]pyridin-2-yl}methylene]thiazolidine-2,4-dione;
37) (Z)-5-[{7-(5-bromopyridin-3-yl)furo[3,2-c]pyridin-2-yl}methylene]thiazolidine-2,4-dione;
38) (Z)-5-([7-{3-fluoro-4-(5-oxo-1-propyl-1H-1,2,4-triazol-4(5H)-yl)phenyl}furo[3,2-c]pyridin-2-yl]methylene)thiazolidine-2,4-dione;
39) (Z)-5-[{7-(pyrimidin-5-yl)furo[3,2-c]pyridin-2-yl}methylene]thiazolidine-2,4-dione;
40) (Z)-5-([7-{4-(methylsulfonyl)phenyl}furo[3,2-c]pyridin-2-yl]methylene)thiazolidine-2,4-dione;
41) (Z)-5-([7-{6-(methylthio)pyridin-3-yl}furo[3,2-c]pyridin-2-yl]methylene)thiazolidine-2,4-dione;

42) (Z)-5-[{7-(6-fluoropyridin-3-yl)furo[3,2-c]pyridin-2-yl}methylene]thiazolidine-2,4-dione;
43) (Z)-5-[{7-(2-chloropyridin-4-yl)furo[3,2-c]pyridin-2-yl}methylene]thiazolidine-2,4-dione;
44) (Z)-5-[{7-(6-bromopyridin-3-yl)furo[3,2-c]pyridin-2-yl}methylene]thiazolidine-2,4-dione;
45) (Z)-5-[{7-(6-chloropyridin-3-yl)furo[3,2-c]pyridin-2-yl}methylene]thiazolidine-2,4-dione;
46) (Z)-5-[{7-(3-chloro-4-methoxyphenyl)furo[3,2-c]pyridin-2-yl}methylene]thiazolidine-2,4-dione;
47) (Z)-5-[{7-(3-fluoro-4-methoxyphenyl)furo[3,2-c]pyridin-2-yl}methylene]thiazolidine-2,4-dione;
48) (Z)-5-[{7-(4-methoxy-3-methylphenyl)furo[3,2-c]pyridin-2-yl}methylene]thiazolidine-2,4-dione;
49) (Z)-5-[{7-(3-chloro-4-isopropoxyphenyl)furo[3,2-c]pyridin-2-yl}methylene]thiazolidine-2,4-dione;
50) (Z)-5-[{7-(5,6-dimethoxypyridin-3-yl)furo[3,2-c]pyridin-2-yl}methylene]thiazolidine-2,4-dione;
51) (Z)-5-[{7-(3-chloro-4-ethoxyphenyl)furo[3,2-c]pyridin-2-yl}methylene]thiazolidine-2,4-dione;
52) (Z)-5-[{7-(3-fluoro-4-isopropoxyphenyl)furo[3,2-c]pyridin-2-yl}methylene]thiazolidine-2,4-dione;
53) (Z)-5-[{7-(6-aminopyridin-3-yl)furo[3,2-c]pyridin-2-yl}methylene]thiazolidine-2,4-dione;
54) (Z)-5-[{7-(4-ethoxy-3-fluorophenyl)furo[3,2-c]pyridin-2-yl}methylene]thiazolidine-2,4-dione;
55) (Z)-5-[{7-(4-ethoxy-3,5-dimethylphenyl)furo[3,2-c]pyridin-2-yl}methylene]thiazolidine-2,4-dione;
56) (Z)-5-[{7-(4-ethylsulfanylphenyl)furo[3,2-c]pyridin-2-yl}methylene]thiazolidine-2,4-dione;
57) (Z)-5-[{7-(4-methoxy-3-trifluoromethylphenyl)furo[3,2-c]pyridin-2-yl}methylene]thiazolidine-2,4-dione;
58) 5-[{7-(5-amino-6-methoxypyridin-3-yl)furo[3,2-c]pyridin-2-yl}methylene]thiazolidine-2,4-dione;
59) (Z)-5-[{7-(5-chloro-6-methoxypyridin-3-yl)furo[3,2-c]pyridin-2-yl}methylene]thiazolidine-2,4-dione;
60) (Z)-5-[2-{(2,4-dioxothiazolidin-5-ylidene)methyl}furo[3,2-c]pyridin-7-yl]picolinonitrile;
61) (Z)-5-([7-{2-(methylthio)pyrimdiin-5-yl}furo[3,2-c]pyridin-2-yl]methylene)thiazolidine-2,4-dione;
62) (Z)-5-([7-{2,4-(dimethoxy)pyrimidin-5-yl}furo[3,2-c]pyridin-2-yl]methylene)thiazolidine-2,4-dione;
63) (Z)-5-[{7-(6-fluoro-5-methylpyridin-3-yl)furo[3,2-c]pyridin-2-yl}methylene]thiazolidine-2,4-dione;
64) (Z)-5-[{7-(6-chloro-5-methylpyridin-3-yl)furo[3,2-c]pyridin-2-yl}methylene]thiazolidine-2,4-dione;
65) (Z)-5-[{7-(6-chloro-5-fluoropyridin-3-yl)furo[3,2-c]pyridin-2-yl}methylene]thiazolidine-2,4-dione;
66) (Z)-5-[{7-(6-methylpyridin-3-yl)furo[3,2-c]pyridin-2-yl}methylene]thiazolidine-2,4-dione;
67) (Z)-5-[{7-(6-chloro-5-methoxypyridin-3-yl)furo[3,2-c]pyridin-2-yl}methylene]thiazolidine-2,4-dione;
68) (Z)-5-([7-{6-methoxy-5-(trifluoromethyl)pyridin-3-yl}furo[3,2-c]pyridin-2-yl]methylene)thiazolidine-2,4-dione;
69) (Z)-5-[{7-(2,3-dihydrobenzofuran-5-yl)furo[3,2-c]pyridin-2-yl}methylene]thiazolidine-2,4-dione;
70) (Z)-5-([7-{4-(methoxymethyl)phenyl}furo[3,2-c]pyridin-2-yl]methylene)thiazolidine-2,4-dione;
71) (Z)-5-[{7-(3,5-dimethylphenyl)furo[3,2-c]pyridin-2-yl}methylene]thiazolidine-2,4-dione;
72) (Z)—N-(tert-butyl)-4-[2-{(2,4-dioxothiazolidin-5-ylidene)methyl}furo[3,2-c]pyridin-7-yl]benzenesulfonamide;
73) (Z)-5-[{7-(4-methoxy-3,5-dimethylphenyl)furo[3,2-c]pyridin-2-yl}methylene]thiazolidine-2,4-dione;
74) (Z)-5-[{7-(3,5-dimethyl-4-propoxyphenyl)furo[3,2-c]pyridin-2-yl}methylene]thiazolidine-2,4-dione;
75) (Z)-5-[{7-(4-isopropoxy-3,5-dimethylphenyl)furo[3,2-c]pyridin-2-yl}methylene]thiazolidine-2,4-dione;
76) (Z)-5-([7-{6-(2,2,2-trifluoroethoxy)pyridin-3-yl}furo[3,2-c]pyridin-2-yl]methylene)thiazolidine-2,4-dione;
77) (Z)-5-[{7-(3,4,5-trimethoxyphenyl)furo[3,2-c]pyridin-2-yl}methylene]thiazolidine-2,4-dione;
78) (Z)-5-([7-{2-fluoro-4-(methylthio)phenyl}furo[3,2-c]pyridin-2-yl]methylene)thiazolidine-2,4-dione;
79) (Z)-5-[{7-(4-hydroxy-3-methoxyphenyl)furo[3,2-c]pyridin-2-yl}methylene]thiazolidine-2,4-dione;
80) (Z)-5-[{7-(4-hydroxy-3,5-dimethylphenyl)furo[3,2-c]pyridin-2-yl}methylene]thiazolidine-2,4-dione;
81) (Z)-5-[{7-(2-methoxypyrimidin-5-yl)furo[3,2-c]pyridin-2-yl}methylene]thiazolidine-2,4-dione;
82) (Z)-5-([7-{4-methyl-3,4-dihydro-2H-benzo[b][1,4]oxazin-7-yl}furo[3,2-c]pyridin-2-yl]methylene)thiazolidine-2,4-dione;
83) (Z)-5-[{7-(4-isopropoxy-3-methylphenyl)furo[3,2-c]pyridin-2-yl}methylene]thiazolidine-2,4-dione;
84) (Z)-5-[{7-(4-ethoxy-3-methylphenyl)furo[3,2-c]pyridin-2-yl}methylene]thiazolidine-2,4-dione;
85) (Z)-5-[{7-(4-hydroxyphenyl)furo[3,2-c]pyridin-2-yl}methylene]thiazolidine-2,4-dione;
86) (Z)-5-[{7-(5-amino-6-chloropyridin-3-yl)furo[3,2-c]pyridin-2-yl}methylene]thiazolidine-2,4-dione;
87) (Z)-5-[{7-(3,5-dichloro-4-methoxyphenyl)furo[3,2-c]pyridin-2-yl}methylene]thiazolidine-2,4-dione;
88) (Z)-5-([7-{4-(hydroxymethyl)-3-methylphenyl}furo[3,2-c]pyridin-2-yl]methylene)thiazolidine-2,4-dione;
89) (Z)-5-([7-{3-fluoro-4-(trifluoromethoxy)phenyl}furo[3,2-c]pyridin-2-yl]methylene)thiazolidine-2,4-dione;
90) (Z)-5-([7-{4-methoxy-3-(trifluoromethyl)phenyl}furo[3,2-c]pyridin-2-yl]methylene)thiazolidine-2,4-dione;
91) (Z)-5-[{7-(4H-benzo[d][1,3]dioxin-6-yl)furo[3,2-c]pyridin-2-yl}methylene]thiazolidine-2,4-dione;
92) (Z)-5-[2-{(2,4-dioxothiazolidin-5-ylidene)methyl}furo[3,2-c]pyridin-7-yl]-2-methoxybenzonitrile;
93) (Z)-5-[{7-(3-chloro-4-hydroxy-5-methoxyphenyl)furo[3,2-c]pyridin-2-yl}methylene]thiazolidine-2,4-dione;
94) (Z)-5-([7-{4-ethoxy-3-(trifluoromethyl)phenyl}furo[3,2-c]pyridin-2-yl]methylene)thiazolidine-2,4-dione;
95) (Z)-5-[{7-(2,2-difluorobenzo[d][1,3]dioxol-5-yl)furo[3,2-c]pyridin-2-yl}methylene]thiazolidine-2,4-dione;
96) (Z)-5-([7-{4-(tert-butoxymethyl)phenyl}furo[3,2-c]pyridin-2-yl]methylene)thiazolidine-2,4-dione;
97) (Z)-5-[{7-(2-ethoxypyrimidin-5-yl)furo[3,2-c]pyridin-2-yl}methylene]thiazolidine-2,4-dione;
98) (Z)-5-[{7-(5-fluoro-6-methoxypyridin-3-yl)furo[3,2-c]pyridin-2-yl}methylene]thiazolidine-2,4-dione;
99) (Z)-5-[{7-(2,6-dichloropyridin-4-yl)furo[3,2-c]pyridin-2-yl}methylene]thiazolidine-2,4-dione;
100) (Z)-5-[{7-(4-cyclopropylphenyl)furo[3,2-c]pyridin-2-yl}methylene]thiazolidine-2,4-dione;
101) (Z)-5-[{7-(5-chloro-6-ethoxypyridin-3-yl)furo[3,2-c]pyridin-2-yl}methylene]thiazolidine-2,4-dione;
102) (Z)-5-[{7-(6-methoxy-5-methylpyridin-3-yl)furo[3,2-c]pyridin-2-yl}methylene]thiazolidine-2,4-dione;
103) (Z)-5-[{7-(6-ethoxy-5-methylpyridin-3-yl)furo[3,2-c]pyridin-2-yl}methylene]thiazolidine-2,4-dione;
104) (Z)-5-[{7-(5-chloro-6-isopropoxypyridin-3-yl)furo[3,2-c]pyridin-2-yl}methylene]thiazolidine-2,4-dione;

105) (Z)-5-[{7-(2-methoxypyridin-4-yl)furo[3,2-c]pyridin-2-yl}methylene]thiazolidine-2,4-dione;
106) (Z)-5-[{7-(2-methylpyridin-4-yl)furo[3,2-c]pyridin-2-yl}methylene]thiazolidine-2,4-dione;
107) (Z)-5-([7-{2-(trifluoromethyl)pyridin-4-yl}furo[3,2-c]pyridin-2-yl]methylene)thiazolidine-2,4-dione;
108) (Z)-5-[{7-(2-ethoxy-6-fluoropyridin-4-yl)furo[3,2-c]pyridin-2-yl}methylene]thiazolidine-2,4-dione;
109) (Z)-2-(3-[2-{(2,4-dioxothiazolidin-5-ylidene)methyl}furo[3,2-c]pyridin-7-yl]phenyl)acetonitrile;
110) (Z)-5-([7-{3-(2,2,2-trifluoroethoxy)phenyl}furo[3,2-c]pyridin-2-yl]methylene)thiazolidine-2,4-dione;
111) (Z)-5-[{7-(3-fluoro-5-methylphenyl)furo[3,2-c]pyridin-2-yl}methylene]thiazolidine-2,4-dione;
112) (Z)—N-(3-[2-{(2,4-dioxothiazolidin-5-ylidene)methyl}furo[3,2-c]pyridin-7-yl]phenyl)methanesulfonamide;
113) (Z)-5-[{7-(3-amino-4-methylphenyl)furo[3,2-c]pyridin-2-yl}methylene]thiazolidine-2,4-dione;
114) (Z)-5-[{7-(4-amino-3-fluorophenyl)furo[3,2-c]pyridin-2-yl}methylene]thiazolidine-2,4-dione;
115) (Z)-5-([7-{3,5-bis(trifluoromethyl)phenyl}furo[3,2-c]pyridin-2-yl]methylene)thiazolidine-2,4-dione;
116) (Z)-5-[{7-(benzo[c][1,2,5]thiadiazol-5-yl)furo[3,2-c]pyridin-2-yl}methylene]thiazolidine-2,4-dione;
117) (Z)-5-[{7-(quinolin-6-yl)furo[3,2-c]pyridin-2-yl}methylene]thiazolidine-2,4-dione;
118) (Z)-5-([7-{2-(cyclopropylamino)pyrimidin-5-yl}furo[3,2-c]pyridin-2-yl]methylene)thiazolidine-2,4-dione;
119) (Z)-5-[{7-(3-methoxypropyn-1-yl)furo[3,2-c]pyridin-2-yl}methylene]thiazolidine-2,4-dione;
120) (Z)-5-[{7-(5-methyl-6-morpholinopyridin-3-yl)furo[3,2-c]pyridin-2-yl}methylene]thiazolidine-2,4-dione;
121) (Z)-5-([7-{6-(dimethylamino)pyridin-3-yl}furo[3,2-c]pyridin-2-yl]methylene)thiazolidine-2,4-dione;
122) (Z)-5-[{7-(1H-indazol-5-yl)furo[3,2-c]pyridin-2-yl}methylene]thiazolidine-2,4-dione;
123) (Z)-5-[{7-(1H-benzo[d]imidazol-5-yl)furo[3,2-c]pyridin-2-yl}methylene]thiazolidine-2,4-dione;
124) (Z)-5-[{7-(1H-pyrazol-4-yl)furo[3,2-c]pyridin-2-yl}methylene]thiazolidine-2,4-dione;
125) (Z)-5-[{7-(phenylethynyl)furo[3,2-c]pyridin-2-yl}methylene]thiazolidine-2,4-dione;
126) (Z)-5-[{7-(propyn-1-yl)furo[3,2-c]pyridin-2-yl}methylene]thiazolidine-2,4-dione;
127) (Z)-5-[{7-(6-morpholinopyridin-3-yl)furo[3,2-c]pyridin-2-yl}methylene]thiazolidine-2,4-dione;
128) (Z)-5-[{7-(2-aminopyrimidin-5-yl)furo[3,2-c]pyridin-2-yl}methylene]thiazolidine-2,4-dione;
129) (Z)-5-([7-{4-(1H-tetrazol-1-yl)phenyl}furo[3,2-c]pyridin-2-yl]methylene)thiazolidine-2,4-dione;
130) (Z)-5-[{7-(3-hydroxyphenyl)furo[3,2-c]pyridin-2-yl}methylene]thiazolidine-2,4-dione;
131) (Z)-5-([7-{3-(morpholinomethyl)phenyl}furo[3,2-c]pyridin-2-yl]methylene)thiazolidine-2,4-dione;
132) (Z)-5-([7-{3-(piperidin-1-ylmethyl)phenyl}furo[3,2-c]pyridin-2-yl]methylene)thiazolidine-2,4-dione;
133) (Z)-5-([7-{4-(morpholinomethyl)phenyl}furo[3,2-c]pyridin-2-yl]methylene)thiazolidine-2,4-dione;
134) (Z)-5-{(7-[4-{(4-methylpiperazin-1-yl)methyl}phenyl]furo[3,2-c]pyridin-2-yl)methylene}thiazolidine-2,4-dione;
135) (Z)-4-[2-{(2,4-dioxothiazolidin-5-ylidene)methyl}furo[3,2-c]pyridin-7-yl]benzoic acid;
136) (Z)-5-[{7-(4-isopropoxyphenyl)furo[3,2-c]pyridin-2-yl}methylene]thiazolidine-2,4-dione;
137) (Z)-5-[{7-(3-isopropoxyphenyl)furo[3,2-c]pyridin-2-yl}methylene]thiazolidine-2,4-dione;
138) (Z)-2-(3-[2-{(2,4-dioxothiazolidin-5-ylidene)methyl}furo[3,2-c]pyridin-7-yl]phenoxy)benzonitrile;
139) (Z)-5-([7-{3-(pyridin-4-yloxy)phenyl}furo[3,2-c]pyridin-2-yl]methylene)thiazolidine-2,4-dione;
140) (Z)-5-([7-{3-(pyrimidin-5-yloxy)phenyl}furo[3,2-c]pyridin-2-yl]methylene)thiazolidine-2,4-dione;
141) (Z)—N-(3-[2-{(2,4-dioxothiazolidin-5-ylidene)methyl}furo[3,2-c]pyridin-7-yl]phenyl)benzenesulfonamide;
142) (Z)-2-thioxo-5-([7-{4-(trifluoromethoxy)phenyl}furo[3,2-c]pyridin-2-yl]methylene)thiazolidin-4-one;
143) (Z)-5-[{7-(4-aminophenyl)furo[3,2-c]pyridin-2-yl}methylene]-2-thioxothiazolidin-4-one;
144) (Z)-5-[{7-(5-chlorothiophen-2-yl)furo[3,2-c]pyridin-2-yl}methylene]-2-thioxothiazolidin-4-one;
145) (Z)-5-[{7-(3-chloro-4-fluorophenyl)furo[3,2-c]pyridin-2-yl}methylene]-2-thioxothiazolidin-4-one;
146) (Z)-5-[{7-(3-fluoro-4-methylphenyl)furo[3,2-c]pyridin-2-yl}methylene]-2-thioxothiazolidin-4-one;
147) (Z)-5-([7-{4-fluoro-3-(trifluoromethyl)phenyl}furo[3,2-c]pyridin-2-yl]methylene)-2-thioxothiazolidin-4-one;
148) (Z)-5-[{7-(thiazol-2-yl)furo[3,2-c]pyridin-2-yl}methylene]-2-thioxothiazolidin-4-one;
149) (Z)-5-([7-{4-(methylthio)phenyl}furo[3,2-c]pyridin-2-yl]methylene)-2-thioxothiazolidin-4-one;
150) (Z)-5-([7-{4-(methylsulfonyl)phenyl}furo[3,2-c]pyridin-2-yl]methylene)-2-thioxothiazolidin-4-one;
151) (Z)-5-[{7-(5-bromopyridin-3-yl)furo[3,2-c]pyridin-2-yl}methylene]-2-thioxothiazolidin-4-one;
152) (Z)-5-[{7-(4-methoxyphenyl)furo[3,2-c]pyridin-2-yl}methylene]-2-thioxothiazolidin-4-one;
153) (Z)-5-[{7-(6-fluoropyridin-3-yl)furo[3,2-c]pyridin-2-yl}methylene]-2-thioxothiazolidin-4-one;
154) (Z)-5-[{7-(thiophen-3-yl)furo[3,2-c]pyridin-2-yl}methylene]-2-thioxothiazolidin-4-one;
155) (Z)-5-[{7-(pyridin-3-yl)furo[3,2-c]pyridin-2-yl}methylene]-2-thioxothiazolidin-4-one;
156) (Z)-5-[{7-(6-bromopyridin-3-yl)furo[3,2-c]pyridin-2-yl}methylene]-2-thioxothiazolidin-4-one;
157) (Z)-5-[{7-(6-chloropyridin-3-yl)furo[3,2-c]pyridin-2-yl}methylene]-2-thioxothiazolidin-4-one;
158) (Z)-5-[{7-(4-isopropoxyphenyl)furo[3,2-c]pyridin-2-yl}methylene]-2-thioxothiazolidin-4-one;
159) (Z)-5-[{7-(3-isopropoxyphenyl)furo[3,2-c]pyridin-2-yl}methylene]-2-thioxothiazolidin-4-one;
160) (Z)-5-[{7-(3-chloro-4-methoxyphenyl)furo[3,2-c]pyridin-2-yl}methylene]-2-thioxothiazolidin-4-one;
161) (Z)-5-[{7-(3-fluoro-4-methoxyphenyl)furo[3,2-c]pyridin-2-yl}methylene]-2-thioxothiazolidin-4-one;
162) (Z)-5-[{7-(2,3-dihydrobenzo[1,4]dioxin-6-yl)furo[3,2-c]pyridin-2-yl}methylene]-2-thioxothiazolidin-4-one;
163) (Z)-5-[{7-(5,6-dimethoxypyridin-3-yl)furo[3,2-c]pyridin-2-yl}methylene]-2-thioxothiazolidin-4-one;
164) (Z)-5-[{7-(3-fluoro-4-isopropoxyphenyl)furo[3,2-c]pyridin-2-yl}methylene]-2-thioxothiazolidin-4-one;
165) (Z)-5-[{7-(6-aminopyridin-3-yl)furo[3,2-c]pyridin-2-yl}methylene]-2-thioxothiazolidin-4-one;
166) (Z)-5-[{7-(4-ethoxy-3-fluorophenyl)furo[3,2-c]pyridin-2-yl}methylene]-2-thioxothiazolidin-4-one;
167) (Z)-2-isopropoxy-5-[2-{(4-oxo-2-thioxothiazolidin-5-ylidene)methyl}furo[3,2-c]pyridin-7-yl]benzaldehyde;

168) (Z)-5-[{7-(2-dimethylaminopyrimidin-5-yl)furo[3,2-c]pyridin-2-yl}methylene]-2-thioxothiazolidin-4-one;
169) (Z)-5-[{7-(6-methoxypyridin-3-yl)furo[3,2-c]pyridin-2-yl}methylene]-2-thioxothiazolidin-4-one;
170) (Z)-5-[{7-(6-ethoxypyridin-3-yl)furo[3,2-c]pyridin-2-yl}methylene]-2-thioxothiazolidin-4-one;
171) (Z)-2-fluoro-4-[2-{(4-oxo-2-thioxothiazolidin-5-ylidene)methyl}furo[3,2-c]pyridin-7-yl]benzonitrile;
172) (Z)-5-[{7-(4-methoxy-3-trifluoromethylphenyl)furo[3,2-c]pyridin-2-yl}methylene]-2-thioxothiazolidin-4-one;
173) (Z)-5-[{7-(5-amino-6-methoxypyridin-3-yl)furo[3,2-c]pyridin-2-yl}methylene]-2-thioxothiazolidin-4-one;
174) (Z)-5-[{7-(6-isopropoxypyridin-3-yl)furo[3,2-c]pyridin-2-yl}methylene]-2-thioxothiazolidin-4-one;
175) (Z)-5-[{7-(5-chloro-6-methoxypyridin-3-yl)furo[3,2-c]pyridin-2-yl}methylene]-2-thioxothiazolidin-4-one;
176) (Z)-5-[2-{(4-oxo-2-thioxothiazolidin-5-ylidene)methyl}furo[3,2-c]pyridin-7-yl]picolinonitrile;
177) (Z)-5-{(7-[4-methoxy-3-{(E)-(4-oxo-2-thioxothiazolidin-5-ylidene)methyl}phenyl]furo[3,2-c]pyridin-2-yl)methylene}-2-thioxothiazolidin-4-one;
178) (Z)-5-[{7-(4-ethansulfonylphenyl)furo[3,2-c]pyridin-2-yl}methylene]-2-thioxothiazolidin-4-one;
179) (Z)-5-[{7-(4-cyclohexylphenyl)furo[3,2-c]pyridin-2-yl}methylene]-2-thioxothiazolidin-4-one;
180) (Z)-5-([7-{2-(methylthio)pyrimidin-5-yl}furo[3,2-c]pyridin-2-yl]methylene)-2-thioxothiazolidin-4-one;
181) (Z)-5-[{7-(2,4-dimethoxypyrimidin-5-yl)furo[3,2-c]pyridin-2-yl}methylene]-2-thioxothiazolidin-4-one;
182) (Z)-5-[{7-(6-chloro-5-methylpyridin-3-yl)furo[3,2-c]pyridin-2-yl}methylene]-2-thioxothiazolidin-4-one;
183) (Z)-5-[{7-(6-chloro-5-fluoropyridin-3-yl)furo[3,2-c]pyridin-2-yl}methylene]-2-thioxothiazolidin-4-one;
184) (Z)-5-[{7-(4-hydroxyphenyl)furo[3,2-c]pyridin-2-yl}methylene]-2-thioxothiazolidin-4-one;
185) (Z)-5-[{7-(6-dimethylamino-5-fluoropyridin-3-yl)furo[3,2-c]pyridin-2-yl}methylene]-2-thioxothiazolidin-4-one;
186) (Z)-5-[{7-(6-methoxy-5-trifluoromethylpyridin-3-yl)furo[3,2-c]pyridin-2-yl}methylene]-2-thioxothiazolidin-4-one;
187) (Z)-5-[{7-(2,3-dihydrobenzofuran-5-yl)furo[3,2-c]pyridin-2-yl}methylene]-2-thioxothiazolidin-4-one;
188) (Z)-5-[{7-(6-chloro-5-methoxypyridin-3-yl)furo[3,2-c]pyridin-2-yl}methylene]-2-thioxothiazolidin-4-one;
189) (Z)-5-[{7-(2,5-difluoro-4-methoxyphenyl)furo[3,2-c]pyridin-2-yl}methylene]-2-thioxothiazolidin-4-one;
190) (Z)-5-[{7-(4-methoxymethylphenyl)furo[3,2-c]pyridin-2-yl}methylene]-2-thioxothiazolidin-4-one;
191) (Z)—N-methyl-4-[2-{(4-oxo-2-thioxothiazolidin-5-ylidene)methyl}furo[3,2-c]pyridin-7-yl]benzenesulfonamide;
192) (Z)—N-(tert-butyl)-4-[2-{(4-oxo-2-thioxothiazolidin-5-ylidene)methyl}furo[3,2-c]pyridin-7-yl]benzenesulfonamide;
193) (Z)-5-([7-{4-(morpholinosulfonyl)phenyl}furo[3,2-c]pyridin-2-yl]methylene)-2-thioxothiazolidin-4-one;
194) (Z)-5-[7-{4-(piperidine-1-sulfonyl)phenyl}-furo[3,2-c]pyridin-2-yl]methylene]-2-thioxothiazolidin-4-one;
195) (Z)-5-[7-(6-fluoro-5-methylpyridin-3-yl)-furo[3,2-c]pyridin-2-ylmethylene]-2-thioxothiazolidin-4-one;
196) (Z)-5-[7-(4-methoxy-3,5-dimethylphenyl)furo[3,2-c]pyridin-2-ylmethylene]-2-thioxothiazolidin-4-one;
197) (Z)-5-[{7-(4-isopropoxy-3,5-dimethylphenyl)furo[3,2-c]pyridin-2-yl}methylene]-2-thioxothiazolidin-4-one;
198) (Z)-2-thioxo-5-([7-{6-(2,2,2-trifluoroethoxy)pyridin-3-yl}furo[3,2-c]pyridin-2-yl]methylene)thiazolidin-4-one;
199) (Z)-5-{(7-[3-{(4-methoxybenzyl)oxy}phenyl]furo[3,2-c]pyridin-2-yl)methylene}-2-thioxothiazolidin-4-one;
200) (Z)-2-thioxo-5-[{7-(3,4,5-trimethoxyphenyl)furo[3,2-c]pyridin-2-yl}methylene]thiazolidin-4-one;
201) (Z)-5-[{7-(4-hydroxy-3-methoxyphenyl)furo[3,2-c]pyridin-2-yl}methylene]-2-thioxothiazolidin-4-one;
202) (Z)-5-[{7-(4-hydroxy-3,5-dimethylphenyl)furo[3,2-c]pyridin-2-yl}methylene]-2-thioxothiazolidin-4-one;
203) (Z)-5-[{7-(2-methoxypyrimidin-5-yl)furo[3,2-c]pyridin-2-yl}methylene]-2-thioxothiazolidin-4-one;
204) (Z)-5-[{7-(4-methyl-3,4-dihydro-2H-benzo[b][1,4]oxazin-7-yl)furo[3,2-c]pyridin-2-yl}methylene]-2-thioxothiazolidin-4-one;
205) (Z)-5-[{7-(4-isopropoxy-3-methylphenyl)furo[3,2-c]pyridin-2-yl}methylene]-2-thioxothiazolidin-4-one;
206) (Z)-5-[{7-(4-ethoxy-3-methylphenyl)furo[3,2-c]pyridin-2-yl}methylene]-2-thioxothiazolidin-4-one;
207) (Z)-5-([7-{4-(tert-butoxymethyl)phenyl}furo[3,2-c]pyridin-2-yl]methylene)-2-thioxothiazolidin-4-one;
208) (Z)-5-[{7-(5-amino-6-chloropyridin-3-yl)furo[3,2-c]pyridin-2-yl}methylene]-2-thioxothiazolidin-4-one;
209) (Z)-5-[{7-(3,5-dichloro-4-methoxyphenyl)furo[3,2-c]pyridin-2-yl}methylene]-2-thioxothiazolidin-4-one;
210) (Z)-5-([7-{3-methyl-4-(trifluoromethoxy)phenyl}furo[3,2-c]pyridin-2-yl]methylene)-2-thioxothiazolidin-4-one;
211) (Z)-2-(4-[2-{(4-oxo-2-thioxothiazolidin-5-ylidene)methyl}furo[3,2-c]pyridin-7-yl]phenoxy)acetonitrile;
212) (Z)-5-([7-{4-(hydroxymethyl)-3-methylphenyl}furo[3,2-c]pyridin-2-yl]methylene)-2-thioxothiazolidin-4-one;
213) (Z)-5-([7-{3-fluoro-4-(trifluoromethoxy)phenyl}furo[3,2-c]pyridin-2-yl]methylene)-2-thioxothiazolidin-4-one;
214) (Z)-5-([7-{4-methoxy-3-(trifluoromethyl)phenyl}furo[3,2-c]pyridin-2-yl]methylene)-2-thioxothiazolidin-4-one;
215) (Z)-5-[{7-(4H-benzo[d][1,3]dioxin-6-yl)furo[3,2-c]pyridin-2-yl}methylene]-2-thioxothiazolidin-4-one;
216) (Z)-2-methoxy-5-[2-{(4-oxo-2-thioxothiazolidin-5-ylidene)methyl}furo[3,2-c]pyridin-7-yl]benzonitrile;
217) (Z)-5-[{7-(3-chloro-4-hydroxy-5-methoxyphenyl)furo[3,2-c]pyridin-2-yl}methylene]-2-thioxothiazolidin-4-one;
218) (Z)-5-[{7-(4-ethoxy-3-(trifluoromethyl)phenyl)furo[3,2-c]pyridin-2-yl}methylene]-2-thioxothiazolidin-4-one;
219) (Z)-5-[{7-(2,2-difluorobenzo[d][1,3]dioxol-5-yl)furo[3,2-c]pyridin-2-yl}methylene]-2-thioxothiazolidin-4-one;
220) (Z)-4-[2-{(4-oxo-2-thioxothiazolidin-5-ylidene)methyl}furo[3,2-c]pyridin-7-yl]benzyl acetate;
221) (Z)-5-[{7-(2-ethoxypyrimidin-5-yl)furo[3,2-c]pyridin-2-yl}methylene]-2-thioxothiazolidin-4-one;
222) (Z)-5-[{7-(2,6-dichloropyridin-4-yl)furo[3,2-c]pyridin-2-yl}methylene]-2-thioxothiazolidin-4-one;
223) (Z)-5-[{7-(4-cyclopropylphenyl)furo[3,2-c]pyridin-2-yl}methylene]-2-thioxothiazolidin-4-one;

224) (Z)-5-[{7-(5-chloro-6-ethoxypyridin-3-yl)furo[3,2-c]pyridin-2-yl}methylene]-2-thioxothiazolidin-4-one;
225) (Z)-5-[{7-(6-methoxy-5-methylpyridin-3-yl)furo[3,2-c]pyridin-2-yl}methylene]-2-thioxothiazolidin-4-one;
226) (Z)-5-[{7-(5-fluoro-6-methoxypyridin-3-yl)furo[3,2-c]pyridin-2-yl}methylene]-2-thioxothiazolidin-4-one;
227) (Z)-5-[{7-(5-chloro-6-isopropoxypyridin-3-yl)furo[3,2-c]pyridin-2-yl}methylene]-2-thioxothiazolidin-4-one;
228) (Z)-5-[{7-(2-methoxypyridin-4-yl)furo[3,2-c]pyridin-2-yl}methylene]-2-thioxothiazolidin-4-one;
229) (Z)-5-[{7-(2-methylpyridin-4-yl)furo[3,2-c]pyridin-2-yl}methylene]-2-thioxothiazolidin-4-one;
230) (Z)-5-[{7-(3-amino-4-fluorophenyl)furo[3,2-c]pyridin-2-yl}methylene]-2-thioxothiazolidin-4-one;
231) (Z)-2-thioxo-5-([7-{2-(trifluoromethyl)pyridin-4-yl}furo[3,2-c]pyridin-2-yl]methylene)thiazolidin-4-one;
232) (Z)-5-[{7-(2-ethoxy-6-fluoropyridin-4-yl)furo[3,2-c]pyridin-2-yl}methylene]-2-thioxothiazolidin-4-one;
233) (Z)-2-(3-[2-{(4-oxo-2-thioxothiazolidin-5-ylidene)methyl}furo[3,2-c]pyridin-7-yl]phenyl)acetonitrile;
234) (Z)-2-thioxo-5-([7-{3-(2,2,2-trifluoroethoxy)phenyl}furo[3,2-c]pyridin-2-yl]methylene)thiazolidin-4-one;
235) (Z)-5-([7-{3-(methylsulfinyl)phenyl}furo[3,2-c]pyridin-2-yl]methylene)-2-thioxothiazolidin-4-one;
236) (Z)-5-[{7-(3-fluoro-5-methylphenyl)furo[3,2-c]pyridin-2-yl}methylene]-2-thioxothiazolidin-4-one;
237) (Z)—N-(3-[2-{(4-oxo-2-thioxothiazolidin-5-ylidene)methyl}furo[3,2-c]pyridin-7-yl]phenyl)methanesulfonamide;
238) (Z)-5-[{7-(2-fluoropyridin-4-yl)furo[3,2-c]pyridin-2-yl}methylene]-2-thioxothiazolidin-4-one;
239) (Z)-5-[{7-(3-amino-4-methylphenyl)furo[3,2-c]pyridin-2-yl}methylene]-2-thioxothiazolidin-4-one;
240) (Z)-5-[{7-(4-amino-3-fluorophenyl)furo[3,2-c]pyridin-2-yl}methylene]-2-thioxothiazolidin-4-one;
241) (Z)-5-([7-{3,5-bis(trifluoromethyl)phenyl}furo[3,2-c]pyridin-2-yl]methylene)-2-thioxothiazolidin-4-one;
242) (Z)-5-[{7-(1H-benzo[d]imidazol-5-yl)furo[3,2-c]pyridin-2-yl}methylene]-2-thioxothiazolidin-4-one;
243) (Z)-5-[{7-(1H-pyrazol-4-yl)furo[3,2-c]pyridin-2-yl}methylene]-2-thioxothiazolidin-4-one;
244) (Z)-5-[{7-(phenylethynyl)furo[3,2-c]pyridin-2-yl}methylene]-2-thioxothiazolidin-4-one;
245) (Z)-5-[{7-(propyn-1-yl)furo[3,2-c]pyridin-2-yl}methylene]-2-thioxothiazolidin-4-one;
246) (Z)-5-[{7-(1-methyl-1H-pyrazol-4-yl)furo[3,2-c]pyridin-2-yl}methylene]-2-thioxothiazolidin-4-one;
247) (Z)-5-[{7-(6-morpholinopyridin-3-yl)furo[3,2-c]pyridin-2-yl}methylene]-2-thioxothiazolidin-4-one;
248) (Z)-5-[{7-(2-aminopyrimidin-5-yl)furo[3,2-c]pyridin-2-yl}methylene]-2-thioxothiazolidin-4-one;
249) (Z)-5-([7-{4-(1H-tetrazol-1-yl)phenyl}furo[3,2-c]pyridin-2-yl]methylene)-2-thioxothiazolidin-4-one;
250) (Z)-5-[{7-(3-hydroxyphenyl)furo[3,2-c]pyridin-2-yl}methylene]-2-thioxothiazolidin-4-one;
251) (Z)-ethyl 3-[2-{(2,4-dioxothiazolidin-5-ylidene)methyl}furo[3,2-c]pyridin-7-yl]benzoate;
252) (Z)-5-([7-{3-(trifluoromethoxy)phenyl}furo[3,2-c]pyridin-2-yl]methylene)thiazolidine-2,4-dione;
253) (Z)-4-[2-{(2,4-dioxothiazolidin-5-ylidene)methyl}furo[3,2-c]pyridin-7-yl]benzenesulfonamide;
254) (Z)-3-[2-{(2,4-dioxothiazolidin-5-ylidene)methyl}furo[3,2-c]pyridin-7-yl]benzenesulfonamide;
255) (Z)-3-chloro-4-[2-{(2,4-dioxothiazolidin-5-ylidene)methyl}furo[3,2-c]pyridin-7-yl]benzenesulfonamide;
256) (Z)-5-([7-{4-chloro-3-(trifluoromethyl)phenyl}furo[3,2-c]pyridin-2-yl]methylene)thiazolidine-2,4-dione;
257) (Z)-3-chloro-4-[2-{(2,4-dioxothiazolidin-5-ylidene)methyl}furo[3,2-c]pyridin-7-yl]-N-isopropylbenzenesulfonamide;
258) (Z)-5-([7-{2-chloro-4-(morpholinosulfonyl)phenyl}furo[3,2-c]pyridin-2-yl]methylene)thiazolidine-2,4-dione;
259) (Z)-5-([7-{2-chloro-4-(piperidin-1-ylsulfonyl)phenyl}furo[3,2-c]pyridin-2-yl]methylene)thiazolidine-2,4-dione;
260) (Z)-3-chloro-4-[2-{(2,4-dioxothiazolidin-5-ylidene)methyl}furo[3,2-c]pyridin-7-yl]-N-(2-hydroxyethyl)benzenesulfonamide;
261) (Z)-5-([7-{4-(4-propylpiperazin-1-ylsulfonyl)phenyl}furo[3,2-c]pyridin-2-yl]methylene)thiazolidine-2,4-dione;
262) (Z)-5-([7-{4-(piperidin-1-ylsulfonyl)phenyl}furo[3,2-c]pyridin-2-yl]methylene)thiazolidine-2,4-dione;
263) (Z)-4-[2-{(2,4-dioxothiazolidin-5-ylidene)methyl}furo[3,2-c]pyridin-7-yl]-N-(2-hydroxyethyl)benzenesulfonamide;
264) (Z)-5-([7-{4-(morpholinosulfonyl)phenyl}furo[3,2-c]pyridin-2-yl]methylene)thiazolidine-2,4-dione;
265) (Z)-4-[2-{(2,4-dioxothiazolidin-5-ylidene)methyl}furo[3,2-c]pyridin-7-yl]-N-methylbenzenesulfonamide;
266) (Z)-4-[2-{(2,4-dioxothiazolidin-5-ylidene)methyl}furo[3,2-c]pyridin-7-yl]-N-isopropylbenzenesulfonamide;
267) (Z)-4-[2-{(2,4-dioxothiazolidin-5-ylidene)methyl}furo[3,2-c]pyridin-7-yl]benzamide;
268) (Z)-5-[2-{(2,4-dioxothiazolidin-5-ylidene)methyl}furo[3,2-c]pyridin-7-yl]thiophene-2-sulfonamide;
269) (Z)-5-[{7-(benzo[d]thiazol-2-yl)furo[3,2-c]pyridin-2-yl}methylene]thiazolidine-2,4-dione;
270) (Z)-5-[{7-(6-methoxypyridazin-3-yl)furo[3,2-c]pyridin-2-yl}methylene]thiazolidine-2,4-dione;
271) (Z)-5-[{7-(1H-indol-5-yl)furo[3,2-c]pyridin-2-yl}methylene]thiazolidine-2,4-dione;
272) (Z)-4-[2-{(2,4-dioxothiazolidin-5-ylidene)methyl}furo[3,2-c]pyridin-7-yl]-N,N-dimethylbenzenesulfonamide;
273) (Z)-5-[{7-(3-chloro-4-hydroxyphenyl)furo[3,2-c]pyridin-2-yl}methylene]thiazolidine-2,4-dione;
274) (Z)-5-[{7-(4-hydroxy-3-methylphenyl)furo[3,2-c]pyridin-2-yl}methylene]thiazolidine-2,4-dione;
275) (Z)-5-[{7-(3-fluoro-4-hydroxyphenyl)furo[3,2-c]pyridin-2-yl}methylene]thiazolidine-2,4-dione;
276) (Z)-5-[2-{(2,4-dioxothiazolidin-5-ylidene)methyl}furo[3,2-c]pyridin-7-yl]-2-hydroxybenzonitrile;
277) (Z)-5-[{7-(4-hydroxy-3-propionylphenyl)furo[3,2-c]pyridin-2-yl}methylene]thiazolidine-2,4-dione;
278) (Z)-5-[2-{(2,4-dioxothiazolidin-5-ylidene)methyl}furo[3,2-c]pyridin-7-yl]-2-methoxynicotinonitrile;
279) (Z)-4-[2-{(2,4-dioxothiazolidin-5-ylidene)methyl}furo[3,2-c]pyridin-7-yl]-2-fluoro-N-methylbenzenesulfonamide;

280) (Z)-4-[2-{(2,4-dioxothiazolidin-5-ylidene)methyl}furo[3,2-c]pyridin-7-yl]-2-fluoro-N,N-dimethylbenzenesulfonamide;
281) (Z)-5-([7-{3-fluoro-4-(morpholinosulfonyl)phenyl}furo[3,2-c]pyridin-2-yl]methylene)thiazolidine-2,4-dione;
282) (Z)-5-([7-{3,5-difluoro-4-(methylsulfonyl)phenyl}furo[3,2-c]pyridin-2-yl]methylene)thiazolidine-2,4-dione;
283) (Z)-5-([7-{3-fluoro-4-(methylsulfonyl)phenyl}furo[3,2-c]pyridin-2-yl]methylene)thiazolidine-2,4-dione;
284) (Z)-methyl 4-[2-{(2,4-dioxothiazolidin-5-ylidene)methyl}furo[3,2-c]pyridin-7-yl]-2,6-difluorobenzoate;
285) (Z)-5-[{7-(4-amino-3,5-difluorophenyl)furo[3,2-c]pyridin-2-yl}methylene]thiazolidine-2,4-dione;
286) (Z)-5-[{7-(4-amino-3,5-dimethylphenyl)furo[3,2-c]pyridin-2-yl}methylene]thiazolidine-2,4-dione;
287) (Z)-2,6-dichloro-4-[2-{(2,4-dioxothiazolidin-5-ylidene)methyl}furo[3,2-c]pyridin-7-yl]-N-methylbenzenesulfonamide;
288) (Z)-2,6-dichloro-4-[2-{(2,4-dioxothiazolidin-5-ylidene)methyl}furo[3,2-c]pyridin-7-yl]-N,N-dimethylbenzenesulfonamide;
289) (Z)-5-([7-{3,5-dichloro-4-(morpholinosulfonyl)phenyl}furo[3,2-c]pyridin-2-yl]methylene)thiazolidine-2,4-dione;
290) (Z)-2,6-dichloro-4-[2-{(2,4-dioxothiazolidin-5-ylidene)methyl}furo[3,2-c]pyridin-7-yl]-N-ethylbenzenesulfonamide;
291) (Z)-2,6-dichloro-4-[2-{(2,4-dioxothiazolidin-5-ylidene)methyl}furo[3,2-c]pyridin-7-yl]-N-isopropylbenzenesulfonamide;
292) (Z)-4-[2-{(2,4-dioxothiazolidin-5-ylidene)methyl}furo[3,2-c]pyridin-7-yl]-N-methyl-2-(trifluoromethoxy)benzenesulfonamide;
293) (Z)-4-[2-{(2,4-dioxothiazolidin-5-ylidene)methyl}furo[3,2-c]pyridin-7-yl]-N,N-dimethyl-2-(trifluoromethoxy)benzenesulfonamide;
294) (Z)-5-([7-{4-(morpholinosulfonyl)-3-(trifluoromethoxy)phenyl}furo[3,2-c]pyridin-2-yl]methylene)thiazolidine-2,4-dione;
295) (Z)-4-[2-{(2,4-dioxothiazolidin-5-ylidene)methyl}furo[3,2-c]pyridin-7-yl]-3-fluoro-N,N-dimethylbenzenesulfonamide;
296) (Z)—N-tert-butyl-2,6-dichloro-4-[2-{(2,4-dioxothiazolidin-5-ylidene)methyl}furo[3,2-c]pyridin-7-yl]benzenesulfonamide;
297) (Z)-2,6-dichloro-4-[2-{(2,4-dioxothiazolidin-5-ylidene)methyl}furo[3,2-c]pyridin-7-yl]-N-(2-hydroxyethyl)benzenesulfonamide;
298) (Z)-4-[2-{(2,4-dioxothiazolidin-5-ylidene)methyl}furo[3,2-c]pyridin-7-yl]-N,N,3-trimethylbenzenesulfonamide;
299) (Z)-methyl 4-[2-{(2,4-dioxothiazolidin-5-ylidene)methyl}furo[3,2-c]pyridin-7-yl]-2-methoxybenzoate;
300) (Z)-methyl 4-[2-{(2,4-dioxothiazolidin-5-ylidene)methyl}furo[3,2-c]pyridin-7-yl]-2-fluorobenzoate;
301) (Z)-methyl 3-[2-{(2,4-dioxothiazolidin-5-ylidene)methyl}furo[3,2-c]pyridin-7-yl]-5-fluorobenzoate;
302) (Z)-methyl 2-chloro-5-[2-{(2,4-dioxothiazolidin-5-ylidene)methyl}furo[3,2-c]pyridin-7-yl]benzoate;
303) (Z)—N-(4-[2-{(2,4-dioxothiazolidin-5-ylidene)methyl}furo[3,2-c]pyridin-7-yl]phenyl)methanesulfonamide;
304) (Z)-3-[2-{(2,4-dioxothiazolidin-5-ylidene)methyl}furo[3,2-c]pyridin-7-yl]-N,N-dimethylbenzamide;
305) (Z)—N-(4-[2-{(2,4-dioxothiazolidin-5-ylidene)methyl}furo[3,2-c]pyridin-7-yl]-2,6-dimethylphenyl)methanesulfonamide;
306) (Z)-4-[2-{(2,4-dioxothiazolidin-5-ylidene)methyl}furo[3,2-c]pyridin-7-yl]-N,2-dimethylbenzenesulfonamide;
307) (Z)-5-([7-{3-methyl-4-(morpholinosulfonyl)phenyl}furo[3,2-c]pyridin-2-yl]methylene)thiazolidine-2,4-dione;
308) (Z)-4-[2-{(2,4-dioxothiazolidin-5-ylidene)methyl}furo[3,2-c]pyridin-7-yl]-N-ethyl-2-methylbenzenesulfonamide;
309) (Z)-4-[2-{(2,4-dioxothiazolidin-5-ylidene)methyl}furo[3,2-c]pyridin-7-yl]-N-isopropyl-2-methylbenzenesulfonamide;
310) (Z)—N-tert-butyl-4-[2-{(2,4-dioxothiazolidin-5-ylidene)methyl}furo[3,2-c]pyridin-7-yl]-2-methylbenzenesulfonamide;
311) (Z)-2-amino-5-[2-{(2,4-dioxothiazolidin-5-ylidene)methyl}furo[3,2-c]pyridin-7-yl]benzonitrile;
312) (Z)-5-([7-{4-amino-3-(trifluoromethyl)phenyl}furo[3,2-c]pyridin-2-yl]methylene)thiazolidine-2,4-dione;
313) (Z)-5-[{7-(6-amino-5-methylpyridin-3-yl)furo[3,2-c]pyridin-2-yl}methylene]thiazolidine-2,4-dione;
314) (Z)-5-([7-{4-(1-methyl-5-oxo-1H-1,2,4-trizol-4(5H)-yl)phenyl}furo[3,2-c]pyridin-2-yl]methylene)thiazolidine-2,4-dione;
315) (Z)-5-([7-{4-(1-isopropyl-5-oxo-1H-1,2,4-triazol-4(5H)-yl)phenyl}furo[3,2-c]pyridin-2-yl]methylene)thiazolidine-2,4-dione;
316) (Z)-5-([7-{2-methoxy-5-(pyrrolidin-1-ylmethyl)phenyl}furo[3,2-c]pyridin-2-yl]methylene)thiazolidine-2,4-dione;
317) (Z)-5-([7-{2-methoxy-5-(morpholinomethyl)phenyl}furo[3,2-c]pyridin-2-yl]methylene)thiazolidine-2,4-dione;
318) (Z)-5-([7-{2-methoxy-5-(piperidin-1-ylmethyl)phenyl}furo[3,2-c]pyridin-2-yl]methylene)thiazolidine-2,4-dione;
319) (Z)-5-([7-{6-(methylsulfonyl)pyridin-3-yl}furo[3,2-c]pyridin-2-yl]methylene)-2-thioxothiazolidin-4-one;
320) (Z)—N,N-dimethyl-3-[2-{(4-oxo-2-thioxothiazolidin-5-ylidene)methyl}furo[3,2-c]pyridin-7-yl]benzenesulfonamide;
321) (Z)—N,N-dimethyl-4-[2-{(4-oxo-2-thioxothiazolidin-5-ylidene)methyl}furo[3,2-c]pyridin-7-yl]benzenesulfonamide;
322) (Z)-5-[{7-(3-chloro-4-hydroxyphenyl)furo[3,2-c]pyridin-2-yl}methylene]-2-thioxothiazolidin-4-one;
323) (Z)-5-[{7-(4-hydroxy-3-methylphenyl)furo[3,2-c]pyridin-2-yl}methylene]-2-thioxothiazolidin-4-one;
324) (Z)-2-hydroxy-5-[2-{(4-oxo-2-thioxothiazolidin-5-ylidene)methyl}furo[3,2-c]pyridin-7-yl]benzonitrile;
325) (Z)-5-[{7-(4-hydroxy-3-propionylphenyl)furo[3,2-c]pyridin-2-yl}methylene]-2-thioxothiazolidin-4-one;
326) (Z)-5-[{7-(3-acetyl-4-hydroxyphenyl)furo[3,2-c]pyridin-2-yl}methylene]-2-thioxothiazolidin-4-one;
327) (Z)-5-[{7-(3-fluoro-4-hydroxyphenyl)furo[3,2-c]pyridin-2-yl}methylene]-2-thioxothiazolidin-4-one;
328) (Z)-2-methoxy-5-[2-{(4-oxo-2-thioxothiazolidin-5-ylidene)methyl}furo[3,2-c]pyridin-7-yl]nicotinonitrile;
329) (Z)-2-fluoro-N-methyl-4-[2-{(4-oxo-2-thioxothiazolidin-5-ylidene)methyl}furo[3,2-c]pyridin-7-yl]benzenesulfonamide;
330) (Z)-2-fluoro-N,N-dimethyl-4-[2-{(4-oxo-2-thioxothiazolidin-5-ylidene)methyl}furo[3,2-c]pyridin-7-yl]benzenesulfonamide;

331) (Z)-5-([7-{3-fluoro-4-(morpholinosulfonyl) phenyl}furo[3,2-c]pyridin-2-yl]methylene)-2-thioxothiazolidin-4-one;
332) (Z)-5-([7-{3,5-difluoro-4-(methylsulfonyl) phenyl}furo[3,2-c]pyridin-2-yl]methylene)-2-thioxothiazolidin-4-one;
333) (Z)-5-([7-{3-fluoro-4-(methylsulfonyl)phenyl}furo[3,2-c]pyridin-2-yl]methylene)-2-thioxothiazolidin-4-one;
334) (Z)-methyl 2,6-difluoro-4-[2-{(4-oxo-2-thioxothiazolidin-5-ylidene)methyl}furo[3,2-c]pyridin-7-yl] benzoate;
335) (Z)-5-[{7-(4-amino-3,5-difluorophenyl)furo[3,2-c] pyridin-2-yl}methylene]-2-thioxothiazolidin-4-one;
336) (Z)-5-[{7-(4-amino-3,5-dimethylphenyl)furo[3,2-c] pyridin-2-yl}methylene]-2-thioxothiazolidin-4-one;
337) (Z)-5-[{7-(4-amino-3-methylphenyl)furo[3,2-c] pyridin-2-yl}methylene]-2-thioxothiazolidin-4-one;
338) (Z)—N-methyl-4-[2-{(4-oxo-2-thioxothiazolidin-5-ylidene)methyl}furo[3,2-c]pyridin-7-yl]-2-(trifluoromethoxy)benzenesulfonamide;
339) (Z)—N,N-dimethyl-4-[2-{(4-oxo-2-thioxothiazolidin-5-ylidene)methyl}furo[3,2-c]pyridin-7-yl]-2-(trifluoromethoxy)benzenesulfonamide;
340) (Z)-5-([7-{4-(morpholinosulfonyl)-3-(trifluoromethoxy)phenyl}furo[3,2-c]pyridin-2-yl]methylene)-2-thioxothiazolidin-4-one;
341) (Z)-2,6-dichloro-N-methyl-4-[2-{(4-oxo-2-thioxothiazolidin-5-ylidene)methyl}furo[3,2-c]pyridin-7-yl]benzenesulfonamide;
342) (Z)-2,6-dichloro-N,N-dimethyl-4-[2-{(4-oxo-2-thioxothiazolidin-5-ylidene)methyl}furo[3,2-c]pyridin-7-yl]benzenesulfonamide;
343) (Z)-5-([7-{3,5-dichloro-4-(morpholinosulfonyl) phenyl}furo[3,2-c]pyridin-2-yl]methylene)-2-thioxothiazolidin-4-one;
344) (Z)-2,6-dichloro-N-ethyl-4-[2-{(4-oxo-2-thioxothiazolidin-5-ylidene)methyl}furo[3,2-c]pyridin-7-yl] benzenesulfonamide;
345) (Z)-2,6-dichloro-N-isopropyl-4-[2-{(4-oxo-2-thioxothiazolidin-5-ylidene)methyl}furo[3,2-c]pyridin-7-yl]benzenesulfonamide;
346) (Z)—N-tert-butyl-2,6-dichloro-4-[2-{(4-oxo-2-thioxothiazolidin-5-ylidene)methyl}furo[3,2-c]pyridin-7-yl]benzenesulfonamide;
347) (Z)-2,6-dichloro-N-(2-hydroxyethyl)-4-[2-{(4-oxo-2-thioxothiazolidin-5-ylidene)methyl}furo[3,2-c]pyridin-7-yl]benzenesulfonamide;
348) (Z)—N,N,3-trimethyl-4-[2-{(4-oxo-2-thioxothiazolidin-5-ylidene)methyl}furo[3,2-c]pyridin-7-yl]benzenesulfonamide;
349) (Z)-methyl 2-methoxy-4-[2-{(4-oxo-2-thioxothiazolidin-5-ylidene)methyl}furo[3,2-c]pyridin-7-yl]benzoate;
350) (Z)-methyl 2-fluoro-4-[2-{(4-oxo-2-thioxothiazolidin-5-ylidene)methyl}furo[3,2-c]pyridin-7-yl]benzoate;
351) (Z)-methyl 3-fluoro-5-[2-{(4-oxo-2-thioxothiazolidin-5-ylidene)methyl}furo[3,2-c]pyridin-7-yl]benzoate;
352) (Z)-methyl 2-chloro-5-[2-{(4-oxo-2-thioxothiazolidin-5-ylidene)methyl}furo[3,2-c]pyridin-7-yl]benzoate;
353) (Z)—N-(4-[2-{(4-oxo-2-thioxothiazolidin-5-ylidene)methyl}furo[3,2-c]pyridin-7-yl]phenyl)methanesulfonamide;
354) (Z)—N,N-dimethyl-3-[2-{(4-oxo-2-thioxothiazolidin-5-ylidene)methyl}furo[3,2-c]pyridin-7-yl]benzamide;
355) (Z)—N-(2,6-dimethyl-4-[2-{(4-oxo-2-thioxothiazolidin-5-ylidene)methyl}furo[3,2-c]pyridin-7-yl]phenyl)methanesulfonamide;
356) (Z)—N-ethyl-2-methyl-4-[2-{(4-oxo-2-thioxothiazolidin-5-ylidene)methyl}furo[3,2-c]pyridin-7-yl] benzenesulfonamide;
357) (Z)—N-isopropyl-2-methyl-4-[2-{(4-oxo-2-thioxothiazolidin-5-ylidene)methyl}furo[3,2-c]pyridin-7-yl]benzenesulfonamide;
358) (Z)—N-tert-butyl-2-methyl-4-[2-{(4-oxo-2-thioxothiazolidin-5-ylidene)methyl}furo[3,2-c]pyridin-7-yl]benzenesulfonamide;
359) (Z)—N-(2-hydroxyethyl)-2-methyl-4-[2-{(4-oxo-2-thioxothiazolidin-5-ylidene)methyl}furo[3,2-c]pyridin-7-yl]benzenesulfonamide;
360) (Z)-2-amino-5-[2-{(4-oxo-2-thioxothiazolidin-5-ylidene)methyl}furo[3,2-c]pyridin-7-yl]benzonitrile;
361) (Z)-5-([7-{4-amino-3-(trifluoromethyl)phenyl}furo [3,2-c]pyridin-2-yl]methylene)-2-thioxothiazolidin-4-one;
362) (Z)-5-([7-{4-(1-methyl-5-oxo-1H-1,2,4-triazol-4 (5H)-yl)phenyl}furo[3,2-c]pyridin-2-yl]methylene)-2-thioxothiazolidin-4-one;
363) (Z)-5-([7-{4-(1-isopropyl-5-oxo-1H-1,2,4-triazol-4 (5H)-yl)phenyl}furo[3,2-c]pyridin-2-yl]methylene)-2-thioxothiazolidin-4-one;
364) (Z)-5-([7-{4-(isopropylsulfonyl)piperazin-1-yl}furo [3,2-c]pyridin-2-yl]methylene)thiazolidine-2,4-dione;
365) (Z)-5-{(7-morpholinofuro[3,2-c]pyridin-2-yl) methylene}thiazolidine-2,4-dione;
366) (Z)-5-[{7-(piperidin-1-yl)furo[3,2-c]pyridin-2-yl}methylene]thiazolidine-2,4-dione;
367) (Z)-5-[{7-(4-methylpiperazin-1-yl)furo[3,2-c]pyridin-2-yl}methylene]thiazolidine-2,4-dione;
368) (Z)-5-[{7-(phenylamino)furo[3,2-c]pyridin-2-yl}methylene]thiazolidine-2,4-dione;
369) (Z)-5-[{7-(benzylamino)furo[3,2-c]pyridin-2-yl}methylene]thiazolidine-2,4-dione;
370) (Z)-ethyl 4-[2-{(2,4-dioxothiazolidin-5-ylidene) methyl}furo[3,2-c]pyridin-7-ylamino]benzoate;
371) (Z)-5-[{7-(4-chlorophenylamino)furo[3,2-c]pyridin-2-yl}methylene]thiazolidine-2,4-dione;
372) (Z)-3-[2-{(2,4-dioxothiazolidin-5-ylidene) methyl}furo[3,2-c]pyridin-7-ylamino]benzonitrile;
373) (Z)-5-([7-{6-(trifluoromethyl)pyridin-3-ylamino}furo[3,2-c]pyridin-2-yl]methylene)thiazolidine-2,4-dione;
374) (Z)-5-[{7-(2-chloropyridin-4-ylamino)furo[3,2-c] pyridin-2-yl}methylene]thiazolidine-2,4-dione;
375) (Z)-5-[{7-(6-chloropyridin-3-ylamino)furo[3,2-c] pyridin-2-yl}methylene]thiazolidine-2,4-dione;
376) (Z)-5-([7-{2-(thiophen-2-yl)ethylamino}furo[3,2-c] pyridin-2-yl]methylene)thiazolidine-2,4-dione;
377) (Z)-5-[{7-(3-methoxyphenethylamino)furo[3,2-c] pyridin-2-yl}methylene]thiazolidine-2,4-dione;
378) (Z)-5-[{7-(3-phenylpropylamino)furo[3,2-c]pyridin-2-yl}methylene]thiazolidine-2,4-dione;
379) (Z)-5-([7-{3-(trifluoromethyl)benzylamino}furo[3, 2-c]pyridin-2-yl]methylene)thiazolidine-2,4-dione;
380) (Z)-5-[{7-(2,4-dichlorophenethylamino)furo[3,2-c] pyridin-2-yl}methylene]thiazolidine-2,4-dione;
381) (Z)-5-[{7-(thiophen-2-ylmethylamino)furo[3,2-c] pyridin-2-yl}methylene]thiazolidine-2,4-dione;

382) (Z)-4-[2-{(2,4-dioxothiazolidin-5-ylidene)methyl}furo[3,2-c]pyridin-7-yl]piperazine-1-sulfonamide;
384) (Z)-1-methyl-5-([7-{3-(trifluoromethoxy)phenyl}furo[3,2-c]pyridin-2-yl]methylene)imidazolidine-2,4-dione;
385) (Z)-4-[2-{(2,4-dioxothiazolidin-5-ylidene)methyl}furo[3,2-c]pyridin-7-yl]-N,N-dimethyl-5,6-dihydropyridine-1(2H)-sulfonamide;
386) (Z)-5-([7-{1-(cyclopropylsulfonyl)-1,2,3,6-tetrahydropyridin-4-yl}furo[3,2-c]pyridin-2-yl]methylene)thiazolidine-2,4-dione;
387) (Z)—N,N-dimethyl-4-[2-{(4-oxo-2-thioxothiazolidin-5-ylidene)methyl}furo[3,2-c]pyridin-7-yl]-5,6-dihydropyridine-1(2H)-sulfonamide;
388) (Z)-5-([7-{1-(cyclopropylsulfonyl)-1,2,3,6-tetrahydropyridin-4-yl}furo[3,2-c]pyridin-2-yl]methylene)-2-thioxothiazolidin-4-one;
389) (Z)-2-(benzylamino)-5-[{7-(4-methoxyphenyl)furo[3,2-c]pyridin-2-yl}methylene]thiazol-4(5H)-one;
390) (Z)-5-[{7-(4-methoxyphenyl)furo[3,2-c]pyridin-2-yl}methylene]-2-morpholinothiazol-4(5H)-one;
391) (Z)-5-[{7-(4-methoxyphenyl)furo[3,2-c]pyridin-2-yl}methylene]-2-(phenethylamino)thiazol-4(5H)-one;
392) (Z)-2-{(4-methoxyphenyl)amino}-5-[{7-(4-methoxyphenyl)furo[3,2-c]pyridin-2-yl}methylene]thiazol-4(5H)-one;
393) (Z)-2-amino-5-[{7-(4-methoxyphenyl)furo[3,2-c]pyridin-2-yl}methylene]thiazol-4(5H)-one;
394) (Z)-5-[{7-(3-fluoro-4-isopropoxyphenyl)furo[3,2-c]pyridin-2-yl}methylene]-2-(methylamino)thiazol-4(5H)-one;
395) (Z)-5-[{7-(3-fluoro-4-isopropoxyphenyl)furo[3,2-c]pyridin-2-yl}methylene]-2-(piperazin-1-yl)thiazol-4(5H)-one;
396) (Z)-3-(2-hydroxyethyl)-5-[{7-(4-methoxyphenyl)furo[3,2-c]pyridin-2-yl}methylene]thiazolidine-2,4-dione;
397) (Z)-5-[{7-(4-methoxyphenyl)furo[3,2-c]pyridin-2-yl}methylene]-3-methyl-2-thioxothiazolidin-4-one;
398) (Z)-5-[{7-(4-(methylthio)phenyl)furo[3,2-c]pyridin-2-yl}methylene]-2-thioxoimidazolidin-4-one;
399) (Z)-5-[{7-(6-fluoropyridin-3-yl)furo[3,2-c]pyridin-2-yl}methylene]-2-thioxoimidazolidin-4-one;
400) (Z)-5-[{7-(3-methoxyphenyl)furo[3,2-c]pyridin-2-yl}methylene]imidazolidine-2,4-dione;
401) (Z)-4-[2-{(2,4-dioxothiazolidin-5-ylidene)methyl}furo[3,2-c]pyridin-7-yl]-N-(2-hydroxyethyl)benzamide;
402) (Z)-4-[2-{(2,4-dioxothiazolidin-5-ylidene)methyl}furo[3,2-c]pyridin-7-yl]-N-propylbenzamide;
403) (Z)-4-[2-{(2,4-dioxothiazolidin-5-ylidene)methyl}furo[3,2-c]pyridin-7-yl]-N-isopropylbenzamide;
410) (Z)-5-[1-{7-(4-methoxyphenyl)furo[3,2-c]pyridin-2-yl}ethylidene]thiazolidine-2,4-dione;
411) (Z)-5-(1-[7-{6-methoxy-5-(trifluoromethyl)pyridin-3-yl}furo[3,2-c]pyridin-2-yl]ethylidene)thiazolidine-2,4-dione;
412) (Z)-2-{(2,4-dioxothiazolidin-5-ylidene)methyl}-N-(2-methoxyphenyl)furo[3,2-c]pyridine-7-carboxamide;
413) (Z)-2-{(2,4-dioxothiazolidin-5-ylidene)methyl}-N-(3-methoxyphenyl)furo[3,2-c]pyridine-7-carboxamide;
414) (Z)-2-{(2,4-dioxothiazolidin-5-ylidene)methyl}-N-(4-methoxyphenyl)furo[3,2-c]pyridine-7-carboxamide;
415) (Z)—N-butyl-2-{(2,4-dioxothiazolidin-5-ylidene)methyl}furo[3,2-c]pyridine-7-carboxamide;
416) (Z)—N-(4-chlorobenzyl)-2-{(2,4-dioxothiazolidin-5-ylidene)methyl}furo[3,2-c]pyridine-7-carboxamide;
417) (Z)-2-{(2,4-dioxothiazolidin-5-ylidene)methyl}-N-(4-methoxybenzyl)furo[3,2-c]pyridine-7-carboxamide;
418) (Z)-5-{(7-(piperidine-1-carbonyl)furo[3,2-c]pyridin-2-yl)methylene}thiazolidine-2,4-dione;
419) (Z)-2-{(2,4-dioxothiazolidin-5-ylidene)methyl}-N-phenethylfuro[3,2-c]pyridine-7-carboxamide;
420) (Z)-2-{(2,4-dioxothiazolidin-5-ylidene)methyl}-N-methylfuro[3,2-c]pyridine-7-carboxamide;
421) (Z)-2-{(2,4-dioxothiazolidin-5-ylidene)methyl}-N-(3-phenylpropyl)furo[3,2-c]pyridine-7-carboxamide;
422) (Z)—N-cyclohexyl-2-{(2,4-dioxothiazolidin-5-ylidene)methyl}furo[3,2-c]pyridine-7-carboxamide;
423) (Z)—N-(2-methoxyphenyl)-2-{(4-oxo-2-thioxothiazolidin-5-ylidene)methyl}furo[3,2-c]pyridine-7-carboxamide;
424) (Z)—N-(3-methoxyphenyl)-2-{(4-oxo-2-thioxothiazolidin-5-ylidene)methyl}furo[3,2-c]pyridine-7-carboxamide;
425) (Z)—N-(4-methoxyphenyl)-2-{(4-oxo-2-thioxothiazolidin-5-ylidene)methyl}furo[3,2-c]pyridine-7-carboxamide;
426) (Z)—N-butyl-2-{(4-oxo-2-thioxothiazolidin-5-ylidene)methyl}furo[3,2-c]pyridine-7-carboxamide;
427) (Z)—N-(4-chlorobenzyl)-2-{(4-oxo-2-thioxothiazolidin-5-ylidene)methyl}furo[3,2-c]pyridine-7-carboxamide;
428) (Z)—N-(4-methoxybenzyl)-2-{(4-oxo-2-thioxothiazolidin-5-ylidene)methyl}furo[3,2-c]pyridine-7-carboxamide;
429) (Z)-5-[{7-(piperidine-1-carbonyl)furo[3,2-c]pyridin-2-yl}methylene]-2-thioxothiazolidin-4-one;
430) (Z)-2-{(4-oxo-2-thioxothiazolidin-5-ylidene)methyl}-N-phenethylfuro[3,2-c]pyridine-7-carboxamide;
431) (Z)—N-methyl-2-{(4-oxo-2-thioxothiazolidin-5-ylidene)methyl}furo[3,2-c]pyridine-7-carboxamide;
432) (Z)-2-{(4-oxo-2-thioxothiazolidin-5-ylidene)methyl}-N-(3-phenylpropyl)furo[3,2-c]pyridine-7-carboxamide;
433) (Z)—N-cyclohexyl-2-{(4-oxo-2-thioxothiazolidin-5-ylidene)methyl}furo[3,2-c]pyridine-7-carboxamide;
434) (Z)-5-[{7-(cyclopropylethynyl)furo[3,2-c]pyridin-2-yl}methylene]thiazolidine-2,4-dione;
435) (Z)-5-[{7-(cyclopentylethynyl)furo[3,2-c]pyridin-2-yl}methylene]thiazolidine-2,4-dione;
436) (Z)-5-[{7-(cyclohexylethynyl)furo[3,2-c]pyridin-2-yl}methylene]thiazolidine-2,4-dione;
437) (Z)-5-([7-{(4-methoxyphenyl)ethynyl}furo[3,2-c]pyridin-2-yl]methylene)thiazolidine-2,4-dione;
438) (Z)-5-[{7-(3,3-dimethylbutyn-1-yl)furo[3,2-c]pyridin-2-yl}methylene]thiazolidine-2,4-dione;
439) (Z)-5-[{7-(pentyn-1-yl)furo[3,2-c]pyridin-2-yl}methylene]thiazolidine-2,4-dione;
440) (Z)-5-{(7-[{4-(trifluoromethyl)phenyl}ethynyl]furo[3,2-c]pyridin-2-yl)methylene}thiazolidine-2,4-dione;
441) (Z)-5-{(7-[{3-(trifluoromethyl)phenyl}ethynyl]furo[3,2-c]pyridin-2-yl)methylene}thiazolidine-2,4-dione;
442) (Z)-5-([7-{(2-methoxyphenyl)ethynyl}furo[3,2-c]pyridin-2-yl]methylene)thiazolidine-2,4-dione;

443) (Z)-5-([7-{(3-methoxyphenyl)ethynyl}furo[3,2-c]pyridin-2-yl]methylene)thiazolidine-2,4-dione;
444) (Z)-5-([7-{(3-fluorophenyl)ethynyl}furo[3,2-c]pyridin-2-yl]methylene)thiazolidine-2,4-dione;
445) (Z)-5-([7-{(4-fluorophenyl)ethynyl}furo[3,2-c]pyridin-2-yl]methylene)thiazolidine-2,4-dione;
446) (Z)-5-[{7-(pyridin-2-ylethynyl)furo[3,2-c]pyridin-2-yl}methylene]thiazolidine-2,4-dione;
447) (Z)-5-[{7-(pyridin-3-ylethynyl)furo[3,2-c]pyridin-2-yl}methylene]thiazolidine-2,4-dione;
448) (Z)-5-([7-{(4-(dimethylamino)phenyl)ethynyl}furo[3,2-c]pyridin-2-yl]methylene)thiazolidine-2,4-dione;
449) (Z)-5-([7-{(4-methoxy-2-methylphenyl)ethynyl}furo[3,2-c]pyridin-2-yl]methylene)thiazolidine-2,4-dione;
450) (Z)-5-([7-{(3,5-dimethoxyphenyl)ethynyl}furo[3,2-c]pyridin-2-yl]methylene)thiazolidine-2,4-dione;
451) (Z)-5-([7-{(3,4-difluorophenyl)ethynyl}furo[3,2-c]pyridin-2-yl]methylene)thiazolidine-2,4-dione;
452) (Z)-5-[{7-(naphthalen-1-ylethynyl)furo[3,2-c]pyridin-2-yl}methylene]thiazolidine-2,4-dione;
453) (Z)-5-([7-{(4-fluoro-3-methylphenyl)ethynyl}furo[3,2-c]pyridin-2-yl]methylene)thiazolidine-2,4-dione;
454) (Z)-5-[{7-(o-tolylethynyl)furo[3,2-c]pyridin-2-yl}methylene]thiazolidine-2,4-dione;
455) (Z)-5-([7-{(2-chlorophenyl)ethynyl}furo[3,2-c]pyridin-2-yl]methylene)thiazolidine-2,4-dione;
456) (Z)-5-([7-{(3-hydroxyphenyl)ethynyl}furo[3,2-c]pyridin-2-yl]methylene)thiazolidine-2,4-dione;
457) (Z)-5-([7-{(2,4,5-trimethylphenyl)ethynyl}furo[3,2-c]pyridin-2-yl]methylene)thiazolidine-2,4-dione;
458) (Z)-5-([7-{(3,4-dichlorophenyl)ethynyl}furo[3,2-c]pyridin-2-yl]methylene)thiazolidine-2,4-dione;
459) (Z)-5-([7-{(4-butylphenyl)ethynyl}furo[3,2-c]pyridin-2-yl]methylene)thiazolidine-2,4-dione;
460) (Z)-2-{4-([2-{(2,4-dioxothiazolidin-5-ylidene)methyl}furo[3,2-c]pyridin-7-yl]ethynyl)phenyl}acetonitrile;
461) (Z)-5-{(7-[{3-(trifluoromethoxy)phenyl}ethynyl]furo[3,2-c]pyridin-2-yl)methylene}thiazolidine-2,4-dione;
462) (Z)—N-{4-([2-{(2,4-dioxothiazolidin-5-ylidene)methyl}furo[3,2-c]pyridin-7-yl]ethynyl)phenyl}methanesulfonamide;
463) (Z)-3-([2-{(2,4-dioxothiazolidin-5-ylidene)methyl}furo[3,2-c]pyridin-7-yl]ethynyl)benzonitrile;
464) (Z)-5-([7-{(4-propylphenyl)ethynyl}furo[3,2-c]pyridin-2-yl]methylene)thiazolidine-2,4-dione;
465) (Z)-5-([7-{(4-ethoxyphenyl)ethynyl}furo[3,2-c]pyridin-2-yl]methylene)thiazolidine-2,4-dione;
466) (Z)-5-[{7-(mesitylethynyl)furo[3,2-c]pyridin-2-yl}methylene]thiazolidine-2,4-dione;
467) (Z)-5-{(7-[{2-(hydroxymethyl)phenyl}ethynyl]furo[3,2-c]pyridin-2-yl)methylene}thiazolidine-2,4-dione;
468) (Z)-5-([7-{(2-aminophenyl)ethynyl}furo[3,2-c]pyridin-2-yl]methylene)thiazolidine-2,4-dione;
469) (Z)-5-([7-{(3,4-dimethoxyphenyl)ethynyl}furo[3,2-c]pyridin-2-yl]methylene)thiazolidine-2,4-dione;
470) (Z)-2-([2-{(2,4-dioxothiazolidin-5-ylidene)methyl}furo[3,2-c]pyridin-7-yl]ethynyl)benzonitrile;
471) (Z)-5-([7-{(4-isopropylphenyl)ethynyl}furo[3,2-c]pyridin-2-yl]methylene)thiazolidine-2,4-dione;
472) (Z)-5-[{7-(naphthalen-2-ylethynyl)furo[3,2-c]pyridin-2-yl}methylene]thiazolidine-2,4-dione;
473) (Z)-5-{(7-[{4-(piperidin-1-yl)phenyl}ethynyl]furo[3,2-c]pyridin-2-yl)methylene}thiazolidine-2,4-dione;
474) (Z)-5-{(7-[{2-(trifluoromethoxy)phenyl}ethynyl]furo[3,2-c]pyridin-2-yl)methylene}thiazolidine-2,4-dione;
475) (Z)-5-[{7-(cyclopropylethynyl)furo[3,2-c]pyridin-2-yl}methylene]-2-thioxothiazolidin-4-one;
476) (Z)-5-[{7-(4-hydroxybutyn-1-yl)furo[3,2-c]pyridin-2-yl}methylene]-2-thioxothiazolidin-4-one;
477) (Z)-5-[{7-(3-hydroxybutyn-1-yl)furo[3,2-c]pyridin-2-yl}methylene]-2-thioxothiazolidin-4-one;
478) (Z)-methyl 3-[2-{(4-oxo-2-thioxothiazolidin-5-ylidene)methyl}furo[3,2-c]pyridin-7-yl]propiolate;
479) (Z)-5-[{7-(cyclopentylethynyl)furo[3,2-c]pyridin-2-yl}methylene]-2-thioxothiazolidin-4-one;
480) (Z)-5-[{7-(cyclohexylethynyl)furo[3,2-c]pyridin-2-yl}methylene]-2-thioxothiazolidin-4-one;
481) (Z)-5-([7-{(4-methoxyphenyl)ethynyl}furo[3,2-c]pyridin-2-yl]methylene)-2-thioxothiazolidin-4-one;
482) (Z)-5-[{7-(3,3-dimethylbutyn-1-yl)furo[3,2-c]pyridin-2-yl}methylene]-2-thioxothiazolidin-4-one;
483) (Z)-5-[{7-(3,3-diethoxypropyn-1-yl)furo[3,2-c]pyridin-2-yl}methylene]-2-thioxothiazolidin-4-one;
484) (Z)-2-thioxo-5-{(7-[{4-(trifluoromethyl)phenyl}ethynyl]furo[3,2-c]pyridin-2-yl)methylene}thiazolidin-4-one;
485) (Z)-2-thioxo-5-{(7-[{3-(trifluoromethyl)phenyl}ethynyl]furo[3,2-c]pyridin-2-yl)methylene}thiazolidin-4-one;
486) (Z)-5-([7-{(2-methoxyphenyl)ethynyl}furo[3,2-c]pyridin-2-yl]methylene)-2-thioxothiazolidin-4-one;
487) (Z)-5-([7-{(3-methoxyphenyl)ethynyl}furo[3,2-c]pyridin-2-yl]methylene)-2-thioxothiazolidin-4-one;
488) (Z)-5-([7-{(3-fluorophenyl)ethynyl}furo[3,2-c]pyridin-2-yl]methylene)-2-thioxothiazolidin-4-one;
489) (Z)-5-([7-{(4-fluorophenyl)ethynyl}furo[3,2-c]pyridin-2-yl]methylene)-2-thioxothiazolidin-4-one;
490) (Z)-5-[{7-(pyridin-2-ylethynyl)furo[3,2-c]pyridin-2-yl}methylene]-2-thioxothiazolidin-4-one;
491) (Z)-5-[{7-(pyridin-3-ylethynyl)furo[3,2-c]pyridin-2-yl}methylene]-2-thioxothiazolidin-4-one;
492) (Z)-5-{(7-[{4-(dimethylamino)phenyl}ethynyl]furo[3,2-c]pyridin-2-yl)methylene}-2-thioxothiazolidin-4-one;
493) (Z)-5-([7-{(4-methoxy-2-methylphenyl)ethynyl}furo[3,2-c]pyridin-2-yl]methylene)-2-thioxothiazolidin-4-one;
494) (Z)-5-([7-{(3,5-dimethoxyphenyl)ethynyl}furo[3,2-c]pyridin-2-yl]methylene)-2-thioxothiazolidin-4-one;
495) (Z)-5-([7-{(3,4-difluorophenyl)ethynyl}furo[3,2-c]pyridin-2-yl]methylene)-2-thioxothiazolidin-4-one;
496) (Z)-5-[{7-(naphthalen-1-ylethynyl)furo[3,2-c]pyridin-2-yl}methylene]-2-thioxothiazolidin-4-one;
497) (Z)-5-([7-{(4-fluoro-3-methylphenyl)ethynyl}furo[3,2-c]pyridin-2-yl]methylene)-2-thioxothiazolidin-4-one;
498) (Z)-2-thioxo-5-[{7-(o-tolylethynyl)furo[3,2-c]pyridin-2-yl}methylene]thiazolidin-4-one;
499) (Z)-5-([7-{(2-chlorophenyl)ethynyl}furo[3,2-c]pyridin-2-yl]methylene)-2-thioxothiazolidin-4-one;
500) (Z)-5-([7-{(3-hydroxyphenyl)ethynyl}furo[3,2-c]pyridin-2-yl]methylene)-2-thioxothiazolidin-4-one;
501) (Z)-2-thioxo-5-([7-{(2,4,5-trimethylphenyl)ethynyl}furo[3,2-c]pyridin-2-yl]methylene)thiazolidin-4-one;
502) (Z)-5-([7-{(3,4-dichlorophenyl)ethynyl}furo[3,2-c]pyridin-2-yl]methylene)-2-thioxothiazolidin-4-one;
503) (Z)-5-([7-{(4-butylphenyl)ethynyl}furo[3,2-c]pyridin-2-yl]methylene)-2-thioxothiazolidin-4-one;

504) (Z)-2-{4-([2-{(4-oxo-2-thioxothiazolidin-5-ylidene)methyl}furo[3,2-c]pyridin-7-yl]ethynyl)phenyl}acetonitrile;
505) (Z)-2-thioxo-5-{(7-[{3-(trifluoromethoxy)phenyl}ethynyl]furo[3,2-c]pyridin-2-yl)methylene}thiazolidin-4-one;
506) (Z)—N-{4-([2-{(4-oxo-2-thioxothiazolidin-5-ylidene)methyl}furo[3,2-c]pyridin-7-yl]ethynyl)phenyl}methanesulfonamide;
507) (Z)-3-([2-{(4-oxo-2-thioxothiazolidin-5-ylidene)methyl}furo[3,2-c]pyridin-7-yl]ethynyl)benzonitrile;
508) (Z)-5-([7-{(4-propylphenyl)ethynyl}furo[3,2-c]pyridin-2-yl]methylene)-2-thioxothiazolidin-4-one;
509) (Z)-5-([7-{(4-ethoxyphenyl)ethynyl}furo[3,2-c]pyridin-2-yl]methylene)-2-thioxothiazolidin-4-one;
510) (Z)-5-[{7-(mesitylethynyl)furo[3,2-c]pyridin-2-yl}methylene]-2-thioxothiazolidin-4-one;
511) (Z)-5-{(7-[{2-(hydroxymethyl)phenyl}ethynyl]furo[3,2-c]pyridin-2-yl)methylene}-2-thioxothiazolidin-4-one;
512) (Z)-5-([7-{(3,4-dimethoxyphenyl)ethynyl}furo[3,2-c]pyridin-2-yl]methylene)-2-thioxothiazolidin-4-one;
513) (Z)-2-([2-{(4-oxo-2-thioxothiazolidin-5-ylidene)methyl}furo[3,2-c]pyridin-7-yl]ethynyl)benzonitrile;
514) (Z)-5-([7-{(4-isopropylphenyl)ethynyl}furo[3,2-c]pyridin-2-yl]methylene)-2-thioxothiazolidin-4-one;
515) (Z)-5-[{7-(naphthalen-2-ylethynyl)furo[3,2-c]pyridin-2-yl}methylene]-2-thioxothiazolidin-4-one;
516) (Z)-5-{(7-[{4-(piperidin-1-yl)phenyl}ethynyl]furo[3,2-c]pyridin-2-yl}methylene)-2-thioxothiazolidin-4-one;
517) (Z)-2-thioxo-5-{(7-[{2-(trifluoromethoxy)phenyl}ethynyl]furo[3,2-c]pyridin-2-yl)methylene}thiazolidin-4-one;
518) (Z)-5-{(7-[{4-(diethylamino)phenyl}ethynyl]furo[3,2-c]pyridin-2-yl)methylene}-2-thioxothiazolidin-4-one;
519) 5-[{7-(m-tolylethynyl)furo[3,2-c]pyridin-2-yl}methyl]thiazolidine-2,4-dione;
520) 5-[{7-(p-tolylethynyl)furo[3,2-c]pyridin-2-yl}methyl]thiazolidine-2,4-dione;
521) (Z)-4-([2-{(2,4-dioxothiazolidin-5-ylidene)methyl}furo[3,2-c]pyridin-7-yl]ethynyl)benzonitrile;
522) (Z)-5-([7-{(2-hydroxyphenyl)ethynyl}furo[3,2-c]pyridin-2-yl]methylene)thiazolidine-2,4-dione;
523) (Z)-5-([7-{(4-hydroxyphenyl)ethynyl}furo[3,2-c]pyridin-2-yl]methylene)thiazolidine-2,4-dione;
524) (Z)-5-([7-{(2-acetylphenyl)ethynyl}furo[3,2-c]pyridin-2-yl]methylene)thiazolidine-2,4-dione;
525) (Z)-5-([7-{(4-acetylphenyl)ethynyl}furo[3,2-c]pyridin-2-yl]methylene)thiazolidine-2,4-dione;
526) (Z)-5-{(7-[{(2-trifluoromethyl)phenyl}ethynyl]furo[3,2-c]pyridin-2-yl)methylene}thiazolidine-2,4-dione;
527) (Z)-5-([7-{(2-isopropylphenyl)ethynyl}furo[3,2-c]pyridin-2-yl]methylene)-2-thioxothiazolidin-4-one;
528) (Z)-5-[{7-(thiophen-3-ylethynyl)furo[3,2-c]pyridin-2-yl}methylene]thiazolidine-2,4-dione;
529) (Z)-5-([7-{(4-tert-butylphenyl)ethynyl}furo[3,2-c]pyridin-2-yl]methylene)thiazolidine-2,4-dione;
530) (Z)-5-([7-{(2-ethylphenyl)ethynyl}furo[3,2-c]pyridin-2-yl]methylene)thiazolidine-2,4-dione;
531) (Z)-Methyl 2-([2-{(2,4-dioxothiazolidin-5-ylidene)methyl}furo[3,2-c]pyridin-7-yl]ethynyl)benzoate;
532) (Z)-Methyl 4-([2-{(2,4-dioxothiazolidin-5-ylidene)methyl}furo[3,2-c]pyridin-7-yl]ethynyl)benzoate;
533) (Z)-5-{(7-[{4-(trifluoromethoxy)phenyl}ethynyl]furo[3,2-c]pyridin-2-yl)methylene}thiazolidine-2,4-dione;
534) (Z)-5-([7-{(3-chlorophenyl)ethynyl}furo[3,2-c]pyridin-2-yl]methylene)thiazolidine-2,4-dione;
535) (Z)-5-([7-{(2,6-dichlorophenyl)ethynyl}furo[3,2-c]pyridin-2-yl]methylene)thiazolidine-2,4-dione;
536) (Z)-4-([2-{(2,4-dioxothiazolidin-5-ylidene)methyl}furo[3,2-c]pyridin-7-yl]ethynyl)-N-methyl-benzenesulfonamide;
537) (Z)-5-{(7-[{4-(morpholinosulfonyl)phenyl}ethynyl]furo[3,2-c]pyridin-2-yl)methylene}thiazolidine-2,4-dione;
538) (Z)-4-([2-{(2,4-dioxothiazolidin-5-ylidene)methyl}furo[3,2-c]pyridin-7-yl]ethynyl)-N-isopropyl-benzenesulfonamide;
539) (Z)—N-tert-butyl-4-([2-{(2,4-dioxothiazolidin-5-ylidene)methyl}furo[3,2-c]pyridin-7-yl]ethynyl)benzenesulfonamide;
540) (Z)-4-([2-{(2,4-dioxothiazolidin-5-ylidene)methyl}furo[3,2-c]pyridin-7-yl]ethynyl)-N-(2-hydroxyethyl)benzenesulfonamide;
541) (Z)-5-([7-{(4-chlorophenyl)ethynyl}furo[3,2-c]pyridin-2-yl]methylene)thiazolidine-2,4-dione;
542) (Z)-methyl 3-([2-{(2,4-dioxothiazolidin-5-ylidene)methyl}furo[3,2-c]pyridin-7-yl]ethynyl)benzoate;
543) (Z)-5-([7-{(3-acetylphenyl)ethynyl}furo[3,2-c]pyridin-2-yl]methylene)thiazolidine-2,4-dione;
544) (Z)-4-([2-{(2,4-dioxothiazolidin-5-ylidene)methyl}furo[3,2-c]pyridin-7-yl]ethynyl)-N,N-dimethylbenzenesulfonamide;
545) (Z)-4-([2-{(2,4-dioxothiazolidin-5-ylidene)methyl}furo[3,2-c]pyridin-7-yl]ethynyl)-N-ethylbenzenesulfonamide;
546) 2-thioxo-5-[{7-(m-tolylethynyl)furo[3,2-c]pyridin-2-yl}methyl]thiazolidin-4-one;
547) 2-thioxo-5-[{7-(p-tolylethynyl)furo[3,2-c]pyridin-2-yl}methyl]thiazolidin-4-one;
548) (Z)-4-([2-{(4-oxo-2-thioxothiazolidin-5-ylidene)methyl}furo[3,2-c]pyridin-7-yl]ethynyl)benzonitrile;
549) (Z)-5-([7-{(2-hydroxyphenyl)ethynyl}furo[3,2-c]pyridin-2-yl]methylene)-2-thioxothiazolidin-4-one;
550) (Z)-5-([7-{(4-hydroxyphenyl)ethynyl}furo[3,2-c]pyridin-2-yl]methylene)-2-thioxothiazolidin-4-one;
551) (Z)-5-([7-{(2-acetylphenyl)ethynyl}furo[3,2-c]pyridin-2-yl]methylene)-2-thioxothiazolidin-4-one;
552) (Z)-5-([7-{(4-acetylphenyl)ethynyl}furo[3,2-c]pyridin-2-yl]methylene)-2-thioxothiazolidin-4-one;
553) (Z)-2-thioxo-5-{(7-[{2-(trifluoromethyl)phenyl}ethynyl]furo[3,2-c]pyridin-2-yl)methylene}thiazolidin-4-one;
554) (Z)-5-([7-{(2-isopropylphenyl)ethynyl}furo[3,2-c]pyridin-2-yl]methylene)-2-thioxothiazolidin-4-one;
555) (Z)-5-[{7-(thiophen-3-ylethynyl)furo[3,2-c]pyridin-2-yl}methylene]-2-thioxothiazolidin-4-one;
556) (Z)-5-([7-{(4-tert-butylphenyl)ethynyl}furo[3,2-c]pyridin-2-yl]methylene)-2-thioxothiazolidin-4-one;
557) (Z)-5-([7-{(2-ethylphenyl)ethynyl}furo[3,2-c]pyridin-2-yl]methylene)-2-thioxothiazolidin-4-one;
558) (Z)-methyl 2-([2-{(4-oxo-2-thioxothiazolidin-5-ylidene)methyl}furo[3,2-c]pyridin-7-yl]ethynyl)benzoate;
559) (Z)-methyl 4-([2-{(4-oxo-2-thioxothiazolidin-5-ylidene)methyl}furo[3,2-c]pyridin-7-yl]ethynyl)benzoate;

560) (Z)-2-thioxo-5-{(7-[{4-(trifluoromethoxy) phenyl}ethynyl]furo[3,2-c]pyridin-2-yl) methylene}thiazolidin-4-one;
561) (Z)-5-([7-{(3-chlorophenyl)ethynyl}furo[3,2-c] pyridin-2-yl]methylene)-2-thioxothiazolidin-4-one;
562) (Z)-5-([7-{(2,6-dichlorophenyl)ethynyl}furo[3,2-c] pyridin-2-yl]methylene)-2-thioxothiazolidin-4-one;
563) (Z)—N-methyl-4-([2-{(4-oxo-2-thioxothiazolidin-5-ylidene)methyl}furo[3,2-c]pyridin-7-yl]ethynyl)benzenesulfonamide;
564) (Z)-5-{(7-[{4-(morpholinosulfonyl)phenyl}ethynyl] furo[3,2-c]pyridin-2-yl)methylene}-2-thioxothiazolidin-4-one;
565) (Z)—N-isopropyl-4-([2-{(4-oxo-2-thioxothiazolidin-5-ylidene)methyl}furo[3,2-c]pyridin-7-yl]ethynyl) benzenesulfonamide;
566) (Z)—N-tert-butyl-4-([2-{(4-oxo-2-thioxothiazolidin-5-ylidene)methyl}furo[3,2-c]pyridin-7-yl]ethynyl) benzenesulfonamide;
567) (Z)—N-(2-hydroxyethyl)-4-([2-{(4-oxo-2-thioxothiazolidin-5-ylidene)methyl}furo[3,2-c]pyridin-7-yl]ethynyl)benzenesulfonamide;
568) (Z)-5-([7-{(4-chlorophenyl)ethynyl}furo[3,2-c] pyridin-2-yl]methylene)-2-thioxothiazolidin-4-one;
569) (Z)-methyl 3-([2-{(4-oxo-2-thioxothiazolidin-5-ylidene)methyl}furo[3,2-c]pyridin-7-yl]ethynyl)benzoate;
570) (Z)-5-([7-{(3-acetylphenyl)ethynyl}furo[3,2-c]pyridin-2-yl]methylene)-2-thioxothiazolidin-4-one;
571) (Z)—N,N-dimethyl-4-([2-{(4-oxo-2-thioxothiazolidin-5-ylidene)methyl}furo[3,2-c]pyridin-7-yl]ethynyl) benzenesulfonamide;
572) (Z)—N-ethyl-4-([2-{(4-oxo-2-thioxothiazolidin-5-ylidene)methyl)furo[3,2-c]pyridin-7-yl]ethynyl)benzenesulfonamide;
573) (Z)-5-[6-(4-methoxyphenyl)furo[3,2-c]pyridin-2-yl}methylene]thiazolidine-2,4-dione;
574) (Z)-5-([6-{4-(trifluoromethoxy)benzyl}furo[3,2-c] pyridin-2-yl]methylene)thiazolidine-2,4-dione; and
575) (Z)-5-[{6-(2-methoxyphenyl)furo[3,2-c]pyridin-2-yl}methylene]-2-thioxothiazolidin-4-one, or a pharmaceutically acceptable salt thereof.

7. A method for preparing the compound of formula (Ie), which comprises: (i) subjecting the compound of formula (IIa) to a hydrolysis reaction to obtain the compound of formula (IIb); and (ii) converting the compound of formula (IIb) into the compound of formula (Ie):

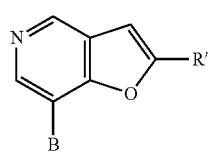

(Ie)

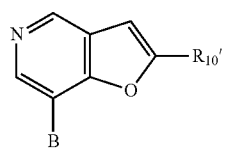

(IIa)

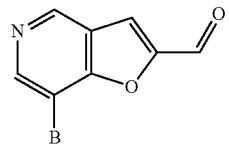

(IIb)

wherein,

B is; —(C≡C)$R_1$; —$(CH_2)_mQ$; —(CH═CH)$(CH_2)_mQ$; —(C≡C)$(CH_2)_mQ$; —NH$(CH_2)_pQ$; —O$(CH_2)_mQ$; —(CONH)$(CH_2)_mQ$; or —CON$R_1R_2$, m is an integer from 0 to 3, p is an integer from 0 to 3, Q is phenyl; pyridyl; pyrazolyl; thiophenyl; pyrimidinyl; thiazolyl; pyridazinyl; piperazinyl; morpholinyl; piperidinyl; tetrahydropyridyl; naphthyl; benzothiophenyl; benzodioxolyl; dihydrobenzofuranyl; dihydrobenzoxazinyl; benzodioxinyl; benzothiadiazolyl; quinolyl; indazolyl; benzoimidazolyl; dihydrobenzodioxinyl; benzothiazolyl; or indolyl, wherein Q is optionally substituted with one or more substituents selected from the group consisting of hydroxy; amino; halogen; cyano; $C_1$-$C_{10}$alkyl optionally substituted with one or more substituents selected from the group consisting of halogen, hydroxy, cyano, $C_1$-$C_6$alkoxy and $C_1$-$C_6$alkylcarbonyloxy; $C_2$-$C_{10}$alkenyl; 4-oxo-2-thioxothiazolidin-5-ylidenyl; $C_2$-$C_{10}$alkynyl; $C_3$-$C_{10}$cycloalkyl; 5- to 7-membered heterocycloalkyl-$C_1$-$C_4$alkyl, wherein, said heterocycloalkyl is optionally substituted with $C_1$-$C_4$alkyl; $C_6$-$C_{12}$aryl; 5- to 12-membered heteroaryl optionally substituted with $C_1$-$C_4$alkyl; 3- to 12-membered heterocycloalkyl optionally substituted with $C_1$-$C_6$alkyl; $C_1$-$C_{10}$alkoxy optionally substituted with one or more substituents selected from halogen and cyano; $C_3$-$C_{10}$cycloalkyloxy; $C_6$-$C_{12}$aryl-$C_1$-$C_{10}$alkyloxy, wherein, said aryl is optionally substituted with $C_1$-$C_3$alkoxy; $C_6$-$C_{12}$aryloxy optionally substituted with one or more substituents selected from the group consisting of hydroxy, amino, halogen, hydroxycarbonyl, cyano and nitro; 5- to 12-membered heteroaryloxy, wherein, said heteroaryl is optionally substituted with one or more substituents selected from the group consisting of hydroxy, amino, halogen, hydroxycarbonyl, cyano and nitro; $C_1$-$C_{10}$alkylcarbonyloxy; $C_1$-$C_{10}$alkylthio; mono- or di-$C_1$-$C_{10}$alkylamino; mono- or di-$C_3$-$C_7$cycloalkylamino; $C_6$-$C_{12}$arylamino; 5- to 12-membered heteroarylamino; $C_1$-$C_{10}$alkylsulfonylamino; $C_6$-$C_{12}$arylsulfonylamino; 5- to 12-membered heteroarylsulfonylamino; $C_1$-$C_{10}$alkylcarbonylamino; $C_6$-$C_{12}$arylcarbonylamino; 5- to 12-membered heteroarylcarbonylamino; formyl; $C_1$-$C_{10}$alkylcarbonyl; $C_6$-$C_{12}$arylcarbonyl; 5- to 12-membered heteroarylcarbonyl; $C_1$-$C_{10}$alkoxycarbonyl; hydroxycarbonyl; $C_6$-$C_{12}$aryloxycarbonyl; 5- to 12-membered heteroaryloxycarbonyl; aminocarbonyl; mono- or di-$C_1$-$C_{10}$alkylaminocarbonyl, wherein said alkyl is optionally substituted with hydroxy; $C_6$-$C_{12}$arylaminocarbonyl; 5- to 12-membered heteroarylaminocarbonyl; aminosulfonyl; mono- or di-$C_1$-$C_{10}$alkylaminosulfonyl, wherein, said alkyl is optionally substituted with hydroxy; $C_3$-$C_7$cycloalkylaminosulfonyl; $C_1$-$C_{10}$alkylsulfonyl optionally substituted with hydroxy; 5- to 7-membered heterocycloalkyl-sulfonyl, wherein, said heterocycloalkyl is optionally substituted with $C_1$-$C_4$alkyl; $C_6$-$C_{12}$arylaminosulfonyl; 5- to 12-membered heteroarylaminosulfonyl; $C_1$-$C_{10}$alkylsulfinyl; $C_1$-$C_{10}$alkylcarbamoyloxy; and $C_1$-$C_{10}$alkylureido, $R_1$ and $R_2$ are each independently hydrogen; $C_1$-$C_{10}$alkyl optionally substituted with one or more substituents selected from hydroxy and $C_1$-$C_6$alkoxy; $C_3$-$C_{10}$cycloalkyl optionally substituted with one or more substituents selected from the group consisting of halogen, hydroxy, $C_1$-$C_6$alkoxy and $C_1$-$C_6$alkylcarbonyloxy; $C_1$-$C_{10}$alkoxycarbonyl; $C_1$-$C_{10}$alkylcarbonyl; or $R_1$ join together to form a 5- to 12-membered ring optionally containing a heteroatom selected from N and O, R' is

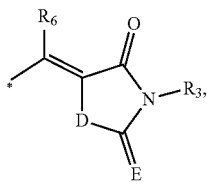

D is $NR_7$, O or S,

E is O or S, $R_3$ is hydrogen; or $C_1$-$C_{10}$alkyl optionally substituted with hydroxy, $R_6$ is hydrogen or $C_1$-$C_{10}$alkyl, $R_7$ is hydrogen or $C_1$-$C_{10}$alkyl, $R_{10}'$ is di-$C_1$-$C_{10}$alkoxymethyl.

8. A pharmaceutical composition comprising, as an active ingredient, a compound according to claim 1 or a pharmaceutically acceptable salt thereof, as an active ingredient.

9. A method for manufacturing a medicament, said method comprising formulating the compound according to claim 1 or a pharmaceutically acceptable salt and a pharmaceutically acceptable carrier into a medicament.

10. A pharmaceutical composition comprising, as an active ingredient, a compound according to claim 2 or a pharmaceutically acceptable salt thereof, as an active ingredient.

11. A pharmaceutical composition comprising, as an active ingredient, a compound according to claim 3 or a pharmaceutically acceptable salt thereof, as an active ingredient.

12. A pharmaceutical composition comprising, as an active ingredient, a compound according to claim 4 or a pharmaceutically acceptable salt thereof, as an active ingredient.

13. A pharmaceutical composition comprising, as an active ingredient, a compound according to claim 5 or a pharmaceutically acceptable salt thereof, as an active ingredient.

14. A pharmaceutical composition comprising, as an active ingredient, a compound according to claim 6 or a pharmaceutically acceptable salt thereof, as an active ingredient.

* * * * *